(12) United States Patent
Shanmugam et al.

(10) Patent No.: US 7,098,009 B2
(45) Date of Patent: Aug. 29, 2006

(54) PRODUCTION OF CHEMICALS FROM LIGNOCELLULOSE, BIOMASS OR SUGARS

(75) Inventors: Keelnatham T. Shanmugam, Gainesville, FL (US); Lonnie O'Neal Ingram, Gainesville, FL (US); Milind A. Patel, Gainesville, FL (US); Mark S. Ou, Gainesville, FL (US); Roberta Harbrucker, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 10/793,568

(22) Filed: Mar. 4, 2004

(65) Prior Publication Data

US 2005/0250192 A1    Nov. 10, 2005

(51) Int. Cl.
    *C12P 7/56* (2006.01)
    *C12N 1/20* (2006.01)
(52) U.S. Cl. .............. 435/139; 435/252.1; 435/252.5
(58) Field of Classification Search ............ 435/252.1, 435/252.5, 139
    See application file for complete search history.

(56) References Cited

U.S. PATENT DOCUMENTS

| | | | |
|---|---|---|---|
| 5,079,164 A | * | 1/1992 | Kirkovits et al. ......... 435/252.5 |
| 5,801,025 A | * | 9/1998 | Ohara et al. ................ 435/139 |
| 2004/0203122 A1 | * | 10/2004 | Otto .......................... 435/139 |

OTHER PUBLICATIONS

Bergey's Manual of Systematic Bacteriology (vol. 2, Sneath et al, eds., pp. 1122, 1123, 1131, and 1132 (1987)).*
Patel et al. (2003) "Second generation biocatalysts for production of fuels and chemicals from biomass" IN: *Proceedings of the 25th Symposium on Biotechnology for Fuels and Chemicals*, Breckenridge, CO, May 4-7, 2003.
16S rRNA Sequence alignments of ATCC 23498 *Bacillus* isolates 17C5, 36D1 and P4-102B.

* cited by examiner

Primary Examiner—Francisco Prats
(74) Attorney, Agent, or Firm—Saliwanchik, Lloyd & Saliwanchik

(57) ABSTRACT

The subject invention relates to newly isolated organisms from nature that produce L(+)-lactic acid high yield from hexose and pentose sugars found in biomass. Organisms and processes or methods for the production of lactic acid and other industrially important chemicals from cellulose and hemicellulose are also provided.

13 Claims, 19 Drawing Sheets

The bar represents number of nucleotide substitutions per site.

The bar represents number of nucleotide substitutions per site.

The bar represents 1% divergence between sequences.

Figure 6A
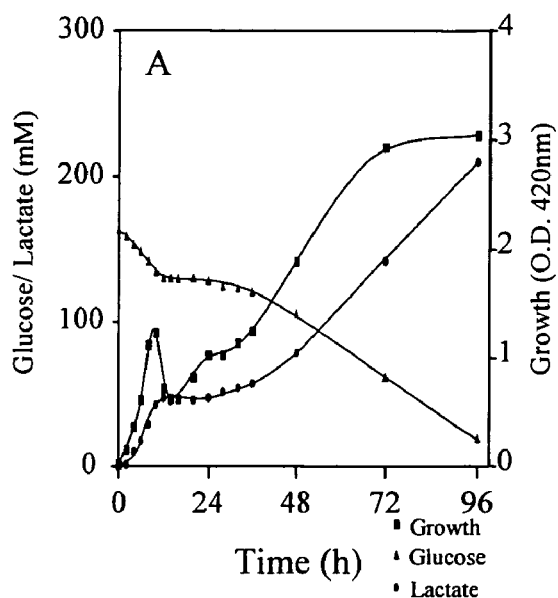
Figure 6B
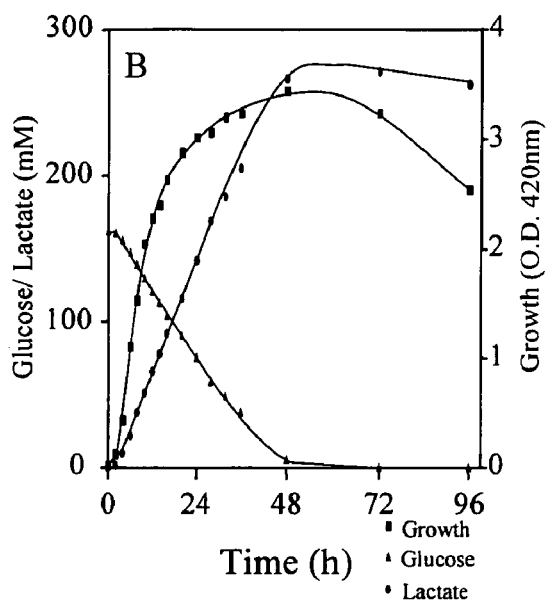
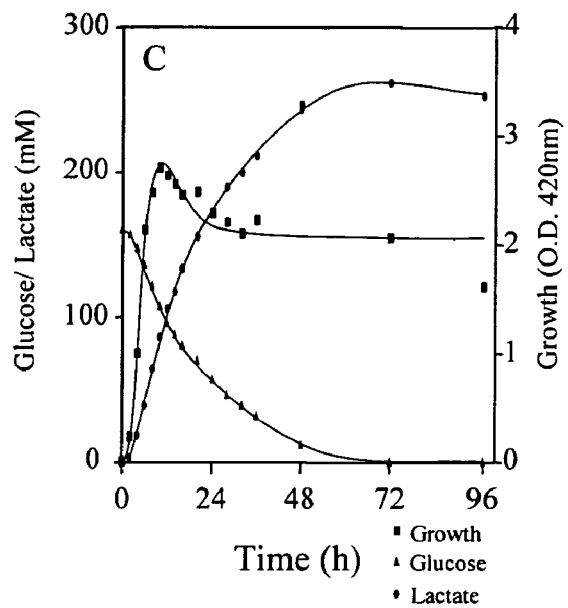
Figure 6B
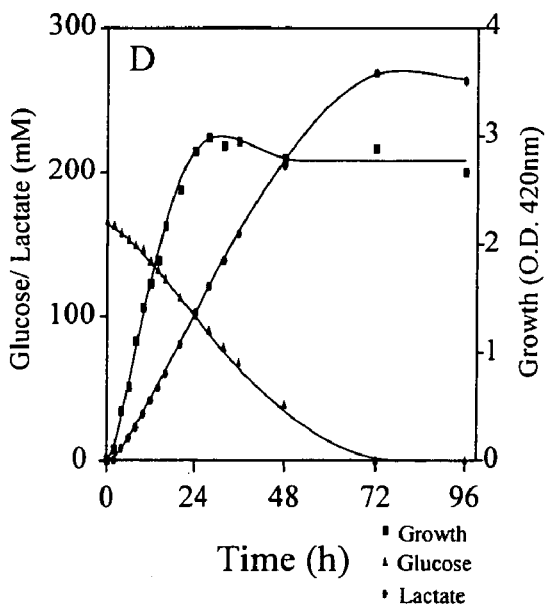
Figure 6D Figure 7A
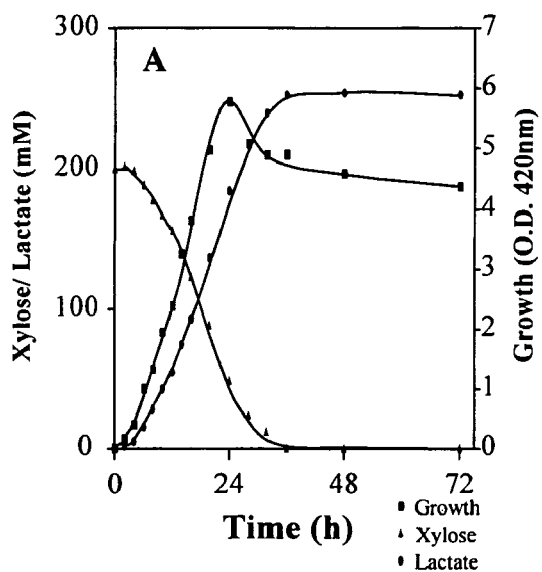
Figure 7C
Figure 7B
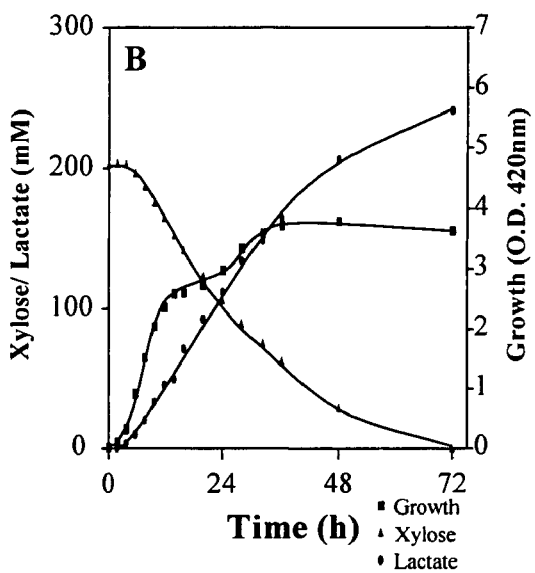
Figure 7D
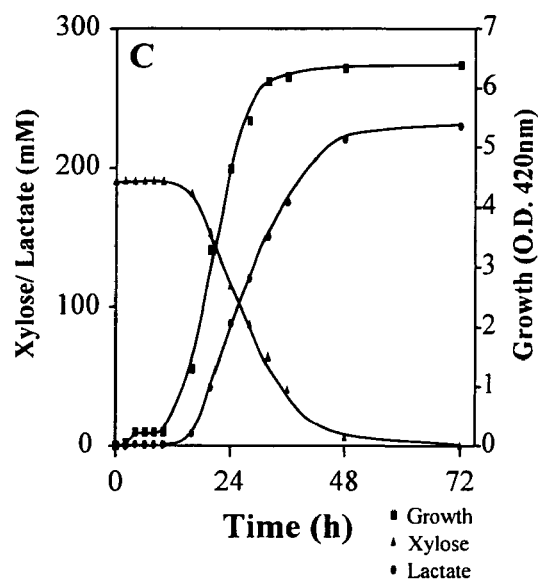
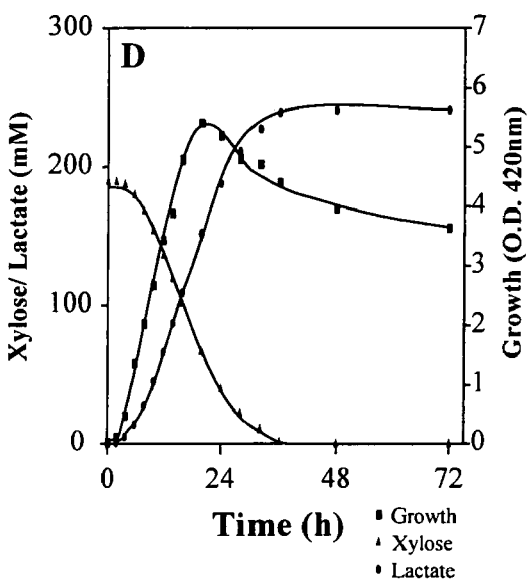

PRODUCTION OF CHEMICALS FROM LIGNOCELLULOSE, BIOMASS OR SUGARS

This invention was made with government support under NREL Sub-contract # XXL-9-29034-01 and DOE Grant # DE-FC36-01GO11073. The government may have certain rights in this invention.

TECHNICAL FIELD

The subject invention relates to newly isolated organisms from nature that produce L(+)-lactic acid at high yield from hexose and pentose sugars. Organisms and processes or methods for the production of lactic acid and other industrially important chemicals are also provided.

BACKGROUND OF THE INVENTION

Lactic acid is widely used in food, pharmaceutical and textile industries. It is also used as a source of lactic acid polymers which are being used as biodegradable plastics (Brown, S. F., 2003, Fortune, 148:92–94; Datta, R., et al., 1995, FEMS Microbiol. Rev. 16:221–231). The physical properties and stability of polylactides can be controlled by adjusting the proportions of the L(+)- and D(−)-lactides (Tsuji, F., 2002, Polymer 43:1789–1796). Optically pure lactic acid is currently produced by the fermentation of glucose derived from corn starch using various lactic acid bacteria (Carr, F. J., et al., 2002, Crit. Rev. Microbiol. 28:281–370; Hofvendahl, K. and Hahn-Hagerdal, B., 2000, Enz. Microb. Technol. 26:87–107). However, the fastidious lactic acid bacteria have complex nutritional requirements (Chopin, A., 1993, FEMS Microbiol. Rev. 12:21–38) and the use of corn as the feedstock competes directly with the food and feed uses.

Lignocellulosic biomass represents a potentially inexpensive and renewable source of sugars for fermentation (Duff, S. J. B. and Murray, W. D., 1996, Bioresource Technol. 55:1–33; Parajo, J. C., et al., 1996, Process Biochem. 31:271–280; Wyman, C. E., 1999, Ann. Rev. Energy Env. 24:189–226). The hemicellulose portion of biomass contains up to 35% of the total carbohydrate and can be readily hydrolyzed to monomeric sugars by dilute sulfuric acid (Saha, B. and Bothast, R. J., 1999, Appl. Biochem. Biotechnol. 76:65–77). With crop residues and hardwoods, this hemicellulose syrup contains primarily xylose. During acid hydrolysis, an assortment of microbial inhibitors is also produced which must be removed by treatment with lime (Amartey, S. and Jeffries, T., 1996, World J. Microbiol. Biotechnol. 12:281–283; Clark, T. A. and Mackie, K. L., 1984, J. Chem. Technol. Biotechnol. 34B:101–110; Martinez, A., et al., 2001, Biotechnol. Prog. 17:287–293).

*Lactobacillus* spp. are used extensively in industry for starch-based lactic acid production, the majority of which lack the ability to ferment pentose sugars such as xylose and arabinose (Carr, F. J., et al., 2002, Crit. Rev. Microbiol. 28:281–370). Although, *Lactobacillus pentosus, Lb. brevis* and *Lactococcus lactis* ferment pentoses to lactic acid, pentoses are metabolized using the phosphoketolase pathway which is inefficient for lactic acid production (Garde, A., et al., 2002, Bioresource Technol. 81:217–223; Tanaka, K., et al., 2002, Appl. Microbiol. Biotechnol. 60:160–167). In the phosphoketolase pathway, xylulose 5-phosphate is cleaved to glyceraldehyde 3-phosphate and acetyl-phosphate. With this pathway, the maximum theoretical yield of lactic acid is limited to one per pentose (0.6 g lactic acid per g xylose) due to the loss of two carbons to acetic acid.

BRIEF SUMMARY OF THE INVENTION

We have recently isolated new organisms (sometimes referred to herein as "second generation biocatalysts", "second generation organisms" or "biocatalyst(s)") from nature that produce L(+) lactic acid at high yield from hexose and pentose sugars. These organisms have the added advantage of performing well under conditions that are optimal for cellulose enzymes (pH of about 5 and temperatures of about 50° C.). As the cost of cellulose enzymes is currently quite high, matching an organism that can produce a desired chemical compound from hexose and pentose sugars with optimal conditions for this enzyme offers the potential for considerable cost savings by reducing the amount of cellulose enzyme needed. Organisms provided by the subject invention can also ferment dilute acid hydrolysates of hemicellulose. Organisms can also ferment hemicellulose and cellulose sugars together in a single unified fermentation. The subject invention also provides organisms and processes or methods for the production of L(+)-lactic acid from cellulose and hemicellulose. Organisms of the subject invention can also be engineered for the production of additional products, such as (and not limited to), 1,3-propanediol, 1,2-propanediol, succinic acid, ethanol, and D(−)-lactic acid. The subject invention also provides polynucleotides and polypeptides encoding D-lactate dehydrogenase (d-ldh; D-LDH). Additionally, the subject invention also provides a DNA fragment that encodes pyruvate formate lyase (pfl; PFL).

These newly isolated organisms, as exemplified by *Bacillus* sp. strain 17C5, ferment sugars in hemicellulose hydrolysate to L(+)-lactic acid at high yields using a simple salts medium supplemented with 0.5% corn steep liquor. The L(+)-lactate product had an optical purity of greater than 99% and comprised 90% of the sugar weight. These organisms, and genetically modified derivatives thereof, can be used for the conversion of pentose-rich feedstocks such as corn stover, corn fiber, bagasse, rice hulls, rice straw, or other forms of biomass into commodity chemicals such as L(+)-lactic acid.

BRIEF DESCRIPTION OF THE DRAWINGS

FIG. 2: Phylogenetic relationship based on the first 525 base pair sequence of 16S rRNA (DNA) between various organisms of the subject invention and known *Bacillus* species (e.g., isolates are close to *B. coagulans* on the basis of the sequence analysis).

FIG. 5: Glucose fermentation and lactic acid production by selected isolates in LB+ glucose (3%) in a pH-stat at pH 5.0 and 50° C.

FIG. 6: Glucose fermentation and lactic acid production by selected isolates in glucose (3%) minimal medium with 1% corn steep liquor in a pH-stat at pH 5.0 and 50° C. FIG. 6A—Isolate 17C5; FIG. 6B—Isolate 36D1; FIG. 6C—Isolate P4-74B; and FIG. 6D—Isolate P4-102B.

FIG. 7: Xylose fermentation and lactic acid production by selected isolates in LB+ xylose (3%) in a pH-stat at pH 5.0 and 50° C. FIG. 7A—Isolate 17C5; FIG. 7B—Isolate 36D1; FIG. 7C—Isolate P4-74B; and FIG. 7D—Isolate P4-102B.

FIG. 8: Xylose fermentation and lactic acid production by selected isolates in xylose (3%)—minimal medium with 1% corn steep liquor in a pH-stat at pH 5.0 and 50° C.

BRIEF DESCRIPTION OF THE SEQUENCES

Figure 1:
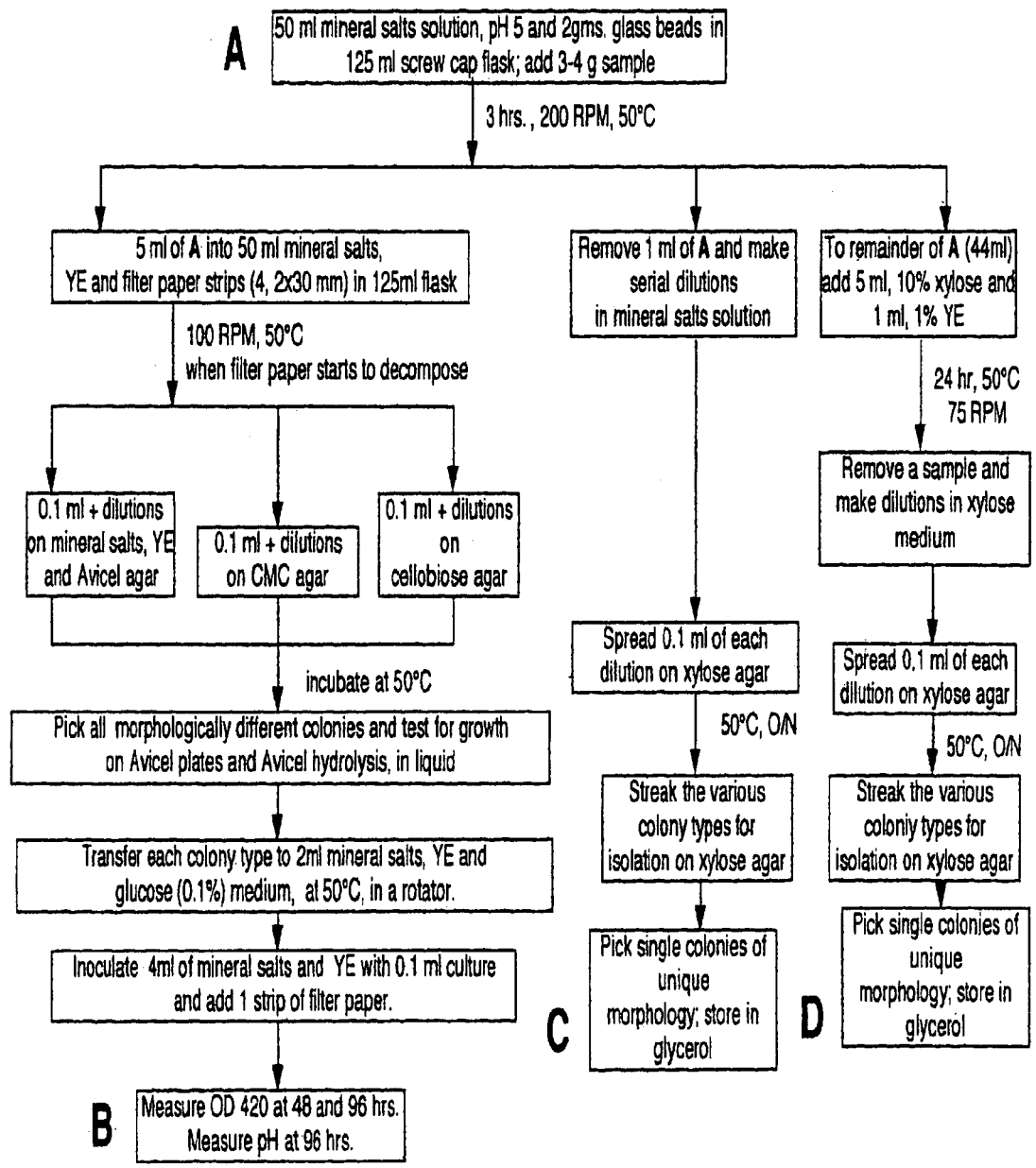
FIG. 1: An illustrative isolation protocol for identifying and isolating organisms according to the subject invention.
Figure 1:
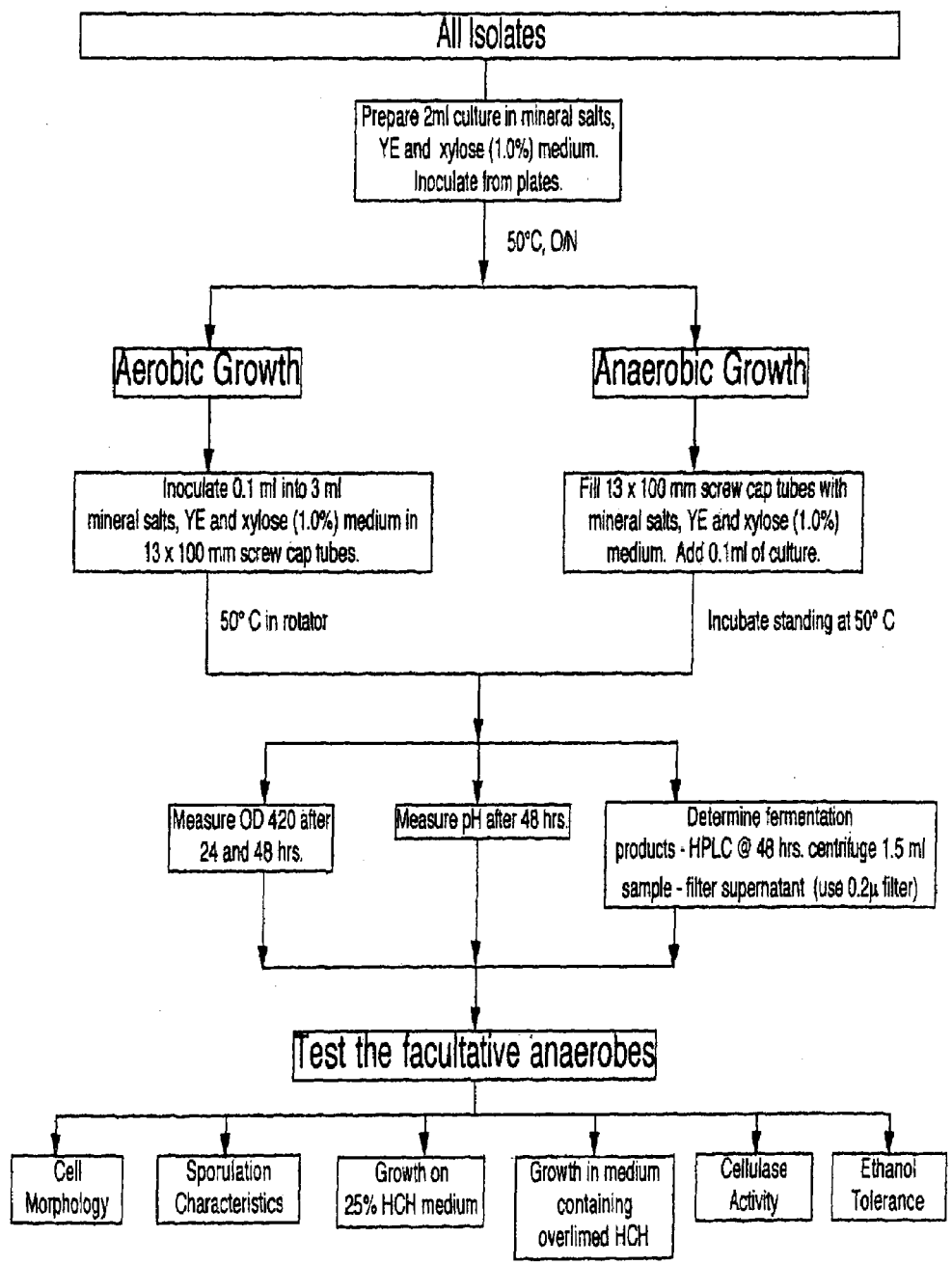
Figure 1:
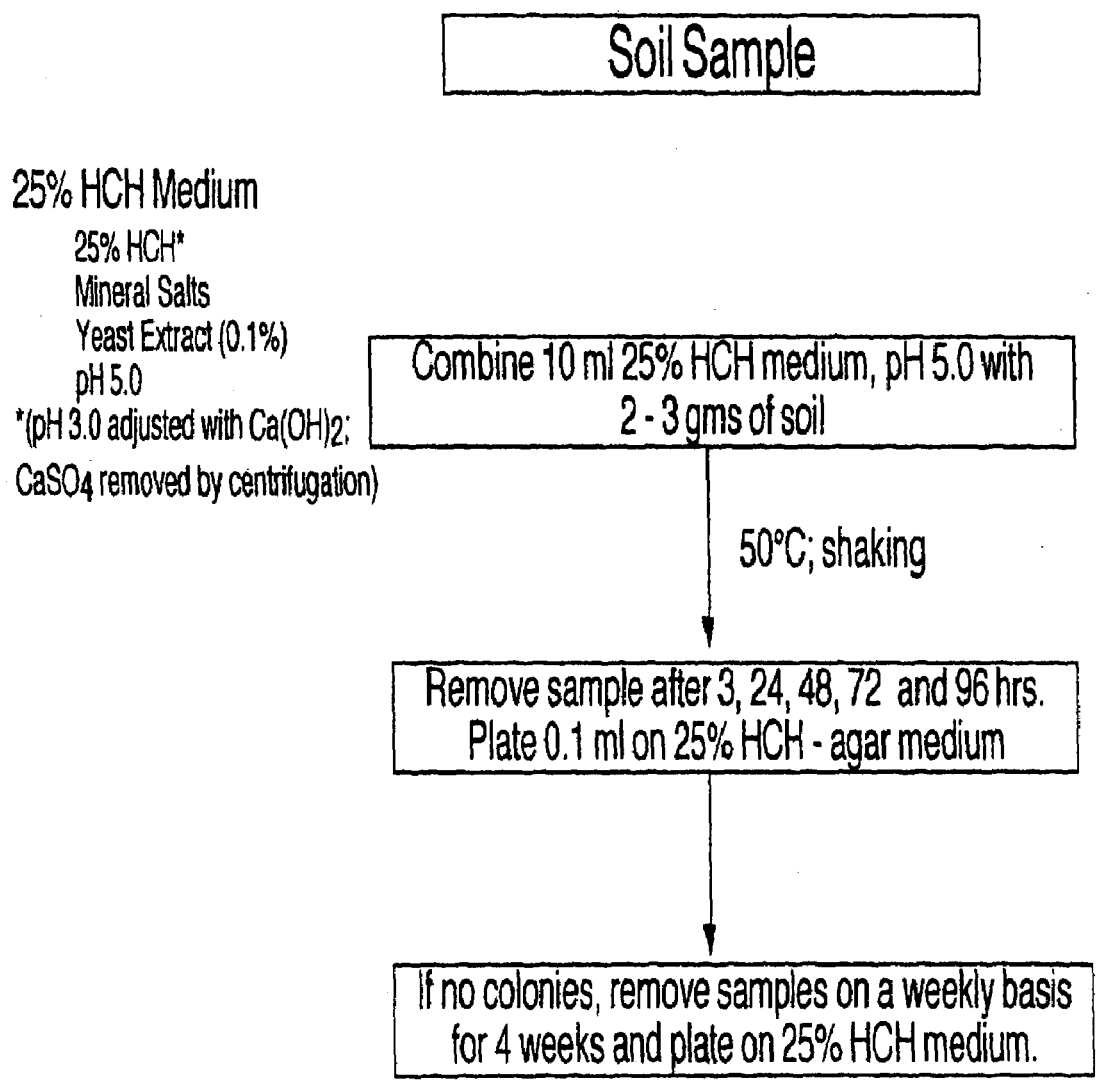

SEQ ID NOs: 1 and 2 are the polynucleotide and polypeptide sequences encoding D-lactate dehydrogenase (d-ldh; D-LDH).

SEQ ID NOs: 3–39 are nucleic acid sequences encoding 16S rRNA (partial; 525 nucleotides) of various isolates of the subject invention.

SEQ ID NOs: 40–42 are longer length nucleic acid sequences encoding 16S rRNA of isolates 36D1, 17C5 and P4-102B of the subject invention.

BRIEF DESCRIPTION OF THE TABLES

Table 1 provides locations from which organisms of the subject invention were isolated.

Table 2 illustrates various properties of organisms isolated according to the subject invention. Where *Bacillus coagulans* is indicated in the "Identification" column, this isolate is related to *B. coagulans* based on the first 500 bp of the 16s rRNA sequence; these organisms are not *B. coagulans* (on the basis of the 16S rRNA sequence analysis). Isolate Y56 is *Bacillus smithii* while isolate 57H2 is closely related to *B. smithii*. *B. coagulans* in the "Isolate" column represents an ATCC culture (ATCC 7050). T and W represent two different colony forms obtained from the culture. Additional legend information: blank space—indicates test not performed; CSL—corn steep liquor; GLU—glucose; HCH—hemicellulose hydrolysate; MS—minimal salts medium; XYL—xylose; YE—yeast extract; and +—denotes positive character for the growth or activity tested. An increase in the number of + signs represents an appropriate increase in the final cell yield of the culture. This same Table legend applies to all other Tables.

Table 3 shows various properties for *Bacillus coagulans*-like isolates that have been grouped on the basis of 16S rRNA sequences.

Table 4 provides growth and fermentation profiles of selected organisms in 3% glucose.

Table 5 illustrates growth and fermentation profiles of selected isolates in 3% xylose.

Table 6 shows fermentation profiles of various selected isolates in 5% sugars.

Table 7 relates to growth and fermentation profiles of selected isolates in minimal salts medium.

Table 8 provides growth and fermentation profiles of select isolates in hemicellulose hydrolysates.

Table 9 is a fermentation profile of 3% glucose in LB medium and in minimal medium with 1% corn steep liquor at pH 5.0 and 50° C. for isolates 17C5, 36D1, P4-102B, and P4-74B.

Table 10 is a fermentation profile of 3% xylose in LB medium and in minimal medium with 1% corn steep liquor at pH 5.0 and 50° C. for isolates 17C5, 36D1, P4-102B, and P4-74B.

Table 11 provides analysis of the lactic acid produced by isolates 17C5, 36D1, P4-102B, and P4-74B.

Table 12 provides $^{13}$C-enrichment ratios for fermentation products produced from $^{13}$C$_1$-xylose.

Table 13 is the SSF profile of strain 36D1 in mineral salts medium at different pH and temperature.

Table 14 relates to sugar cane bagasse hemicellulose hydrolysate fermentation by *Bacillus* sp. strain 17C5.

DETAILED DISCLOSURE OF THE INVENTION

*Bacillus* isolates 17C5, 36D1 and P4-102B were deposited with the American Type Culture Collection (10801 University Blvd., Manassas, Va. 20110-2209 USA) on Mar. 2, 2004 and have accession numbers PTA-5826, PTA-5827, and PTA-5828, respectively. In various embodiments, the subject invention provides isolates that have not been genetically modified (e.g., a non-transformed isolate selected from the group consisting of isolates 17C5, 36D1 and P4-102B). Also included within the scope of the subject invention are subclones, progeny, and subcultures of these isolates.

The culture deposited for the purposes of this patent application was deposited under conditions that assure that access to the culture is available during the pendency of this patent application to one determined by the Commissioner of Patents and Trademarks entitled thereto under 37 C.F.R. § 1.14 and 35 U.S.C. § 122. The deposit will be available as required by foreign patent laws in countries wherein counterparts of the subject application, or its progeny, are filed. However, it should be understood that the availability of a deposit does not constitute a license to practice the subject invention in derogation of patent rights granted by government action.

Further, the subject culture deposit will be stored and made available to the public in accord with the provisions of the Budapest Treaty for the deposit of biological materials, i.e., they will be stored with all the care necessary to keep them viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of a deposit. All restrictions on the availability to the public of the subject culture deposit will be irrevocably removed upon the granting of a patent disclosing it.

In one embodiment, the subject invention provides novel isolated Gram positive organisms capable of producing L(+) lactic acid at high yield from hexose and pentose sugars. In certain embodiments, the organisms are isolated from nature and have not been modified by recombinant DNA technologies. The organisms of the subject invention also have the added advantage of performing well under conditions that are optimal for cellulose enzymes, growing well in media maintained at a pH of about 5 and temperatures of 50° C.

Accordingly, one aspect of the subject invention provides for novel Gram positive organisms that have not been recombinantly modified, are isolated from nature and comprise at least one of, or any combination of, the following characteristics:

a) able to grow under anaerobic conditions;
b) able to grow and ferment glucose, xylose, arabinose, galactose, mannose, sucrose, cellobiose, or various combinations of these carbohydrate sources;
c) able to grow in minimal-salts medium with and without corn steep liquor;
d) able to grow in, and ferment, sugar cane bagasse hemicellulose hydrolysate, crystalline cellulose;
e) can perform simultaneous saccharification and fermentation (SSF) of crystalline cellulose;
f) are classified into the unique phylogenetic group of organisms on the subject invention on the basis of 16S rRNA sequences of at least 50, 150, 200, 250, 300, 350, 400, 450, 500, 525, 550 or 600 consecutive nucleotides or on the basis of the full length 16S rRNA sequence of the organisms of the subject invention (e.g., similarity scores of at least 0.95, 0.96, 0.97, 0.98, or 0.99 or a similarity score 1.00 as compared to at least one, any combination, or all, of the sequences of SEQ ID NOs: 3–42);
g) generation of L(+)-lactic acid yields in excess of 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99%, wherein the L(+)-lactic acid produced by the organisms has an optical purity of at least 80, 81, 82, 83, 84, 85, 86, 87, 88, 89, 90, 91, 92, 93, 94, 95, 96, 97, 98, or 99%;
h) utilization of pentose sugars in fermentation pathways;
i) utilization of hexose sugars in fermentation pathways;
j) utilization of both hexose and pentose sugars in fermentation pathways; and/or
k) use of the pentose phosphate pathway in pentose fermentation;
l) spore-forming organism;
m) classification as a member of the family *Bacillaceae*; and/or
n) classification as a member of the genus *Bacillus*.

In certain embodiments of the subject invention, the novel organisms of the subject invention have at least two, three, four, five, six, seven, eight, nine, ten, eleven, twelve, or thirteen of the aforementioned characteristics. In other embodiments, the novel organisms of the subject invention have all fourteen of the aforementioned characteristics. As would be apparent to the skilled artisan, the organisms of the subject invention can have any combination of the aforementioned characteristics and the various combinations of these characteristics have not been set forth in this specification in the interests of not unduly lengthening the subject specification. Additionally, any of the aforementioned characteristics can be specifically included or excluded from the characteristics of organisms of the subject invention.

The subject invention also provides methods of isolating these organisms comprising the steps provided in FIG. 1 and microorganisms that have been isolated according to the methods of the subject invention. Thus, in one embodiment, the subject invention provides a method of isolating an organism having those characteristics disclosed herein or supra comprising the steps of:

a) obtaining an environmental sample from soils, compost, wood chips, food products, mulch, animal waste, or any other environmental source;
b) pre-incubating and resuspending the sample;
c) enriching for cellulose positive organisms;
d) isolating hemicellulose fermenting organisms;
e) enriching for hemicellulose fermenting organisms;
f) isolating organisms enriched in step e); and
g) analyzing said isolated organisms for desired properties.

Thus, in one embodiment, a sample obtained from the environment is added to a composition comprising a sterile mineral salts solution and beads at a pH of about 5 to form a first liquid culture composition. For example, about 3–4 grams of a sample (for example a soil sample) is added to the sterile mineral salt solution and the subsequent incubation of the resulting mixture in a shaker at 50° C. for 3 hours to dislodge the bacteria from particles.

After the bacteria have been dislodged from particles, enrichment for cellulase-positive bacteria is performed according to methods known to the skilled artisan. For example, about 5 ml of the suspended particle sample can be added to 50 ml of a composition comprising mineral salts and yeast extract [mineral salts-yeast extract medium (1 g/L YE)] and a filter paper strip to form a first culture to form a second liquid culture composition. This second culture composition can be incubated in the shaker at 50° C. (100 RPM) and the filter paper structure monitored visually. After filter paper appears to be decomposed, a loopful of medium can be removed and streaked out for the isolation of colonies on complete medium containing 2 g/L Avicel or Sigmacel 50 cellulose. Dilutions, typically ten-fold dilutions, can also be made and the various dilutions plated on complete medium containing 2 g/L Avicel or Sigmacel 50 cellulose, a medium containing carboxymethylcellulose (CMC) and/or cellobiose (0.2%). Incubate all the plates at 50° C. in plastic boxes. Colonies thus isolated are then picked and tested for growth in Sigmacel plates and for filter paper hydrolysis in liquid medium (a third liquid culture composition) in tubes (e.g., 4 ml of medium with one strip of filter paper). After 48 and 96 hours of growth, the OD420 nm and pH of the cultures are determined.

Hemicellulose fermenting organisms can then be isolated using solid and/or liquid medium. Where solid medium is used, remove 1 ml of a sample from the suspended culture (third liquid culture composition) and make serial dilutions (e.g., 10-fold) in mineral salts solution. Spread 0.1 ml samples on xylose medium containing 10 g xylose per liter and incubate the plates at 50° C. overnight. Pick colonies to a new plate and grow overnight at 50° C. Streak the colonies for isolation on xylose medium and pick single colonies from each morphological type to store in glycerol and also patch for routine use. Isolates which are facultative can be tested for growth in the presence of 25% hemicellulose hydrolysate in plates as well as in medium containing overlimed hemicellulose hydrolysate.

When using liquid medium, add nutrients to the third liquid culture medium. In one embodiment, 5 ml of 10% xylose and 1 ml of 1% YE (pH 5, filter sterilized) can be added to 44 ml of the suspended sample in said third liquid culture medium to form a fourth liquid culture medium. Incubate said fourth liquid culture medium for 24 hours at 50° C., shaking. Remove a sample from said fourth liquid culture medium and make serial dilutions (e.g., 10-fold) in mineral salts solution. Spread 0.1 ml samples on xylose medium with 10 g xylose per liter and incubate the plates at 50° C., overnight. Pick colonies to a new plate and grow overnight at 50° C. and streak the colonies for isolation on xylose medium. Pick single colonies from each morphological type and store in glycerol and also patch for routine use.

In the analysis step of the subject method, each isolate can be tested for other properties in complete medium with 10 g/L xylose. These properties include, and are not limited to: 1) growth under aerobic and anaerobic conditions in rich medium as well as in minimal salts medium with or without supplements such as yeast extract or corn steep liquor at a starting pH of 5.0 or 6.8; 2) fermentation profile of facultative organisms; 3) growth in hemicellulose hydrolysate both overlimed as well as not-overlimed, at a starting pH of 5.0; 4) ethanol tolerance; 5) ability to grow at a starting medium pH of less than 5.0; 6) ability to produce xylanase; or 7) ability to hydrolyze crystalline cellulose (e.g., Avicel) as well as amorphous cellulose, carboxymethyl cellulose (CMC). In various embodiments of the subject invention, the organisms isolated according to these methods have at least one of the properties listed in this paragraph. Other embodiments provide for organisms of the subject invention to have any combination of 2, 3, 4, 5 or 6 of the aforementioned properties. Yet other embodiments provide for the identification of organisms, as well as isolated organisms, that all seven of the properties mentioned in this paragraph.

As set forth supra, isolated organisms of the subject invention can, as a characteristic, be classified into the unique phylogenetic group of organisms of the subject invention on the basis of 16S rRNA sequences. In this regard, the organisms are classified on the basis of the sequence of at least 50, 150, 200, 250, 300, 350, 400, 450, 500, 525, 550 or 600 consecutive nucleotides of the 16S rRNA sequence or on the basis of the full length 16S rRNA sequence. In this aspect of the invention, organisms can be compared against the 16S rRNA sequences provided in the appended sequence listing or the Ribosomal Database at web site: rdp.cme.msu.edu/html/citation.html. Organisms within the scope of the subject invention can have a similarity score of 1.00 or a similarity score of at least (or greater than) 0.95, 0.96, 0.97, 0.98, or 0.99. As discussed herein, organisms with a similarity score of 0.99 to 1.00 can be grouped within the same species with confidence. Methods for classifying organisms on the basis of 16S rRNA sequences are well known to those skilled in the art (and one method for such an analysis is provided in the Examples described herein). Specifically excluded from the scope of the instant invention are those organisms that can be, or are, classified as *Bacillus coagulans, B. smithii*, or *B. coagulans*, strain IDSp on the basis of the 16S rRNA sequence information.

The subject invention further provides genetically modified organisms useful for the production of industrially useful chemicals. Non-limiting examples of such chemicals include ethanol, 1,3-propanediol, 1,2-propanediol, succinic acid, and D(−)-lactic acid. In this embodiment of the invention, organisms isolated according to the methods taught herein are genetically modified to express those enzymes necessary for the production of a desired chemical. Sources of nucleic acids suitable for the transformation or genetic engineering of organisms of the subject invention can be obtained from the ATCC. "ATCC" refers to the American Type Culture Collection depository (P.O. Box 1549, Manassas, Va. 20108, USA). Alternatively, nucleotide sequences encoding the enzymes discussed in the following paragraphs can be obtained from other sources that include, and are not limited to, GENBANK, EMBL, or the NCBI database (maintained by the National Library of Medicine (USA)).

In one aspect of the invention, the organisms of the subject invention can be engineered to inactivate the L-lactate dehydrogenase (l-ldh) gene via methods known in the art (for example, chromosomal deletion, insertion or inactivation). Other genes may also be inactivated in the construction of recombinant organisms for use in the production of industrially useful chemicals. For example, genes encoding fumarate reductase (frd), alcohol/aldehyde dehydrogenase (adh), pyruvate formate lyase (pfl), acetate kinase gene (ack), and/or the phosphoenolpyruvate carboxylase (ppc) may be, optionally, inactivated. Other aspects of the invention allow for the use of organisms in which the l-ldh gene is, or other genes are, not inactivated; additionally, any of the aforementioned genes can be singly inactivated or any combination of said genes can be inactivated according to methods known in the art. The organisms can then be transformed with various vectors containing those genes necessary for the production of a desired chemical and recombinant organism and vectors are known in the art for the production of chemicals, such as the non-limiting examples provided infra.

For example, U.S. Pat. Nos. 6,136,576 and 6,025,184 (each of which is hereby incorporated by reference in its entirety) are directed to genetically engineered organisms that produce 1,3-propanediol and methods of producing such engineered organisms. Accordingly, isolated organisms of the subject invention can be engineered to produce 1-3-propanediol using the vectors taught therein. Alternatively, new vectors can be constructed that contain genes and/or enzymes taught in these patents that allow for the production of 1,3-propanediol in the organisms of the subject invention. For the production of 1,2-propanediol, vectors, genes, and/or enzymes taught in U.S. Pat. Nos. 6,303,352 and 6,087,140 (each of which is hereby incorporated by reference in its entirety) can be used to engineer organisms of the subject invention.

For the production of 1,3-propanediol, *E. coli* host cell W1485 harboring plasmids pDT20 and pAH42 (Accession Number ATCC 98188 and deposited in the ATCC under the terms of the Budapest Treaty) can be used as sources of nucleic acids that encode glycerol-3-phosphate dehydrogenase (G3PDH), glycerol-3-phosphatase (G3Phosphatase), glycerol dehydratase (dhaB), and 1,3-propanediol oxidoreductase (dhaT). Alternatively, *S. cerevisiae* YPH500 (deposited as ATCC 74392 under the terms of the Budapest Treaty) harboring plasmids pMCK10, pMCK17, pMCK30 and pMCK35 containing genes encoding glycerol-3-phosphate dehydrogenase (G3PDH), glycerol-3-phosphatase (G3P phosphatase), glycerol dehydratase (dhaB), and 1,3- propanediol oxidoreductase (dhaT) can be used as a source of genetic material for the production of recombinant organisms capable of producing 1,3-propanediol. Yet another source of readily available genetic material for the production of recombinant organisms capable of producing 1,3-propanediol is *E. coli* DH5α containing pKP1 which has about 35 kb insert of a Klebsiella genome which contains glycerol dehydratase, protein X and proteins 1, 2 and 3 (deposited with the ATCC under the terms of the Budapest Treaty and designated ATCC 69789); *E. coli* DH5α cells containing pKP4 comprising a portion of the Klebsiella genome encoding diol dehydratase enzyme, including protein X was deposited with the ATCC under the terms of the Budapest Treaty and was designated ATCC 69790. Preferred enzymes for the production of 1,2-propanediol are aldose reductase, glycerol dehydrogenase, or both. Exemplary sources of these enzymes are rat lens aldose reductase and *E. coli* glycerol dehydrogenase. Aldose reductase sequences are highly conserved, thus the source of the aldose reductase gene is not critical to the present invention. The source of the glycerol dehydrogenase gene is not critical. Other genes that can be used in the practice of this aspect of the invention include: carbonyl reductase (EC 1.1.1.84), glycerol dehydrogenase (EC 1.1.1.6, EC 1.1.1.156), aldehyde reductase (EC 1.1.1.2), methylglyoxal reductase (also known as 2-oxoaldehyde reductase and lactaldehyde dehydrogenase, EC 1.1.1.78), L-glycol dehydrogenase (EC 1.1.1.185), alcohol dehydrogenase EC 1.1.1.1, EC 1.1.1.2), 1,2-propanediol dehydrogenase, (lactaldehyde reductase, EC 1.1.1.55), and 1,2-propanediol oxidoreductase, (lactaldehyde reductase, EC 1.1.1.77).

Where succinic acid is a contemplated end product for production by recombinant organisms of the subject invention, the methods and materials of U.S. Patent Application Publication No. US 2003/0017559 A1 (which is hereby incorporated by reference in its entirety) can be used in the engineering of organisms provided by the subject invention. The inactivation of genes, such as l-ldh, pta, adh, ack, and pfl of the organisms of the subject invention, can be, optionally, inactivated in the engineered organisms. In one embodiment, pfl and ldh (and, optionally pts) genes are inactivated in the cells provided by the subject invention to redirect the metabolic products into the metabolic pathways that produce succinic acid (succinate). The production of succinic acid can be further enhanced by the optional addition of one or more heterologous genes encoding malic enzyme and/or fumarate reductase to the cells of the invention by recombinant means known to those skilled in the art.

Engineering of D(−)-lactic acid production into organisms of the subject invention can be performed according to the teachings of Zhou et al. ((Applied and Environmental Microbiology, 2003, 69(1):399–407) which is hereby incorporated by reference in its entirety). Briefly, genes encoding L-lactate dehydrogenase (l-ldh), fumarate reductase (frd), alcohol/aldehyde dehydrogenase (adh), and pyruvate formate lyase (pfl) are, optionally, inactivated by chromosomal deletion. In some embodiments, the acetate kinase gene (ack) can be mutated or inactivated to further increase yields. Cells are then engineered with the D-lactate dehydrogenase gene, provided in SEQ ID No: 1.

In the production of ethanol, the organisms of the subject invention can be engineered with nucleic acids, such as those disclosed in U.S. Pat. No. 5,000,000 (which is hereby incorporated by reference in its entirety). In this aspect of the invention, the d-ldh, l-ldh, ppc, ack, pfl genes of organisms provided by the subject invention are, optionally, inactivated. Organisms can then be transformed with the nucleic acids taught in this patent can then be used in methods of producing ethanol. For example, genes coding for the alcohol dehydrogenase II and pyruvate decarboxylase activities together with appropriate regulatory sequences are used to transform host cells provided by the subject invention (the regulatory sequences may consist of promoters, inducers, operators, ribosomal binding sites, terminators, and/or other regulatory sequences).

The subject invention provides methods of making an industrially useful chemical comprising the steps of: a) providing a recombinant or non-recombinant organism having at least one of the characteristics set forth for isolated organisms provided by the subject invention (or any combination of said characteristics); and b) culturing said microorganism in the presence of at least one carbon source capable of being converted to said industrially useful chemical under conditions suitable for the production of said chemical. The method may further comprise the optional step of recovering the industrially useful chemical. Non-limiting examples of chemical compounds that can be produced according to the subject invention include L(+)-lactic acid, 1,3-propanediol, 1,2-propanediol, succinic acid, ethanol and D(−)-lactic acid.

In various aspects of the aforementioned methods of making industrially useful compounds, any variety of carbon sources can be used. In certain aspects of the invention, the carbon source is a hexose or pentose sugar. Non-limiting examples of these sugars include glucose, galactose, mannose, xylose, and arabinose. Optionally, the carbon source can be a disaccharide, such as cellobiose. Other carbon sources useful in the practice of the subject invention include lignocellulose; hemicellulose hydrolysates from sugar cane bagasse, corn fiber, corn stover, straw, or other forms of hardwood, softwood or agricultural residue; and/or crystalline cellulose. Conditions useful in the aforementioned methods include maintaining a pH of between 4 and 6, 4.5 and 5.5, or a pH of about 5 and temperatures ranging from 45° C. to 60° C., 45° C. to 55° C., or temperatures that are maintained at about 50° C. The pH of fermentation systems used in the production of industrially useful chemicals as taught herein can be maintained according to well-known methods in the art (e.g., pH stats).

The subject invention further provides nucleic acid and polypeptide sequence for newly isolated enzyme D-lactate dehydrogenase (d-ldh; D-LDH [see SEQ ID Nos: 1–2]). The subject invention also provides a nucleic acid fragment derived from organisms disclosed herein that encodes a pyruvate formate lyase pfl; PFL). This polynucleotide fragment was derived from isolate P4-102B (ATCC PTA-5828) and was obtained using Sau3A as a restriction enzyme. The fragment is about 4 kilobases in length and has been used to reconstitute PFL activity in a strain of *E. coli* that is defective in this regard (the plasmid containing this insert was able to complement an *E. coli* pflB mutant). Of course, other restriction enzymes can be used to obtain polynucleotide fragments encoding PFL and these various polynucleotide fragments can be screened (according to methods known in the art) in organisms that are pfl defective to determine if they are able to reconstitute PFL function. The subject invention also encompasses degenerate polynucleotide sequences that encode the PFL and D-LDH enzymes provided herein. Degenerate polynucleotide sequences for these enzymes can be obtained by inputting the amino acids sequences provided herein into a variety of commercially available software suites. Non-limiting examples of such software suites include: Bio/Chem Lab Assistant (Dundee Scientific Ltd., Dundee Scotland UK) or DNATools (available for download at crc.dk/dnatools/dnatools.htm).

Accordingly, the subject invention further provides:

a) a polynucleotide sequence having at least about 20% to 99.99% identity to a polynucleotide of SEQ ID No: 1.

b) a polynucleotide fragment derived or obtained from isolate P4-102B (ATCC PTA-5828) that can reconstitute PFL activity and/or encodes pyruvate formate lyase (pfl; PFL);

c) a polynucleotide sequence encoding a polypeptide fragment or variant of the PFL and D-LDH enzymes, wherein said fragment or variant has substantially the same serologic activity as the native polypeptide or said fragment of variant has substantially the same enzymatic activity as the native full-length polypeptide; or d) a polynucleotide sequence that is complementary to the polynucleotides of a), b), or c).

Nucleotide sequence, polynucleotide or nucleic acid are understood to mean, according to the present invention, either a double-stranded DNA, a single-stranded DNA or products of transcription of the said DNAs (e.g., RNA molecules).

As indicated supra, the subject invention also provides nucleotide sequences complementary to the sequences disclosed herein. Thus, the invention is understood to include any DNA whose nucleotides are complementary to those of the sequence of the invention, and whose orientation is reversed (e.g., anti-sense sequences). These sequences may be complementary over the full length of the nucleic acids that encode the PFL and D-LDH enzymes or over fragments of these nucleic acids.

The present invention further comprises fragments of the sequences of the instant invention as well as fragments of the gene products contained within the polynucleotide sequences provided herein. Representative fragments of the polynucleotide sequences according to the invention will be understood to mean any nucleotide fragment having at least 8 successive nucleotides, preferably at least 12 successive nucleotides, and still more preferably at least 15 or at least 20 successive nucleotides of the sequence from which it is derived. The upper limit for such fragments is the total number of polynucleotides found in the full length sequence (or, in certain embodiments, of the full length open reading frame (ORF) identified herein). It is understood that such fragments refer only to portions of the disclosed polynucleotide sequences that are not listed in a publicly available database.

In some embodiments, the subject invention includes those fragments capable of hybridizing under stringent conditions with a nucleotide sequence according to the invention. Hybridization under conditions of high or intermediate stringency, are defined below. Thus, conditions are chosen such that they allow hybridization to be maintained between two complementary DNA fragments. Hybridization conditions described above for a polynucleotide of about 300 bases in size can be adapted by persons skilled in the art for larger- or smaller-sized oligonucleotides, according to the teaching of Sambrook et al., 1989.

The nucleic acid sequences described herein have other uses as well. For example, the nucleic acids of the subject invention can be useful as probes to identify complementary sequences within other nucleic acid molecules or genomes. Such use of probes can be applied to methods to identify or distinguish organisms. As is well known in the art, probes can be made by labeling the nucleic acid sequences of interest according to accepted nucleic acid labeling procedures and techniques.

Various degrees of stringency of hybridization can be employed. The more severe the conditions, the greater the complimentarily that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak [1987] DNA Probes, Stockton Press, New York, N.Y., pp. 169–170.

Examples of various stringency conditions are provided herein. Hybridization of immobilized DNA on Southern blots with $^{32}$P-labeled gene-specific probes can be performed by standard methods (Maniatis et al. [1982] Molecular Cloning: A Laboratory Manual, Cold Spring Harbor Laboratory, New York). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20–25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. [1983] Methods in Enzymology, R. Wu, L. Grossman and K. Moldave [eds.] Academic Press, New York 100:266–285).

$Tm=81.5°$ C.$+16.6$ Log[Na+]$+0.41$(% $G+C$)$-0.61$(% formamide)$-600$/length of duplex in base pairs.

Washes are typically carried out as follows:
(1) twice at room temperature for 15 minutes in 1×SSPE, 0.1% SDS (low stringency wash);
(2) once at Tm−20° C. for 15 minutes in 0.2×SSPE, 0.1% SDS (moderate stringency wash).

For oligonucleotide probes, hybridization can be carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes can be determined by the following formula:

$Tm$ (° C.)$=2$(number $T/A$ base pairs)$+4$(number $G/C$ base pairs)

(Suggs et al. [1981] ICN-UCLA Symp. Dev. Biol. Using Purified Genes, D. D. Brown [ed.], Academic Press, New York, 23:683–693).

Washes can be carried out as follows:
(1) twice at room temperature for 15 minutes 1×SSPE, 0.1% SDS (low stringency wash);
(2) once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

| Low: | 1 or 2× SSPE, room temperature |
|---|---|
| Low: | 1 or 2× SSPE, 42° C. |
| Moderate: | 0.2× or 1× SSPE, 65° C. |
| High: | 0.1× SSPE, 65° C. |

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5–20×10$^6$ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47–9.57; and Ausubel et al., 1989, Current Protocols in Molecular Biology, Green Publishing Associates and Wiley Interscience, N.Y. are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47–9.57; and Ausubel et al., 1989, Current Protocols in Molecular Biology, Green Publishing Associates and Wiley Interscience, N.Y. are incorporated herein in their entirety.

Duplex formation and stability depend on substantial complimentarily between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al. [1982] *Molecular Cloning: A Laboratory Manual*, Cold Spring Harbor Laboratory, New York; Wei et al. [1983] *J. Biol. Chem.* 258:13006–13512.

Thus, the subject invention also provides nucleic acid based methods for the identification of the presence of the pfl and d-ldh genes in an organism or a sample. These methods can utilize the nucleic acids of the subject invention and are well known to those skilled in the art (see, for example, Sambrook et al. (1989). Among the techniques useful in such methods are enzymatic gene amplification (or PCR), Southern blots, Northern blots, or other techniques utilizing hybridization for the identification of polynucleotide sequences in a sample.

The subject invention also provides for modified nucleotide sequences. Modified nucleic acid sequences will be understood to mean any nucleotide sequence that has been modified, according to techniques well known to persons skilled in the art, and exhibiting modifications in relation to the native, naturally occurring nucleotide sequences. One non-limiting example of a "modified nucleotide sequences" includes mutations in regulatory and/or promoter sequences of a polynucleotide sequence that result in a modification of the level of expression of the polypeptide. A modified nucleotide sequence will also be understood to mean any nucleotide sequence encoding a modified polypeptide as defined below.

The subject invention also provides detection probes (e.g., fragments of the disclosed polynucleotide sequences) for hybridization with a target sequence or the amplicon generated from the target sequence. Such a detection probe will advantageously have as sequence a sequence of at least 12, 15, 20, 25, 30, 35, 40, 45, 50, 55, 60, 65, 70, 75, 80, 85, 90, 95, or 100 nucleotides. The detection probes can also be used as labeled probe or primer in the subject invention. Labeled probes or primers are labeled with a radioactive compound or with another type of label. Alternatively, non-labeled nucleotide sequences may be used directly as probes or primers; however, the sequences are generally labeled with a radioactive element ($^{32}P$, $^{33}P$, $^{35}S$, $^{3}H$, $^{125}I$) or with a molecule such as biotin, acetylaminofluorene, digoxigenin, 5-bromo-deoxyuridine, or fluorescein to provide probes that can be used in numerous applications.

The nucleotide sequences according to the invention may also be used in analytical systems, such as DNA chips. DNA chips and their uses are well known in the art and (see for example, U.S. Pat. Nos. 5,561,071; 5,753,439; 6,214,545; Schena et al., BioEssays, 1996, 18:427–431; Bianchi et al., Clin. Diagn. Virol., 1997, 8:199–208; each of which is hereby incorporated by reference in their entireties) and/or are provided by commercial vendors such as Affymetrix, Inc. (Santa Clara, Calif.).

Another aspect of the invention provides vectors for the cloning and/or the expression of a polynucleotide sequence taught herein. Vectors of this invention can also comprise elements necessary to allow the expression and/or the secretion of the said nucleotide sequences in a given host cell. The vector can contain a promoter, signals for initiation and for termination of translation, as well as appropriate regions for regulation of transcription. In certain embodiments, the vectors can be stably maintained in the host cell and can, optionally, contain signal sequences directing the secretion of translated protein. These different elements are chosen according to the host cell used. Vectors can integrate into the host genome or, optionally, be autonomously-replicating vectors.

The subject invention also provides for the expression of a polypeptide, peptide, derivative, or analog encoded by a polynucleotide sequence disclosed herein. The disclosed sequences can also be regulated by a second nucleic acid sequence so that the protein or peptide is expressed in a host transformed with the recombinant DNA molecule. For example, expression of a protein or peptide may be controlled by any promoter/enhancer element known in the art. Promoters which may be used to control expression include, but are not limited to, the CMV promoter, the SV40 early promoter region (Bemoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al, 1982, Nature 296:39–42); prokaryotic vectors containing promoters such as the β-lactamase promoter (Villa-Kamarof, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., 1983, Nature 303:209–213) or the cauliflower mosaic virus 35S RNA promoter (Gardner, et al., 1981,Nucl. Acids Res. 9:2871), and the promoter of the photosynthetic enzyme ribulose bisphosphate carboxylase (Herrera-Estrella et al., 1984, Nature 310:115–120); promoter elements from yeast or fungi such as the Gal 4 promoter, the ADC (alcohol dehydrogenase) promoter, PGK (phosphoglycerol kinase) promoter, and/or the alkaline phosphatase promoter The vectors according to the invention are, for example, vectors of plasmid or viral origin. In a specific embodiment, a vector is used that comprises a promoter operably linked to a protein or peptide-encoding nucleic acid sequence contained within the disclosed polynucleotide sequences, one or more origins of replication, and, optionally, one or more selectable markers (e.g., an antibiotic resistance gene). Expression vectors comprise regulatory sequences that control gene expression, including gene expression in a desired host cell. Exemplary vectors for the expression of the polypeptides of the invention include the pET-type plasmid vectors (Novagen) or pBAD plasmid vectors (Invitrogen) or those provided in the examples below. Furthermore, the vectors according to the invention are useful for transforming host cells so as to clone or express the nucleotide sequences of the invention.

The invention also encompasses the host cells transformed by a vector according to the invention. These cells may be obtained by introducing into host cells a nucleotide sequence inserted into a vector as defined above, and then culturing the said cells under conditions allowing the replication and/or the expression of the transfected nucleotide sequence.

The host cell may be chosen from eukaryotic or prokaryotic systems, such as for example bacterial cells, (Gram negative or Gram positive), yeast cells, animal cells (such as Chinese hamster ovary (CHO) cells), plant cells, and/or insect cells using baculovirus vectors. In some embodiments, the host cells for expression of the polypeptides include, and are not limited to, those taught in U.S. Pat. Nos. 6,319,691, 6,277,375, 5,643,570, or 5,565,335, each of which is incorporated by reference in its entirety, including all references cited within each respective patent.

Furthermore, a host cell strain may be chosen which modulates the expression of the inserted sequences, or modifies and processes the gene product in the specific fashion desired. Expression from certain promoters can be elevated in the presence of certain inducers; thus, expression of the genetically engineered polypeptide may be controlled. Furthermore, different host cells have characteristic and specific mechanisms for the translational and post-translational processing and modification (e.g., glycosylation, phosphorylation) of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

The subject invention also provides one or more isolated polypeptides comprising:
  a) a polypeptide encoded by a polynucleotide sequence selected from the group consisting of SEQ ID NOs: 1;
  b) a polypeptide comprising pyruvate formate lyase (pfl; PFL) that is encoded by a polynucleotide fragment derived from isolate P4-102B (said polynucleotide being obtained, for example, using Sau3A as restriction enzyme); or
  c) a polypeptide fragment or variant of a) or b), wherein said fragment or variant has substantially the same serologic or enzymatic activity as the native, full-length polypeptide.

The subject invention also provides fragments of at least 5 amino acids of a polypeptide encoded by the polynucleotides of the instant invention. In some embodiments, the polypeptide fragments are reactive with antibodies generated against the full-length polypeptides set forth in the immediately preceding paragraph. In the context of the instant invention, the terms polypeptide, peptide and protein are used interchangeably; however, it should be understood that the invention does not relate to the polypeptides in natural form, that is to say that they are not taken in their natural environment but that they may have been isolated or obtained by purification from natural sources, obtained from host cells prepared by genetic manipulation (e.g., the polypeptides, or fragments thereof, are recombinantly produced by host cells, or by chemical synthesis). Polypeptides according to the instant invention may also contain non-natural amino acids, as will be described below.

A homologous (or modified) polypeptide will be understood to designate a polypeptide exhibiting, in relation to the natural polypeptide, certain modifications. These modifications can include a deletion, addition, or substitution of at least one amino acid, a truncation, an extension, a chimeric fusion, a mutation, or polypeptides exhibiting post-translational modifications. Among the homologous polypeptides, those whose amino acid sequences exhibit between at least (or at least about) 20.00% to 99.99% (inclusive) identity to the native, naturally occurring polypeptide are another aspect of the invention. The aforementioned range of percent identity is to be taken as including, and providing written description and support for, any fractional percentage, in intervals of 0.01%, between 20.00% and, up to, including 99.99%. These percentages are purely statistical and differences between two polypeptide sequences can be distributed randomly and over the entire sequence length.

Homologous polypeptides can, alternatively, have 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent identity with the polypeptide sequences of the instant invention. The expression equivalent amino acid is intended here to designate any amino acid capable of being substituted for one of the amino acids in the basic structure without, however, essentially modifying the biological activities of the corresponding peptides (e.g., its enzymatic activity).

By way of example, amino acid substitutions can be carried out without resulting in a substantial modification of the biological activity of the corresponding modified polypeptides; for example, the replacement of leucine with valine or isoleucine, of aspartic acid with glutamic acid, of glutamine with asparagine, of arginine with lysine, and the like, the reverse substitutions can be performed without substantial modification of the biological activity of the polypeptides.

In other specific embodiments, the polypeptides, peptides or derivatives, or analogs thereof may be expressed as a fusion, or chimeric protein product (comprising the protein, fragment, analog, or derivative joined via a peptide bond to a heterologous protein sequence (e.g., a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

The subject invention further provides antibodies to the polypeptides of SEQ ID NOs 2 or the fragments thereof. These antibodies can be used in any variety of methods including affinity purification of the PFL and D-LDH enzymes (or related enzymes). Other uses for such antibodies including contacting a sample with the antibodies and assaying for the presence of an antigen-antibody complex. In this aspect of the invention, either the antibodies to the PFL and D-LDH enzymes can be directly labeled with a marker or another antibody that is appropriately labeled can be used to detect the presence of an antibody-antigen complex.

The terms "comprising", "consisting of" and "consisting essentially of" are defined according to their standard meaning. The terms may be substituted for one another throughout the instant application in order to attach the specific meaning associated with each term.

All percentages are by weight and all solvent mixture proportions are by volume unless otherwise noted. It should be understood that the examples and embodiments described herein are for illustrative purposes only and that various modifications or changes in light thereof will be suggested to persons skilled in the art and are to be included within the spirit and purview of this application and the scope of the appended claims. All publications, patents, and/or patent applications cited in this patent application are hereby incorporated by reference in their entireties.

EXAMPLE 1

Isolation and Characterization of Organisms

Environmental samples from 77 locations (Table 1) were collected and bacteria which grew in xylose medium at a pH of 5.0 and at 50° C. were isolated. The protocol followed for the enrichment and isolation is presented in FIG. 1. Using this enrichment, a total of 380 bacterial isolates were obtained. After initial screen, isolates were analyzed for various characteristics and the results obtained with 334 isolates are presented in Table 2.

Characteristics analyzed included: 1) Growth under aerobic and anaerobic conditions in rich medium as well as in minimal salts medium (with or without supplements such as yeast extract or corn steep liquor) at a starting pH of 5.0 or 6.8; 2) Fermentation profile of facultative organisms; 3) Growth in hemicellulose hydrolysate (both overlimed and not-overlimed) at a starting pH of 5.0; 4) Ethanol tolerance; 5) Ability to grow at a starting medium pH of less than 5.0; 6) Ability to produce xylanase; and 7) Ability to hydrolyze crystalline cellulose (Avicel) as well as amorphous cellulose, carboxymethyl cellulose (CMC).

Based on the growth characteristics, 100 isolates were found to be strict aerobes when grown at pH 5.0. However, 27 of these 100 isolates grew under anaerobic conditions when the starting pH of the medium was increased to 6.8. This difference could be related to the inability of the isolates to grow when the medium pH dropped below 4.5 since the medium pH of all the isolates decreased from a starting pH of 5.0 to less than 4.5 within 6 hours even during aerobic growth. This decrease in pH is due to the accumulation of lactate in the medium. When cultured in glucose-supplemented medium, all the isolates produced lactate as the main fermentation product. With xylose as the carbon source, lactate was still the major fermentation product but small amounts of acetate, ethanol and, with some isolates, formate were detected. The presence of formate in the spent medium suggests that during xylose-dependent growth, pyruvate formate lyase is also produced by the isolates.

Sixteen of the isolates produced cellulase activity based on hydrolysis of carboxymethyl cellulose. These cellulase-positive isolates did not hydrolyze crystalline cellulose such as Avicel or Sigmacel. All 16 cellulolytic isolates are strict aerobes. Seventeen isolates produced xylanase activity detected as hydrolysis of remazol brilliant blue R-o-xylan (RBB-xylan). Five of the xylanase-positive isolates are also facultative anaerobes.

Based on the growth characteristics of these isolates under anaerobic conditions in a glucose or xylose medium as well as in various other media (Table 2), 44 of the 380 isolates were selected for identification using the sequence of first 500 bases of the DNA coding for the 16S rRNA. 16S rRNA gene sequence was determined by MIDI Labs using their specific protocol for isolating and sequencing 16S rRNA gene from bacteria. Specifically, the 16S rRNA gene was PCR amplified from genomic DNA using primers corresponding to E. coli positions 005 and 531. This PCR product is expected to be about 500 base pairs of the first part of the 16S rRNA gene. The DNA after amplification was sequenced by cycle-sequencing using AmpliTaq FS DNA polymerase and dRhodamine dye terminators. The DNA sequence was obtained after electrophoresis on an ABI Prism DNA sequencer and analyzed using PE/Applied Biosystems DNA editing and assembly software. These sequences are presented in SEQ ID # 3–39.

Similar methods were used to determine 16S rRNA (DNA) sequence of over 1500 bp. The primers used correspond to E. coli positions 005 and 1540 by the MIDI Labs for isolates 17C5 and Bacillus coagulans ATCC 7050 (ATCC type strain for B. coagulans). Sequence of over 1500 bp for 16S rRNA(DNA) for strains 36D1 and P4-102B were determined at the University of Florida, Dept. of Microbiology and Cell Science DNA sequencing facility. Appropriate DNA was PCR-amplified using two primers based on E. coli 16S rRNA sequence; Primer 1, GAGTTTGATCCTG-GCTCAG (SEQ ID No: 43); Primer 2, AGAAAGGAGGT-GATCCAGCC (SEQ ID No: 44) (Suzuki, T. and Yamasato, K. (1994) Phylogeny of spore-forming lactic acid bacteria based on 16S rRNA gene sequences, FEMS Microbiol. Letters 115:13–18). The amplified product was cloned into vector plasmid PCR-II TOPO (Invitrogen) and sequenced. The DNA insert was also sub-cloned into vector plasmid pUC19 for convenience of sequencing. These three sequences are presented in SEQ ID # 40–42. DNA sequence was analyzed for sequence similarity using the Ribosomal Database Project II (web site rdp.cme.msu.edu/html/citation.html) (Cole J R, Chai B, Marsh T L, Farris R J, Wang Q, Kulam S A, Chandra S, McGarrell D M, Schmidt T M, Garrity G M, Tiedje J M. The Ribosomal Database Project (RDP-II): previewing a new autoaligner that allows regular updates and the new prokaryotic taxonomy. 2003. Nucleic Acids Research 31(1):442–443).

Figure 2:
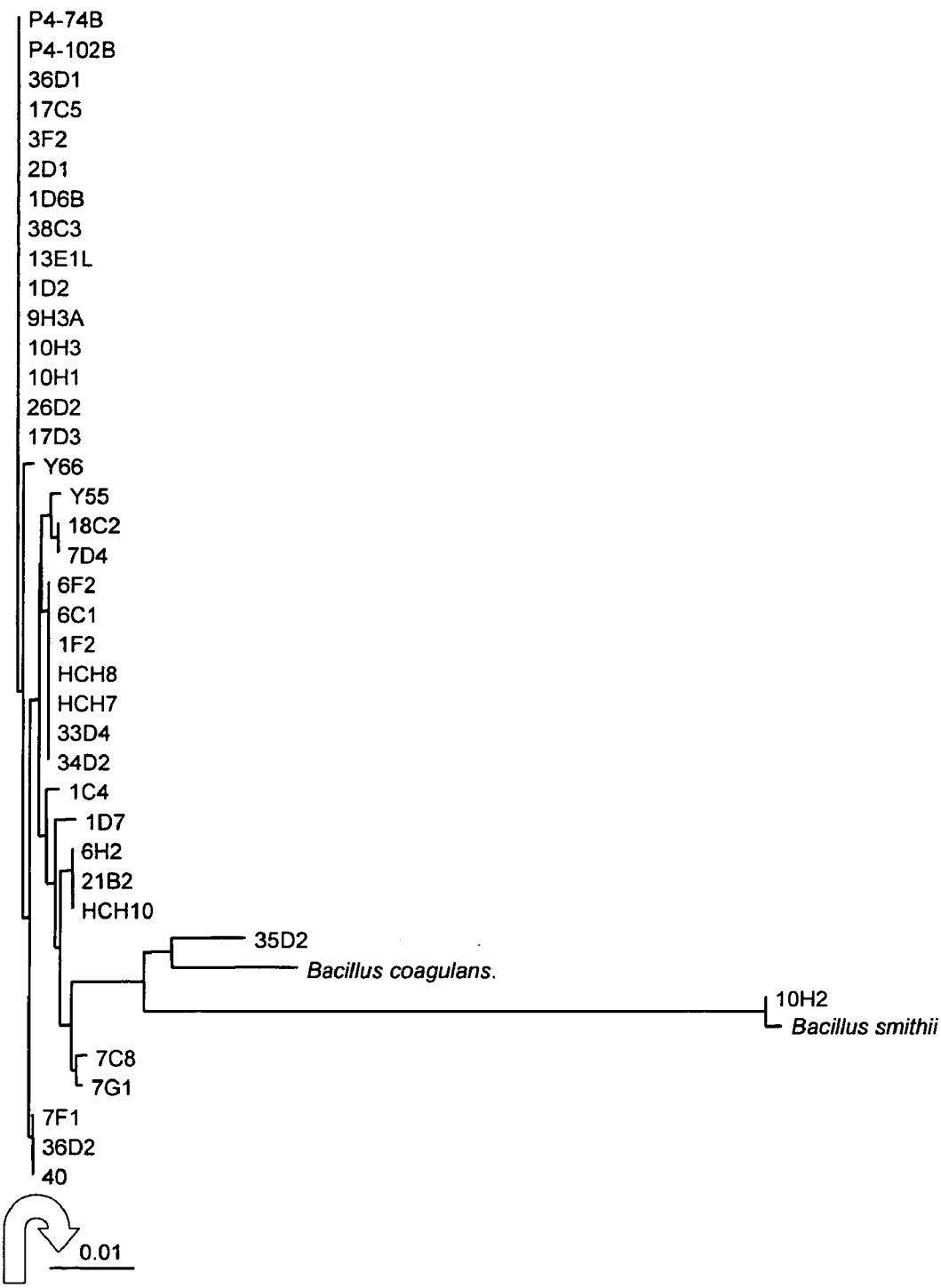
FIG. 2: Phylograms of isolates of the subject invention based on rRNA (16S) sequences.

Using the RDP database, the similarity scores between the closest Bacillus organism (B. coagulans IDSP) and three isolates (17C5, 36D1 and P4-102B; SEQ ID# 40–42) were determined. These values are 0.978 (17C5), 0.969 (36D1) and 0.975 (P4-102B). A similarity score between 0.99 and 1.000 would indicate that the two bacteria can be grouped with confidence in the same species. A similarity score of 0.97 or lower suggests that the two bacteria can only be identified at the genus level with confidence. (Suzuki, T. and K. Yamasato. 1994. Phylogeny of spore-forming lactic acid bacteria based on 16S rRNA gene sequences. FEMS Microbiol. Letters 115:13–18). The similarity scores between the current isolates and RDP database entries which are also Bacillus coagulans type strains from various collections vary from 0.87 to 0.95. Thus, it is difficult to group these new isolates at the species level with Bacillus coagulans strictly based on 16S rRNA gene sequence information. It is possible that these new isolates represent a new Bacillus species closely related to Bacillus coagulans. Phylograms representing 38 of the 44 isolates is presented in FIG. 2. Only one of the isolate, Y56, was identified as Bacillus smithii. Other isolates could not be identified at the species level although all are *Bacillus* and spores can be readily detected under normal growth conditions in several of these isolates confirming their *Bacillus* designation. One isolate, 10H2, is closely related to *Bacillus smithii*. Based on the 16S rRNA sequence, the nearest relative of all the other isolates is *Bacillus coagulans*.

Figure 3:
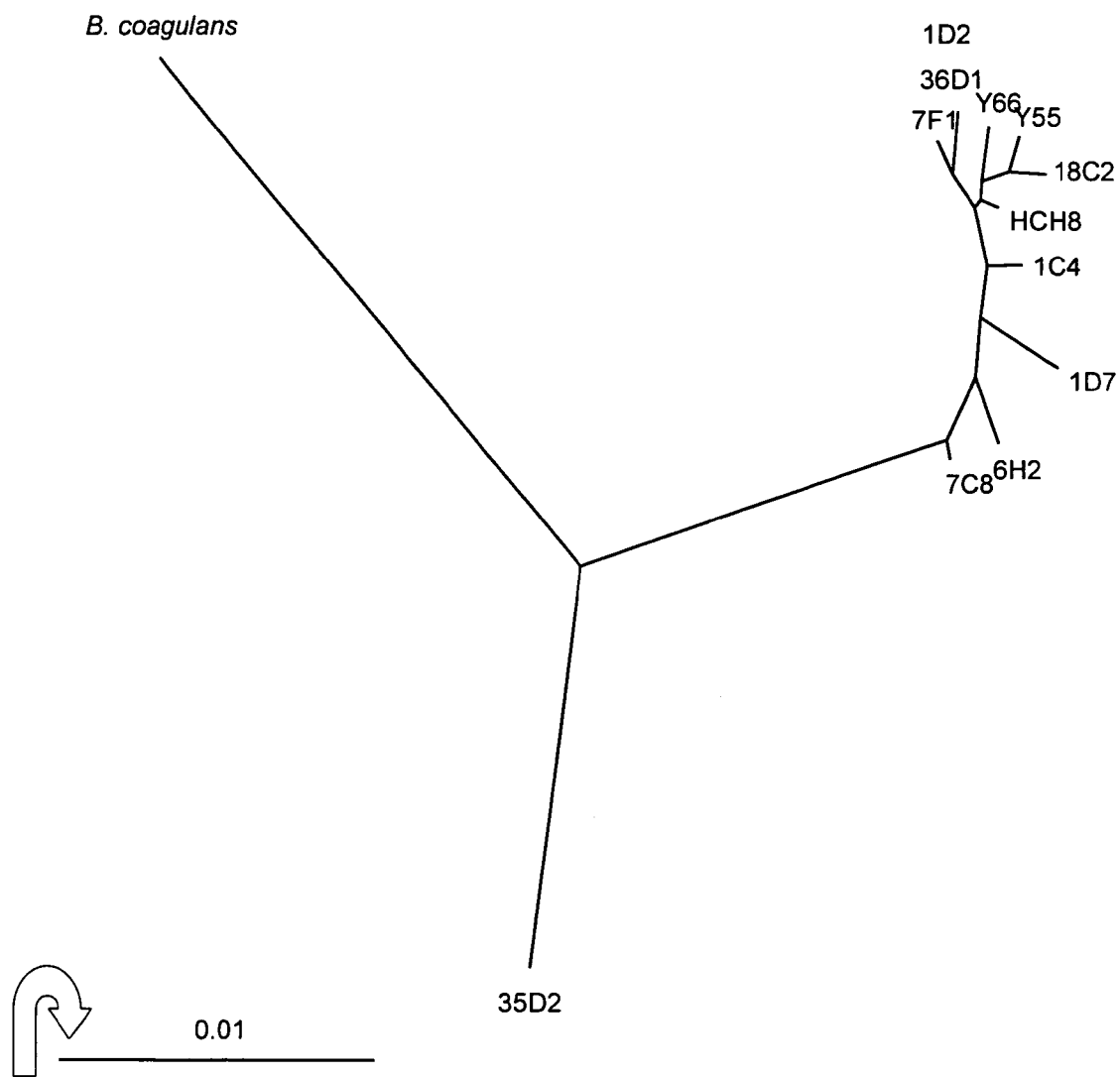
FIG. 3: Unrooted radial phylogenetic tree of isolates related to *Bacillus coagulans* from the various groups.

An authentic *Bacillus coagulans* obtained from American Type Culture Collection (ATCC 7050) (Hammer, B. W., 1915. Iowa Agric. Exp. Stn. Res. Bull. 19:119–131) was found to be xylose-negative and also differed in other physiological properties. The 37 *B. coagulans*-like isolates can be grouped into 12 groups (FIG. 2; Table 3). Some of these groups have only one representative isolate while others have several isolates; for example Group 1 has 15 isolates with identical first 500 bases of their 16S rRNA sequence but these isolates came from 8 different locations within Florida, Georgia, South Carolina and California (Table 1). Although differences in the rRNA sequence allowed the separation of these isolates into different groups, phylogenetically they cluster together and away from *Bacillus coagulans* (FIG. 3).

Thirty two of the 41 identified isolates completely fermented the 1% glucose or xylose present in the medium within 24 hours in a pH-stat operating at pH 5.0 and at 50° C. (Table 3). Recovery of glucose carbon in products was about 95% with lactate accounting for about 90% to 100% of the fermentation products produced by the glucose cultures. Significant amounts of acetate, formate and ethanol were also produced by these isolates when xylose served as the C-source. For example, isolate 18C2 converted 93% of glucose and 98% of xylose to products when grown in rich medium with 1% sugar. Under these conditions, lactate fraction of the total products was 95% with glucose and 77% with xylose.

Based on the rate of sugar utilization (1%) in the pH-stat, as well as other physiological characteristics, 76 isolates were selected for detailed fermentation analysis. When the sugar concentration in the rich medium was increased to 3%, 7 isolates converted both glucose and xylose to products within 48 hours; isolates 13E1L, 36D1, HCH8, Y40, P4-74B, P4-85 and P4-102B (Tables 4 & 5). When analyzed after 72 hours of growth and fermentation, 5 additional isolates were also found to ferment 3% of glucose and xylose to completion (isolates 3F2, 17C5, HCH7, HCH10 and Y55). These 12 isolates fermented glucose to lactate with a conversion efficiency of about 85–90%. Lactate accounted for more than 95% of the total products produced from glucose. The lactate produced by 15 isolates was found to be L-(+)-lactate by HPLC analysis and the highest amount of lactate produced by these isolates was about 0.30 M (27 g/L lactic acid). When grown with xylose, the lactate fraction of the fermentation products only accounted for about 80% of the total while the remainder included acetate, ethanol, formate and small amounts of succinate.

Fourteen isolates were further tested for their ability to ferment 5% sugar in the same rich medium. Increasing the sugar concentration to 5% also increased the lactate production. With one exception (isolate P4-102B) none of the isolates completely fermented the added sugar (Table 6). The highest level of lactate produced by isolate P4-102B grown in LB+ glucose (5%) was about 0.45 M (40.5 g/L lactic acid). Trace amounts of ethanol and acetate were also detected in the fermentation broths. Most of the other isolates produced varying levels of lactate ranging from 0.25 to 0.4 M. Again, lactate accounted for more than 95% of the products from glucose. The fermentation profile of the isolates grown in 5% xylose was not different from that obtained at lower xylose concentration and the highest amount of lactate detected was about 0.34 M (Table 6).

These isolates were also grown in minimal salts medium supplemented with 1% corn steep liquor with either glucose or xylose (3%) as the C-source (Table 7). Only one isolate, 36D1 fermented both sugars in this medium in about 48 hours. Two other isolates, 17C5 and P4-74B, completely fermented both sugars by about 72–96 hours. These three along with three other isolates (selected on their ability to utilize xylose) were also tested for their ability to ferment the sugars present in hemicellulose hydrolysate (HCH). For these fermentations, either 25% HCH (Batch T6-#5) adjusted to pH 5.0 with Ca(OH)$_2$ or 50% overlimed HCH (Batch BCI-November 99) was used in a minimal salts medium base with 1% corn steep liquor. A number of the isolates completely fermented the sugars present in the HCH (Table 8).

EXAMPLE 2

Additional Analysis of Isolates 17C5, 36D1, P4-102B, and P4-74B

Four isolates were selected for further study (isolates 17C5, 36D1, P4-102B, and P4-74B). Isolates 17C5 and 36D1 grew and fermented the sugars in sugar cane bagasse hemicellulose hydrolysate as well as SSF of crystalline cellulose, Solka Floc, in minimal-salts medium with 1% corn steep liquor. Isolate P4-102B was easily transformable by plasmid DNA. Isolate P4-74B was included because of its growth and fermentation characteristics.

Taxonomy of the New Isolates

Figure 4:
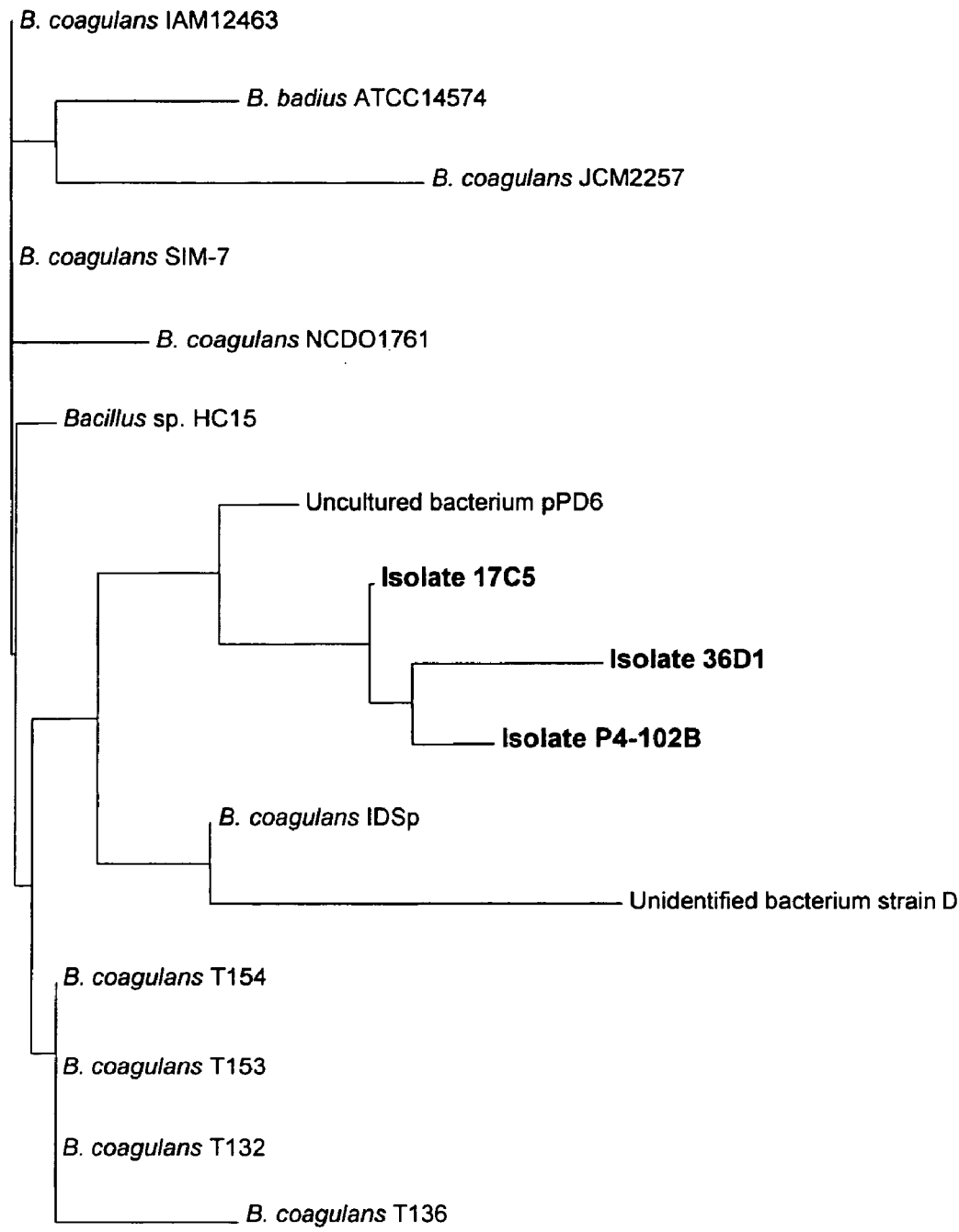
FIG. 4: An additional phylogenetic relationship of selected second generation biocatalysts to *Bacillus coagulans* and other closely related bacteria based on longer sequences of DNA coding for 16S rRNA.
Figure 5A:
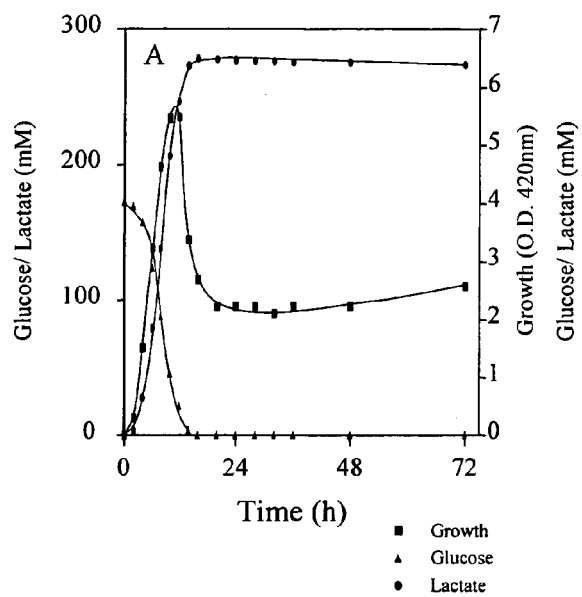
FIG. 5A—Isolate 17C5.
Figure 5B:
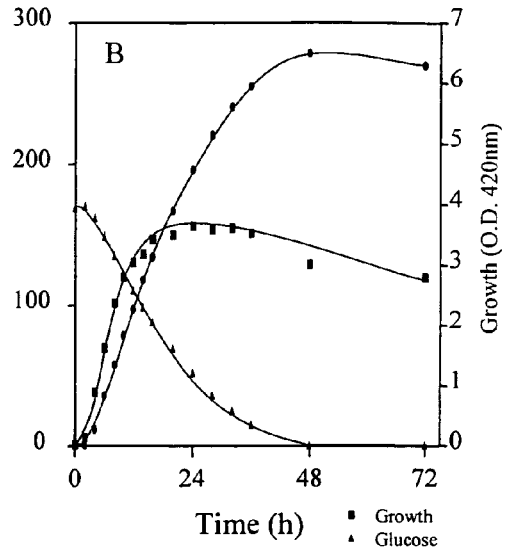
FIG. 5B—Isolate 36D1.
Figure 5C:
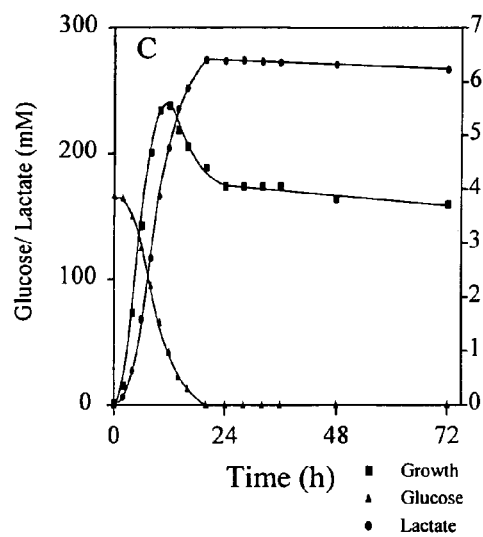
FIG. 5C—Isolate P4-74B.
Figure 5D:
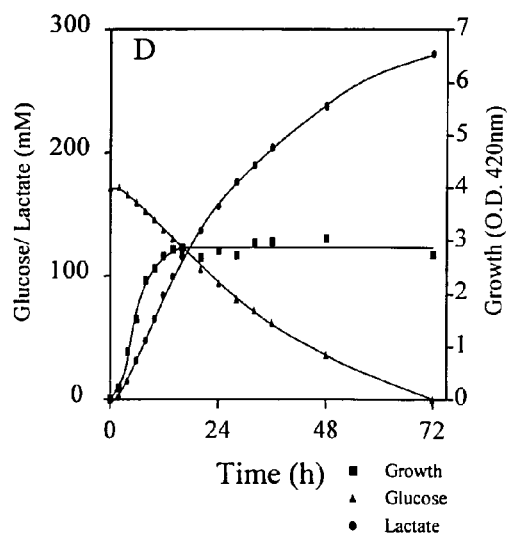
FIG. 5D—Isolate P4-102B.
Figure 8A:
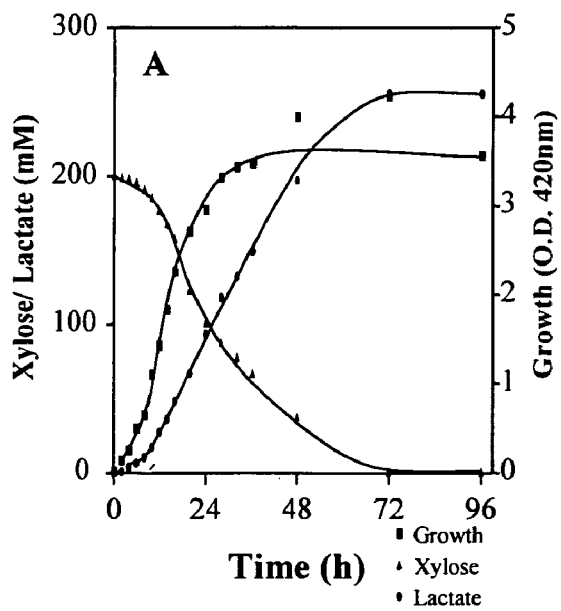
FIG. 8A—Isolate 17C5.
Figure 8B:
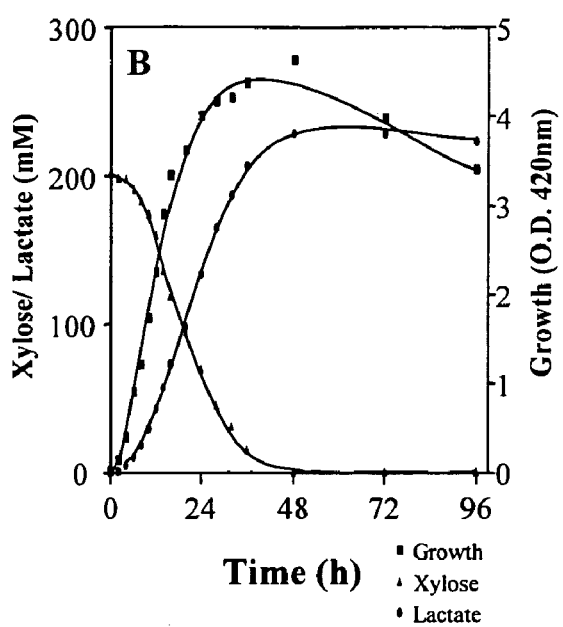
FIG. 8B—Isolate 36D1.
Figure 8C:
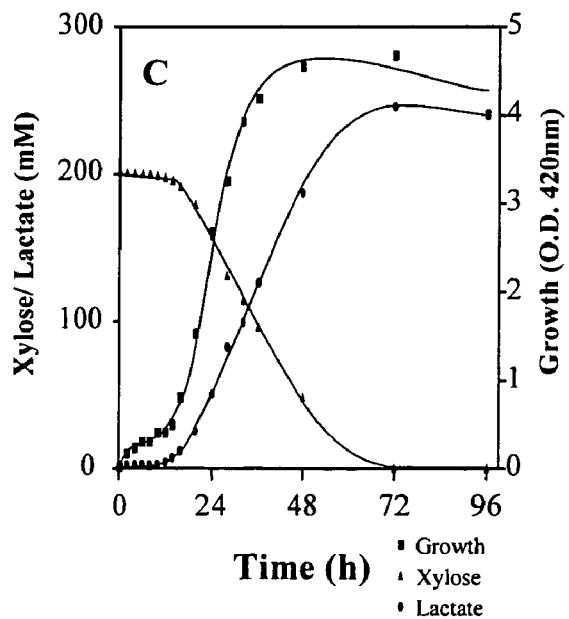
FIG. 8C—Isolate P4-74B.
Figure 8D:
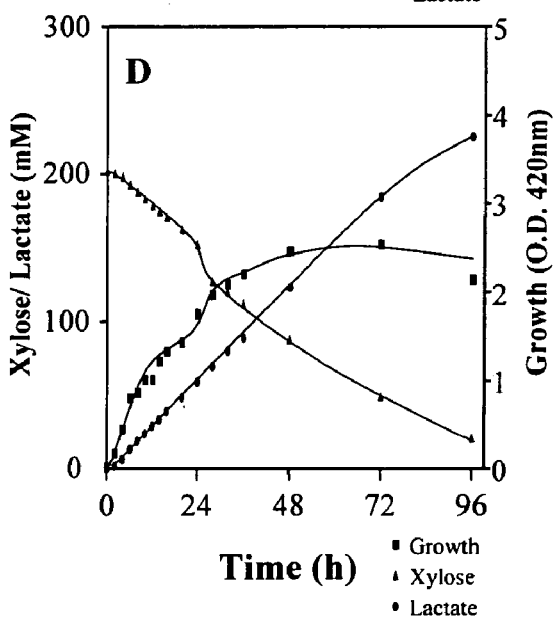
FIG. 8D—Isolate P4-102B.

Based on the sequence of first 500 bp of the 16S rRNA sequence (as discussed in Example 1), 37 of the 39 tested isolates, including the four selected strains, were found to form a unique phylogenetic group with the nearest neighbor being *Bacillus coagulans*. To confirm these identities, the DNA encoding the entire 16S rRNA from three of the isolates, 17C5, 36D1 and P4-102B, was sequenced and these sequences were compared to other sequences in the rRNA sequence database. Based on full length sequence, isolates 17C5, 36D1 and P4-102B formed a unique phylogenetic group with the nearest neighbor being *Bacillus coagulans* (see FIG. 4) although the three strains were initially isolated from different geographical locations within the country (Table 1). As presented in FIG. 4, bacteria identified as *B. coagulans* form a very diverse phylogenetic group and except for one strain of *B. coagulans*, strain IDSp, other bacteria identified as *B. coagulans* in the database are phylogenetically distinct from these new isolates. The *B. coagulans* ATCC type strain, ATCC 7050, also differed from the new isolates by its inability to utilize xylose. These isolates may constitute a new species of *Bacillus* and may be referred herein as *Bacillus* spp. (or second generation isolates) in accordance with their unique phylogeny. The ability to produce lactic acid as the major fermentation product and the phylogenetic grouping with *B. coagulans* indicates that these organisms are part of a larger sporogenic lactic acid bacteria group.

Fermentation of Glucose

Detailed growth and fermentation profiles of four of the selected second generation isolates on glucose are presented in Table 9 and FIGS. 5–6. Lactic acid production was used to establish the general physiological and fermentation characteristics of these second generation isolates. In these experiments, the cultures were grown in fermentation units at 50° C. and a constant pH of 5.0, maintained by addition of 2N KOH. Cultures were mixed by a magnetic stirrer bar at 200 RPM. The gas phase above the 250 ml of liquid in a 500 ml vessel was air. Inoculum for these experiments was grown under aerobic conditions at 50° C. in LB+glucose (1%) (LB; tryptone, 1%; yeast extract, 0.5%; NaCl, 0.5%) to mid-exponential phase of growth.

After a very short lag (less than 2 hours), LB+glucose cultures grew in a linear manner until the maximal cell density was reached in about 12 hours (FIG. 5). Glucose utilization and lactate production followed the growth of the biocatalyst and continued until all the sugar (30 g/L) was exhausted from the medium. A culture maintained under strict anaerobic conditions with an argon gas phase grew very slowly suggesting that the initial build-up of cell mass required micro-aerobic conditions. Continued fermentation of glucose by the second generation isolates was independent of the gas phase.

Cell yield of strains 17C5 and P4-74B were significantly higher in rich medium with glucose than the other two strains although the cell density of strains 17C5 and P4-74B decreased significantly when they reached stationary phase (FIG. 5). All 4 cultures reached the same final yield of lactic acid and the time for complete fermentation of the added glucose was directly proportional to the highest observed cell density of the cultures with strain 17C5 fermenting 30 g/L glucose in about 16 hours with the highest volumetric productivity of lactate (2.5 g $L^{-1}$ $h^{-1}$).

All four strains grew in glucose-minimal medium supplemented with 1% corn steep liquor with strain P4-74B growing at the highest growth rate (FIG. 6). Strain 36D1 had the second highest growth rate and reached the stationary phase by about 24 hours. Strain 17C5 had the lowest growth rate. However, the final cell yield in glucose-minimal medium was about the same for all four strains. The amount of time required to completely ferment the 30 g/L glucose depended on the growth rate and cell yield and varied between 48 and 96 hours. Corn steep liquor provided for optimum growth when organisms were grown in minimal medium.

The main fermentation product of all four strains from glucose was lactate (Table 9). Acetate and ethanol accounted for about 5% of the total products produced irrespective of the medium composition. In rich medium, strains 36D1 and P4-74B had the highest specific glucose consumption rate and corresponding lactate production rate. In minimal medium, the specific rate of glucose consumption and lactate production were about the same for strains 3 6D 1, P4-74B and P4-102B. Total product yield from glucose was about 85%.

Fermentation of Xylose.

Xylose is the primary sugar in the hemicellulose fraction of hardwood and agricultural residues such as sugar cane bagasse, corn fiber, corn stover, straw, and other biomass. All four isolates used in this detailed study, strains 17C5, 36D1, P4-74B and P4-102B, grew and fermented xylose in both rich medium and minimal-salts medium supplemented with corn steep liquor (Table 10; FIGS. 7–8). Following various lengths of lag period, all four strains grew in LB+xylose linearly. Specific xylose consumption rate and lactate production rate were highest with strain 36D 1 cultured in rich medium with strain P4-1 02B as the second highest (Table 10). In xylose-containing minimal-medium, the specific xylose consumption rate and lactate production rate of strains 17C5 and 36D 1 were comparable and were the highest of the four select isolates. The level of acetate and ethanol among fermentation products varied between 9 and 18% depending on the strain and medium. Strain 17C5 had the lowest level of these co-products (about 10%) while strain 36D1 had the highest level (about 18%). This reduced the lactate yield of strain 36D1 to 68% of the expected value in xylose-minimal medium although the total product yield of the two strains were comparable at 85%.

In minimal medium strain 36D1 was most effective in fermenting xylose converting 30 g/L xylose in less than 48 hours (FIG. 8). Based on these fermentation profiles, strain 36D1 emerged as the most effective glucose and xylose fermenting biocatalyst, especially in minimal salts medium supplemented with only corn steep liquor (volumetric productivity of 0.6 g $L^{-1}$ $h^{-1}$). Increasing the sugar concentration to 50 g/L marginally increased the lactic acid yield beyond that with 30 g/L sugar, probably due to inhibition of fermentation by lactic acid. Production of lactic acid at a concentration higher than 0.4 M (about 35 g/L) was found to progressively inhibit fermentation. The lactic acid produced by the four isolates was found to be L(+)-isomer with D(−)-isomer contributing to less than 4% of the total (Table 11).

Xylose Utilization Pathway

Many of the lactic acid bacteria used at the industrial level do not ferment pentoses such as xylose. The few lactic acid bacteria capable of fermenting pentoses, such as *Lactobacillus pentosus, Lb. arabinosus*, etc. utilize phosphoketolase pathway for pentose utilization. The key enzyme of this pathway, phosphoketolase, cleaves xylulose-5-phosphate in the presence of inorganic phosphate to one molecule each of glyceraldehyde-3-phosphate and acetyl phosphate. The products of pentose fermentation by these bacteria are an equimolar amount of lactic acid and acetic acid plus ethanol. The loss of ⅔ of the xylose carbons to acetyl phosphate will reduce the amount of xylose carbon that can be channeled to lactic acid or to ethanol in ethanologenic constructs by about 40%.

The main product produced by the isolated second generation biocatalysts is lactic acid (about 80 to 90% of fermentation products). Acetic acid and ethanol represented only 10–20% of the products produced from the pentose xylose suggesting that these biocatalysts utilize an alternate pathway, the pentose phosphate pathway, for xylose fermentation. In order to confirm that the pentose-phosphate pathway is used by the second generation biocatalysts for xylose metabolism, we determined the distribution pattern of C1-carbon of xylose into fermentation products since glyceraldehyde-3-phosphate directly yields pyruvate and products derived from pyruvate, lactate, acetate and ethanol. During the cleavage of xylulose-5-phosphate by phosphoketolase, carbon at 1-position of xylose is the C-2 carbon of acetate and ethanol. The lactic acid carbon skeleton is derived from the carbons 3–5 of xylose and in an organism with phosphoketolase pathway $^{13}C_1$-label in xylose will not be found in lactate. If the pentose-phosphate pathway is the main pathway by which the pentose is metabolized, ⅔ of the C3-carbon of glyceraldehyde-3-phosphate will be derived from C1-carbon of xylose while ⅓ of the C1-carbon of glyceraldehyde-3-phosphate will originate from C1-carbon of xylose. The presence of $^{13}C$-label in lactate will confirm the metabolism of xylose through the pentose-phosphate pathway.

Figure 9:
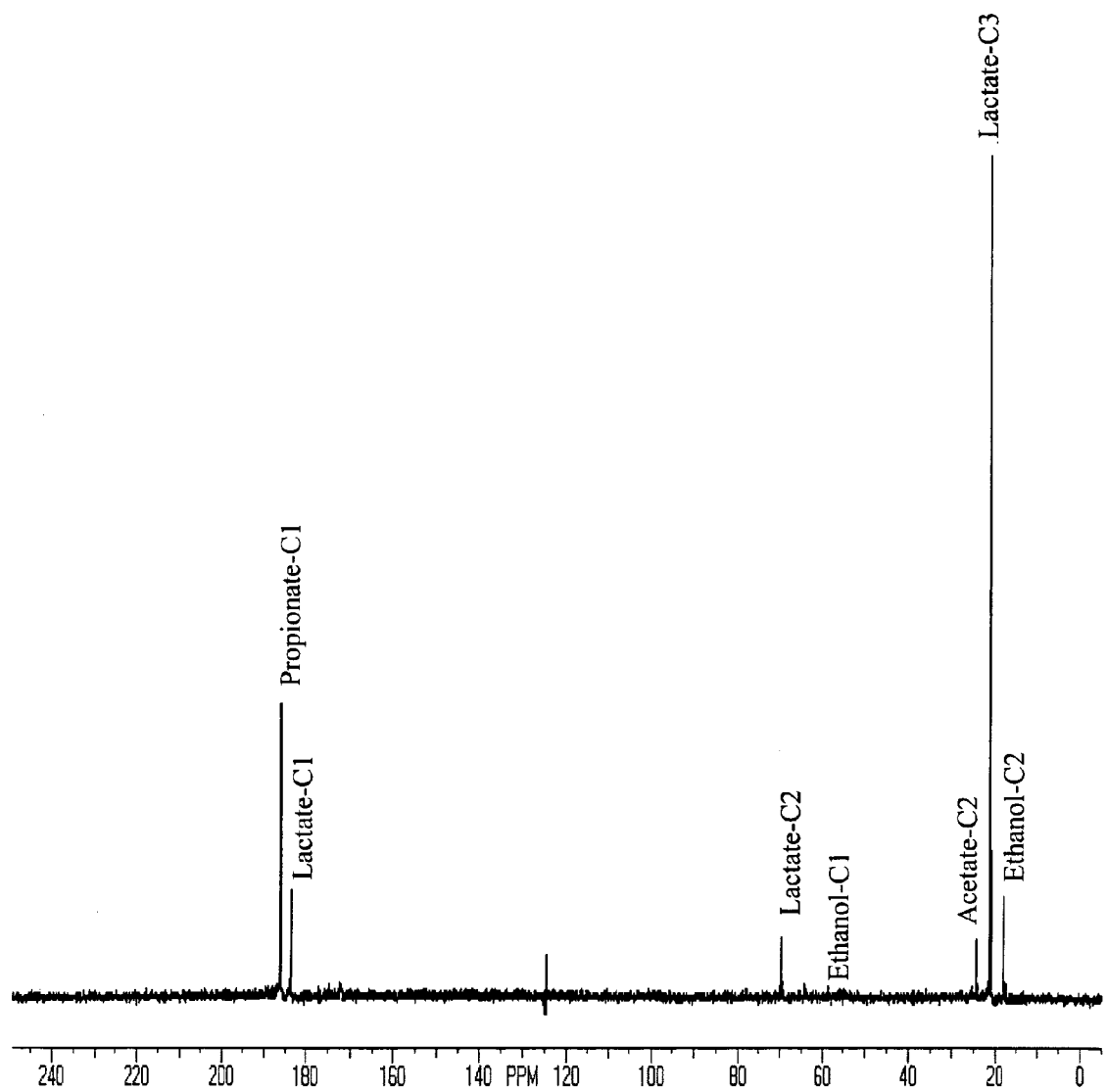
FIG. 9: $^{13}$C-NMR spectrum of spent medium of strain 36D1 grown in LB+ $^{13}$C1-Xylose (1.2%; 20.8% $^{13}$C enrichment) at 50° C. pH of the culture was maintained between 6.0 and 7.0 by manual addition of 0.5 N KOH. $^{13}$C1-propionic acid (50 mM) served as a standard.

For these experiments, we used $^{13}C_1$-xylose and followed the products produced by strains 36D1 and P4-102B by $^{13}C$-NMR. A typical $^{13}C$-NMR spectrum obtained with the $^{13}C_1$-xylose fermentation products of strain 36D1 is presented in FIG. 9. Carbon 3 of lactate had the highest amount of $^{13}C$ originating from C1-xylose. Carbon 1 of lactate also carried significant amount of $^{13}C$. The C2 position of lactate is not expected to originate from C1-xylose except for a small amount derived by randomization of carbon by the pentose-phosphate pathway. With C2 of lactate as a reference, C1 of lactate was enriched by about 5-fold and the C3 of lactate was enriched by about 17-fold by $^{13}C$ (Table 12). These results clearly show that the pentose phosphate pathway is the main pathway of xylose utilization in these second generation biocatalysts. Since pyruvate carbon is enriched with $^{13}C$, the acetate and ethanol are also expected to carry $^{13}C$-label. The $^{13}C$-label was found only at the C2 position of acetate and ethanol. The inability to detect $^{13}C$ in C1 of acetate and ethanol is due to the small amount of $^{13}C$-label entering the C2-position of pyruvate (contributing to C1 of acetate and ethanol) combined with the low concentration of these two compounds in the fermentation broth. Small amount of $^{13}C$-label was detected in formate with non-growing cells indicating that pyruvate formatelyase is responsible for the acetate and ethanol produced by strain 36D1.

The presence and operation of pentose phosphate pathway in these biocatalysts is significant since all the xylose carbon will be routed through pyruvate. This supports complete recovery of xylose carbon as ethanol by decarboxylation of pyruvate to acetaldehyde and further reduction to ethanol in engineered organisms. Xylose metabolism through phosphoketolase, on the other hand, would be expected to yield one glyceraldehyde-3-phosphate and one acetyl phosphate leading to production of one ethanol from pyruvate with at least 40% of xylose carbon lost as acetate.

Simultaneous Saccharification and Fermentation of Crystalline Cellulose (SSF)

The optimal conditions reported for commercially used fungal cellulases are pH 5.0 and 50° C. The biocatalysts we have isolated and characterized grew and fermented both hexoses and pentoses at 50° C. and pH 5.0. All four selected biocatalysts were found to be competent in SSF of crystalline cellulose (Solka Floc). Since strain 36D1 fermented both glucose and xylose effectively in minimal salts medium with corn steep liquor, this strain was used to evaluate the SSF characteristics of these second generation biocatalysts.

Figure 10:
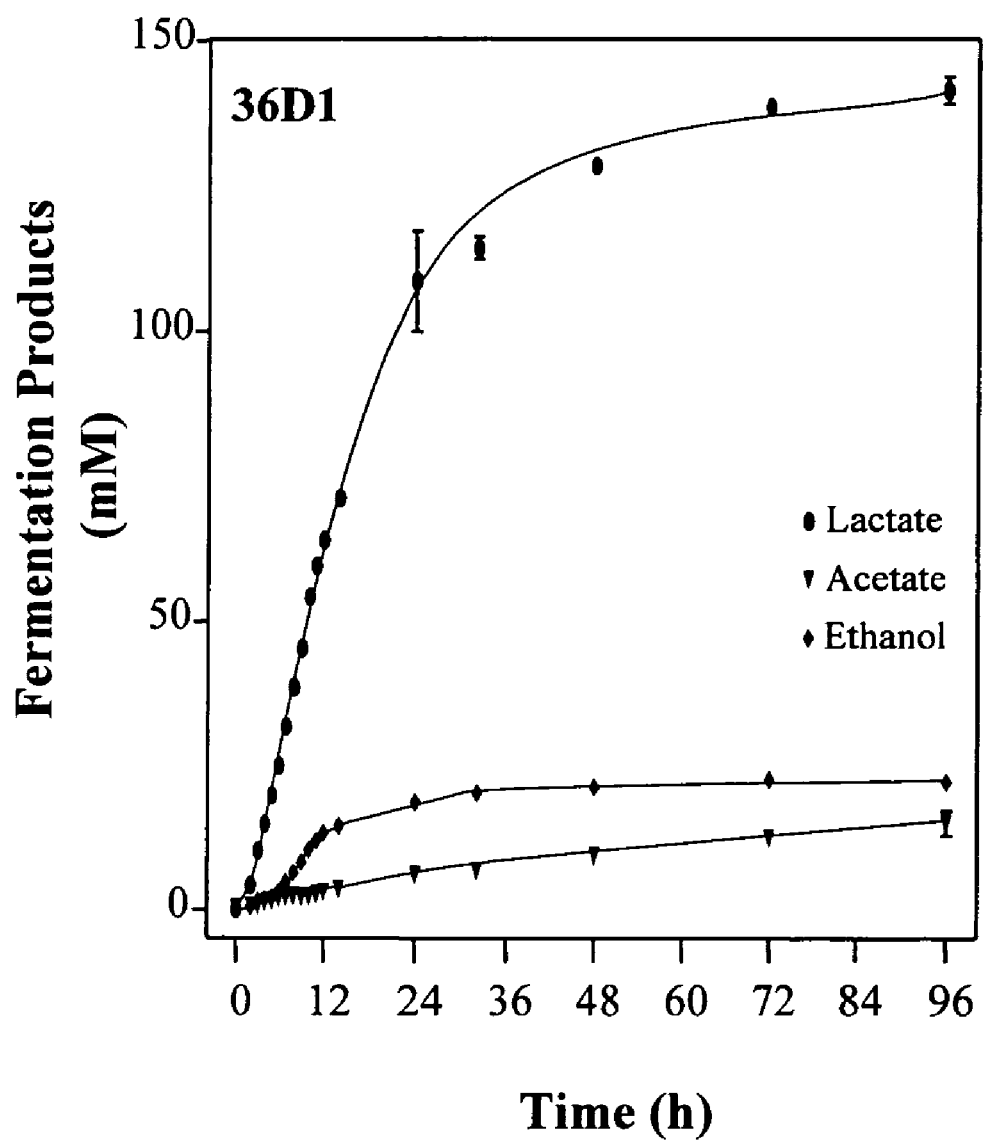
FIG. 10: Simultaneous saccharification and fermentation (SSF) of Solka-Floc (2%) by strain 36D1 in the presence of 15 FPU Spezyme CE (Genencor)/g Solka-Floc in mineral salts medium with 1% corn steep liquor in a pH-stat at pH 5.0 and 50° C.

In the first set of experiments, SSF of Solka Floc (2%; 117 mM glucose equivalent with a 5% moisture content) was carried out in minimal salts medium with 1% corn steep liquor with 15 FPU/g glucan of fungal cellulases (Spezyme CE; generously provided by Genencor) at 50° C. and pH 5.0 (FIG. 10). The amount of lactate and other products produced from 2% Solka Floc over a 96 hours period was determined. From these values, volumetric productivity of the major product, lactic acid, was calculated. Volumetric productivity represents indirectly the rate at which cellulases are releasing glucose for growth and fermentation. In all of these SSF experiments, the inoculum size was 5% to minimize free glucose accumulation in the medium. The amount of free glucose in the medium was less than 3 mM during the first 24 hours of SSF indicating that the sugar released by the cellulases was consumed rapidly by the isolate.

At 15 FPU/g glucan cellulase level, lactate production started after a lag of about an hour and was linear for about 18 hours. Small amount of acetate and ethanol were also produced between 6 and 12 hours of fermentation. After about 36 hours, lactate production reached a slow phase and continued at this low rate past 96 hours. Volumetric productivity of lactate was 6.2 mmol $L^{-1}$ $h^{-1}$, the same as that of free glucose fermentation in minimal salts medium (Table 13). The product yield from cellulose at 96 hours of 180 mM is 77% of the expected maximum. Lactic acid accounted for about 78% of the products.

Figure 11:
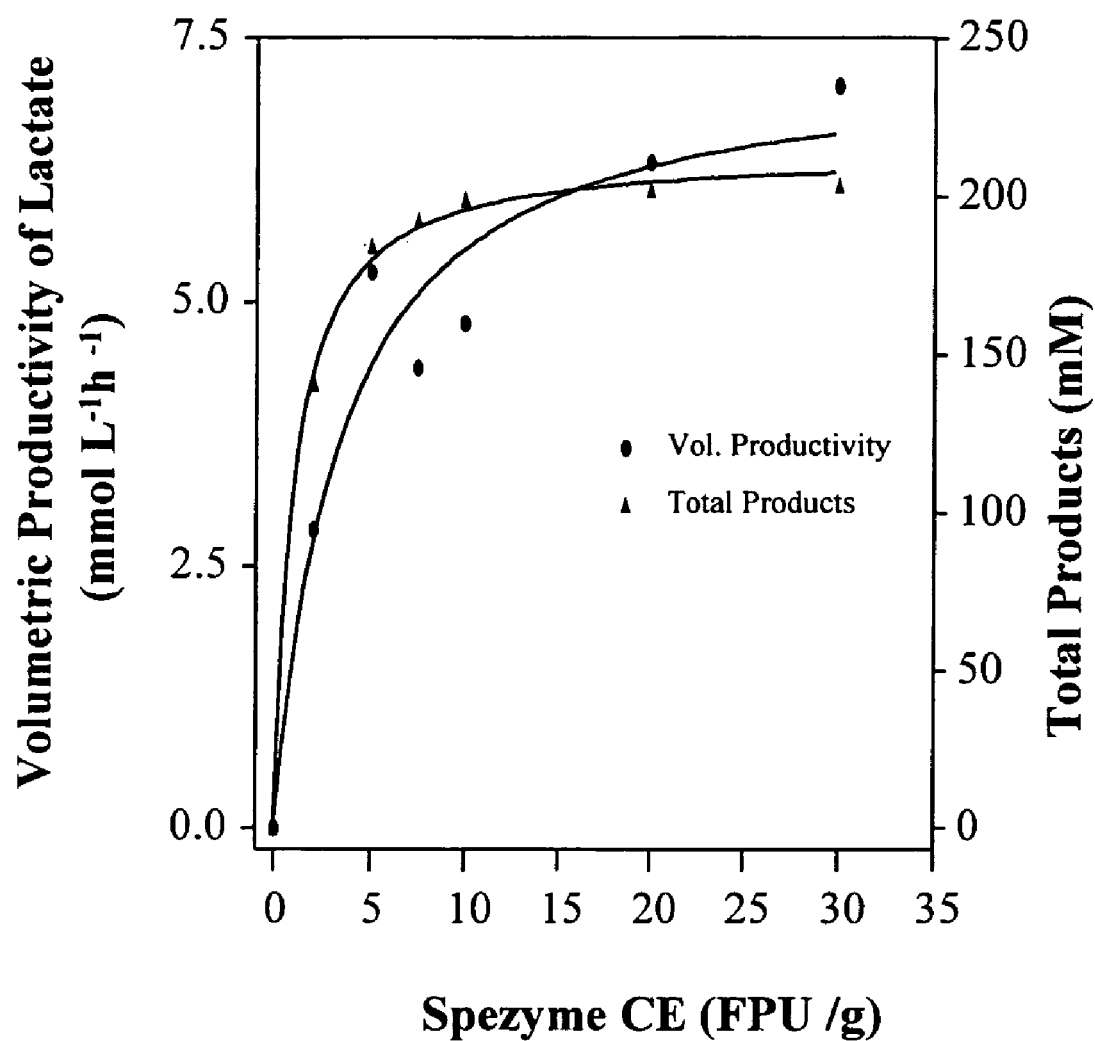
FIG. 11: Effect of Spezyme CE (a commercial cellulase) concentration on SSF of crystalline cellulose, Solka-Floc in mineral salts medium with 1% corn steep liquor in a pH-stat at pH 5.0 and 50° C., by strain 36D1. Total products represent lactate, acetate, ethanol and succinate.

In order to determine the minimum amount of cellulase required for optimal SSF, fermentations were carried out at different cellulase concentrations (FIG. 11). Volumetric productivity of lactate as well as the total product yield increased linearly with cellulase concentration from 0 to about 5 FPU/g glucan (FIG. 11). Increasing the cellulase concentration beyond this level led to a smaller rate of increase in volumetric productivity until about 30 FPU/g glucan was reached. Under these SSF conditions, the highest volumetric productivity of 7.1 mmol $L^{-1}$ $h^{-1}$ was reached at about 30 FPU/g glucan and this value is less than 2-fold higher for a 6-fold increase in enzyme concentration from 5 to 30 FPU/g glucan. At 15 FPU/g glucan, the volumetric productivity was 84% of the value with 30 FPU/g glucan. Total product yield at 96 hours was about 199.5±5 mM between the cellulase levels of 7.5 and 30 FPU/g glucan. These results show that an increase in cellulase level from 15 to 30 FPU/g glucan only increased the volumetric productivity by 1.12-fold without any change in either lactic acid or total product yield. In subsequent SSF, a Spezyme CE concentration of 15 FPU/g glucan was used.

Figure 12:
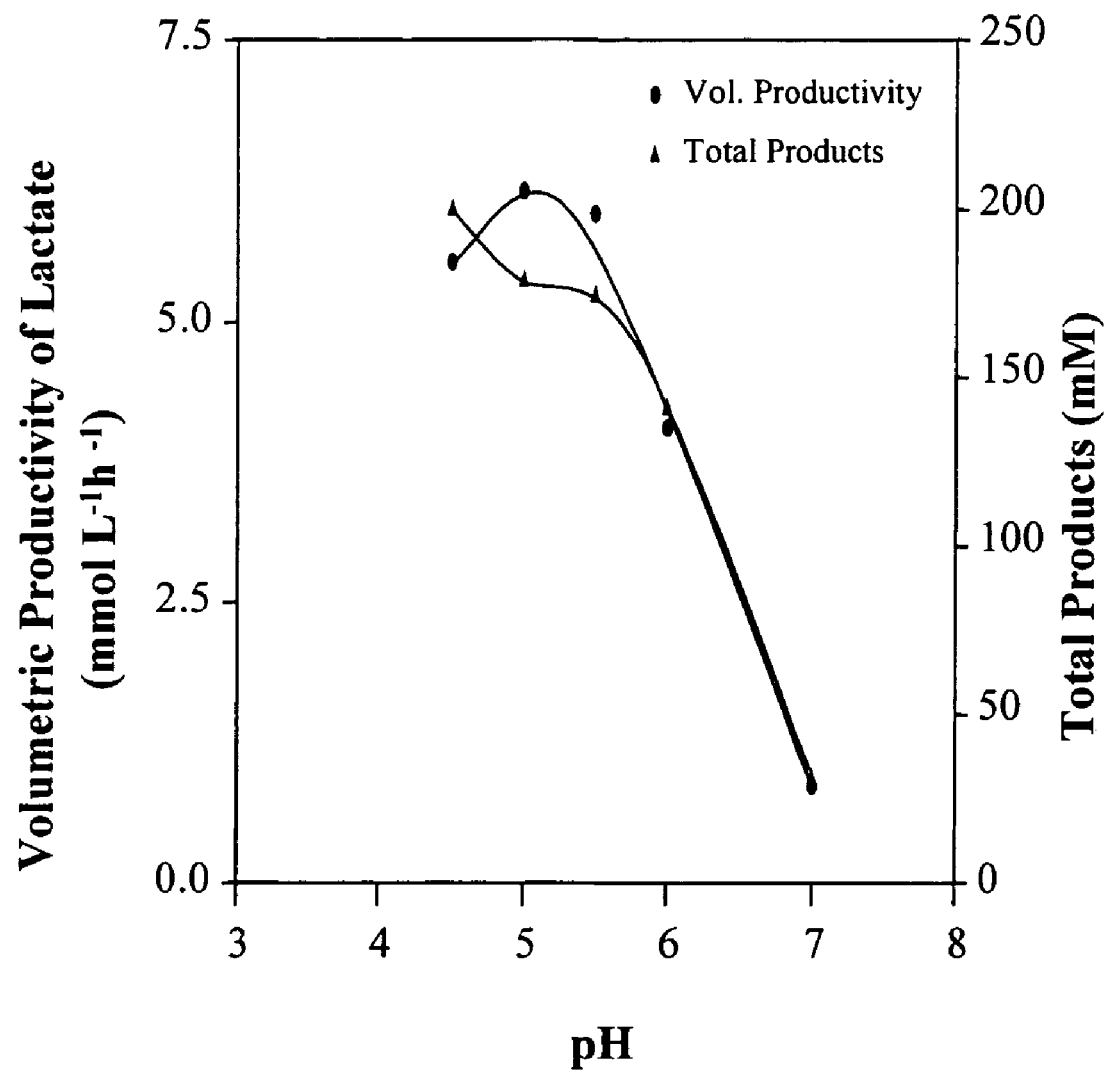
FIG. 12: pH profile of SSF of Solka-Floc by strain 36D1 with 15 FPU Spezyme CE/g Solka-Floc in mineral salts medium with 1% corn steep liquor in a pH-stat at 50° C. Total products represent lactate, acetate, ethanol and succinate.

The optimal pH for the SSF of Solka Floc using strain 36D1 was between 5.0 and 5.5 (FIG. 12). Although the volumetric productivity of lactate was highest at pH 5.0, product yield was maximum at pH 4.5 reaching 85% of the theoretical yield after 96 hours of SSF (Table 13). Apparently, the optimum pH for SSF of cellulose by strain 36D1 is between 4.5 and 5.0. The amount of acetate and ethanol produced by the culture also increased with increasing culture pH.

Figure 13:
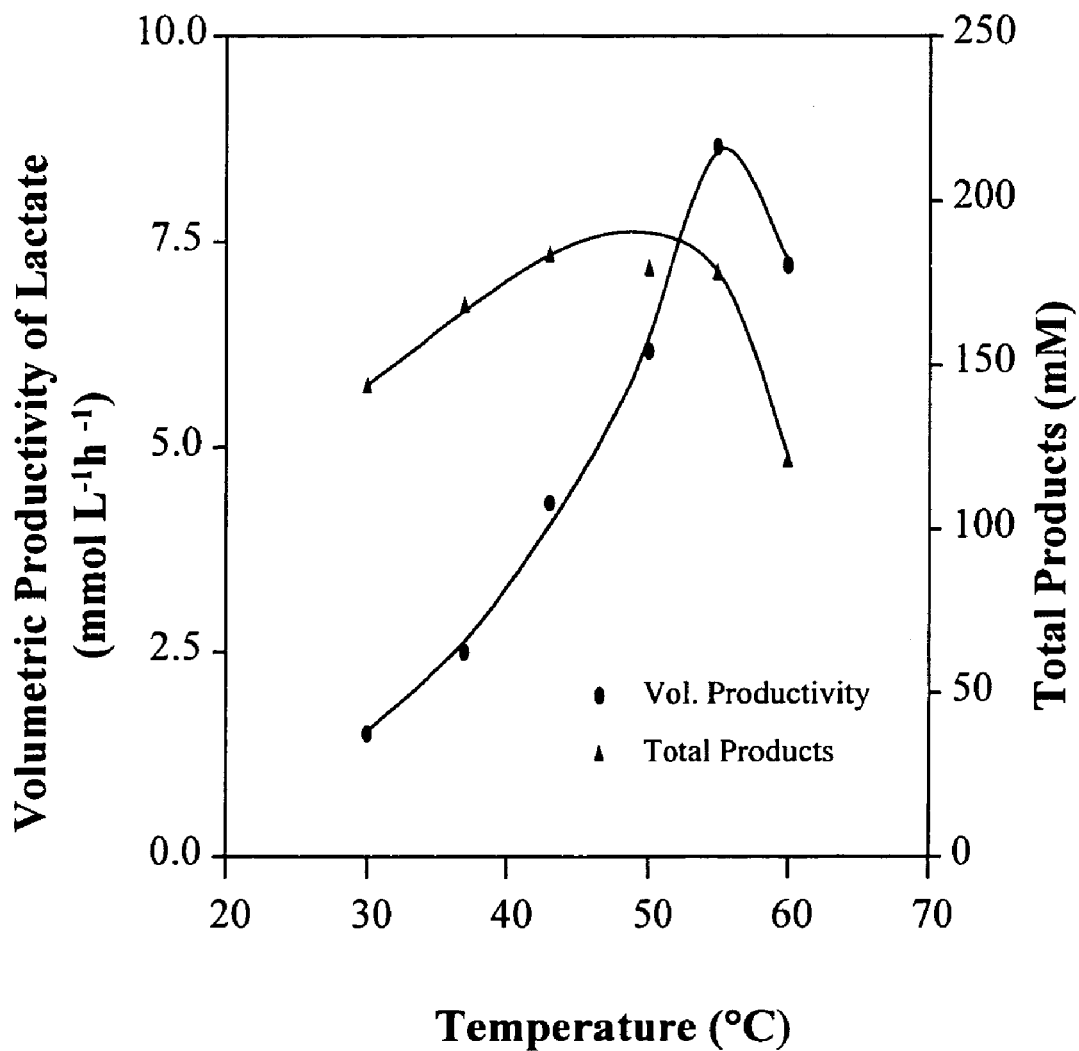
FIG. 13: Temperature profile of SSF by strain 36D1 with 15 FPU Spezyme CE/g Solka-Floc in mineral salts medium with 1% corn steep liquor in a pH-stat at pH 5.0. Total products represent lactate acetate, ethanol and succinate.

At a cellulase concentration of 15 FPU/g glucan and at pH 5.0, the rate of SSF of cellulose by strain 36D1 was highest at 55° C. Although the product yield did not significantly change between 43° C. and 55° C., the volumetric productivity of lactate was about 2-times higher at 55° C. than the 4.3 mmol $L^{-1}$ $h^{-1}$ at 43° C. (FIG. 13).

Fermentation of Sugar Cane Bagasse Hemicellulose Hydrolysate

The sugar cane bagasse hemicellulose acid hydrolysate was generously provided by BC International. This hydrolysate had a total sugar concentration of 81.6 g/L with xylose accounting for 86.5% of the total. Small amount of glucose (11.5 g/L) and arabinose (1.2 g/L) were also present in the hydrolysate. The hydrolysate was adjusted to pH 5.0 with calcium hydroxide. The resulting calcium sulfate was removed by centrifugation and the supernatant was used in fermentations. Isolates 17C5 and 36D1 fermented hemicellulose hydrolysate at a concentration of 25% in mineral salts medium with 0.5% corn steep liquor. Increasing the hydrolysate concentration to 50% led to inhibition of fermentation. To minimize inhibition, the hemicellulose hydrolysate was over-limed with calcium hydroxide and the final pH was adjusted to 5.0.

Figure 15A:
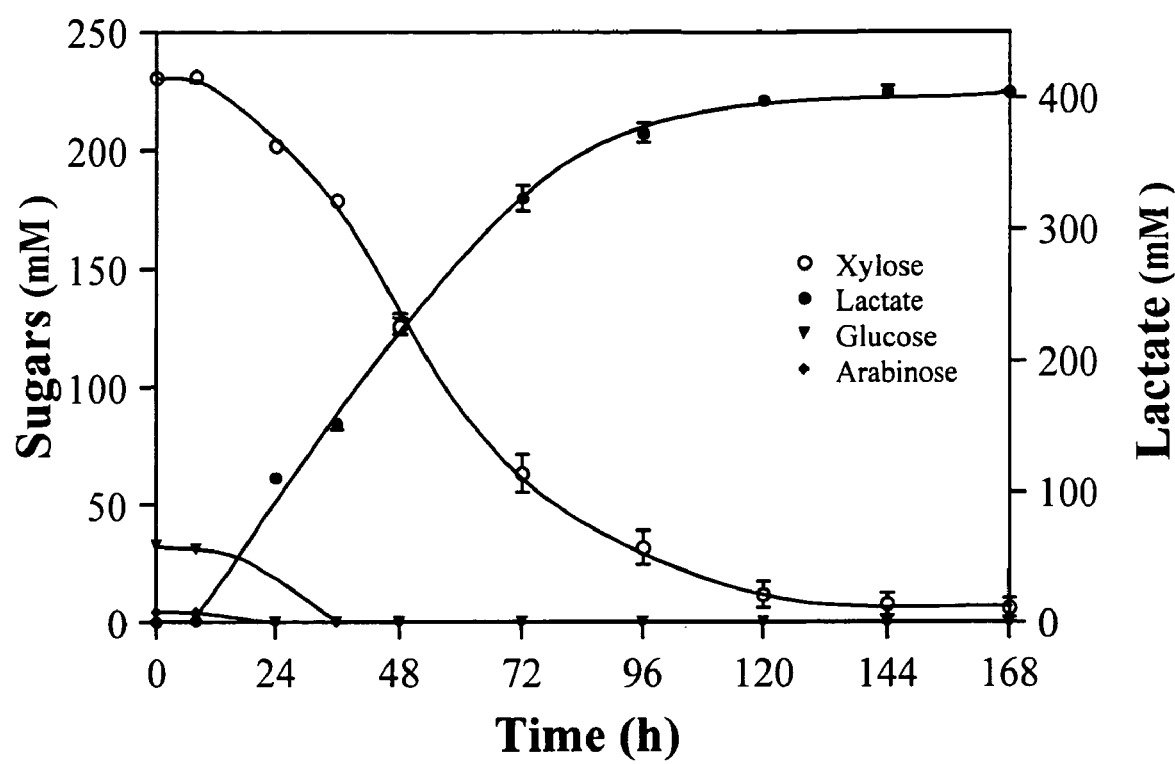
FIG. 15: Fermentation of sugar cane bagasse hemicellulose acid-hydrolysate (over-limed). Fermentations were conducted using three levels of total sugar: 256 mM (FIG. 15A), 412 mM (FIG. 15B), and 483 mM (FIG. 15C). In all fermentations, glucose and arabinose were metabolized first followed by xylose. Fermentation profiles were generally similar for all three levels of sugar although fermentation times increased with substrate. With 256 mM sugar (40 g L$^{-1}$), lactate production was measurable after 8 hours and fermentation was completed within 120 h. With 412 mM sugar (60 g L$^{-1}$), fermentation proceeded at a constant rate until the lactate concentration reached about 0.4 M (36 g L$^{-1}$ lactic acid). Complete fermentation of all sugars in this fermentation to 617 mM lactate (55.5 g L$^{-1}$) required an additional 144 hours due to a progressively declining fermentation rate. With the highest level of sugar tested (483 mM; 72 g L$^{-1}$), 78 mM xylose remained after 192 h of incubation.
Figure 15B:
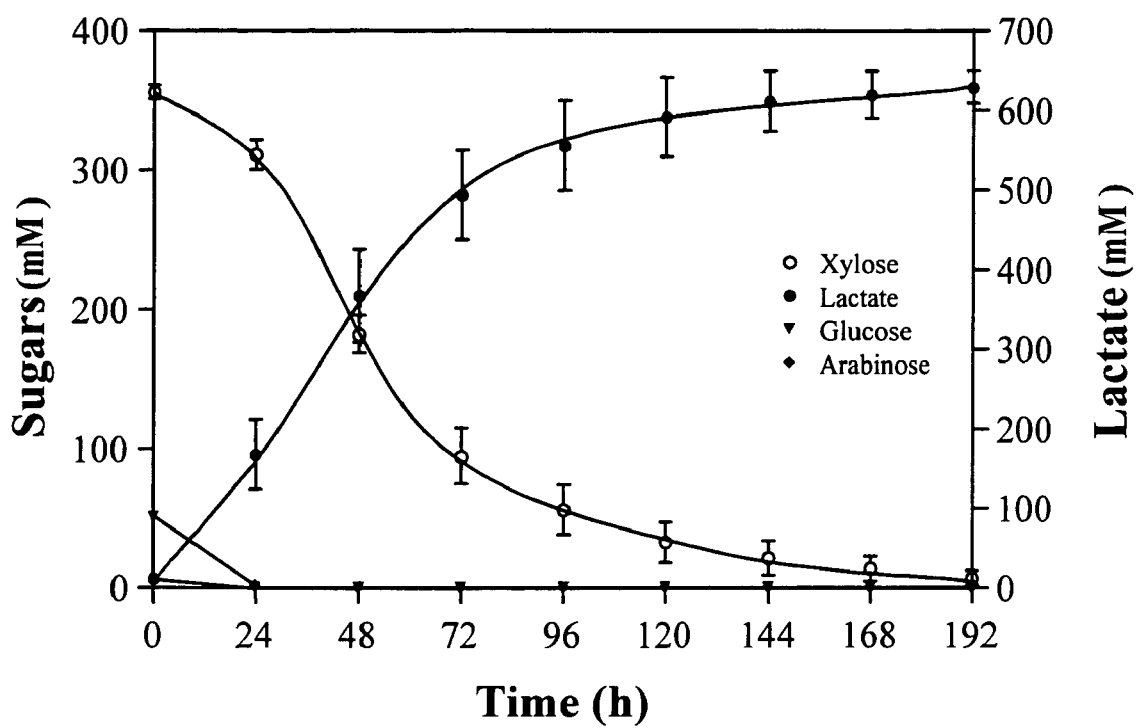
Figure 15C:
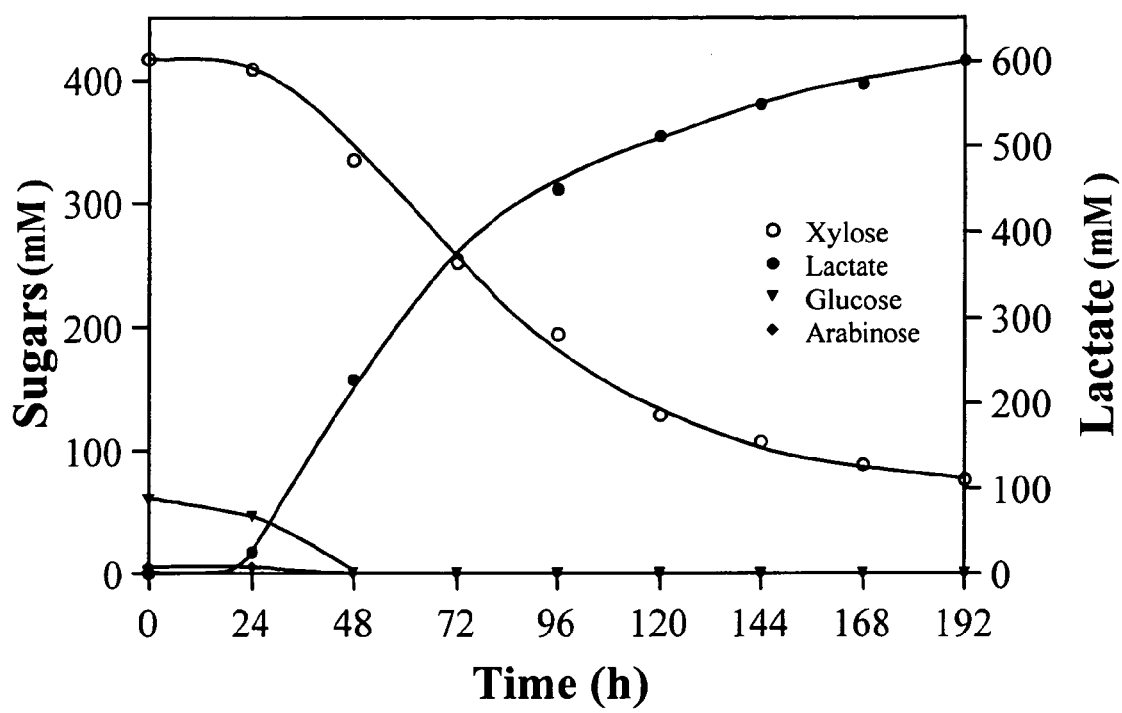

Fermentations were conducted using three levels of total sugar: 256 mM (FIG. 15A), 412 mM (FIG. 15B), and 483 mM (FIG. 15C). In all fermentations, glucose and arabinose were metabolized first followed by xylose. Fermentation profiles were generally similar for all three levels of sugar although fermentation times increased with substrate. With 256 mM sugar (40 g $L^{-1}$), lactate production was measurable after 8 hours and fermentation was completed within 120 h. With 412 mM sugar (60 g $L^{-1}$), fermentation proceeded at a constant rate until the lactate concentration reached about 0.4 M (36 g L$^{-1}$ lactic acid). Complete fermentation of all sugars in this fermentation to 617 mM lactate (55.5 g L$^{-1}$) required an additional 144 hours due to a progressively declining fermentation rate. With the highest level of sugar tested (483 mM; 72 g L$^{-1}$), 78 mM xylose remained after 192 h of incubation. These results suggest that fermentation is inhibited by lactate concentrations above 0.4 M. Even at the highest sugar concentration of 483 mM (about 72 g L$^{-1}$) lactate titer did not increase beyond 0.6 M (54 g L$^{-1}$), consistent with 617 mM (55.8 g L$^{-1}$) lactate (Table 14) representing a near upper limit for strain 17C5 at pH 5.0 (50° C.) in this medium. Irrespective of the initial sugar concentration, the lactic acid produced by strain 17C5 was L(+)-lactic acid at an optical purity higher than 99%.

Lactate yields were calculated based on sugar utilized and ranged from 0.9 g lactate per g sugar for the lower two sugar concentrations to 0.86 g lactate per g sugar for the highest sugar concentration (Table 14). Maximal volumetric rate of sugar metabolism was determined to be 5.5 mmol xylose L$^{-1}$ h$^{-1}$ (approximately 0.8 g sugar L$^{-1}$ h$^{-1}$).

Simultaneous Saccharification and Co-fermentation

Figure 14A:
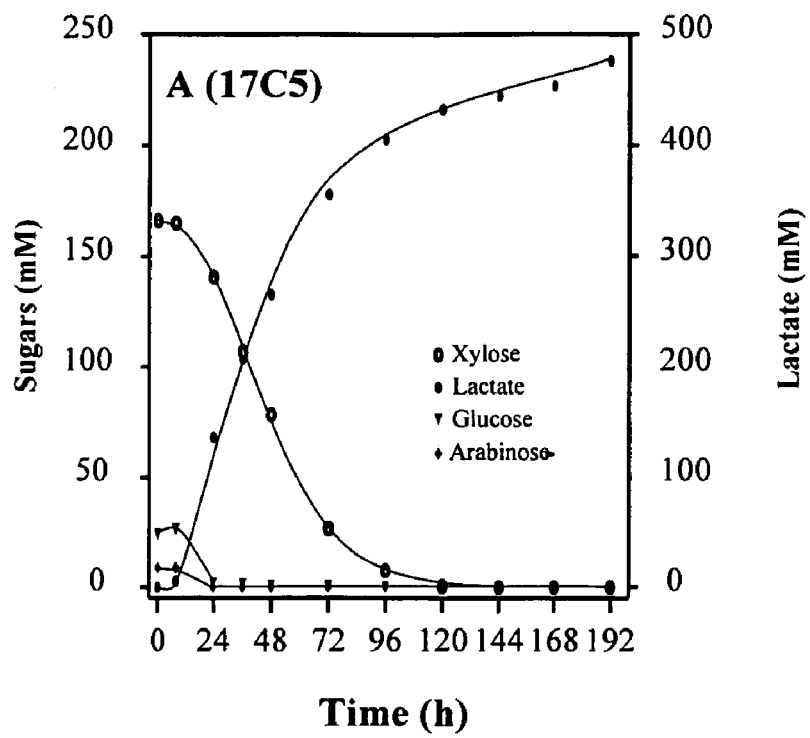
FIG. 14: Simultaneous saccharification and co-fermentation (SSCF) of sugars present in overlimed sugarcane bagasse hemicellulose hydrolysate (40%) and Solka-Floc (2%) in the presence of 10FPU Spezyme CE/g Solka-Floc by strains 17C5 (FIG. 14A) and 36D1 (FIG. 14B) in mineral salts medium with 0.5% corn steep liquor in a pH-stat at pH 5.0 and 50° C.
Figure 14B:
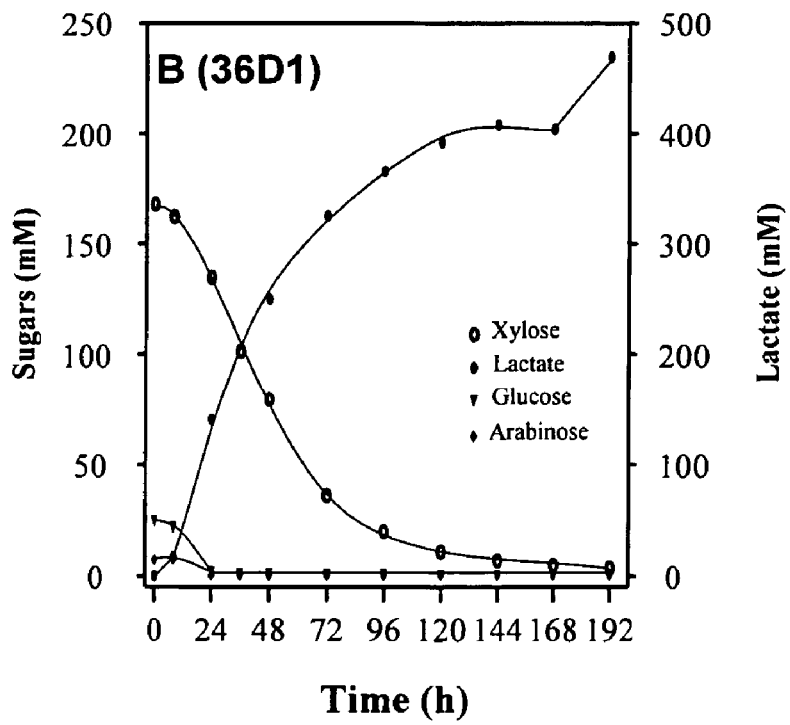

In the next set of experiments strains 17C5 and 36D1 were evaluated for their ability to ferment sugar cane bagasse hemicellulose hydrolysate (over-limed) and Solka Floc (cellulose) simultaneously. Results of these experiments are presented in FIG. 14. Strain 17C5 fermented all the sugars in the hydrolysate and most of the sugars released from cellulose by about 96 hours yielding about 400 mM lactate (36 g/L). SSCF continued at a lower rate past 192 hours when the experiment was terminated. The rate of SSCF by strain 36D1 was slightly lower than strain 17C5.These results show that these new biocatalysts are capable of fermenting both the xylose-rich hemicellulose hydrolysate and cellulose simultaneously (with minimum amounts of commercial cellulose).

EXAMPLE 3

Analysis of *Bacillus* sp. Isolate 17C5

*Bacillus* sp. isolate 17C5 was isolated from Old Faithful Geyser of California (Calistoga, Calif.) and grown on L-broth (tryptone, 1%; yeast extract; 0.5%, NaCl, 0.5%). Sugar cane bagasse hemicellulose hydrolysate was prepared using dilute sulfuric acid under proprietary conditions and was kindly provided by BC International, Dedham, Mass. This hydrolysate was treated with lime as described previously (Martinez A, Rodriguez M E, Wells M L, York S W, Preston J F, Ingram L O (2001) Detoxification of dilute acid hydrolysates of lignocellulose with lime. Biotechnol. Prog. 17: 287–93). Total sugar content after lime treatment was 81.3 g/l (xylose, 68.6 g/l; glucose, 11.5 g/l; arabinose, 1.2 g/l). Media used in fermentation experiments contained per liter: 50% to 90% v/v lime-treated hydrolysate; 6.25 g Na$_2$HPO$_4$, 0.75 g KH$_2$PO$_4$, 2.0 g NaCl, 0.2 g MgSO$_4$.7 H$_2$0, 1.0 g (NH$_4$)$_2$SO$_4$, 10 mg FeSO$_4$.7H$_2$0, 10 mg Na$_2$MoO$_4$.2H$_2$O, 1 ml trace mineral solution (Allen M B, Arnon D I (1955) Studies on nitrogen-fixing blue-green algae: I. Growth and nitrogen fixation by *Anabaena cylindrica* Lemm. Plant Physiol. 30: 366–372), and 5 ml corn steep liquor (50% dry solids; Grain Processing Corp., Muscatine, Iowa). Sterile concentrated solutions of salts and corn steep liquor were added to the lime-treated hemicellulose hydrolysate prior to pH adjustment to 5.0 and inoculation.

Optical purity of lactic acid was determined by HPLC using Chiralpak M A(+) column (Chiral Technologies Inc., Exton, Pa.) with 2 mM CuSO$_4$ as the mobile phase at 0.4 ml per min (32° C.). Corn steep liquor used in the fermentations contained a racemic mixture of D(−)- and L(+)-lactic acids and 0.5% initial concentration used in these experiments introduced 2.6 mM D(−)-lactic acid and 3.4 mM L(+)-lactic acid into the fermentations.

Batch fermentations were carried out as previously described (Beall D S, Ohta K, Ingram L O (1991) Parametric studies of ethanol production from xylose and other sugars by recombinant *Escherichia coli*. Biotechnol. Bioeng. 38: 296–303) except at 50° C. and pH of 5.0. Broth pH was controlled by automatic addition of 2 M KOH. Fresh overnight cultures from L-agar were inoculated into L-broth (pH 5.0) with glucose (1%). After incubation for 2.5 h at 50° C. with shaking (200 rpm), this mid-exponential phase culture was used to provide a 1% v/v inoculum for pH-controlled fermenters. Sugar and fermentation products were measured using HPLC (Underwood S A, Zhou S, Causey T B, Yomano L P, Shanmugam K T, Ingram L O (2002) Genetic changes to optimize carbon partitioning between ethanol and biosynthesis in ethanologenic *Escherichia coli*. Appl. Environ. Microbiol. 68: 6263–6272).

Fermentations were conducted at an initial sugar concentration of 256 mM (FIG. 15A), 412 mM (FIG. 15B) or 483 mM (FIG. 15C). In lime-treated hemicellulose hydrolysate from sugar cane bagasse, xylose (86%) was the most abundant sugar with smaller amounts of glucose (12.5%) and arabinose (1.5%). In all fermentations, glucose and arabinose were metabolized first followed by xylose. Fermentation profiles were generally similar for all three levels of sugar although fermentation times increased with substrate. With 256 mM sugar (40 g/l), lactate production was measurable after 8 hours and fermentation was completed within 120 h. With 412 mM sugar (60 g/l), fermentation proceeded at a constant rate until the lactate concentration reached about 0.4 M (36 g/l lactic acid). Complete fermentation of all sugars in this fermentation to 617 mM lactate (55.5 g/l) required an additional 144 hours due to a progressively declining fermentation rate. With the highest level of sugar tested (483 mM; 72 g/l), 78 mM xylose remained after 192 h of incubation. These results suggest that fermentation is inhibited by lactate concentrations above 0.4 M. Even at the highest sugar concentration of 483 mM (about 72 g/l) lactate titer did not increase beyond 0.6 M (54 g/l), consistent with 617 mM (55.8 g/l) lactate (Table 14) representing a near upper limit for strain 17C5 at pH 5.0 (50° C.) in this medium. Irrespective of the initial sugar concentration, the lactic acid produced by strain 17C5 was L(+)-lactic acid at an optical purity of higher than 99%.

Lactate yields were calculated based on sugar utilized and ranged from 0.9 g lactate per g sugar for the lower two sugar concentrations to 0.86 g lactate per g sugar for the highest sugar concentration (Table 14). Maximal volumetric rates of sugar metabolism were determined to be 5.5 mM xylose/l.h (approximately 0.8 g sugar/l.h).

An analysis of products at the end of fermentation provides a quantitative basis to evaluate potential metabolic pathways for xylose metabolism in strain 17C5. Each mole of glucose can be converted into 2 moles lactate by all major glycolytic pathways for hexoses. Two primary pathways are known for pentose metabolism: the transaldolase/transketolase pathway and the phosphoketolase pathway. The transaldolase/transketolase pathway quantitatively converts the pentose sugars (xylose and arabinose) into the three carbon intermediate, pyruvate, providing the potential to produce 1.67 moles lactate per mole pentose. In contrast, the phosphoketolase pathway common to most lactic acid bacteria (Garde A, Jonsson G, Schmidt A S, Ahring B K (2002) Lactic acid production from wheat straw hemicellulose hydrolysate by *Lactobacillus pentosus* and *Lactobacillus brevis. Bioresoure Technol.* 81: 217–23) (Tanaka K, Komiyama A, Sonomoto K, Ishizaki A, Hall S J, Stanbury P E (2002) Two different pathways for D-xylose metabolism and the effect of xylose concentration on the yield coefficient of L-lactate in mixed-acid fermentation by the lactic acid bacterium *Lactococcus lactis* IO-1. *Appl. Microbiol. Biotechnol.* 60: 160–167), cleaves a five-carbon intermediate into glyceraldehyde 3-phosphate and acetyl-phosphate. The maximum yield from the phosphoketolase pathway is 1 mole lactate per mole pentose accompanied by equimolar acetate. Since lactate yields from strain 17C5 averaged over 100-fold that of acetate, strain 17C5 can be presumed to utilize the transaldolase/transketolase pathway for pentose metabolism. Observed lactate yields were about 90% of the theoretical yield calculated with this assumption. Small amounts of succinate, formate and ethanol were also produced during fermentation. With the transaldolase/transketolase pathway, the maximum theoretical yield for lactate is the same for both pentose and hexose sugars on weight basis (1 g lactate per g sugar).

TABLE 1

Sample Sources for Isolation of Organisms

| First Number in Isolate Name | Source |
| --- | --- |
| 1 | Newberry High School, Newberry, FL - Compost, Lower cup |
| 2 | Hollywood, FL - Dumpster |
| 3 | Newberry High School, Newberry, FL - Compost, Upper cup |
| 4 | Newberry High School, Newberry, FL - Compost, Baggy |
| 5 | Gainesville, FL - Coleman Flower bed |
| 6 | Lake Worth, FL - Banyon |
| 7 | Pompano Beach, FL - *Ficus* |
| 8 | Brush Pile, KFC |
| 9 | Lake Worth, FL - Service Plaza |
| 10 | Whitewater Falls, NC - Service Plaza |
| 11 | Whitewater Falls, NC |
| 12 | Oconee Fish Hatchery, SC |
| 13 | Oconee Fish Hatchery, SC - under Hemlocks |
| 14 | Clemson, SC - Bog, Botanical Gardens |
| 15 | Dannon Fat-free Yogurt |
| 16 | GA-HWY 121, Sparkman Creek Bridge, Just north of FL border |
| 17 | GA-HWY 121, five miles north of FL border |
| 18 | Okeefenokee Natl. Wildlife Refuge, GA - #2 Boardwalk |
| 19 | Okeefenokee Natl. Wildlife Refuge, GA - #1 Boardwalk |
| 20 | Organic Yogurt |
| 21 | RMH Pine nugget mulch |
| 22 | Near Lake Alice, UF campus - hemicellulose hydrolysate enrichment |
| 23 | FL Beach Sample, Sand |
| 24 | FL Beach Sample, Dirt |
| 25 | FL Beach Sample, Rabbit Pellets |
| 26 | FL Beach Sample, Rabbit Pellets |
| 27 | FL Beach Sample, Rabbit Pellets |
| 28 | FL Beach Sample, Rabbit Pellets |
| 29 | FL Beach Sample, Rabbit Pellets |
| 30 | FL Beach Sample, Sea Shell |
| 31 | FL Beach Sample, Driftwood |
| 32 | Pecan Bayou, TX - Muck Soil sent by Angel (Dr. Aldrich's friend) |
| 33 | Calistoga, CA - Geyser #3 |
| 34 | El Capitan State Beach, CA - under *Eucalyptus* |
| 35 | Riverside, CA - Brooks Coleman's Flower Bed |
| 36 | Calistoga, CA - Geyser #1 |
| 37 | San Simeon, CA - under Pine |
| 38 | Woodland Hills, CA - Aldrich's Clay Compost Pile |
| 39 | Brookdale, CA - State Road 9, under Redwood |
| 40 | Big Basin Redwoods State Park, CA #1 |
| 41 | Big Basin Redwoods State Park, CA #2 |
| 42 | San Luis Obispo, CA |
| 43 | Calistoga, CA - Geysor #2 |
| 44 | San Simeon, CA - Moonstone Beach |
| 45 | Big Sur, CA - under Redwood |
| 46 | Lyndon, VT - Rest Stop |
| 47 | Lebanon, NH - Ferns and Conifers |
| 48 | NH - Soil under *Prunus* tree |
| 49 | Burke, VT - Wet Meadow |
| 50 | Quebec City, Canada - *Sphagnum* |
| 51 | Quebec City, Canada - Peat Bog |
| 52 | Yuma Desert, CA - 30 minutes from Calexico |
| 53 | El Centro, imperial Valley, CA - Grain field |
| 54 | CA, off I-8, near Laguna Mountain Recreation Area, Elev., 4,000 ft |
| 55 | Cuyamaca Rancho State Park, CA |
| 56 | Southern US - Paper Mill |
| 57 | Southern US - Paper Mill |
| Isolates with Y prefix | |
| 1 | Gainesville, FL - Morningside Nature Center, Pitcher Plant |
| 2 | Alachua County, FL - CR121 & 231 near CNB Bank |
| 3 | Gainesville, FL - Raceway |
| 4 | Alachua County, FL - 0.7 mile into Austin Cary Forest |
| 5 | Alachua County, FL - 0.9 mile, ditch on road in Austin Cary Forest |
| 6 | Gainesville, FL - Morningside Nature Center, Cypress Dome |
| 7 | Sugarcane Bagasse Storage Area, Acidic |
| 8 | Near Las Vegas, NV - Desert |
| 9 | Rotting Tomato |
| 10 | I-10 Exit 8 (MS) - Ditch with Hatpins |
| 11 | I-10 Exit 8 (MS) - Field by Stucky's Restaurant |
| 12 | I-10 Exit 7 (MS) - Ditch, red clay |
| 13 | SR252 - mile 9 |
| 14 | SR252 - mile 10 |
| 15 | Near Las Vegas, NV - Desert soil (6 samples) |
| 16 | Decomposing coffee ground |
| 17 | Southern Cotton Gin |
| 18 | Southern Pickle Co. (2 samples) |
| 19 | Warm Springs, GA |
| 20 | Compost, 108, 1250 - Tampa area |

Isolates starting with a "P" represent enrichment at pH 4.0 before isolation. For this enrichment, soil samples from various sources were mixed and used as a source of inoculum.

TABLE 2

Properties of all the Isolates

| Isolate | Identification[a] (16S rRNA) | Xylanase 72 hr | CMCase 72 hr | Cellobiose MS (0.1% YE) pH 5.0 72 hr | Growth at pH 5.0 | | | | | | | | | | | | |
|---|---|---|---|---|---|---|---|---|---|---|---|---|---|---|---|---|---|
| | | | | | LB Xylose (1%) | | | | | | LB Glucose (1%) | | | | | | |
| | | | | | Anaerobic | | | | Aerobic | | Anaerobic | | | | Aerobic | | |
| | | | | | O.D. 420 nm | | pH | | O.D. 420 nm | pH | O.D. 420 nm | | pH | | O.D. 420 nm | | pH |
| | | | | | 24 hrs | 48 hrs | 48 hrs | 24 hrs | 48 hrs | 48 hrs | 24 hrs | 48 hrs | 48 hrs | 24 hrs | 48 hrs | 48 hrs |
| 1C1 | | − | − | + | 0.34 | 0.33 | 4.20 | 2.80 | 3.90 | 4.37 | 0.42 | 0.40 | 4.35 | 1.70 | 1.70 | 4.32 |
| 1C2 | | + | + | + | 0.10 | 0.09 | 5.03 | 0.60 | 1.15 | 5.15 | 0.07 | 0.05 | 4.97 | 0.71 | 0.96 | 5.41 |
| 1C3 | B. coagulans | − | − | + | 0.10 | 0.39 | 4.32 | 1.20 | 1.50 | 4.29 | 0.25 | 0.45 | 4.32 | 1.21 | 1.55 | 4.26 |
| 1C4 | B. coagulans | − | − | + | 0.45 | 0.58 | 4.30 | 1.95 | 1.80 | 4.30 | 0.31 | 0.40 | 4.31 | 1.60 | 1.85 | 4.33 |
| 1D1 | B. coagulans | − | − | + | 0.35 | 0.35 | 4.17 | 2.20 | 2.20 | 4.16 | 0.48 | 0.60 | 4.34 | 1.60 | 1.88 | 4.29 |
| 1D2 | | − | − | + | 0.30 | 0.32 | 4.22 | 1.90 | 2.15 | 4.28 | 0.38 | 0.36 | 4.37 | 1.48 | 3.00 | 4.26 |
| 1D5 | | − | − | + | 0.36 | 0.51 | 4.44 | 1.80 | 1.75 | 4.40 | 0.30 | 0.30 | 4.45 | 1.80 | 1.95 | 4.40 |
| 1D6A | | − | − | − | 0.13 | 0.39 | 4.28 | 1.90 | 1.75 | 4.29 | 0.21 | 0.37 | 4.31 | 0.28 | 0.39 | 4.23 |
| 1D6B | B. coagulans | − | − | + | 0.15 | 0.31 | 4.18 | 1.75 | 3.90 | 4.39 | 0.19 | 0.43 | 4.30 | 0.59 | 0.80 | 4.16 |
| 1D7 | B. coagulans | − | − | + | 0.40 | 0.40 | 4.26 | 1.85 | 2.00 | 4.23 | 0.55 | 0.66 | 4.32 | 1.90 | 3.40 | 4.25 |
| 1F1 | | − | − | + | 0.22 | 0.25 | 4.47 | 1.30 | 1.20 | 4.36 | 0.16 | 0.30 | 4.44 | 1.01 | 4.60 | 4.50 |
| 1F2 | B. coagulans | − | − | + | 0.40 | 0.45 | 4.12 | 2.10 | 2.30 | 4.13 | 0.43 | 0.66 | 4.26 | 1.93 | 1.93 | 4.19 |
| 2C2 | | − | − | + | 0.15 | 0.24 | 5.02 | 0.70 | 1.00 | 5.85 | 0.18 | 0.15 | 4.94 | 0.65 | 1.19 | 5.72 |
| 2C3 | | + | + | + | 0.32 | 0.31 | 4.28 | 1.60 | 1.50 | 4.17 | 0.35 | 0.37 | 4.22 | 1.34 | 1.38 | 4.18 |
| 2C3-1 | | + | − | + | 0.02 | 0.02 | 4.95 | 0.00 | 0.00 | 5.01 | 0.02 | 0.00 | 4.94 | 0.00 | 0.00 | 4.90 |
| 2D1 | B. coagulans | − | − | + | 0.33 | 0.26 | 4.38 | 2.10 | 3.20 | 4.32 | 0.44 | 0.42 | 4.26 | 1.80 | 1.80 | 4.23 |
| 2D2 | B. coagulans | + | − | + | 0.21 | 0.34 | 4.52 | 1.45 | 2.60 | 4.55 | 0.49 | 0.45 | 4.29 | 1.95 | 3.30 | 4.38 |
| 2D3 | B. coagulans | + | − | + | 0.35 | 0.40 | 4.29 | 1.40 | 2.20 | 4.34 | 0.31 | 0.31 | 4.35 | 1.08 | 1.85 | 4.28 |
| 2D3M | | − | − | + | 0.18 | 0.20 | 4.56 | 1.40 | 2.70 | 4.60 | 0.36 | 0.41 | 4.39 | 2.81 | 4.50 | 4.48 |
| 2D10 | | − | − | + | 0.35 | 0.33 | 4.34 | 1.70 | 2.50 | 4.33 | 0.44 | 0.68 | 4.39 | 1.40 | 2.65 | 4.36 |
| 2D11 | | − | − | + | 0.27 | 0.37 | 4.15 | 1.30 | 2.70 | 4.23 | 0.41 | 0.45 | 4.28 | 2.41 | 4.30 | 4.25 |
| 2F1 | | − | − | + | 0.11 | 0.11 | 5.02 | 0.60 | 1.00 | 5.79 | 0.13 | 0.12 | 5.01 | 0.70 | 0.91 | 5.93 |
| 2F2 | | − | − | + | 0.33 | 0.34 | 4.28 | 1.70 | 2.60 | 4.28 | 0.24 | 0.45 | 4.13 | 0.99 | 1.85 | 4.27 |
| 2G1 | | − | − | − | 0.02 | 0.09 | 5.04 | 0.75 | 1.30 | 5.68 | 0.07 | 0.12 | 5.06 | 0.95 | 1.40 | 5.24 |
| 2G2 | | − | − | + | 0.31 | 0.23 | 4.51 | 1.20 | 1.20 | 4.47 | 0.22 | 0.23 | 4.52 | 0.75 | 0.85 | 4.56 |
| 2G3 | | − | − | + | 0.13 | 0.11 | 4.98 | 1.05 | 2.30 | 6.54 | 0.20 | 0.24 | 4.96 | 0.83 | 2.90 | 6.58 |
| 2G4 | | − | − | + | 0.14 | 0.17 | 4.97 | 0.65 | 1.00 | 5.73 | 0.20 | 0.20 | 4.98 | 0.65 | 2.30 | 6.50 |
| 3D1 | | − | − | + | 0.23 | 0.24 | 4.38 | 1.50 | 1.95 | 4.43 | 0.23 | 0.27 | 4.29 | 1.53 | 1.55 | 4.39 |
| 3F1 | | − | − | + | 0.38 | 0.39 | 4.15 | 1.75 | 1.90 | 4.14 | 0.40 | 0.44 | 4.17 | 1.73 | 1.73 | 4.21 |
| 3F2 | B. coagulans | − | − | + | 0.38 | 0.41 | 4.15 | 1.90 | 1.95 | 4.17 | 0.52 | 0.51 | 4.23 | 1.85 | 3.50 | 4.20 |
| 4D1 | | − | − | − | 0.20 | 0.09 | 4.91 | 0.55 | 0.65 | 5.46 | 0.08 | 0.07 | 4.86 | 0.55 | 0.55 | 4.94 |
| 4D2 | | − | − | + | 0.34 | 0.30 | 4.41 | 1.40 | 2.40 | 4.25 | 0.26 | 0.37 | 4.38 | 1.30 | 1.85 | 4.28 |
| 4D3 | | − | − | + | 0.30 | 0.53 | 4.18 | 1.85 | 2.10 | 4.22 | 0.31 | 0.50 | 4.23 | 1.80 | 2.60 | 4.15 |
| 4E2 | | − | − | − | 0.10 | 0.19 | 5.35 | 0.35 | 0.90 | 6.61 | 0.45 | 0.49 | 4.22 | 1.61 | 3.55 | 4.36 |
| 4F1 | | − | − | + | 0.15 | 0.17 | 4.99 | 0.70 | 1.03 | 5.78 | 0.09 | 0.09 | 4.97 | 0.68 | 1.05 | 5.51 |
| 4F2 | | − | − | − | 0.11 | 0.06 | 4.87 | 0.75 | 0.88 | 5.40 | 0.07 | 0.07 | 4.92 | 0.70 | 0.69 | 5.00 |
| 5C3 | | − | − | + | 0.00 | 0.00 | 4.93 | 0.00 | 0.00 | 4.97 | 0.04 | 0.01 | 4.98 | 0.03 | 0.01 | 4.98 |
| 5D1 | | − | − | + | 0.23 | 0.24 | 4.49 | 1.35 | 1.60 | 4.49 | 0.26 | 0.39 | 4.40 | 1.53 | 1.55 | 4.38 |
| 5D2 | | − | − | + | 0.38 | 0.33 | 4.34 | 1.75 | 1.70 | 4.35 | 0.55 | 0.53 | 4.32 | 1.75 | 1.80 | 4.42 |

TABLE 2-continued

Properties of all the Isolates

| Isolate | Stationary Phase Survival – LB (Glucose 1%), (microaerobic), pH 5.0 | | | | | | LB Xylose (1%) Anaerobic OD 420nm 24 hrs | 48 hrs | pH 48 hrs | LB Xylose (1%) Aerobic OD 420nm 24 hrs | 48 hrs | pH 48 hrs | LB Glucose (1%) Anaerobic OD 420nm 24 hrs | 48 hrs | pH 48 hrs | LB Glucose (1%) Aerobic OD 420nm 24 hrs | 48 hrs | pH 48 hrs |
|---|---|---|---|---|---|---|---|---|---|---|---|---|---|---|---|---|---|---|
| | OD 24 hrs | OD 48 hrs | pH 48 hrs | CFU/ml 24 hrs | CFU/ml 48 hrs | notes | | | | | | | | | | | | |
| 5D3 | | | | | | − | 0.20 | 0.22 | 4.45 | 0.65 | 1.15 | 4.49 | 0.22 | 0.26 | 4.53 | 0.76 | 0.73 | 4.47 |
| 5D10 | | | | | | − | 0.33 | 0.39 | 4.46 | 1.90 | 1.83 | 4.44 | 0.45 | 0.43 | 4.43 | 1.20 | 2.00 | 4.48 |
| 5D12 | | | | | | − | 0.20 | 0.20 | 4.51 | 0.70 | 1.48 | 4.33 | 0.16 | 0.20 | 4.54 | 0.44 | 0.30 | 4.47 |
| 5D13 | | | | | | − | 0.33 | 0.31 | 4.22 | 2.10 | 2.20 | 4.24 | 0.11 | 0.60 | 4.34 | 1.30 | 3.10 | 4.31 |
| 5F1 | 1.25 | 1.40 | 4.38 | 1.3 × 10$^7$ | 1.2 × 10$^5$ | + | 0.12 | 0.08 | 4.90 | 0.50 | 0.70 | 5.65 | 0.15 | 0.16 | 4.96 | 0.30 | 0.25 | 5.05 |
| 5F2 | | | | | | + | 0.10 | 0.10 | 4.89 | 0.50 | 0.65 | 5.46 | 0.22 | 0.18 | 4.91 | 0.45 | 0.93 | 2.02 |
| 5F3 | | | | | | + | 0.20 | 0.22 | 4.30 | 1.70 | 2.80 | 4.42 | 0.15 | 0.38 | 4.16 | 1.25 | 1.75 | 4.33 |
| 5G2 | | | | | | + | 0.28 | 0.23 | 4.39 | 1.50 | 1.45 | 4.41 | 0.22 | 0.42 | 4.28 | 1.15 | 1.13 | 4.38 |
| 6C1 | | | | | B. coagulans | + | 0.28 | 0.23 | 4.36 | 1.50 | 1.50 | 4.25 | 0.31 | 0.31 | 4.42 | 1.80 | 2.76 | 4.46 |
| 6D1A | 2.20 | 2.50 | 4.34 | 3.2 × 10$^5$ | nd | − | 0.52 | 0.50 | 4.48 | 2.57 | 2.03 | 4.38 | 1.25 | 0.61 | 4.42 | 1.53 | 1.45 | 4.50 |
| 6D1B | | | | | | − | 0.24 | 0.25 | 4.50 | 1.50 | 1.55 | 4.36 | 0.31 | 0.29 | 4.51 | 1.20 | 1.98 | 4.43 |
| 6D2A | | | | | | − | 0.21 | 0.26 | 4.60 | 1.80 | 2.70 | 4.76 | 0.28 | 0.40 | 4.52 | 1.35 | 4.23 | 4.57 |
| 6D6 | 1.85 | 2.00 | 4.18 | 1.2 × 10$^7$ | 3 × 10$^6$ | + | 0.91 | 0.20 | 4.28 | 1.48 | 2.50 | 4.24 | 0.30 | 0.52 | 4.40 | 0.91 | 1.35 | 4.27 |
| 6F1sm | | | | | | + | 0.24 | 0.25 | 4.50 | 1.52 | 2.69 | 4.49 | 0.10 | 0.39 | 4.47 | 0.90 | 0.83 | 4.47 |
| 6F11g | | | | | | − | 0.27 | 0.27 | 4.39 | 1.45 | 1.50 | 4.54 | 0.26 | 0.32 | 4.36 | 1.05 | 1.10 | 4.38 |
| 6F2 | | | | | B. coagulans | + | 0.45 | 0.60 | 4.53 | 1.71 | 2.35 | 4.62 | 0.40 | 0.63 | 4.19 | 2.15 | 3.08 | 4.22 |

Growth at pH 6.8

| Isolate | LB Xylose (1%) Anaerobic OD 420 nm 24 hrs | 48 hrs | pH 48 hrs | LB Xylose (1%) Aerobic OD 420 nm 24 hrs | 48 hrs | pH 48 hrs | LB Glucose (1%) Anaerobic OD 420 nm 24 hrs | 48 hrs | pH 48 hrs | LB Glucose (1%) Aerobic OD 420 nm 24 hrs | 48 hrs | pH 48 hrs |
|---|---|---|---|---|---|---|---|---|---|---|---|---|
| 1C1 | 1.15 | 1.15 | 4.28 | 2.85 | 2.90 | 4.30 | 1.20 | 1.20 | 4.35 | 2.55 | 2.83 | 4.24 |
| 1C2 | 0.26 | 1.20 | 4.29 | 1.15 | 1.55 | 5.55 | 0.16 | 0.19 | 5.40 | 1.05 | 1.45 | 5.46 |
| 1C3 | 0.55 | 0.85 | 4.31 | 2.50 | 2.60 | 4.39 | 0.85 | 1.08 | 4.13 | 1.85 | 2.20 | 4.35 |
| 1C4 | 1.30 | 1.50 | 4.38 | 2.95 | 3.70 | 4.38 | 1.15 | 1.23 | 4.36 | 3.05 | 3.95 | 4.67 |
| 1D1 | 1.30 | 1.20 | 4.28 | 2.85 | 2.80 | 4.43 | 1.35 | 1.30 | 4.33 | 2.05 | 2.40 | 4.94 |
| 1D2 | 1.15 | 1.05 | 4.28 | 2.75 | 2.60 | 4.39 | 1.35 | 1.20 | 4.25 | 3.65 | 4.10 | 5.18 |
| 1D5 | 0.85 | 0.85 | 4.48 | 3.00 | 3.40 | 4.53 | 1.15 | 1.10 | 4.45 | 1.85 | 3.50 | 4.37 |
| 1D6A | 1.00 | 1.05 | 4.32 | 3.50 | 4.40 | 4.36 | 1.00 | 1.05 | 4.27 | 1.10 | 1.23 | 4.31 |
| 1D6B | 0.40 | 0.75 | 4.27 | 2.30 | 3.40 | 4.29 | 0.85 | 1.03 | 4.23 | 1.75 | 3.15 | 4.25 |
| 1D7 | 1.00 | 1.10 | 4.29 | 2.30 | 2.80 | 4.54 | 1.20 | 1.40 | 4.42 | 2.20 | 2.55 | 4.29 |
| 1F1 | 0.42 | 0.60 | 4.43 | 1.25 | 1.60 | 4.48 | 0.70 | 0.68 | 4.18 | 1.05 | 1.30 | 4.55 |
| 1F2 | 1.10 | 1.05 | 4.27 | 2.70 | 2.00 | 4.17 | 1.30 | 1.30 | 4.33 | 2.33 | 1.85 | 4.25 |
| 2C2 | 0.06 | 0.10 | 6.41 | 2.00 | 2.10 | 6.73 | 0.07 | 0.14 | 6.45 | 0.60 | 0.85 | 6.13 |
| 2C3 | 1.00 | 0.95 | 4.24 | 2.80 | 2.70 | 4.25 | 1.10 | 1.10 | 4.29 | 1.95 | 2.05 | 4.26 |
| 2C3-1 | 0.08 | 0.09 | 6.32 | 0.43 | 0.65 | 6.65 | 0.04 | 0.13 | 5.49 | 1.30 | 2.80 | 5.18 |
| 2D1 | 0.95 | 0.95 | 4.44 | 2.45 | 2.35 | 4.29 | 1.20 | 1.15 | 4.27 | 2.25 | 1.38 | 4.48 |
| 2D2 | 0.80 | 0.90 | 4.57 | 2.60 | 3.10 | 4.72 | 1.30 | 1.25 | 4.30 | 3.13 | 5.00 | 4.18 |
| 2D3 | 1.05 | 1.10 | 4.35 | 1.80 | 2.40 | 4.38 | 1.00 | 0.89 | 4.46 | 1.70 | 1.78 | 4.38 |
| 2D3M | 0.85 | 1.10 | 4.67 | 2.30 | 3.00 | 4.75 | 0.95 | 1.10 | 4.32 | 3.40 | 4.70 | 4.28 |
| 2D10 | 0.80 | 0.90 | 4.42 | 1.65 | 2.50 | 4.59 | 0.95 | 1.30 | 4.31 | 1.85 | 3.20 | 4.36 |
| 2D11 | 0.95 | 1.15 | 4.28 | 2.80 | 4.20 | 4.47 | 1.25 | 1.15 | 4.18 | 5.40 | 9.40 | 5.11 |
| 2F1 | 0.04 | 0.07 | 6.57 | 0.70 | 1.10 | 6.24 | 0.05 | 0.08 | 6.57 | 0.75 | 1.00 | 6.37 |
| 2F2 | 0.75 | 0.80 | 4.50 | 2.00 | 3.00 | 4.23 | 0.85 | 1.05 | 4.30 | 1.50 | 2.25 | 4.29 |

TABLE 2-continued

Properties of all the Isolates

| Isolate | | | | | | | | | | | | |
|---|---|---|---|---|---|---|---|---|---|---|---|---|
| 2G1 | 0.09 | 0.10 | 6.40 | 0.73 | 1.10 | 6.06 | 0.04 | 0.05 | 6.45 | 0.48 | 0.78 | 5.91 |
| 2G2 | 0.70 | 0.70 | 4.42 | 2.20 | 2.50 | 4.30 | 0.85 | 0.75 | 4.42 | 1.55 | 1.63 | 4.32 |
| 2G3 | 0.08 | 0.11 | 6.46 | 0.80 | 1.05 | 6.22 | 0.01 | 0.05 | 6.55 | 0.65 | 1.00 | 6.11 |
| 2G4 | 0.80 | 0.11 | 6.53 | 1.75 | 3.40 | 5.02 | 0.06 | 1.00 | 4.50 | 1.55 | 1.25 | 4.63 |
| 3D1 | 0.08 | 0.80 | 4.47 | 1.85 | 2.40 | 4.81 | 1.00 | 1.00 | 4.39 | 1.50 | 1.65 | 4.57 |
| 3F1 | 1.10 | 1.10 | 4.24 | 2.40 | 2.45 | 4.21 | 1.15 | 1.10 | 4.15 | 2.10 | 3.35 | 4.11 |
| 3F2 | 1.10 | 1.20 | 4.19 | 2.60 | 2.85 | 4.24 | 1.15 | 1.10 | 4.07 | 2.10 | 2.70 | 4.22 |
| 4D1 | 0.09 | 0.14 | 6.31 | 0.73 | 1.10 | 6.22 | 0.04 | 0.09 | 6.38 | 0.75 | 1.25 | 5.77 |
| 4D2 | 0.80 | 0.80 | 4.49 | 1.65 | 2.55 | 4.26 | 0.55 | 1.05 | 4.18 | 1.90 | 2.95 | 4.34 |
| 4D3 | 0.80 | 1.15 | 4.31 | 2.70 | 3.10 | 4.33 | 0.65 | 1.03 | 4.26 | 1.45 | 2.70 | 4.27 |
| 4E2 | 0.11 | 0.08 | 6.70 | 0.85 | 0.90 | 6.89 | 1.10 | 1.05 | 4.22 | 2.10 | 2.33 | 4.44 |
| 4F1 | 0.05 | 0.08 | 6.52 | 1.75 | 1.25 | 7.38 | 0.02 | 0.11 | 5.83 | 0.60 | 1.50 | 5.33 |
| 4F2 | 0.11 | 0.14 | 6.43 | 0.90 | 2.15 | 6.20 | 0.06 | 0.11 | 6.35 | 1.85 | 1.75 | 4.95 |
| 5C3 | 0.12 | 0.15 | 6.49 | 0.45 | 0.73 | 6.67 | 0.03 | 0.13 | 5.41 | 1.75 | 1.75 | 4.92 |
| 5D1 | 0.37 | 0.41 | 4.62 | 1.15 | 1.85 | 4.74 | 0.60 | 0.75 | 4.44 | 1.80 | 1.85 | 4.93 |
| 5D2 | 0.80 | 0.85 | 4.41 | 2.20 | 2.60 | 4.65 | 0.80 | 1.30 | 4.17 | 1.65 | 2.85 | 4.70 |
| 5D3 | 0.70 | 0.75 | 4.49 | 1.23 | 1.55 | 4.29 | 0.80 | 0.80 | 4.44 | 1.55 | 1.85 | 4.42 |
| 5D10 | 1.00 | 1.05 | 4.47 | 2.10 | 2.15 | 4.44 | 1.25 | 1.15 | 4.42 | 1.70 | 1.70 | 4.86 |
| 5D12 | 0.30 | 0.41 | 4.38 | 1.35 | 1.90 | 4.49 | 0.70 | 0.70 | 4.41 | 1.75 | 2.10 | 4.50 |
| 5D13 | 1.15 | 1.05 | 4.33 | 2.95 | 3.20 | 4.74 | 1.35 | 1.20 | 4.22 | 1.75 | 2.65 | 4.60 |
| 5F1 | 0.07 | 0.11 | 6.41 | 1.35 | 2.70 | 6.11 | 0.06 | 0.10 | 6.38 | 1.85 | 1.50 | 5.02 |
| 5F2 | 0.10 | 0.15 | 6.36 | 0.65 | 1.03 | 4.52 | 0.85 | 1.20 | 6.33 | 1.85 | 1.55 | 4.97 |
| 5F3 | 0.95 | 1.05 | 4.35 | 2.75 | 2.90 | 4.60 | 0.14 | 0.21 | 4.18 | 1.80 | 2.70 | 4.65 |
| 5G2 | 0.80 | 0.90 | 4.41 | 0.85 | 1.35 | 4.43 | 0.73 | 0.92 | 5.54 | 1.75 | 1.80 | 4.89 |
| 6C1 | 1.03 | 1.40 | 4.36 | 2.60 | 3.20 | 4.76 | 0.98 | 0.93 | 4.16 | 2.50 | 2.70 | 4.36 |
| 6D1A | 0.63 | 0.70 | 4.48 | 3.80 | 4.10 | 4.42 | 0.80 | 0.95 | 4.37 | 4.60 | 5.80 | 5.07 |
| 6D1B | 0.63 | 0.63 | 4.46 | 1.93 | 2.00 | 4.74 | 0.48 | 0.68 | 4.46 | 1.90 | 2.08 | 4.45 |
| 6D2A | 0.18 | 0.19 | 4.75 | 0.80 | 1.40 | 4.55 | 0.68 | 0.92 | 4.62 | 1.40 | 1.95 | 4.63 |
| 6D6 | 0.50 | 0.70 | 4.25 | 1.80 | 2.20 | 4.61 | 1.00 | 1.08 | 4.32 | 2.20 | 2.80 | 4.42 |
| 6F1sm | 0.70 | 0.80 | 4.56 | 2.20 | 2.35 | 4.59 | 0.85 | 0.90 | 4.47 | 1.75 | 2.75 | 4.41 |
| 6F1lg | 0.55 | 0.68 | 4.56 | 2.90 | 3.60 | 4.65 | 1.00 | 1.08 | 4.40 | 1.80 | 2.85 | 4.33 |
| 6F2 | 0.53 | 0.58 | 4.43 | 1.50 | 1.85 | 4.90 | 0.93 | 1.03 | 4.28 | 1.85 | 2.90 | 4.25 |

Fermentation Products (48 hr) (pH not Controlled)

| | LB (1% Xylose), pH 6.8 | | | | | | | LB (1% Glucose), pH 6.8 | | | | | | |
|---|---|---|---|---|---|---|---|---|---|---|---|---|---|---|
| Isolate | Xylose mM | Succinate mM | Lactate mM | Formate mM | Fumarate μM | Acetate mM | Ethanol mM | Glucose mM | Succinate mM | Lactate mM | Formate mM | Fumarate μM | Acetate mM | Ethanol mM |
| 1C1 | 66.9 | 1.5 | 14.2 | 7.1 | | 6.1 | | 42.8 | 2.2 | 19.0 | | 18.5 | | |
| 1C2 | | | | | | | | 45.9 | 1.5 | 19.2 | | | 3.3 | |
| 1C3 | 47.3 | 2.3 | 16.7 | * | 13.4 | 3.3 | 0.70 | 41.5 | * | 15.9 | | | 3.8 | |
| 1C4 | 68.0 | 1.5 | 13.3 | 4.9 | 10.2 | 3.5 | | 41.6 | | 18.3 | | | | |
| 1D1 | 60.7 | 1.5 | 14.0 | * | | | | 60.7 | 1.1 | | | | | |
| 1D2 | 58.0 | 1.5 | 14.3 | 4.3 | | 2.7 | | 45.2 | 1.1 | 20.9 | | | | |
| 1D5 | 51.2 | 1.3 | 13.1 | 3.7 | | 3.3 | | 40.5 | 2.4 | 15.1 | | | 3.3 | |
| 1D6A | 34.9 | 1.5 | 16.6 | | | 2.1 | | 40.7 | 1.2 | 19.3 | | | | |
| 1D6B | 44.1 | 1.5 | 18.4 | | nd | | | 39.9 | * | 17.6 | | 11.0 | * | |
| 1D7 | 44.4 | 1.5 | 14.5 | | nd | 2.4 | | 42.7 | | 17.3 | | | | |

TABLE 2-continued

Properties of all the Isolates

| Isolate | | | | | | | | | |
|---|---|---|---|---|---|---|---|---|---|
| 1F1 | 48.2 | 1.7 | 15.3 | | | | 43.4 | 1.1 | 15.6 |
| 1F2 | 48.1 | 1.1 | 15.3 | | | | 41.4 | * | 19.9 |
| 2C2 | | | | | | | | | |
| 2C3 | 45.5 | 1.6 | 16.7 | * | | 2.2 | 43.4 | 1.5 | 20.7 |
| 2C3-1 | | | | 6.3 | | 3.1 | | | |
| 2D1 | 44.0 | 1.6 | 13.6 | | | 6.1 | 42.7 | 1.2 | 15.2 |
| 2D2 | 52.5 | * | 3.2 | 9.4 | | 2.7 | 43.6 | 1.1 | 17.8 |
| 2D3 | 45.7 | 1.5 | 19.1 | | * | 6.6 | 40.8 | 1.5 | 14.6 |
| 2D3M | 52.0 | | 1.0 | 8.3 | | 3.9 | 41.4 | 1.1 | 18.8 |
| 2D10 | 47.6 | 1.3 | 9.6 | 4.7 | 2.8 | 6.6 | 39.6 | 1.2 | 18.4 |
| 2D11 | 50.6 | * | 2.6 | 9.2 | 3.5 | | 45.3 | * | 18.5 |
| 2F1 | | | | | | | | | |
| 2F2 | 46.9 | 1.1 | 17.5 | 3.7 | | 2.8 | 42.2 | 1.1 | 18.6 |
| 2G1 | | | | | | | | | |
| 2G2 | 46.2 | 1.5 | 15.0 | | | 4.0 | 43.8 | 1.1 | 14.8 |
| 2G3 | | | | | | | | | |
| 2G4 | | | | | 9.8 | | | | |
| 3D1 | 49.1 | 1.4 | 13.1 | * | | 2.9 | 40.8 | 1.4 | 15.4 |
| 3F1 | 49.8 | 1.6 | 15.5 | * | | 3.2 | 36.0 | * | 17.9 |
| 3F2 | 47.0 | 1.7 | 19.4 | * | | | 38.0 | 1.9 | 22.4 |
| 4D1 | | | | | | | | | |
| 4D2 | 52.2 | 1.3 | 14.5 | * | | 3.9 | 39.6 | 1.1 | 16.8 |
| 4D3 | 46.1 | 1.4 | 17.3 | * | | 5.9 | 40.0 | 1.4 | 17.2 |
| 4E2 | | | | | | | | | |
| 4F1 | | | | | | | | | |
| 4F2 | | | | | | | | | |
| 5C3 | | | | | | | | | |
| 5D1 | 50.1 | 1.4 | 13.9 | | | 3.1 | 43.5 | 1.6 | 14.9 |
| 5D2 | 49.6 | 1.5 | 16.8 | | 7.0 | | 44.1 | 1.1 | 18.6 |
| 5D3 | 53.1 | 1.9 | 15.6 | 8.5 | | | 42.8 | 1.4 | 14.7 |
| 5D10 | 52.0 | 1.4 | 12.4 | 11.9 | | 3.4 | 44.7 | 1.1 | 16.6 |
| 5D12 | | | | | | | | | |
| 5D13 | | | | | | | | | |
| 5F1 | | | | | | | | | |
| 5F2 | 48.3 | 1.6 | 17.2 | * | | 3.0 | 43.1 | 1.2 | 22.6 |
| 5F3 | 51.1 | 1.7 | 15.6 | | 2.6 | 5.1 | 47.1 | 1.2 | 15.8 |
| 5G2 | 45.3 | | 15.5 | | | 4.0 | 22.6 | | 13.5 |
| 6C1 | | | | | | | | | |
| 6D1A | | | | | | | | | |
| 6D1B | | | | | | | | | |
| 6D2A | | | | | | | | | |
| 6D6 | 48.9 | 1.3 | 16.5 | * | | 2.4 | 45.4 | 1.3 | 17.4 |
| 6F1sm | 53.4 | 1.7 | 9.9 | 4.1 | | 4.0 | 48.4 | | 17.3 |
| 6F1lg | 56.0 | | 9.8 | | | 3.0 | 36.7 | | 14.0 |
| 6F2 | 52.1 | | 3.3 | 11.3 | 5.9 | 7.6 | 41.1 | | 19.0 |

TABLE 2-continued

Properties of all the Isolates

Fermentation Products (48 hr) (pHstat)

| | LB (1% Xylose), pH 5.0 | | | | | | LB (1% Glucose), pH 5.0 | | | | | |
|---|---|---|---|---|---|---|---|---|---|---|---|---|
| Isolate | Xylose mM | Lactate mM | Succinate mM | Acetate mM | Ethanol mM | Formate mM | Fumarate μM | Glucose mM | Lactate mM | Succinate mM | Acetate mM | Ethanol mM | Formate mM | Fumarate μM |
| 1C1 | | | | | | | | | | | | | | |
| 1C2 | | | | | | | | | | | | | | |
| 1C3 | | | | | | | | | | | | | | |
| 1C4 | 0.00 | 77.47 | 1.79 | 10.55 | 10.41 | 11.91 | 0.00 | 0.00 | 89.16 | 0.72 | 8.52 | 0.00 | 0.00 | 0.00 |
| 1D1 | 0.00 | 87.05 | 3.08 | 10.73 | 8.35 | 8.38 | 0.00 | 0.00 | 94.79 | 0.00 | 6.69 | 2.20 | 0.00 | 0.00 |
| 1D2 | 0.00 | 74.97 | 0.00 | 10.00 | 17.18 | 9.14 | 0.00 | 0.00 | 88.02 | 0.00 | 3.91 | 0.00 | 0.00 | 0.00 |
| 1D5 | | | | | | | | | | | | | | |
| 1D6A | | | | | | | | | | | | | | |
| 1D6B | 0.00 | 94.01 | 3.78 | 3.35 | 20.58 | 0.00 | 0.00 | 0.00 | 99.78 | 0.97 | 4.90 | 9.07 | 0.00 | 0.00 |
| 1D7 | 0.32 | 71.01 | 1.72 | 9.50 | 10.11 | 8.15 | 0.00 | 0.00 | 91.17 | 0.79 | 0.00 | 0.00 | 0.00 | 0.00 |
| 1F1 | | | | | | | | | | | | | | |
| 1F2 | 0.00 | 93.27 | 2.26 | 9.81 | 13.28 | 3.46 | 0.00 | 0.00 | 97.35 | 0.86 | 7.88 | 0.00 | 0.00 | 0.00 |
| 2C2 | | | | | | | | | | | | | | |
| 2C3 | | | | | | | | | | | | | | |
| 2C3-1 | | | | | | | | | | | | | | |
| 2D1 | 0.00 | 87.16 | 3.37 | 13.05 | 7.62 | 8.79 | 0.00 | 0.00 | 94.28 | 0.97 | 7.76 | 3.41 | 0.00 | 0.00 |
| 2D2 | 36.65 | 6.32 | 1.44 | 20.88 | 18.39 | 31.93 | 0.00 | 0.00 | 105.91 | 0.78 | 1.92 | 4.11 | 0.00 | 0.00 |
| 2D3 | 0.00 | 92.36 | 3.38 | 9.53 | 9.71 | 3.33 | 0.00 | 0.00 | 98.14 | 0.88 | 4.40 | 9.11 | 0.00 | 0.00 |
| 2D3M | | | | | | | | | | | | | | |
| 2D10 | 0.00 | 72.74 | 1.67 | 14.47 | 13.49 | 15.14 | 0.00 | 0.00 | 92.86 | 0.00 | 2.68 | 0.00 | 0.00 | 0.00 |
| 2D11 | 40.99 | 5.72 | 1.58 | 16.65 | 11.33 | 22.48 | 0.00 | 0.00 | 101.16 | 0.67 | 2.08 | 3.27 | 0.00 | 0.00 |
| 2F1 | | | | | | | | | | | | | | |
| 2F2 | 43.39 | 22.98 | 0.98 | 10.97 | 0.00 | 3.88 | 0.00 | 0.00 | 96.75 | 0.72 | 2.30 | 3.73 | 0.00 | 0.00 |
| 2G1 | | | | | | | | | | | | | | |
| 2G2 | | | | | | | | | | | | | | |
| 2G3 | | | | | | | | | | | | | | |
| 2G4 | | | | | | | | | | | | | | |
| 3D1 | | | | | | | | | | | | | | |
| 3F1 | | | | | | | | | | | | | | |
| 3F2 | 0.00 | 85.14 | 3.41 | 9.88 | 10.03 | 6.15 | 0.00 | 0.00 | 99.37 | 1.03 | 8.39 | 0.00 | 0.00 | 0.00 |
| 4D1 | | | | | | | | | | | | | | |
| 4D2 | | | | | | | | | | | | | | |
| 4D3 | | | | | | | | | | | | | | |
| 4E2 | | | | | | | | | | | | | | |
| 4F1 | | | | | | | | | | | | | | |
| 4F2 | | | | | | | | | | | | | | |
| 5C3 | | | | | | | | | | | | | | |
| 5D1 | | | | | | | | | | | | | | |
| 5D2 | | | | | | | | | | | | | | |
| 5D3 | | | | | | | | | | | | | | |
| 5D10 | | | | | | | | | | | | | | |
| 5D12 | | | | | | | | | | | | | | |
| 5D13 | | | | | | | | | | | | | | |

TABLE 2-continued

Properties of all the Isolates

| Isolate | LB Glucose (1%), pH 4.5 O.D. 420 nm 24 hrs | LB Glucose (1%), pH 4.5 O.D. 420 nm 48 hrs | LB Glucose (1%), pH 4.5 pH 48 hrs | LB Xylose (1%), pH 4.5 O.D. 420 nm 24 hrs | LB Xylose (1%), pH 4.5 O.D. 420 nm 48 hrs | LB Xylose (1%), pH 4.5 pH 48 hrs |
|---|---|---|---|---|---|---|
| 5F1 | | | | | | |
| 5F2 | | | | | | |
| 5F3 | | | | | | |
| 5G2 | | | | | | |
| 6C1 | 0.00 | 85.58 | 2.12 | 12.06 | 17.51 | 3.53 |
| 6D1A | | | | | | |
| 6D1B | | | | | | |
| 6D2A | 0.77 | 96.49 | 4.11 | 1.37 | 13.41 | 0.00 |
| 6D6 | | | | | | |
| 6F1sm | | | | | | |
| 6F1g | 29.10 | 54.44 | 1.74 | 7.57 | 5.22 | 5.03 |
| 6F2 | 15.19 | 13.16 | 2.95 | 24.70 | 18.58 | 34.83 |

Anaerobic Growth

| Isolate | MS (0.1% YE) (Xylose 1%), pH 5 O.D. 420 nm 24 hrs | MS (0.1% YE) (Xylose 1%), pH 5 O.D. 420 nm 48 hrs | MS (0.1% YE) (Xylose 1%), pH 5 pH 48 hrs | MS (0.1% YE) (Glucose 1%), pH 5 O.D. 420 nm 24 hrs | MS (0.1% YE) (Glucose 1%), pH 5 O.D. 420 nm 48 hrs | MS (0.1% YE) (Glucose 1%), pH 5 pH 48 hrs | HCH 10% CSL 1%, pH 5 O.D. 420 nm 24 hrs | HCH 10% CSL 1%, pH 5 O.D. 420 nm 48 hrs | HCH 10% CSL 1%, pH 5 pH 48 hrs |
|---|---|---|---|---|---|---|---|---|---|
| 5F1 | | | | | | | | | |
| 5F2 | | | | | | | | | |
| 5F3 | | | | | | | | | |
| 5G2 | | | | | | | | | |
| 6C1 | | 0.00 | | 0.47 | | 2.95 | | 0.00 | |
| 6D1A | | | | | | | | | |
| 6D1B | | | | | | | | | |
| 6D2A | | 0.00 | 100.01 | 1.40 | 7.12 | 5.88 | | 0.00 | |
| 6D6 | | | 104.72 | | | | | | |
| 6F1sm | | | | | | | | | |
| 6F1g | | 0.00 | 106.10 | 0.63 | 2.66 | 3.28 | | 0.00 | |
| 6F2 | | 0.00 | 98.41 | 0.71 | 5.11 | 0.00 | | 0.00 | |
| 1C1 | 0.10 | 0.13 | 4.64 | 0.10 | 0.05 | 4.54 | 0.20 | 0.23 | 4.18 |
| 1C2 | 0.09 | 0.13 | 4.61 | 0.06 | 0.08 | 4.55 | 0.27 | 0.34 | 4.19 |
| 1C3 | 0.13 | 0.22 | 4.66 | 0.15 | 0.16 | 4.50 | 0.34 | 0.39 | 4.14 |
| 1C4 | 0.10 | 0.17 | 4.57 | 0.04 | 0.07 | 4.46 | 0.25 | 0.29 | 4.18 |
| 1D1 | 0.09 | 0.19 | 4.61 | 0.09 | 0.08 | 4.42 | 0.27 | 0.32 | 4.19 |
| 1D2 | 0.13 | 0.17 | 4.70 | 0.17 | 0.06 | 4.56 | 0.12 | 0.19 | 4.19 |
| 1D5 | 0.11 | 0.17 | 4.59 | 0.06 | 0.08 | 4.60 | 0.24 | 0.36 | 4.16 |
| 1D6A | 0.11 | 0.14 | 4.56 | 0.08 | 0.05 | 4.47 | 0.29 | 0.45 | 4.17 |
| 1D6B | 0.22 | 0.12 | 4.62 | 0.12 | 0.13 | 4.50 | 0.17 | 0.24 | 4.19 |
| 1D7 | 0.06 | 0.29 | 4.48 | 0.07 | 0.05 | | 0.14 | 0.17 | 4.19 |
| 1F1 | 0.17 | 0.06 | 4.53 | 0.17 | 0.13 | | 0.30 | 0.26 | 4.48 |
| 1F2 | | 0.24 | | | | | | | 4.17 |
| 2C2 | | | | | | | | | |
| 2C3 | | | | | | | | | |
| 2C3-1 | | | | | | | | | |
| 2D1 | 0.16 | 0.20 | 4.69 | 0.10 | 0.06 | 4.48 | 0.32 | 0.33 | 4.29 |
| 2D2 | 0.23 | 0.30 | 4.77 | 0.08 | 0.09 | 4.54 | 0.31 | 0.25 | 4.21 |
| 2D3 | 0.13 | 0.08 | 4.58 | 0.09 | 0.07 | 4.51 | 0.20 | 0.15 | 4.17 |
| 2D3M | 0.15 | 0.13 | 4.72 | 0.07 | 0.05 | 4.61 | 0.19 | 0.18 | 4.24 |
| 2D10 | 0.00 | 0.00 | 5.07 | 0.07 | 0.09 | 4.58 | 0.34 | 0.25 | 4.19 |
| 2D11 | 0.12 | 0.26 | 4.80 | 0.11 | 0.05 | 4.53 | 0.28 | 0.26 | 4.22 |
| 2F1 | | | | | | | | | |
| 2F2 | 0.09 | 0.11 | 4.56 | 0.06 | 0.03 | 4.48 | 0.14 | 0.09 | 4.21 |
| 2G1 | | | | | | | | | |
| 2G2 | 0.05 | 0.10 | 4.60 | 0.01 | 0.03 | 4.61 | 0.01 | 0.19 | 4.32 |
| 2G3 | | | | | | | | | |
| 2G4 | | | | | | | | | |
| 3D1 | 0.13 | 0.18 | 4.74 | 0.09 | 0.12 | 4.74 | 0.02 | 0.00 | 4.42 |

TABLE 2-continued

Properties of all the Isolates

| Isolate | 0% Ethanol O.D. 420 nm 24 hrs | 0% Ethanol O.D. 420 nm 48 hrs | LB (Glucose 1%, pH 6.8) 4% Ethanol(w/w) O.D. 420 nm 24 hrs | 48 hrs | 5% Ethanol(w/w) O.D. 420 nm 24 hrs | 48 hrs | LB (Glucose 1%, pH 5.0) 0% Ethanol O.D. 420 nm 24 hrs | 48 hrs | 4% Ethanol(w/w) O.D. 420 nm 24 hrs | 48 hrs | 5% Ethanol(w/w) O.D. 420 nm 24 hrs | 48 hrs | 20% HCH 0.1% YE/Glu pH 5.0(V) plates (48 hrs) | 25% HCH 0.1% YE/Glu pH 5.0(V) plates (48 hrs) | 50% HCH overlimed 0.1% YE/Glu pH 5.0(V) plates (48 hrs) |
|---|---|---|---|---|---|---|---|---|---|---|---|---|---|---|---|
| 3F1 | | 0.09 | 0.25 | | | 0.08 | 4.29 | 0.14 | 4.53 | 0.17 | 4.52 | 0.10 | 4.21 | 0.22 | |
| 3F2 | | 0.14 | 0.15 | | | 0.12 | 4.32 | 0.10 | 4.27 | 0.11 | 4.45 | 0.12 | 4.21 | 0.14 | |
| 4D1 | | | | | | | | | | | | | | | |
| 4D2 | | 0.03 | 0.13 | 0.02 | | 0.10 | 4.43 | 0.11 | 4.62 | 0.18 | 4.56 | 0.04 | 4.27 | 0.05 | |
| 4D3 | | 0.04 | 0.11 | 0.01 | | 0.14 | 4.42 | 0.14 | 4.53 | 0.16 | 4.48 | 0.09 | 4.43 | 0.17 | |
| 4E2 | | | | | | | | | | | | | | | |
| 4f1 | | | | | | | | | | | | | | | |
| 4F2 | | | | | | | | | | | | | | | |
| 5C3 | | | | | | | | | | | | | | | |
| 5D1 | | 0.01 | 0.00 | 0.01 | | 0.02 | 4.53 | 0.10 | 4.64 | 0.11 | 4.79 | 0.01 | 4.36 | 0.01 | |
| 5D2 | | 0.01 | 0.14 | 0.12 | | 0.14 | 4.34 | 0.12 | 4.62 | 0.17 | 4.26 | 0.05 | 4.55 | 0.11 | |
| 5D3 | | 0.01 | 0.00 | 0.01 | | 0.01 | 4.53 | 0.05 | 4.56 | 0.11 | 4.56 | 0.02 | 4.49 | 0.00 | |
| 5D10 | | 0.01 | 0.01 | 0.01 | | 0.01 | 4.53 | 0.12 | 4.52 | 0.19 | 4.27 | 0.09 | 4.55 | 0.12 | |
| 5D12 | | | | | | | | | | | | | | | |
| 5D13 | | | | | | | | | | | | | | | |
| 5F1 | | | | | | | | | | | | | | | |
| 5F2 | | | | | | | | | | | | | | | |
| 5F3 | | 0.00 | 0.11 | 0.01 | | 0.11 | 4.32 | 0.12 | 4.53 | 0.19 | 4.26 | 0.05 | 4.57 | 0.24 | |
| 5G2 | | 0.00 | 0.08 | 0.11 | | 0.11 | 4.52 | 0.08 | 4.60 | 0.15 | 4.24 | 0.01 | 4.57 | 0.12 | |
| 6C1 | | 0.02 | 0.03 | 0.04 | | 0.04 | 4.47 | 0.20 | 4.48 | 0.20 | 4.43 | 0.05 | 4.10 | 0.10 | |
| 6D1A | | | | | | | | | | | | | | | |
| 6D1B | | | | | | | | | | | | | | | |
| 6D2A | | | | | | | | | | | | | | | |
| 6D6 | | 0.12 | 0.16 | 0.14 | | 0.21 | 4.38 | 0.13 | 4.44 | 0.15 | 4.59 | 0.29 | 4.72 | 0.15 | |
| 6F1sm | | 0.11 | 0.19 | 0.15 | | 0.18 | 4.38 | 0.12 | 4.49 | 0.17 | 4.53 | + | 4.13 | 0.02 | |
| 6F1lg | | 0.07 | 0.15 | 0.11 | | 0.15 | 4.41 | 0.10 | 4.57 | 0.15 | 4.55 | + | 4.21 | 0.01 | |
| 6F2 | | 0.11 | 0.15 | 0.15 | | 0.22 | 4.44 | 0.15 | 4.57 | 0.20 | 4.47 | 0.04 | 4.12 | 0.07 | |

| Isolate | 0% Ethanol O.D. 420 nm 24 hrs | 48 hrs | LB (Glucose 1%, pH 5.0) 4% Ethanol(w/w) O.D. 420 nm 24 hrs | 48 hrs | 4.5% Ethanol(w/w) O.D. 420 nm 24 hrs | 48 hrs | 5% Ethanol(w/w) O.D. 420 nm 24 hrs | 48 hrs | 20% HCH 0.1% YE/Glu pH 5.0(V) plates (48 hrs) | 25% HCH 0.1% YE/Glu pH 5.0(V) plates (48 hrs) | 50% HCH overlimed 0.1% YE/Glu pH 5.0(V) plates (48 hrs) |
|---|---|---|---|---|---|---|---|---|---|---|---|
| 1C1 | | | | | | | | | +++ | + | − |
| 1C2 | 0.85 | 0.90 | 0.03 | 0.06 | 0.05 | 0.06 | 0.03 | 0.03 | − | − | − |
| 1C3 | | | 0.02 | 0.16 | 0.15 | 0.17 | 0.02 | 0.02 | +++ | + | + |
| 1C4 | | | 0.09 | 0.27 | 0.17 | 0.16 | 0.09 | 0.15 | +++ | + | − |
| 1D1 | | | | | | | | | +++ | + | − |
| 1D2 | 0.75 | 0.90 | 0.04 | 0.11 | 0.08 | 0.08 | 0.07 | 0.12 | +++ | + | − |
| 1D5 | | | 0.04 | 0.02 | 0.05 | 0.07 | 0.04 | 0.03 | +++ | + | − |
| 1D6A | | | | | | | | | +++ | + | + |
| 1D6B | | | | | | | | | +++ | − | − |
| 1D7 | | | | | | | | | +++ | + | − |
| 1F1 | 1.00 | 1.15 | 0.04 | 0.16 | 0.11 | 0.11 | 0.09 | 0.08 | − | − | − |
| 1F2 | | | | | | | | | +++ | + | − |
| 2C2 | | | | | | | | | − | − | − |
| 2C3 | | | | | | | | | − | − | − |

TABLE 2-continued

Properties of all the Isolates

| Isolate | C1 | C2 | C3 | C4 | C5 | C6 | C7 | C8 | C9 | C10 | C11 | C12 | C13 | C14 | S1 | S2 | S3 |
|---|---|---|---|---|---|---|---|---|---|---|---|---|---|---|---|---|---|
| 2C3-1 | 0.95 | | | | | | | | | | | | | | – | – | – |
| 2D1 | | | | | | | 0.54 | 0.58 | 0.25 | 0.24 | 0.07 | 0.07 | 0.07 | 0.07 | – | + | – |
| 2D2 | | | | | | | 0.41 | 0.58 | 0.22 | 0.23 | 0.12 | 0.13 | 0.13 | 0.14 | +++ | + | – |
| 2D3 | | | | | | | 0.51 | 0.44 | 0.13 | 0.19 | 0.10 | 0.13 | 0.07 | 0.07 | +++ | + | – |
| 2D3M | | | | | | | | | | | | | | | +++ | + | – |
| 2D10 | | | | | | | | | | | | | | | ++ | + | + |
| 2D11 | | | | | | | | | | | | | | | ++ | ++ | + |
| 2F1 | | | | | | | | | | | | | | | – | – | – |
| 2F2 | | | | | | | | | | | | | | | + | + | – |
| 2G1 | | | | | | | | | | | | | | | – | – | – |
| 2G2 | | | | | | | | | | | | | | | – | – | – |
| 2G3 | | | | | | | | | | | | | | | – | – | – |
| 2G4 | | | | | | | | | | | | | | | – | – | – |
| 3D1 | | | | | | | | | | | | | | | + | – | – |
| 3F1 | 0.95 | 1.10 | | | | | | | | | | | | | + | + | – |
| 3F2 | | | | | | | 0.58 | 0.66 | 0.30 | 0.34 | 0.02 | 0.11 | 0.01 | 0.01 | – | – | – |
| 4D1 | | | | | | | | | | | | | | | ++ | + | – |
| 4D2 | | | | | | | | | | | | | | | +++ | + | – |
| 4D3 | | | | | | | | | | | | | | | ++ | – | – |
| 4E2 | | | | | | | | | | | | | | | +++ | ++ | + |
| 4F1 | | | | | | | | | | | | | | | – | – | – |
| 4F2 | | | | | | | | | | | | | | | – | + | – |
| 5C3 | | | | | | | | | | | | | | | + | – | – |
| 5D1 | | | | | | | | | | | | | | | – | – | – |
| 5D2 | | | | | | | | | | | | | | | ++ | – | – |
| 5D3 | | | | | | | | | | | | | | | +++ | – | – |
| 5D10 | | | | | | | | | | | | | | | – | – | – |
| 5D12 | | | | | | | | | | | | | | | +++ | – | – |
| 5D13 | | | | | | | | | | | | | | | +++ | + | – |
| 5F1 | | | | | | | | | | | | | | | – | + | – |
| 5F2 | | | | | | | | | | | | | | | – | – | – |
| 5F3 | | | | | | | | | | | | | | | + | + | – |
| 5G2 | 0.95 | | 0.14 | 0.46 | 0.04 | 0.05 | 0.04 | | | 0.14 | 0.07 | 0.07 | 0.09 | 0.08 | + | + | – |
| 6C1 | 0.95 | | 0.14 | 0.46 | 0.04 | 0.05 | 0.04 | 0.47 | 0.49 | 0.14 | 0.14 | 0.07 | 0.07 | 0.09 | 0.08 | + | + | – |
| 6D1A | 0.95 | | 0.39 | 0.41 | 0.09 | 0.38 | 0.08 | 0.07 | 0.45 | 0.50 | 0.11 | 0.11 | 0.03 | 0.03 | 0.03 | ++ | ++ | + |
| 6D1B | 0.75 | | 0.55 | 0.56 | 0.08 | 0.06 | 0.08 | 0.08 | 0.50 | 0.55 | 0.24 | 0.26 | 0.11 | 0.11 | 0.08 | ++ | + | – |
| 6D2A | 0.80 | 1.05 | 0.05 | 0.04 | 0.04 | 0.05 | 0.03 | 0.50 | 0.55 | 0.04 | 0.06 | 0.02 | 0.02 | 0.01 | 0.00 | – | – | – |
| 6D6 | | | | | | | | | | | | | | | – | – | – |
| 6F1sm | | | | | | | | | | | | | | | ++ | – | – |
| 6F1lg | | | | | | | | | | | | | | | ++ | + | – |
| 6F2 | | | | | | | | | | | | | | | + | – | – |

TABLE 2-continued

Properties of all the Isolates

| | Aerobic (pH 5.0) | | | | | | | | | | | | Antibiotic Sensitivity | | | |
|---|---|---|---|---|---|---|---|---|---|---|---|---|---|---|---|---|
| | 25% HCH (0.1% YE) | | | 10% HCH (1% CSL) | | | 25% Overlimed HCH | | | 50% Overlimed HCH (0.1% YE) | | | | | | |
| | CFU/ml | | pH | CFU/ml | | pH | CFU/ml | | pH | CFU/ml | | pH | Tetracycline | Chloramphenicol | Kanamycin | Ampicillin |
| Isolate | 24 hrs | 48 hrs | 48 hrs | 24 hrs | 48 hrs | 48 hrs | 24 hrs | 48 hrs | 48 hrs | 24 hrs | 48 hrs | 48 hrs | 20 mg/L | 30 mg/L | 50 mg/L | 100 mg/L |
| 1C1 | | | | | | | | | | | | | | | | |
| 1C2 | | | | | | | | | | | | | | | | |
| 1C3 | | | | | | | | | | | | | | | | |
| 1C4 | | | | | | | | | | | | | + | | | |
| 1D1 | | | | | | | | | | | | | − | − | − | − |
| 1D2 | | | | | | | | | | | | | − | − | − | − |
| 1D5 | | | | | | | | | | | | | | | | |
| 1D6A | | | | | | | | | | | | | | | | |
| 1D6B | | | | | | | | | | | | | | | | |
| 1D7 | | | | | | | | | | | | | | | | |
| 1F1 | | | | | | | | | | | | | | | | |
| 1F2 | | | | | | | | | | | | | | | | |
| 2C2 | | | | | | | | | | | | | | | | |
| 2C3 | | | | | | | | | | | | | | | | |
| 2C3-1 | | | | | | | | | | | | | | | | |
| 2D1 | | | | | | | | | | | | | | | | |
| 2D2 | | | | | | | | | | | | | | | | |
| 2D3 | | | | | | | | | | | | | | | | |
| 2D3M | | | | | | | | | | | | | | | | |
| 2D10 | | | | | | | | | | | | | | | | |
| 2D11 | | | | | | | | | | | | | | | | |
| 2F1 | | | | | | | | | | | | | | | | |
| 2F2 | | | | | | | | | | | | | | | | |
| 2G1 | | | | | | | | | | | | | | | | |
| 2G2 | | | | | | | | | | | | | | | | |
| 2G3 | | | | | | | | | | | | | | | | |
| 2G4 | | | | | | | | | | | | | | | | |
| 3D1 | | | | | | | | | | | | | | | | |
| 3F1 | | | | | | | | | | | | | | | | |
| 3F2 | | | | | | | | | | | | | | | | |
| 4D1 | | | | | | | | | | | | | | | | |
| 4D2 | | | | | | | | | | | | | | | | |
| 4D3 | | | | | | | | | | | | | | | | |
| 4E2 | $4 \times 10^3$ | − | 4.46 | $1 \times 10^7$ | $2 \times 10^4$ | 4.39 | $5 \times 10^4$ | − | 4.52 | $2 \times 10^5$ | $10^5$ | 4.77 | | | | |
| 4F1 | | | | | | | | | | | | | | | | |
| 4F2 | | | | | | | | | | | | | | | | |
| 5C3 | | | | | | | | | | | | | | | | |
| 5D1 | | | | | | | | | | | | | | | | |
| 5D2 | | | | | | | | | | | | | | | | |
| 5D3 | | | | | | | | | | | | | | | | |
| 5D10 | | | | | | | | | | | | | | | | |
| 5D12 | | | | | | | | | | | | | | | | |

TABLE 2-continued

Properties of all the Isolates

| Isolate | Identification[a] (16S rRNA) | Xylanase 72 hr | CMCase 72 hr | Cellobiose MS (0.1% YE) pH 5.0 72 hr | Growth at pH 5.0 | | | | | | | | | | | | |
|---|---|---|---|---|---|---|---|---|---|---|---|---|---|---|---|---|
| | | | | | LB Xylose (1%) | | | | | | LB Glucose (1%) | | | | | |
| | | | | | Anaerobic | | | Aerobic | | | Anaerobic | | | Aerobic | | |
| | | | | | O.D. 420 nm | | pH | O.D. 420 nm | | pH | O.D. 420 nm | | pH | O.D. 420 nm | | pH |
| | | | | | 24 hrs | 48 hrs | 48 hrs | 24 hrs | 48 hrs | 48 hrs | 24 hrs | 48 hrs | 48 hrs | 24 hrs | 48 hrs | 48 hrs |
| 5D13 | 3 × 10⁵ | − | 4.34 | | | | | | | | | | | | | | |
| 5F1 | | | | | | | | | | | | | | | | | |
| 5F2 | | | | | | | | | | | | | | | | | |
| 5F3 | | | | | | | | | | | | | | | | | |
| 5G2 | | | | | | | | | | | | | | | | | |
| 6C1 | 2 × 10⁶ | − | | 3 × 10⁶ | | | | | | | | | | | | | |
| 6D1A | | | | | | | | | | | | | | | | | |
| 6D1B | | | | | | | | | | | | | | | | | |
| 6D2A | | | | | | | | | | | | | | | | | |
| 6D6 | 4.74 | | | 3 × 10³ | 4.70 | | | 2 × 10⁵ | | | 4 × 10³ | 3 × 10⁵ | 4.73 | + | | | |
| 6F1sm | | | | | | | | | | | | | | − | − | − | − |
| 6F1lg | | | | | | | | | | | | | | − | − | − | − |
| 6F2 | | | | | | | | | | | | | | − | − | − | − |
| 6F3A | | − | − | | 0.11 | 0.21 | 4.59 | 0.70 | 0.70 | 4.26 | 0.21 | 0.22 | 4.55 | 0.83 | 0.95 | 4.54 |
| 6F3B | | − | − | | 0.09 | 0.11 | 4.44 | 0.29 | 0.42 | 4.51 | 0.20 | 0.21 | 4.51 | 1.73 | 1.80 | 4.21 |
| 6H1A | | − | − | | 0.08 | 0.14 | 4.99 | 0.70 | 1.05 | 5.66 | 0.15 | 0.20 | 4.96 | 0.55 | 1.00 | 5.34 |
| 6H1B | | − | − | | 0.33 | 0.36 | 4.23 | 2.00 | 2.00 | 4.26 | 0.40 | 0.45 | 4.33 | 1.40 | 1.43 | 4.17 |
| 6H2 | B. coagulans | − | + | + | 0.31 | 0.37 | 4.20 | 1.50 | 1.45 | 4.35 | 0.38 | 0.40 | 4.35 | 1.78 | 1.73 | 4.37 |
| 6H3 | | − | − | − | 0.07 | 0.40 | 4.48 | 0.35 | 1.33 | 4.27 | 0.20 | 0.21 | 4.56 | 0.95 | 0.82 | 4.50 |
| 7C1 | | − | − | + | 0.05 | 0.10 | 4.99 | 0.70 | 1.09 | 5.65 | 0.08 | 0.10 | 4.72 | 1.70 | 1.05 | 5.15 |
| 7C2 | | − | − | + | 0.02 | 0.05 | 5.16 | 0.72 | 0.55 | 5.94 | 0.06 | 0.07 | 5.14 | 0.65 | 0.98 | 5.57 |
| 7C4 | | − | − | + | 0.41 | 0.50 | 4.31 | 2.48 | 2.50 | 4.53 | 0.04 | 0.60 | 4.39 | 3.00 | 3.00 | 4.30 |
| 7C5 | | − | − | + | 0.10 | 0.15 | 4.58 | 0.80 | 1.09 | 4.45 | 0.10 | 0.20 | 4.69 | 1.20 | 1.24 | 4.50 |
| 7C6 | | − | − | + | 0.00 | 0.00 | 5.04 | 0.00 | 0.00 | 5.04 | 0.00 | 0.00 | 5.06 | 0.00 | 0.00 | 5.06 |
| 7C8 | B. coagulans | − | − | + | 0.49 | 0.50 | 4.28 | 2.30 | 2.18 | 4.52 | 0.08 | 0.65 | 4.40 | 2.15 | 1.87 | 4.40 |
| 7D1 | | − | − | + | 0.05 | 0.10 | 5.07 | 0.55 | 0.78 | 5.95 | 0.08 | 0.16 | 5.07 | 0.80 | 1.10 | 5.60 |
| 7D3 | | − | − | + | 0.35 | 0.30 | 4.46 | 1.92 | 2.10 | 4.44 | 0.35 | 0.55 | 4.47 | 1.40 | 2.14 | 4.46 |
| 7D4 | B. coagulans | − | − | + | 0.48 | 0.45 | 4.34 | 1.90 | 1.75 | 4.38 | 0.52 | 0.70 | 4.43 | 1.85 | 1.73 | 4.31 |
| 7E1 | | − | − | + | 0.08 | 0.15 | 4.41 | 1.10 | 1.01 | 4.43 | 0.25 | 0.27 | 4.48 | 0.90 | 1.48 | 4.63 |
| 7F1-smooth | B. coagulans | − | − | + | 0.27 | 0.26 | 4.34 | 1.63 | 1.80 | 4.32 | 0.35 | 0.40 | 4.36 | 1.50 | 1.43 | 4.36 |
| 7F1-rough | | − | − | | 0.25 | 0.23 | 4.35 | 1.53 | 1.65 | 4.37 | 0.34 | 0.37 | 4.39 | 1.35 | 1.40 | 4.41 |
| 7F2 | | − | − | + | 0.06 | 0.10 | 4.85 | 0.73 | 1.42 | 5.37 | 0.60 | 0.88 | 4.31 | 2.20 | 3.02 | 4.27 |
| 7G1 | B. coagulans | − | − | + | 0.42 | 0.50 | 4.29 | 2.55 | 2.15 | 4.39 | 0.40 | 0.56 | 4.39 | 2.10 | 2.93 | 4.34 |
| 7G2 | | − | − | − | 0.06 | 0.12 | 5.07 | 0.62 | 1.18 | 5.86 | 0.11 | 0.19 | 5.06 | 0.80 | 1.15 | 5.75 |
| 7G3 | | − | − | + | 0.03 | 0.07 | 5.07 | 0.51 | 0.99 | 5.78 | 0.04 | 0.13 | 5.07 | 2.75 | 2.58 | 6.69 |
| 7G4 | | − | − | + | 0.24 | 0.33 | 4.33 | 2.09 | 3.15 | 4.52 | 0.35 | 0.60 | 4.40 | 1.80 | 1.43 | 4.32 |
| 8D1 | | − | − | + | 0.16 | 0.19 | 4.47 | 1.31 | 1.45 | 4.55 | 0.25 | 0.30 | 4.35 | 0.31 | 0.31 | 4.49 |
| 8D2 | | − | − | + | 0.25 | 0.29 | 4.31 | 1.78 | 1.95 | 4.55 | 0.40 | 0.60 | 4.30 | 1.93 | 1.74 | 4.34 |

TABLE 2-continued

Properties of all the Isolates

| Isolate | 24 hrs | 48 hrs | | | 24 hrs | 48 hrs | | |
|---|---|---|---|---|---|---|---|---|
| 8D3 | 0.04 | 0.11 | 5.09 | 0.41 | 0.95 | 5.82 | 0.10 | 0.18 | 5.05 | 0.85 | 1.22 | 5.64 |

| Isolate | | | | | | | | | | | | |
|---|---|---|---|---|---|---|---|---|---|---|---|---|
| 8D3 | − | 0.04 | 0.11 | 5.09 | 0.41 | 0.95 | 5.82 | 0.10 | 0.18 | 5.05 | 0.85 | 1.22 | 5.64 |
| 8F1 | + | 0.35 | 0.37 | 4.36 | 1.08 | 2.20 | 4.46 | 0.80 | 0.80 | 4.18 | 3.98 | 2.90 | 4.39 |
| 8F2 | + | 0.05 | 0.10 | 4.84 | 0.68 | 0.72 | 5.99 | 0.50 | 0.50 | 4.28 | 1.52 | 1.69 | 4.30 |
| 8F3 | + | 0.25 | 0.31 | 4.43 | 0.49 | 1.60 | 4.25 | 0.35 | 0.35 | 4.33 | 0.55 | 1.25 | 4.47 |
| 9D1 | + | 0.17 | 0.17 | 4.54 | 1.12 | 0.78 | 4.39 | 0.40 | 0.35 | 4.41 | 0.48 | 0.41 | 4.60 |
| 9D2 | + | 0.09 | 0.10 | 4.48 | 1.60 | 2.15 | 4.58 | 0.35 | 0.40 | 4.41 | 0.85 | 0.88 | 4.59 |
| 10D1 | + | 0.10 | 0.14 | 4.58 | 0.85 | 0.78 | 4.42 | 0.20 | 0.16 | 4.56 | 0.60 | 0.64 | 4.53 |
| 10D2 | + | 0.06 | 0.13 | 4.55 | 0.90 | 0.88 | 4.59 | 0.35 | 0.35 | 4.51 | 0.89 | 0.83 | 4.53 |
| 11D1 | + | 0.15 | 0.09 | 4.53 | 0.85 | 0.80 | 4.35 | 0.35 | 0.22 | 4.47 | 0.87 | 0.83 | 4.41 |
| 11D2 | + | 0.09 | 0.13 | 4.54 | 0.90 | 1.00 | 4.58 | 0.30 | 0.35 | 4.47 | 1.10 | 0.93 | 4.50 |
| 11E1 | + | 0.26 | 0.29 | 4.31 | 2.50 | 2.55 | 4.46 | 0.40 | 0.70 | 4.36 | 2.13 | 0.76 | 4.28 |
| 11F2 | − | 0.05 | 0.09 | 4.66 | 0.60 | 0.87 | 4.61 | 0.10 | 0.40 | 4.56 | 0.78 | 2.40 | 4.55 |
| 12F2 | + | 0.12 | 0.13 | 4.61 | 1.05 | 1.61 | 4.48 | 0.40 | 0.50 | 4.45 | 1.53 | 0.84 | 4.46 |
| 13D1 | + | 0.27 | 0.31 | 4.30 | 1.92 | 2.60 | 4.50 | 0.50 | 0.65 | 4.32 | 1.90 | 2.20 | 4.40 |
| 13E1sm | + | 0.32 | 0.31 | 4.24 | 1.53 | 1.65 | 4.37 | 0.40 | 0.45 | 4.22 | 1.60 | 2.20 | 4.24 |
| 13E1L *B. coagulans* | + | 0.34 | 0.36 | 4.24 | 1.98 | 1.90 | 4.15 | 0.53 | 0.58 | 4.17 | 0.95 | 1.53 | 4.30 |
| 14D1 | + | 0.15 | 0.12 | 4.60 | 0.62 | 0.60 | 4.54 | 0.16 | 0.17 | 4.62 | 0.33 | 1.00 | 4.59 |
| 14D2 | + | 0.07 | 0.12 | 4.55 | 0.98 | 1.82 | 4.49 | 0.30 | 0.35 | 4.41 | 1.44 | 1.17 | 4.47 |
| 14D3 | + | 0.09 | 0.11 | 4.98 | 0.53 | 0.72 | 5.63 | 0.10 | 0.14 | 4.95 | 0.70 | 0.94 | 5.08 |
| 14D4 | + | 0.09 | 0.08 | 4.72 | 0.97 | 1.08 | 4.58 | 0.40 | 0.30 | 4.17 | 1.00 | 1.43 | 4.48 |
| 14E1 | + | 0.06 | 0.16 | 5.01 | 1.32 | 1.68 | 6.85 | 0.06 | 0.08 | 4.96 | 0.63 | 0.98 | 4.93 |
| 14E2 | + | 0.30 | 0.32 | 4.33 | 1.30 | 3.05 | 4.49 | 0.50 | 0.60 | 4.36 | 2.10 | 1.90 | 4.28 |
| 14F1 | + | 0.06 | 0.19 | 5.05 | 0.48 | 0.99 | 5.87 | 0.08 | 0.09 | 4.96 | 0.38 | 0.31 | 5.08 |
| 14F2 | + | 0.07 | 0.15 | 4.99 | 0.68 | 1.50 | 6.08 | 0.08 | 0.10 | 4.93 | 0.44 | 0.83 | 5.11 |
| 15E1 | + | 0.09 | 0.08 | 5.07 | 0.35 | 1.90 | 6.72 | 0.09 | 0.15 | 5.04 | 0.52 | 1.08 | 5.92 |
| 15E2 | + | 0.09 | 0.09 | 5.08 | 0.38 | 0.82 | 5.75 | 0.07 | 0.13 | 5.08 | 0.38 | 0.39 | 5.59 |
| 16C1 | + | 0.06 | 0.09 | 5.08 | 0.62 | 1.91 | 6.28 | 0.14 | 0.27 | 5.12 | 1.58 | 1.28 | 6.29 |
| 16C2 | + | 0.31 | 0.40 | 4.32 | 1.28 | 1.60 | 4.35 | 0.30 | 0.40 | 4.36 | 1.98 | 2.00 | 4.35 |
| 16C3 | + | 0.03 | 0.04 | 5.08 | 0.60 | 1.89 | 6.88 | 0.13 | 0.16 | 5.08 | 0.41 | 0.63 | 5.67 |
| 17C1 | + | 0.07 | 0.06 | 5.06 | 0.62 | 1.00 | 5.83 | 0.08 | 0.14 | 5.07 | 0.42 | 0.93 | 5.92 |

Stationary Phase Survival

| Isolate | LB (Glucose 1%) O.D. 420 nm | | pH | CFU/ml | | Growth at pH 6.8 LB Xylose (1%) Anaerobic O.D. 420 nm | | pH | Aerobic O.D. 420 nm | | pH | LB Glucose (1%) Anaerobic O.D. 420 nm | | pH | Aerobic O.D. 420 nm | | pH |
|---|---|---|---|---|---|---|---|---|---|---|---|---|---|---|---|---|---|
| | 24 hrs | 48 hrs | 48 hrs | 24 hrs | 48 hrs | 24 hrs | 48 hrs | 48 hrs | 24 hrs | 48 hrs | 48 hrs | 24 hrs | 48 hrs | 48 hrs | 24 hrs | 48 hrs | 48 hrs |
| 6F3A | | | | | | | | | | | | 0.02 | 0.04 | 6.36 | 0.03 | 0.04 | 6.62 |
| 6F3B | 0.68 | 1.70 | 5.53 | 2 × 10⁴ | nd | 0.08 | 0.50 | 5.53 | 0.50 | 0.90 | 4.52 | 0.70 | 0.85 | 4.33 | 1.60 | 2.65 | 4.23 |
| 6H1A | 1.43 | 1.48 | 4.17 | <10⁴ | nd | 0.13 | 0.13 | 6.17 | 1.23 | 1.35 | 4.40 | 0.11 | 0.12 | 6.41 | 0.95 | 1.33 | 5.96 |
| 6H1B | 1.40 | 1.25 | 4.08 | <10⁴ | nd | 0.85 | 0.83 | 4.28 | 0.73 | 0.93 | 6.10 | 1.10 | 1.20 | 4.29 | 2.03 | 1.93 | 4.43 |
| 6H2 | | | | | | 0.65 | 0.83 | 4.32 | 2.10 | 2.15 | 4.31 | 0.90 | 1.03 | 4.32 | 1.85 | 2.00 | 4.80 |
| 6H3 | | | | | | 0.01 | 0.01 | 6.52 | 1.85 | 4.00 | 4.36 | 0.01 | 0.00 | 6.75. | 0.01 | 1.75 | 4.56 |
| 7C1 | 2.00 | 2.30 | 4.31 | 1.1 × 10⁶ | nd | 0.08 | 0.12 | 6.54 | 0.50 | 2.00 | 4.34 | 0.06 | 0.10 | 6.49 | 0.70 | 1.40 | 5.99 |
| 7C2 | | | | | | 0.13 | 0.19 | 6.53 | 0.75 | 1.18 | 6.39 | 0.23 | 0.23 | 5.39 | 1.50 | 1.85 | 5.65 |
| 7C4 | | | | | | 0.03 | 0.80 | 4.38 | 0.14 | 1.95 | 4.44 | 0.03 | 1.09 | 4.31 | 0.08 | 2.45 | 4.32 |

TABLE 2-continued

Properties of all the Isolates

| | | | | | | | | | | | | |
|---|---|---|---|---|---|---|---|---|---|---|---|---|
| 7C5 | | | | 0.04 | 0.04 | 6.53 | 0.06 | 0.68 | 5.76 | 0.00 | 0.05 | 6.56 | 0.45 | 1.40 | 4.47 |
| 7C6 | | | | 0.02 | 0.00 | 6.53 | 0.00 | 0.02 | 6.65 | 0.31 | 0.35 | 4.80 | 0.07 | 0.03 | 5.80 |
| 7C8 | 1.65 | 1.80 | 4.30 | 1 × 10⁵ | 0.29 | 2.10 | 4.31 | 0.80 | 1.75 | 4.43 | 0.08 | 1.23 | 4.45 | 1.30 | 3.50 | 4.32 |
| 7D1 | | | | 0.11 | 0.17 | 6.54 | 0.90 | 0.91 | 6.35 | 0.08 | 0.10 | 6.56 | 0.75 | 1.15 | 6.15 |
| 7D3 | | | | 0.79 | 0.95 | 4.52 | 1.70 | 2.30 | 4.33 | 0.83 | 1.14 | 4.48 | 1.70 | 1.75 | 4.59 |
| 7D4 | 1.43 | 1.40 | 4.31 | <10⁴ | 0.83 | 0.95 | 4.41 | 1.90 | 1.28 | 4.76 | 0.74 | 1.37 | 4.32 | 1.80 | 2.40 | 4.18 |
| 7E1 | | | | 0.03 | 0.50 | 4.60 | 0.01 | 0.02 | 6.63 | 0.84 | 0.72 | 4.43 | 0.00 | 0.98 | 4.45 |
| 7F1-smooth | 1.30 | 1.50 | 4.34 | 2.7 × 10⁶ | 0.83 | 0.85 | 4.47 | 2.05 | 2.05 | 6.40 | 0.80 | 1.05 | 4.36 | 1.90 | 2.08 | 4.38 |
| 7F1-rough | 1.25 | 1.20 | 4.39 | <10⁴ | 0.80 | 0.78 | 4.46 | 1.65 | 2.45 | 4.46 | 0.85 | 0.90 | 4.47 | 1.73 | 1.88 | 4.47 |
| 7F2 | | | | 0.10 | 0.15 | 5.64 | 2.40 | 3.14 | 7.20 | 1.10 | 1.44 | 4.27 | 2.20 | 3.20 | 4.18 |
| 7G1 | 1.80 | 1.65 | 4.16 | <10⁴ | 0.73 | 0.90 | 4.38 | 1.90 | 2.14 | 4.36 | 0.73 | 0.95 | 4.42 | 1.40 | 1.60 | 4.46 |
| 7G2 | | | | 0.05 | 0.10 | 6.46 | 0.95 | 1.35 | 5.78 | 0.04 | 0.06 | 6.50 | 0.70 | 1.05 | 6.24 |
| 7G3 | | | | 0.01 | 0.07 | 6.43 | 0.75 | 0.80 | 6.23 | 0.08 | 0.11 | 6.58 | 0.70 | 0.80 | 6.23 |
| 7G4 | | | | 0.35 | 0.38 | 4.25 | 2.50 | 2.60 | 4.44 | 0.61 | 0.73 | 4.41 | 2.60 | 2.80 | 4.46 |
| 8D1 | | | | 0.32 | 0.36 | 4.33 | 0.00 | 2.00 | 4.53 | 0.16 | 0.38 | 4.42 | 0.10 | 1.30 | 4.42 |
| 8D2 | | | | 0.38 | 0.47 | 4.27 | 3.50 | 4.80 | 4.38 | 0.63 | 0.70 | 4.35 | 2.40 | 2.80 | 4.47 |
| 8D3 | | | | 0.03 | 0.07 | 6.44 | 0.70 | 0.90 | 6.22 | 0.03 | 0.06 | 6.49 | 0.40 | 0.80 | 6.27 |
| 8F1 | | | | 0.82 | 0.70 | 4.44 | 2.40 | 2.20 | 4.44 | 1.38 | 1.54 | 4.44 | 3.40 | 3.40 | 4.64 |
| 8F2 | | | | 0.16 | 0.12 | 6.01 | 1.10 | 1.90 | 5.84 | 0.94 | 0.84 | 4.31 | 1.90 | 2.60 | 4.23 |
| 8F3 | | | | 0.70 | 0.60 | 4.44 | 1.40 | 1.80 | 4.36 | 0.70 | 0.70 | 4.51 | 1.02 | 1.80 | 4.54 |
| 9D1 | | | | 0.30 | 0.41 | 4.54 | 1.10 | 1.60 | 4.47 | 0.69 | 0.56 | 4.62 | 1.10 | 1.50 | 4.60 |
| 9D2 | | | | 0.53 | 0.40 | 4.32 | 1.90 | 2.30 | 4.54 | 0.80 | 0.73 | 4.40 | 1.60 | 2.80 | 4.49 |
| 10D1 | | | | 0.62 | 0.48 | 4.45 | 0.95 | 1.80 | 4.35 | 0.53 | 0.52 | 4.41 | 1.80 | 2.00 | 4.46 |
| 10D2 | | | | 0.20 | 0.30 | 4.58 | 1.10 | 1.20 | 5.23 | 0.27 | 0.36 | 4.58 | 1.15 | 1.20 | 4.74 |
| 11D1 | | | | 0.32 | 0.35 | 4.44 | 0.55 | 1.70 | 6.20 | 0.30 | 0.35 | 4.65 | 0.00 | 1.20 | 4.34 |
| 11D2 | | | | 0.23 | 0.32 | 4.58 | 1.70 | 1.30 | 5.40 | 0.68 | 0.82 | 4.56 | 1.05 | 1.60 | 4.64 |
| 11E1 | | | | 0.60 | 0.97 | 4.33 | 1.60 | 1.80 | 5.16 | 0.84 | 1.07 | 4.31 | 1.50 | 3.10 | 4.39 |
| 11F2 | | | | 0.18 | 0.23 | 4.62 | 0.85 | 0.80 | 4.97 | 0.32 | 0.33 | 4.65 | 1.00 | 1.20 | 4.87 |
| 12F2 | | | | 0.19 | 0.24 | 4.66 | 1.30 | 1.70 | 4.57 | 0.68 | 0.68 | 4.53 | 1.65 | 1.70 | 4.60 |
| 13D1 | | | | 0.64 | 0.70 | 4.30 | 2.00 | 2.15 | 4.45 | 1.28 | 1.22 | 4.41 | 2.20 | 3.20 | 4.33 |
| 13E1sm | 1.55 | 1.40 | 4.18 | 6 × 10⁴ | 0.32 | 0.31 | 4.31 | 1.53 | 1.65 | 4.37 | 0.40 | 0.45 | 4.22 | 1.60 | 1.53 | 4.24 |
| 13E1L | 1.55 | 1.50 | 4.32 | 2 × 10⁴ | 0.85 | 1.00 | 4.38 | 2.40 | 2.25 | 4.26 | 1.03 | 1.00 | 4.26 | 2.08 | 1.93 | 4.20 |
| 14D1 | | | | 0.60 | 0.42 | 4.49 | 1.40 | 1.50 | 4.49 | 0.00 | 0.78 | 4.50 | 0.00 | 0.90 | 4.46 |
| 14D2 | | | | 0.18 | 0.28 | 4.65 | 0.70 | 1.30 | 4.82 | 0.56 | 0.50 | 4.58 | 1.02 | 1.75 | 4.75 |
| 14D3 | | | | 0.05 | 0.11 | 6.38 | 0.65 | 1.10 | 6.20 | 0.05 | 0.10 | 6.44 | 0.45 | 1.50 | 6.18 |
| 14D4 | | | | 0.20 | 0.26 | 4.73 | 1.20 | 1.20 | 4.81 | 0.53 | 0.54 | 4.62 | 1.60 | 1.60 | 4.72 |
| 14E1 | | | | 0.00 | 0.05 | 6.42 | 0.30 | 0.50 | 6.42 | 0.00 | 0.02 | 6.52 | 0.00 | 0.40 | 6.03 |
| 14E2 | | | | 0.98 | 0.55 | 4.31 | 1.20 | 1.55 | 4.43 | 0.70 | 0.82 | 4.29 | 1.30 | 2.00 | 4.34 |
| 14F1 | | | | 0.08 | 0.16 | 6.36 | 0.90 | 1.80 | 6.63 | 0.05 | 0.09 | 6.41 | 0.70 | 1.60 | 6.14 |
| 14F2 | | | | 0.05 | 0.12 | 6.34 | 0.95 | 1.05 | 6.25 | 0.05 | 0.10 | 6.45 | 0.90 | 1.60 | 5.85 |
| 15E1 | | | | 0.06 | 0.11 | 6.43 | 0.70 | 1.00 | 6.22 | 0.07 | 0.10 | 6.48 | 0.70 | 0.75 | 6.13 |
| 15E2 | | | | 0.05 | 0.11 | 6.45 | 0.80 | 0.80 | 6.22 | 0.04 | 0.08 | 6.47 | 0.90 | 0.70 | 6.29 |
| 16C1 | | | | 0.05 | 0.10 | 6.50 | 0.70 | 0.90 | 6.22 | 0.05 | 0.08 | 6.51 | 0.70 | 0.90 | 6.26 |
| 16C2 | | | | 0.59 | 0.73 | 4.28 | 2.30 | 2.90 | 4.59 | 0.92 | 1.00 | 4.30 | 2.90 | 5.60 | 4.47 |
| 16C3 | | | | 0.02 | 0.07 | 6.42 | 2.30 | 4.20 | 7.41 | 0.03 | 0.07 | 6.51 | 1.35 | 0.70 | 6.19 |
| 17C1 | | | | 0.02 | 0.07 | 6.43 | 0.80 | 1.30 | 6.26 | 0.03 | 0.08 | 6.50 | 0.72 | 0.70 | 6.36 |

TABLE 2-continued

Properties of all the Isolates

Fermentation Products (48 hr) (pH not Controlled)

| | LB (1% Xylose), pH 6.8 | | | | | | | LB (1% Glucose), pH 6.8 | | | | | | |
|---|---|---|---|---|---|---|---|---|---|---|---|---|---|---|
| Isolate | Xylose mM | Succinate mM | Lactate mM | Formate mM | Fumarate μM | Acetate mM | Ethanol mM | Glucose mM | Succinate mM | Lactate mM | Formate mM | Fumarate μM | Acetate mM | Ethanol mM |
| 6F3A | | | | | | | | | | | | | | |
| 6F3B | | | | | | | | | | | | | | |
| 6H1A | | | | | | | | | | | | | | |
| 6H1B | 47.1 | | 15.6 | | | 5.9 | | 39.1 | | 17.7 | | | | |
| 6H2 | 43.8 | | 15.1 | | | 5.4 | | 38.6 | | 15.2 | | | | |
| 6H3 | | | | | | | | | | | | | | |
| 7C1 | | | | | | | | | | | | | | |
| 7C2 | | | | | | | | | | | | | | |
| 7C3 | | | | | | | | | | | | | | |
| 7C4 | | | | | | | | | | | | | | |
| 7C5 | | | | | | | | | | | | | | |
| 7C6 | | | | | | | | | | | | | | |
| 7C8 | | | | | | | | | | | | | | |
| 7D1 | | | | | | | | | | | | | | |
| 7D3 | 49.4 | | 12.5 | | | 3.8 | | 46.0 | | 15.2 | | | | |
| 7D4 | 48.2 | | 15.1 | | | 2.5 | | 43.6 | | 18.2 | | | | |
| 7E1 | 35.9 | | 9.6 | | | * | | 45.8 | | 15.3 | | | 2.2 | |
| 7F1-smooth | 48.8 | | 14.2 | | | 3.8 | 2.4 | 45.6 | | 19.6 | | | | |
| 7F1-rough | 49.9 | 1.3 | 13.6 | | | 4.4 | 2.7 | 45.5 | | 16.2 | | | | |
| 7F2 | 56.5 | | | | | 4.2 | | 44.9 | | 20.0 | | | | |
| 7G1 | 49.9 | | 16.1 | | | 4.2 | | 47.5 | | 16.4 | | | * | |
| 7G2 | | | | | | | | | | | | | | |
| 7G3 | | | | | | | | | | | | | | |
| 7G4 | 45.6 | | 20.0 | | | 2.1 | | 47.8 | | 17.7 | | | | |
| 8D1 | 45.5 | | 18.9 | | | 2.2 | | 45.4 | | 19.3 | | | | |
| 8D2 | | | | | | | | | | | | | | |
| 8D3 | | | | | | | | | | | | | | |
| 8F1 | 48.1 | | 14.1 | | | 3.5 | | 45.0 | | 16.4 | | | 2.3 | |
| 8F2 | | | | | | | | | | | | | | |
| 8F3 | 50.0 | | 15.5 | | | 2.1 | | 48.6 | | 15.0 | | | 2.1 | |
| 9D1 | 14.7 | | 4.5 | | | | | 50.0 | | 13.1 | | | * | |
| 9D2 | 48.3 | | 16.8 | | | 2.7 | | 47.0 | | 18.5 | | | | |
| 10D1 | 52.6 | 1.3 | 17.4 | | | 2.0 | | 50.0 | 1.3 | 17.6 | | | 2.0 | |
| 10D2 | | | | | | | | | | | | | | |
| 11D1 | | | | | | | | | | | | | | |
| 11D2 | | | | | | | | | | | | | | |
| 11E1 | 45.7 | 1.1 | 17.5 | | | 4.9 | | 61.9 | 1.2 | 20.7 | | | | |
| 11F2 | | | | | | | | | | | | | | |
| 12F2 | | | | | | | | | | | | | | |
| 13D1 | 44.2 | 1.5 | 17.9 | | | 4.9 | 2.4 | 44.1 | 1.2 | 18.5 | | | 2.3 | |
| 13E1sm | 57.0 | 1.7 | 15.3 | 4.2 | | 3.1 | 7.8 | 47.2 | | 23.6 | | | * | |
| 13E1L | 48.3 | 1.6 | 13.5 | 4.2 | | 3.9 | | 45.4 | 1.8 | 22.1 | | | * | |
| 14D1 | 52.0 | | | | | | | | | | | | | |

TABLE 2-continued

Properties of all the Isolates

| Isolate | Xylose mM | Lactate mM | Succinate mM | Acetate mM | Ethanol mM | Formate mM | Fumarate μM | Glucose mM | Lactate mM | Succinate mM | Acetate mM | Ethanol mM | Formate mM | Fumarate μM |
|---|---|---|---|---|---|---|---|---|---|---|---|---|---|---|
| 14D2 | | | | | | | | | | | | | | |
| 14D3 | | | | | | | | | | | | | | |
| 14D4 | | | | | | | | | | | | | | |
| 14E1 | | | | | | | | | | | | | | |
| 14E2 | 45.4 | 1.2 | 16.3 | | | 5.3 | | 46.0 | | 21.5 | | | | |
| 14F1 | | | | | | | | | | | | | | |
| 14F2 | | | | | | | | | | | | | | |
| 15E1 | | | | | | | | | | | | | | |
| 15E2 | | | | | | | | | | | | | | |
| 16C1 | | | | | | | | | | | | | | |
| 16C2 | 48.0 | 1.3 | 19.5 | | | 4.1 | | 43.0 | | 21.6 | | | | |
| 16C3 | | | | | | | | | | | | | | |
| 17C1 | | | | | | | | | | | | | | |

Fermentation Products (48 hr) (pHstat)

| Isolate | LB (1% Xylose), pH 5.0 | | | | | | | LB (1% Glucose), pH 5.0 | | | | | | |
|---|---|---|---|---|---|---|---|---|---|---|---|---|---|---|
| | Xylose mM | Lactate mM | Succinate mM | Acetate mM | Ethanol mM | Formate mM | Fumarate μM | Glucose mM | Lactate mM | Succinate mM | Acetate mM | Ethanol mM | Formate mM | Fumarate μM |
| 6F3A | | | | | | | | | | | | | | |
| 6F3B | | | | | | | | | | | | | | |
| 6H1A | | | | | | | | | | | | | | |
| 6H1B | 0.27 | 82.67 | 3.18 | 22.85 | 13.88 | 0.00 | 0.00 | 0.00 | 100.19 | 0.67 | 4.91 | 3.83 | 0.00 | 0.00 |
| 6H2 | 0.00 | 71.74 | 2.55 | 25.47 | 7.56 | 0.00 | 0.00 | 0.00 | 89.76 | 2.78 | 13.22 | 0.00 | 0.00 | 0.00 |
| 6H3 | | | | | | | | | | | | | | |
| 7C1 | | | | | | | | | | | | | | |
| 7C2 | | | | | | | | | | | | | | |
| 7C3 | | | | | | | | | | | | | | |
| 7C4 | | | | | | | | | | | | | | |
| 7C5 | | | | | | | | | | | | | | |
| 7C6 | | | | | | | | | | | | | | |
| 7C8 | 0.00 | 73.62 | 2.48 | 28.41 | 7.64 | 0.00 | 0.00 | 0.00 | 88.04 | 0.65 | 12.26 | 0.00 | 0.00 | 0.00 |
| 7D1 | | | | | | | | | | | | | | |
| 7D3 | | | | | | | | | | | | | | |
| 7D4 | 10.68 | 78.89 | 1.64 | 7.21 | 6.42 | 0.00 | 0.00 | 9.49 | 86.46 | 0.60 | 0.72 | 4.56 | 0.00 | 0.00 |
| 7E1 | 0.00 | 78.30 | 2.33 | 20.71 | 5.92 | 0.00 | 0.00 | 0.00 | 94.94 | 0.78 | 7.80 | 0.00 | 0.00 | 0.00 |
| 7F1-smooth | | | | | | | | | | | | | | |
| 7F1-rough | | | | | | | | | | | | | | |
| 7F2 | | | | | | | | | | | | | | |
| 7G1 | 0.00 | 79.88 | 1.98 | 18.91 | 9.26 | 1.93 | 0.00 | 0.00 | 92.23 | 0.77 | 6.73 | 4.76 | 0.00 | 0.00 |
| 7G2 | | | | | | | | | | | | | | |
| 7G3 | | | | | | | | | | | | | | |
| 7G4 | | | | | | | | | | | | | | |
| 8D1 | | | | | | | | | | | | | | |
| 8D2 | | | | | | | | | | | | | | |
| 8D3 | | | | | | | | | | | | | | |
| 8F1 | | | | | | | | | | | | | | |
| 8F2 | | | | | | | | | | | | | | |

TABLE 2-continued

Properties of all the Isolates

| Isolate | LB Glucose (1%), pH 4.5 | | | LB Xylose (1%), pH 4.5 | | | Anaerobic Growth | | | | | | | | |
|---|---|---|---|---|---|---|---|---|---|---|---|---|---|---|---|
| | | | | | | | MS (0.1% YE) (Xylose 1%), pH 5 | | | MS (0.1% YE) (Glucose 1%), pH 5 | | | HCH 10% CSL 1%, pH 5 | | |
| | O.D. 420 nm 24 hrs | O.D. 420 nm 48 hrs | pH 48 hrs | O.D. 420 nm 24 hrs | O.D. 420 nm 48 hrs | pH 48 hrs | O.D. 420 nm 24 hrs | O.D. 420 nm 48 hrs | pH 48 hrs | O.D. 420 nm 24 hrs | O.D. 420 nm 48 hrs | pH 48 hrs | O.D. 420 nm 24 hrs | O.D. 420 nm 48 hrs | pH 48 hrs |
| 8F3 | | | | | | | | | | | | | | | |
| 9D1 | | | | | | | | | | | | | | | |
| 9D2 | | | | | | | | | | | | | | | |
| 10D1 | | | | | | | | | | | | | | | |
| 10D2 | | | | | | | | | | | | | | | |
| 11D1 | | | | | | | | | | | | | | | |
| 11D2 | | | | | | | | | | | | | | | |
| 11E1 | | | | | | | | | | | | | | | |
| 11F2 | | | | | | | | | | | | | | | |
| 12F2 | | | | | | | | | | | | | | | |
| 13D1 | | | | | | | | | | | | | | | |
| 13E1sm | | | | | | | | | | | | | | | |
| 13E1L | 0.00 | 90.82 | 2.53 | 12.33 | 11.08 | 11.42 | 0.00 | 0.00 | 106.15 | 0.67 | 3.87 | 3.91 | 0.00 | 0.00 | 0.00 |
| 14D1 | | | | | | | | | | | | | | | |
| 14D2 | | | | | | | | | | | | | | | |
| 14D3 | | | | | | | | | | | | | | | |
| 14D4 | | | | | | | | | | | | | | | |
| 14E1 | | | | | | | | | | | | | | | |
| 14E2 | | | | | | | | | | | | | | | |
| 14F1 | | | | | | | | | | | | | | | |
| 14F2 | | | | | | | | | | | | | | | |
| 15E1 | | | | | | | | | | | | | | | |
| 15E2 | | | | | | | | | | | | | | | |
| 16C1 | | | | | | | | | | | | | | | |
| 16C2 | | | | | | | | | | | | | | | |
| 16C3 | | | | | | | | | | | | | | | |
| 17C1 | | | | | | | | | | | | | | | |
| 6F3A | | | | | | | | | | | | | | | |
| 6F3B | | | | | | | | | | | | | | | |
| 6H1A | | | | | | | | | | | | | | | |
| 6H1B | 0.08 | 0.17 | 4.38 | 0.08 | 0.16 | 4.26 | 0.05 | 0.08 | 4.53 | 0.06 | 0.07 | 4.40 | + | 0.05 | 4.09 |
| 6H2 | 0.03 | 0.08 | 4.48 | 0.04 | 0.14 | 4.42 | 0.19 | 0.17 | 4.45 | 0.08 | 0.07 | 4.49 | 0.08 | 0.00 | 4.10 |
| 6H3 | | | | | | | | | | | | | | | |
| 7C1 | | | | | | | | | | | | | | | |
| 7C2 | | | | | | | | | | | | | | | |
| 7C4 | | | | | | | | | | | | | | | |
| 7C5 | | | | | | | | | | | | | | | |
| 7C6 | | | | | | | 0.09 | 0.12 | 4.30 | 0.10 | 0.14 | 4.29 | 0.20 | 0.22 | 3.98 |
| 7C8 | | | | | | | | | | | | | | | |
| 7D1 | | | | | | | | | | | | | | | |

TABLE 2-continued

Properties of all the Isolates

| | | | | | | | | | | | | | | | |
|---|---|---|---|---|---|---|---|---|---|---|---|---|---|---|---|
| 7D3 | 0.11 | 0.11 | 4.42 | 0.12 | 0.16 | 4.42 | 0.22 | 0.31 | 4.54 | 0.08 | 0.08 | 4.55 | + | + | 4.20 |
| 7D4 | 0.26 | 0.26 | 4.25 | 0.18 | 0.23 | 4.40 | 0.22 | 0.24 | 4.53 | 0.10 | 0.09 | 4.47 | 0.17 | 0.15 | 4.10 |
| 7E1 | 0.02 | 0.02 | 4.51 | 0.00 | 0.00 | 4.39 | 0.09 | 0.08 | 4.51 | 0.08 | 0.11 | 4.44 | 0.00 | 0.00 | 5.00 |
| 7F1-smooth | 0.06 | 0.15 | 4.42 | 0.14 | 0.15 | 4.37 | 0.10 | 0.12 | 4.52 | 0.07 | 0.09 | 4.50 | 0.11 | 0.10 | 4.12 |
| 7F1-rough | | | | | | | | | | | | | | | |
| 7F2 | 0.06 | 0.16 | 4.44 | 0.12 | 0.16 | 4.34 | 0.10 | 0.09 | 4.59 | 0.07 | 0.10 | 4.53 | 0.15 | 0.13 | 4.10 |
| 7G1 | 0.22 | 0.26 | 4.32 | 0.13 | 0.15 | 4.46 | 0.08 | 0.09 | 5.09 | 0.12 | 0.13 | 4.40 | 0.11 | 0.15 | 4.08 |
| 7G2 | 0.03 | 0.14 | 4.38 | 0.02 | 0.15 | 4.40 | 0.18 | 0.18 | 4.45 | 0.12 | 0.13 | 4.45 | 0.17 | 0.22 | 3.97 |
| 7G3 | | | | | | | | | | | | | | | |
| 7G4 | 0.00 | 0.15 | 4.30 | 0.00 | 0.00 | 4.36 | 0.15 | 0.13 | 4.46 | 0.07 | 0.07 | 4.60 | 0.25 | 0.25 | 4.29 |
| 8D1 | 0.09 | 0.13 | 4.40 | 0.00 | 0.00 | 4.36 | 0.15 | 0.17 | 4.45 | 0.04 | 0.04 | 4.61 | 0.13 | 0.21 | 4.30 |
| 8D2 | | | | | | | | | | | | | | | |
| 8D3 | | | | | | | | | | | | | | | |
| 8F1 | 0.15 | 0.18 | 4.38 | 0.00 | 0.00 | 4.36 | 0.15 | 0.21 | 4.60 | 0.08 | 0.08 | 4.60 | 0.00 | 0.00 | 4.30 |
| 8F2 | | | | | | | | | | | | | | | |
| 8F3 | 0.00 | 0.00 | 4.38 | 0.00 | 0.00 | 4.35 | 0.13 | 0.08 | 4.45 | 0.05 | 0.04 | 4.61 | 0.03 | 0.02 | 4.60 |
| 9D1 | 0.00 | 0.00 | 4.40 | 0.00 | 0.00 | 4.34 | 0.14 | 0.11 | 4.45 | 0.04 | 0.08 | 4.67 | 0.06 | 0.00 | 4.49 |
| 9D2 | 0.00 | 0.00 | 4.40 | 0.00 | 0.00 | 4.36 | 0.14 | 0.10 | 4.60 | 0.06 | 0.07 | 4.66 | 0.05 | 0.00 | 4.41 |
| 10D1 | 0.00 | 0.00 | 4.52 | 0.00 | 0.00 | 4.43 | 0.10 | 0.09 | 4.43 | 0.00 | 0.00 | 4.96 | 0.04 | 0.00 | 4.49 |
| 10D2 | | | | | | | | | | | | | | | |
| 11D1 | | | | | | | | | | | | | | | |
| 11D2 | | | | | | | | | | | | | | | |
| 11E1 | 0.00 | 0.03 | 4.43 | 0.03 | 0.07 | 4.43 | 0.45 | 0.46 | 4.40 | 0.08 | 0.07 | 4.54 | 0.13 | 0.09 | 4.31 |
| 11F2 | | | | | | | | | | | | | | | |
| 12F2 | | | | | | | | | | | | | | | |
| 13D1 | 0.03 | 0.02 | 4.48 | 0.00 | 0.00 | 4.37 | 0.19 | 0.10 | 4.48 | 0.06 | 0.07 | 4.58 | 0.09 | 0.06 | 4.30 |
| 13E1sm | 0.20 | 0.24 | 4.18 | 0.18 | 0.16 | 4.24 | 0.05 | 0.03 | 4.67 | 0.07 | 0.07 | 4.43 | 0.09 | 0.16 | 4.07 |
| 13E1L | 0.19 | 0.22 | 4.23 | 0.16 | 0.15 | 4.22 | 0.10 | 0.14 | 4.50 | 0.10 | 0.14 | 4.43 | 0.21 | 0.26 | 4.09 |
| 14D1 | | | | | | | | | | | | | | | |
| 14D2 | | | | | | | | | | | | | | | |
| 14D3 | | | | | | | | | | | | | | | |
| 14D4 | | | | | | | | | | | | | | | |
| 14E1 | | | | | | | | | | | | | | | |
| 14E2 | 0.03 | 0.05 | 4.48 | 0.01 | 0.04 | 4.44 | 0.29 | 0.29 | 4.45 | 0.06 | 0.14 | 5.02 | 0.05 | 0.02 | 4.72 |
| 14F1 | | | | | | | | | | | | | | | |
| 14F2 | | | | | | | | | | | | | | | |
| 15E1 | | | | | | | | | | | | | | | |
| 15E2 | | | | | | | | | | | | | | | |
| 16C1 | | | | | | | | | | | | | | | |
| 16C2 | 0.01 | 0.07 | 4.37 | 0.00 | 0.00 | 4.38 | 0.22 | 0.24 | 4.45 | 0.07 | 0.07 | 4.64 | 0.18 | 0.20 | 4.30 |
| 16C3 | | | | | | | | | | | | | | | |
| 17C1 | | | | | | | | | | | | | | | |

TABLE 2-continued

Properties of all the Isolates

| Isolate | LB (Glucose 1%, pH 6.8) | | | | | | | | LB (Glucose 1%, pH 5.0) | | | | | | | | 20% HCH 0.1% YE/Glu pH 5.0[V] plates (48 hrs) | 25% HCH 0.1% YE/Glu pH 5.0[V] plates (48 hrs) | 50% HCH overlimed 0.1% YE/Glu pH 5.0[V] plates (48 hrs) |
|---|---|---|---|---|---|---|---|---|---|---|---|---|---|---|---|---|---|---|---|
| | 0% Ethanol O.D. 420 nm | | 4% Ethanol(w/w) O.D. 420 nm | | 4.5% Ethanol(w/w) O.D. 420 nm | | 5% Ethanol(w/w) O.D. 420 nm | | 0% Ethanol O.D. 420 nm | | 4% Ethanol(w/w) O.D. 420 nm | | 4.5% Ethanol(w/w) O.D. 420 nm | | 5% Ethanol(w/w) O.D. 420 nm | | | | |
| | 24 hrs | 48 hrs | 24 hrs | 48 hrs | 24 hrs | 48 hrs | 24 hrs | 48 hrs | 24 hrs | 48 hrs | 24 hrs | 48 hrs | 24 hrs | 48 hrs | 24 hrs | 48 hrs | | | |
| 6F3A | | | | | | | | | | | | | | | | | — | — | — |
| 6F3B | | | | | | | | | | | | | | | | | — | — | — |
| 6H1A | | | | | | | | | | | | | | | | | — | — | — |
| 6H1B | 0.75 | 0.95 | 0.10 | 0.25 | 0.06 | 0.06 | 0.05 | 0.05 | 0.25 | 0.50 | 0.11 | 0.11 | 0.05 | 0.06 | 0.02 | 0.01 | — | — | — |
| 6H2 | 0.55 | 0.55 | 0.06 | 0.06 | 0.06 | 0.06 | 0.07 | 0.07 | 0.35 | 0.45 | 0.18 | 0.18 | 0.11 | 0.13 | 0.04 | 0.02 | — | — | — |
| 6H3 | | | | | | | | | | | | | | | | | ++ | — | — |
| 7C1 | 0.05 | 0.05 | 0.01 | 0.01 | 0.02 | 0.02 | 0.02 | 0.02 | 0.30 | 0.40 | 0.04 | 0.04 | 0.02 | 0.02 | 0.03 | 0.02 | — | — | — |
| 7C2 | | | | | | | | | | | | | | | | | + | — | — |
| 7C4 | | | | | | | | | | | | | | | | | — | — | — |
| 7C5 | 0.45 | 0.65 | 0.03 | 0.06 | 0.05 | 0.03 | 0.04 | 0.03 | 0.35 | 0.40 | 0.19 | 0.19 | 0.14 | 0.16 | 0.05 | 0.03 | — | — | — |
| 7C6 | | | | | | | | | | | | | | | | | ++ | + | — |
| 7C8 | | | | | | | | | | | | | | | | | ++ | + | — |
| 7D1 | 0.95 | 1.05 | 0.35 | 0.38 | 0.20 | 0.26 | 0.03 | 0.03 | 0.40 | 0.50 | 0.17 | 0.17 | 0.10 | 0.10 | 0.05 | 0.04 | — | — | — |
| 7D3 | | | | | | | | | | | | | | | | | ++ | + | — |
| 7D4 | | | | | | | | | | | | | | | | | ++ | + | — |
| 7E1 | 0.90 | 0.95 | 0.01 | 0.18 | 0.02 | 0.02 | 0.02 | 0.02 | 0.50 | 0.52 | 0.21 | 0.22 | 0.12 | 0.14 | 0.06 | 0.07 | | | |
| 7F1-smooth | | | | | | | | | | | | | | | | | | | — |
| 7F1-rough | | | | | | | | | | | | | | | | | + | — | — |
| 7F2 | 0.35 | 0.80 | 0.04 | 0.10 | 0.07 | 0.05 | 0.04 | 0.04 | 0.35 | 0.50 | 0.19 | 0.23 | 0.16 | 0.17 | 0.08 | 0.06 | + | + | — |
| 7G1 | | | | | | | | | | | | | | | | | + | + | — |
| 7G2 | | | | | | | | | | | | | | | | | — | — | — |
| 7G3 | | | | | | | | | | | | | | | | | + | + | — |
| 7G4 | | | | | | | | | | | | | | | | | +++ | + | + |
| 8D1 | | | | | | | | | | | | | | | | | ++ | + | — |
| 8D2 | | | | | | | | | | | | | | | | | +++ | + | + |
| 8D3 | | | | | | | | | | | | | | | | | — | — | — |
| 8F1 | | | | | | | | | | | | | | | | | +++ | + | + |
| 8F2 | | | | | | | | | | | | | | | | | +++ | + | + |
| 8F3 | | | | | | | | | | | | | | | | | + | — | — |
| 9D1 | | | | | | | | | | | | | | | | | +++ | + | + |
| 9D2 | | | | | | | | | | | | | | | | | — | — | — |
| 10D1 | | | | | | | | | | | | | | | | | +++ | + | — |
| 10D2 | | | | | | | | | | | | | | | | | ++ | + | — |
| 11D1 | | | | | | | | | | | | | | | | | — | — | — |
| 11D2 | | | | | | | | | | | | | | | | | ++ | + | + |
| 11E1 | | | | | | | | | | | | | | | | | — | — | — |
| 11F2 | | | | | | | | | | | | | | | | | — | + | — |
| 12F2 | | | | | | | | | | | | | | | | | — | — | — |
| 13D1 | | | | | | | | | | | | | | | | | + | + | — |
| 13E1sm | 0.45 | 0.45 | 0.25 | 0.30 | 0.07 | 0.08 | 0.04 | 0.04 | 0.40 | 0.40 | 0.13 | 0.14 | 0.13 | 0.13 | 0.10 | 0.08 | + | — | + |

TABLE 2-continued

Properties of all the Isolates

Aerobic (pH 5.0)

| Isolate | 25% HCH (0.1% YE) CFU/ml 24 hrs | 48 hrs | pH 48 hrs | 10% HCH (1% CSL) CFU/ml 24 hrs | 48 hrs | pH 48 hrs | 25% Overlimed HCH CFU/ml 24 hrs | 48 hrs | pH 48 hrs | 50% Overlimed HCH (0.1% YE) CFU/ml 24 hrs | 48 hrs | pH 48 hrs | Antibiotic Sensitivity Tetracycline 20 mg/L | Chloramphenicol 30 mg/L | Kanamycin 50 mg/L | Ampicillin 100 mg/L |
|---|---|---|---|---|---|---|---|---|---|---|---|---|---|---|---|---|
| 13E1L | 1.00 | 1.10 | 0.15 | 0.38 | 0.14 | 0.40 | 0.05 | 0.05 | 0.65 | 0.65 | 0.26 | 0.26 | 0.16 | 0.15 | 0.09 | 0.10 | ++ | ++ | + | + |
| 14D1 | | | | | | | | | | | | | | | | | − | − | − | − |
| 14D2 | | | | | | | | | | | | | | | | | − | − | − | − |
| 14D3 | | | | | | | | | | | | | | | | | − | − | − | − |
| 14D4 | | | | | | | | | | | | | | | | | − | − | − | − |
| 14E1 | | | | | | | | | | | | | | | | | − | − | − | − |
| 14E2 | | | | | | | | | | | | | | | | | − | − | − | − |
| 14F1 | | | | | | | | | | | | | | | | | − | − | − | − |
| 14F2 | | | | | | | | | | | | | | | | | − | − | − | − |
| 15E1 | | | | | | | | | | | | | | | | | − | − | − | − |
| 15E2 | | | | | | | | | | | | | | | | | − | − | − | − |
| 16C1 | | | | | | | | | | | | | | | | | − | − | − | − |
| 16C2 | | | | | | | | | | | | | | | | | − | − | + | − |
| 16C3 | | | | | | | | | | | | | | | | | − | − | − | − |
| 17C1 | | | | | | | | | | | | | | | | | − | − | − | − |
| 6F3A | | | | | | | | | | | | | | | | | | | | |
| 6F3B | | | | | | | | | | | | | | | | | | | | |
| 6H1A | | | | | | | | | | | | | | | | | | | | |
| 6H1B | | | | | | | | | | | | | | | | | − | − | − | − |
| 6H2 | | | | | | | | | | | | | | | | | − | − | − | − |
| 6H3 | | | | | | | | | | | | | | | | | | | | |
| 7C1 | | | | | | | | | | | | | | | | | | | | |
| 7C2 | | | | | | | | | | | | | | | | | | | | |
| 7C4 | | | | | | | | | | | | | | | | | + | − | − | − |
| 7C5 | | | | | | | | | | | | | | | | | | | | |
| 7C6 | | | | | | | | | | | | | | | | | | | | |
| 7C8 | | | | | | | | | | | | | | | | | − | − | − | − |
| 7D1 | | | | | | | | | | | | | | | | | | | | |
| 7D3 | | | | | | | | | | | | | | | | | | | | |
| 7D4 | | | | | | | | | | | | | | | | | − | − | − | − |
| 7E1 | | | | | | | | | | | | | | | | | | | | |
| 7F1-smooth | | | | | | | | | | | | | | | | | | | | |
| 7F1-rough | | | | | | | | | | | | | | | | | − | − | − | − |
| 7F2 | | | | | | | | | | | | | | | | | | | | |
| 7G1 | | | | | | | | | | | | | | | | | | | | |
| 7G2 | | | | | | | | | | | | | | | | | | | | |
| 7G3 | | | | | | | | | | | | | | | | | | | | |
| 7G4 | | | | | | | | | | | | | | | | | | | | |
| 8D1 | | | | | | | | | | | | | | | | | | | | |
| 8D2 | | | | | | | | | | | | | | | | | | | | |

TABLE 2-continued

Properties of all the Isolates

| Isolate | Identification[a] (16S rRNA) | Xylanase 72 hr | CMCase 72 hr | Cellobiose MS (0.1% YE) pH 5.0 72 hr | LB Xylose (1%) Anaerobic O.D. 420 nm 24 hrs | LB Xylose (1%) Anaerobic O.D. 420 nm 48 hrs | LB Xylose (1%) pH 48 hrs | LB Xylose (1%) Aerobic O.D. 420 nm 24 hrs | LB Xylose (1%) Aerobic O.D. 420 nm 48 hrs | LB Xylose (1%) pH 48 hrs | Growth at pH 5.0 LB Glucose (1%) Anaerobic O.D. 420 nm 24 hrs | Anaerobic O.D. 420 nm 48 hrs | pH 48 hrs | Aerobic O.D. 420 nm 24 hrs | Aerobic O.D. 420 nm 48 hrs | pH 48 hrs |
|---|---|---|---|---|---|---|---|---|---|---|---|---|---|---|---|---|
| 8D3 | | | | | | | | | | | | | | | | |
| 8F1 | | | | | | | | | | | | | | | | |
| 8F2 | | | | | | | | | | | | | | | | |
| 8F3 | | | | | | | | | | | | | | | | |
| 9D1 | | | | | | | | | | | | | | | | |
| 9D2 | | | | | | | | | | | | | | | | |
| 10D1 | | | | | | | | | | | | | | | | |
| 10D2 | | | | | | | | | | | | | | | | |
| 11D1 | | | | | | | | | | | | | | | | |
| 11D2 | | | | | | | | | | | | | | | | |
| 11E1 | | | | | | | | | | | | | | | | |
| 11F2 | | | | | | | | | | | | | | | | |
| 12F2 | | | | | | | | | | | | | | | | |
| 13D1 | | >4 × 10⁷ | − | 2 × 10⁶ | | | | | | | | | | | | |
| 13E1sm | | 7 × 10⁶ | 4.52 | 2 × 10⁶ | 3.95 | >4 × 10⁷ | 3.90 | | | | | | | | + | |
| 13E1L | | | 4.17 | − | 3.99 | 4 × 10⁵ | 3.87 | | | | | | | | − | |
| 14D1 | | | | | | | | | | | | | | | | |
| 14D2 | | | | | | | | | | | | | | | | |
| 14D3 | | | | | | | | | | | | | | | | |
| 14D4 | | | | | | | | | | | | | | | | |
| 14E1 | | | | | | | | | | | | | | | | |
| 14E2 | | | | | | | | | | | | | | | | |
| 14F1 | | | | | | | | | | | | | | | | |
| 14F2 | | | | | | | | | | | | | | | | |
| 15E1 | | | | | | | | | | | | | | | | |
| 15E2 | | | | | | | | | | | | | | | | |
| 16C1 | | | | | | | | | | | | | | | | |
| 16C2 | | | | | | | | | | | | | | | − | |
| 16C3 | | | | | | | | | | | | | | | − | |
| 17C1 | | | | | | | | | | | | | | | | |
| 17C2 | | − | − | + | 0.04 | 0.07 | 5.07 | 0.65 | 1.48 | 5.89 | 0.08 | 0.15 | 5.04 | 1.38 | 2.28 | 7.04 |
| 17C3 | | − | − | + | 0.06 | 0.08 | 5.09 | 2.28 | 4.30 | 7.04 | 0.08 | 0.15 | 5.09 | 1.13 | 1.08 | 5.07 |
| 17C4 | | − | − | + | 0.35 | 0.35 | 4.30 | 1.60 | 1.98 | 5.52 | 0.45 | 0.70 | 4.39 | 2.18 | 1.90 | 4.22 |
| 17C5 | | − | − | + | 0.34 | 0.33 | 4.29 | 2.15 | 2.30 | 4.33 | 0.62 | 0.65 | 4.35 | 2.52 | 3.23 | 4.23 |
| 17D1 | | − | − | + | 0.09 | 0.03 | 5.02 | 0.35 | 0.55 | 5.48 | 0.08 | 0.09 | 4.95 | 0.85 | 2.37 | 6.31 |
| 17D2 | B. coagulans | − | − | + | 0.36 | 0.40 | 4.43 | 1.80 | 1.92 | 4.33 | 0.75 | 0.80 | 4.23 | 1.90 | 1.70 | 4.36 |
| 17D3 | B. coagulans | − | − | + | 0.65 | 0.61 | 4.30 | 1.90 | 1.80 | 4.39 | 0.50 | 0.50 | 4.24 | 1.38 | 1.55 | 4.35 |
| 17E1 | | − | − | + | 0.10 | 0.08 | 5.08 | 0.51 | 0.90 | 5.85 | 0.07 | 0.14 | 5.08 | 0.70 | 1.00 | 5.90 |
| 17E2 | | − | − | + | 0.10 | 0.10 | 5.09 | 0.41 | 1.05 | 5.65 | 0.08 | 0.15 | 5.08 | 0.63 | 0.86 | 5.85 |

TABLE 2-continued

Properties of all the Isolates

| | | | | | | | | | | | | | |
|---|---|---|---|---|---|---|---|---|---|---|---|---|---|
| 18C1 | B. coagulans | − | − | + | 0.10 | 0.11 | 5.09 | 0.41 | 2.32 | 7.06 | 0.06 | 0.15 | 5.08 | 0.67 | 5.90 |
| 18C2 | | − | − | + | 0.63 | 0.52 | 4.25 | 1.55 | 1.55 | 4.39 | 0.40 | 0.40 | 4.36 | 1.58 | 4.34 |
| 18C4 | | − | − | + | 0.06 | 0.06 | 5.00 | 0.50 | 0.78 | 4.36 | 0.03 | 0.05 | 4.99 | 0.35 | 4.91 |
| 18C5 | | − | − | + | 0.36 | 0.34 | 4.47 | 2.15 | 2.75 | 4.56 | 0.50 | 0.50 | 4.27 | 2.53 | 4.41 |
| 18C6 | | − | − | + | 0.10 | 0.10 | 4.60 | 1.08 | 1.15 | 4.35 | 0.15 | 0.14 | 4.54 | 0.90 | 4.49 |
| 18D1 | | − | − | + | 0.39 | 0.45 | 4.26 | 2.10 | 2.15 | 4.27 | 0.50 | 0.50 | 4.32 | 1.98 | 4.37 |
| 18D4 | | − | − | + | 0.11 | 0.12 | 4.88 | 0.20 | 0.62 | 5.81 | 0.45 | 0.50 | 4.43 | 2.32 | 4.44 |
| 18E1 | | − | − | + | 0.12 | 0.15 | 5.01 | 0.93 | 1.63 | 5.44 | 0.15 | 0.18 | 5.03 | 0.88 | 5.33 |
| 18E2 | | − | − | + | 0.13 | 0.18 | 5.01 | 4.05 | 5.00 | 6.55 | 0.19 | 0.17 | 5.05 | 0.73 | 5.56 |
| 18E3 | | − | − | + | 0.10 | 0.14 | 5.11 | 0.78 | 1.17 | 5.47 | 0.17 | 0.21 | 5.04 | 0.85 | 5.50 |
| 19C1 | | − | − | − | 0.21 | 0.22 | 4.41 | 0.93 | 0.95 | 4.27 | 0.21 | 0.19 | 4.35 | 0.60 | 4.44 |
| 19D2 | | − | − | + | 0.13 | 0.18 | 4.91 | 0.40 | 0.70 | 5.32 | 0.65 | 0.80 | 4.14 | 2.23 | 4.32 |
| 19E2 | | − | − | + | 0.14 | 0.18 | 5.11 | 2.20 | 2.05 | 6.02 | 0.13 | 0.18 | 5.03 | 0.85 | 5.60 |
| 21B1 | B. coagulans | − | − | + | 0.12 | 0.15 | 5.08 | 0.55 | 1.08 | 5.55 | 0.06 | 0.13 | 5.06 | 0.41 | 5.48 |
| 21B2 | | − | − | + | 0.73 | 0.75 | 4.26 | 1.78 | 2.60 | 4.29 | 0.80 | 0.78 | 4.15 | 1.60 | 4.32 |
| 21B3 | | − | − | + | 0.12 | 0.16 | 5.04 | 0.98 | 1.30 | 4.67 | 0.15 | 0.20 | 5.04 | 0.85 | 5.44 |
| 21B4 | | − | − | + | 0.15 | 0.15 | 4.94 | 0.58 | 0.80 | 5.35 | 0.04 | 0.06 | 4.89 | 0.85 | 4.93 |
| 21C3 | | − | − | + | 0.17 | 0.38 | 4.28 | 1.10 | 1.03 | 4.44 | 0.24 | 0.30 | 4.44 | 1.18 | 4.42 |
| 21C4 | | − | − | + | 0.17 | 0.13 | 5.00 | 0.60 | 1.08 | 5.79 | 0.13 | 0.09 | 5.07 | 0.75 | 5.54 |
| 21D2 | | − | − | + | 0.18 | 0.24 | 4.51 | 1.08 | 1.03 | 4.43 | 0.30 | 0.29 | 4.40 | 1.05 | 4.43 |
| 21D5 | | − | − | + | 0.06 | 0.06 | 5.02 | 0.58 | 0.85 | 5.34 | 0.07 | 0.07 | 5.01 | 0.41 | 4.98 |
| 21D6 | | − | − | + | 0.13 | 0.12 | 5.04 | 0.70 | 1.28 | 5.80 | 0.11 | 0.09 | 5.01 | 0.68 | 5.32 |
| 22C1 | | + | + | + | 0.07 | 0.07 | 5.21 | 1.63 | 1.50 | 4.37 | 0.12 | 0.11 | 5.14 | 0.73 | 5.52 |
| 22C2 | | − | + | + | 0.06 | 0.08 | 5.17 | 0.78 | 0.68 | 5.67 | 0.05 | 0.07 | 5.07 | 0.09 | 5.23 |
| 22C3 | | − | − | + | 0.08 | 0.06 | 4.99 | 0.37 | 0.28 | 5.34 | 0.33 | 0.28 | 5.08 | 0.36 | 5.01 |
| 22D1 | | − | − | + | 0.13 | 0.14 | 4.94 | 0.50 | 0.80 | 5.47 | 0.12 | 0.13 | 4.97 | 0.39 | 4.95 |
| 22D3 | | − | − | + | 0.25 | 0.25 | 4.34 | 0.98 | 0.95 | 4.28 | 0.28 | 0.27 | 4.30 | 1.23 | 4.44 |
| 23C1 | | − | − | − | 0.17 | 0.20 | 4.58 | 0.65 | 0.98 | 4.55 | 0.23 | 0.25 | 4.44 | 0.90 | 4.39 |
| 23C2 | | − | − | + | 0.10 | 0.18 | 4.53 | 1.10 | 1.10 | 4.52 | 0.18 | 0.26 | 4.43 | 1.00 | 4.46 |
| 23C3 | | − | − | + | 0.13 | 0.17 | 5.04 | 0.60 | 1.10 | 5.50 | 0.13 | 0.19 | 5.04 | 0.70 | 5.52 |
| 23D1 | | − | − | + | 0.13 | 0.16 | 5.01 | 0.78 | 1.25 | 5.57 | 0.16 | 0.32 | 5.09 | 0.90 | 5.29 |
| 23D2 | | − | − | + | 0.14 | 0.17 | 4.98 | 0.75 | 1.10 | 5.61 | 0.15 | 0.20 | 5.04 | 0.43 | 5.47 |
| 24B1 | | − | − | + | 0.14 | 0.16 | 4.97 | 0.70 | 1.20 | 5.64 | 0.17 | 0.18 | 4.98 | 0.75 | 5.38 |
| 24C1 | | − | − | + | 0.09 | 0.13 | 5.02 | 0.63 | 1.20 | 5.62 | 0.05 | 0.17 | 5.05 | 0.68 | 5.37 |
| 24D2 | | − | − | + | 0.24 | 0.30 | 4.43 | 1.23 | 1.75 | 4.59 | 0.38 | 0.54 | 4.36 | 1.50 | 4.44 |
| 25C1 | | − | − | + | 0.12 | 0.15 | 5.04 | 0.48 | 0.85 | 5.70 | 0.12 | 0.18 | 5.08 | 0.40 | 5.77 |
| 25D2 | | − | − | + | 0.12 | 0.20 | 4.98 | 0.65 | 1.20 | 5.68 | 0.11 | 0.19 | 4.98 | 2.20 | 5.91 |
| 25D3 | | − | − | + | 0.12 | 0.19 | 4.99 | 0.70 | 1.20 | 5.57 | 0.13 | 0.19 | 4.99 | 0.65 | 5.41 |
| 26C1 | | − | − | + | 0.08 | 0.13 | 5.06 | 0.48 | 0.85 | 5.83 | 0.10 | 0.16 | 5.06 | 0.35 | 5.70 |
| 26D1 | | − | − | + | 0.13 | 0.19 | 4.99 | 0.75 | 1.70 | 5.70 | 0.13 | 0.22 | 5.01 | 0.83 | 5.26 |
| 26D2 | B. coagulans | − | − | − | 0.42 | 0.28 | 4.20 | 2.00 | 2.20 | 4.34 | 0.75 | 0.72 | 4.14 | 1.85 | 4.34 |
| 27C1 | | − | − | + | 0.12 | 0.26 | 5.04 | 1.25 | 1.10 | 5.66 | 0.11 | 0.18 | 4.99 | 0.65 | 5.49 |
| 27C2 | | − | − | + | 0.14 | 0.17 | 5.00 | 0.60 | 1.15 | 5.65 | 0.13 | 0.22 | 4.96 | 0.63 | 5.46 |
| 27D1 | | − | − | + | 0.11 | 0.16 | 4.97 | 0.45 | 0.90 | 5.47 | 0.14 | 0.20 | 4.99 | 0.43 | 5.32 |
| 28C1 | | − | − | + | 0.13 | 0.18 | 4.96 | 0.70 | 1.25 | 5.50 | 0.15 | 0.23 | 4.99 | 0.65 | 5.49 |
| 28C2 | | − | − | + | 0.18 | 0.28 | 4.44 | 0.85 | 0.90 | 4.56 | 0.25 | 0.30 | 4.37 | 0.80 | 4.47 |
| 28D1 | | − | − | + | 0.07 | 0.16 | 5.00 | 0.35 | 0.78 | 5.51 | 0.23 | 0.33 | 4.34 | 0.95 | 6.19 |

TABLE 2-continued

Properties of all the Isolates

| | Stationary Phase Survival | | | | | Growth at pH 6.8 | | | | | | | | | | | |
|---|---|---|---|---|---|---|---|---|---|---|---|---|---|---|---|---|
| | LB (Glucose 1%), (microaerobic), pH 5.0 | | | | | LB Xylose (1%) | | | | | | LB Glucose (1%) | | | | |
| | O.D. 420 nm | | pH | CFU/ml | | Anaerobic | | | | Aerobic | | Anaerobic | | | | Aerobic | |
| | | | | | | O.D. 420 nm | | pH | O.D. 420 nm | | pH | O.D. 420 nm | | pH | O.D. 420 nm | | pH |
| Isolate | 24 hrs. | 48 hrs | 48 hrs | 24 hrs | 48 hrs | 24 hrs | 48 hrs | 48 hrs | 24 hrs | 48 hrs | 48 hrs | 24 hrs | 48 hrs | 48 hrs | 24 hrs | 48 hrs | 48 hrs |
| 17C2 | | | | | | 0.10 | 0.15 | 6.46 | 2.40 | 4.50 | 7.27 | 0.02 | 0.08 | 6.49 | 0.80 | 0.70 | 6.34 |
| 17C3 | | | | | | 0.04 | 0.08 | 6.41 | 0.60 | 1.05 | 6.19 | 0.04 | 0.09 | 6.49 | 0.80 | 0.60 | 6.38 |
| 17C4 | | | | | | 1.10 | 0.95 | 4.37 | 2.10 | 2.85 | 4.26 | 1.30 | 1.02 | 4.41 | 2.30 | 2.60 | 4.26 |
| 17C5 | | | | | | 1.00 | 0.77 | 4.27 | 2.50 | 2.15 | 4.34 | 1.20 | 1.13 | 4.30 | 2.10 | 2.40 | 4.28 |
| 17D1 | | | | | | 0.06 | 0.16 | 6.39 | 0.65 | 1.00 | 6.28 | 0.80 | 0.50 | 4.23 | 0.70 | 1.10 | 6.13 |
| 17D2 | | | | | | 1.15 | 0.95 | 4.46 | 2.10 | 1.30 | 4.42 | 1.15 | 1.25 | 4.38 | 2.60 | 3.10 | 4.27 |
| 17D3 | 1.78 | 1.78 | 4.30 | 8 × 10⁴ | nd | 0.88 | 0.55 | 4.35 | 2.60 | 3.00 | 4.60 | 1.50 | 1.28 | 4.31 | 2.75 | 2.80 | 4.26 |
| 17E1 | | | | | | 0.02 | 0.07 | 6.44 | 0.75 | 1.75 | 4.33 | 0.05 | 0.08 | 6.54 | 0.85 | 3.30 | 5.74 |
| 17E2 | | | | | | 0.02 | 0.08 | 6.45 | 0.70 | 0.90 | 6.21 | 1.21 | 1.12 | 4.34 | 1.00 | 1.90 | 4.78 |
| 18C1 | | | | | | 0.03 | 0.06 | 6.46 | 0.70 | 0.70 | 6.25 | 0.02 | 0.06 | 6.53 | 0.80 | 0.70 | 6.40 |
| 18C2 | 1.43 | 1.40 | 4.24 | 1.8 × 10⁵ | nd | 1.13 | 0.83 | 4.36 | 2.25 | 3.30 | 4.30 | 1.17 | 1.44 | 4.32 | 2.25 | 2.70 | 4.29 |
| 18C4 | | | | | | 0.05 | 0.12 | 6.37 | 0.85 | 1.35 | 6.32 | 0.05 | 0.10 | 6.44 | 0.70 | 1.15 | 6.06 |
| 18C5 | | | | | | 0.90 | 0.72 | 4.42 | 2.10 | 2.35 | 4.44 | 1.48 | 1.23 | 4.42 | 2.25 | 2.30 | 4.39 |
| 18C6 | | | | | | 0.44 | 0.40 | 4.42 | 1.15 | 1.25 | 4.43 | 0.72 | 0.48 | 4.57 | 0.98 | 1.10 | 4.49 |
| 18D1 | | | | | | 0.93 | 0.98 | 4.29 | 2.30 | 2.90 | 4.45 | 1.40 | 1.13 | 4.33 | 2.50 | 2.55 | 4.56 |
| 18D4 | | | | | | 0.05 | 0.09 | 5.85 | 0.50 | 0.60 | 6.34 | 0.80 | 1.08 | 4.27 | 2.10 | 2.20 | 4.56 |
| 18E1 | | | | | | 0.06 | 0.10 | 6.35 | 0.83 | 1.03 | 6.07 | 0.07 | 0.09 | 6.38 | 0.85 | 1.08 | 5.92 |
| 18E2 | | | | | | 0.06 | 0.10 | 6.40 | 0.80 | 1.03 | 6.10 | 0.07 | 0.07 | 6.45 | 0.75 | 1.03 | 5.95 |
| 18E3 | | | | | | 0.05 | 0.09 | 6.39 | 0.98 | 1.00 | 6.11 | 0.09 | 0.12 | 6.43 | 0.90 | 1.18 | 5.90 |
| 19C1 | | | | | | 0.38 | 0.65 | 4.46 | 1.55 | 1.55 | 4.30 | 0.55 | 0.65 | 4.48 | 1.25 | 1.30 | 4.25 |
| 19D2 | | | | | | 0.05 | 0.30 | 5.05 | 0.73 | 0.45 | 6.50 | 0.90 | 1.10 | 4.31 | 2.40 | 3.25 | 4.43 |
| 19E2 | | | | | | 0.07 | 0.10 | 6.45 | 0.88 | 1.33 | 6.09 | 0.09 | 0.11 | 6.47 | 0.75 | 1.08 | 5.97 |
| 21B1 | | | | | | 0.04 | 0.06 | 6.45 | 0.60 | 1.10 | 6.35 | 0.03 | 0.04 | 6.50 | 0.65 | 1.38 | 5.58 |
| 21B2 | 1.43 | 1.45 | 4.33 | <10⁴ | nd | 1.25 | 1.28 | 4.39 | 2.25 | 3.00 | 4.28 | 1.00 | 1.15 | 4.34 | 2.55 | 3.60 | 4.20 |
| 21B3 | | | | | | 0.06 | 0.09 | 6.32 | 0.95 | 0.85 | 6.19 | 0.05 | 0.07 | 6.49 | 0.70 | 1.35 | 5.81 |
| 21B4 | | | | | | 0.01 | 0.04 | 6.36 | 0.58 | 0.63 | 6.23 | 0.11 | 0.75 | 4.28 | 0.55 | 0.73 | 5.86 |
| 21C3 | | | | | | 0.24 | 0.30 | 4.60 | 1.20 | 1.80 | 4.60 | 0.40 | 0.58 | 4.50 | 1.75 | 2.75 | 4.56 |
| 21C4 | | | | | | 0.07 | 0.14 | 6.34 | 1.38 | 2.15 | 4.29 | 0.07 | 0.13 | 6.42 | 0.75 | 1.20 | 6.13 |
| 21D2 | | | | | | 0.21 | 0.25 | 4.62 | 1.08 | 1.55 | 4.75 | 0.35 | 0.37 | 4.50 | 1.10 | 1.03 | 4.64 |
| 21D5 | | | | | | 0.07 | 0.39 | 4.70 | 1.00 | 0.88 | 6.70 | 0.10 | 0.11 | 6.37 | 0.55 | 1.35 | 5.53 |
| 21D6 | | | | | | 0.09 | 0.19 | 6.36 | 1.10 | 1.38 | 6.95 | 0.07 | 0.15 | 6.34 | 0.75 | 1.20 | 6.13 |
| 22C1 | | | | | | 0.04 | 0.09 | 6.04 | 0.78 | 1.25 | 5.80 | 0.22 | 0.24 | 5.27 | 1.10 | 1.95 | 5.23 |
| 22C2 | | | | | | 0.07 | 0.11 | 6.22 | 0.73 | 0.83 | 5.52 | 0.15 | 0.15 | 5.45 | 1.18 | 1.40 | 5.56 |
| 22C3 | | | | | | 0.10 | 0.18 | 6.32 | 0.60 | 1.08 | 5.75 | 0.09 | 0.14 | 6.39 | 1.40 | 1.95 | 5.86 |
| 22D1 | | | | | | 0.06 | 0.12 | 6.29 | 0.58 | 1.05 | 6.29 | 0.06 | 0.11 | 6.36 | 0.58 | 1.08 | 5.81 |
| 22D3 | | | | | | 0.32 | 0.58 | 4.34 | 1.05 | 1.20 | 4.42 | 0.70 | 0.83 | 4.50 | 1.05 | 1.53 | 4.57 |
| 23C1 | | | | | | 0.21 | 0.29 | 4.57 | 0.70 | 1.45 | 4.82 | 0.31 | 0.32 | 4.49 | 0.90 | 0.83 | 4.71 |
| 23C2 | | | | | | 0.17 | 0.23 | 4.73 | 0.85 | 0.85 | 4.67 | 0.34 | 0.35 | 4.59 | 1.30 | 1.20 | 4.55 |
| 23C3 | | | | | | 0.03 | 0.07 | 6.44 | 0.70 | 0.75 | 6.16 | 0.08 | 0.11 | 6.43 | 0.68 | 0.88 | 5.98 |
| 23D1 | | | | | | 0.05 | 0.08 | 6.47 | 0.70 | 1.10 | 6.12 | 0.10 | 0.10 | 6.45 | 3.30 | 4.60 | 7.09 |

TABLE 2-continued

Properties of all the Isolates

| Isolate | | | | | | | | | | | | |
|---------|------|------|------|------|------|------|------|------|------|------|------|------|
| 23D2 | 0.06 | 6.45 | 0.09 | 1.40 | 6.05 | 0.85 | 1.40 | 0.09 | 6.45 | 1.20 | 1.25 | 4.55 |
| 24B1 | 0.08 | 6.48 | 0.10 | 1.10 | 6.06 | 0.80 | 1.10 | 0.10 | 6.49 | 0.68 | 1.03 | 6.02 |
| 24C1 | 0.06 | 6.41 | 0.08 | 1.10 | 6.06 | 0.70 | 1.10 | 0.09 | 6.60 | 0.70 | 1.00 | 6.28 |
| 24D2 | 0.33 | 4.62 | 0.39 | 1.80 | 4.71 | 1.23 | 1.80 | 0.60 | 4.54 | 1.50 | 2.90 | 4.69 |
| 25C1 | 0.04 | 6.46 | 0.08 | 0.80 | 6.01 | 0.70 | 0.80 | 0.08 | 6.46 | 0.60 | 0.80 | 6.39 |
| 25D2 | 0.07 | 6.45 | 0.09 | 1.00 | 6.03 | 1.00 | 1.00 | 0.13 | 6.42 | 0.65 | 1.08 | 6.02 |
| 25D3 | 0.07 | 6.48 | 0.08 | 1.20 | 6.33 | 0.85 | 1.20 | 0.11 | 6.45 | 0.75 | 1.30 | 5.95 |
| 26C1 | 0.08 | 6.46 | 0.10 | 0.85 | 6.46 | 0.65 | 0.85 | 0.08 | 6.49 | 0.90 | 1.25 | 6.60 |
| 26D1 | 0.06 | 6.47 | 0.07 | 1.15 | 6.06 | 0.80 | 1.15 | 0.10 | 6.48 | 0.70 | 1.13 | 5.95 |
| 26D2 | 1.30 | 4.38 | 1.15 | 1.30 | 4.34 | 2.60 | 1.30 | 1.40 | 4.36 | 2.60 | 3.90 | 4.16 |
| 27C1 | 0.03 | 6.47 | 0.03 | 2.20 | 4.53 | 0.68 | 2.20 | 0.13 | 6.41 | 0.65 | 1.13 | 5.97 |
| 27C2 | 0.06 | 6.44 | 0.06 | 0.95 | 6.13 | 0.65 | 0.95 | 0.10 | 6.45 | 0.60 | 1.05 | 5.91 |
| 27D1 | 0.05 | 6.48 | 0.06 | 0.75 | 6.11 | 0.60 | 0.75 | 0.07 | 6.47 | 0.63 | 1.05 | 5.97 |
| 28C1 | 0.07 | 6.47 | 0.08 | 0.95 | 6.09 | 0.75 | 0.95 | 0.07 | 6.49 | 0.68 | 1.00 | 6.06 |
| 28C2 | 0.27 | 4.74 | 0.29 | 1.35 | 4.88 | 0.85 | 1.35 | 0.58 | 4.63 | 1.15 | 1.65 | 4.69 |
| 28D1 | 0.25 | 4.69 | 0.30 | 1.15 | 4.81 | 0.75 | 1.15 | 0.95 | 4.26 | 1.35 | 1.45 | 4.81 |

Additional values: 1.65, 1.60, 4.26, 1 × 10⁴, nd

Fermentation Products (48 hr) (pH not Controlled)

| | LB (1% Xylose), pH 6.8 | | | | | | | LB (1% Glucose), pH 6.8 | | | | | | |
|---|---|---|---|---|---|---|---|---|---|---|---|---|---|---|
| Isolate | Xylose mM | Succinate mM | Lactate mM | Formate mM | Fumarate μM | Acetate mM | Ethanol mM | Glucose mM | Succinate mM | Lactate mM | Formate mM | Fumarate μM | Acetate mM | Ethanol mM |
| 17C2 | | | | | | | | | | | | | | |
| 17C3 | | | | | | | | | | | | | | |
| 17C4 | 50.4 | 1.3 | 14.8 | 3.5 | | 2.6 | | 47.0 | | 19.0 | | | | |
| 17C5 | 49.4 | 1.2 | 19.4 | | | 2.4 | | 44.6 | | 21.9 | | | | |
| 17D1 | | | | | | | | | | | | | | |
| 17D2 | 49.7 | 1.1 | 15.1 | | | 2.8 | | 44.5 | | 19.4 | | | 2.0 | |
| 17D3 | 57.0 | 1.3 | 14.5 | | | 5.5 | | 46.6 | | 21.5 | | | | |
| 17E1 | | | | | | | | | | | | | | |
| 17E2 | | | | | | | | | | | | | | |
| 18C1 | | | | | | | | | | | | | | |
| 18C2 | 57.0 | 1.3 | 14.7 | | | 2.8 | | 46.3 | | 20.0 | | | | |
| 18C4 | | | | | | | | | | | | | | |
| 18C5 | 53.9 | 1.4 | 15.3 | | | 2.2 | 4.0 | 48.8 | | 19.5 | | | | |
| 18C6 | 58.5 | 1.3 | 17.4 | | | | | 51.0 | | 15.7 | | | | |
| 18D1 | 48.4 | 1.1 | 16.5 | | | 4.1 | | 47.0 | | 21.2 | | | | |
| 18D4 | | | | | | | | | | | | | | |
| 18E1 | | | | | | | | | | | | | | |
| 18E2 | | | | | | | | | | | | | | |
| 18E3 | | | | | | | | | | | | | | |
| 19C1 | | | | | | | | | | | | | | |
| 19D2 | | | | | | | | | | | | | | |
| 19E2 | | | | | | | | | | | | | | |
| 21B1 | | | | | | | | | | | | | | |
| 21B2 | 50.2 | 1.4 | 11.6 | 4.3 | 10.7 | 5.2 | * | 41.9 | 1.3 | 16.5 | | 11.9 | * | |
| 21B3 | | | | | | | | | | | | | | |
| 21B4 | | | | | | | | | | | | | | |

TABLE 2-continued

Properties of all the Isolates

| Isolate | Xylose mM | Lactate mM | Succinate mM | Acetate mM | Ethanol mM | Formate mM | Fumarate μM | Glucose mM | Lactate mM | Succinate mM | Acetate mM | Ethanol mM | Formate mM | Fumarate μM |
|---|---|---|---|---|---|---|---|---|---|---|---|---|---|---|
| 21C3 | | | | | | | | | | | | | | |
| 21C4 | | | | | | | | | | | | | | |
| 21D2 | | | | | | | | | | | | | | |
| 21D5 | | | | | | | | | | | | | | |
| 21D6 | | | | | | | | | | | | | | |
| 22C1 | | | | | | | | | | | | | | |
| 22C2 | | | | | | | | | | | | | | |
| 22C3 | | | | | | | | | | | | | | |
| 22D1 | | | | | | | | | | | | | | |
| 22D3 | 50.9 | 1.5 | 17.4 | | | 2.2 | | | | | | | | 2.2 |
| 23C1 | 57.9 | 1.2 | 14.3 | | | | | | | | | | | |
| 23C2 | | | | | | | | | | | | | | |
| 23C3 | | | | | | | | | | | | | | |
| 23D1 | | | | | | | | | | | | | | |
| 23D2 | | | | | | | | | | | | | | |
| 24B1 | | | | | | | | | | | | | | |
| 24C1 | | | | | | | | | | | | | | |
| 24D2 | | | | | | | | | | | | | | |
| 25C1 | | | | | | | | | | | | | | |
| 25D2 | | | | | | | | | | | | | | |
| 25D3 | | | | | | | | | | | | | | |
| 26C1 | | | | | | | | | | | | | | |
| 26D1 | | | | | | | | | | | | | | |
| 26D2 | 48.1 | 1.3 | 14.3 | | | 5.7 | 2.3 | | | | | | | |
| 27C1 | | | | | | | | | | | | | | |
| 27C2 | | | | | | | | | | | | | | |
| 27D1 | | | | | | | | | | | | | | |
| 28C1 | | | | | | | | | | | | | | |
| 28C2 | 54.0 | | 13.6 | | | * | | 40.0 | 1.3 | 17.5 | | | | |
| 28D1 | | | | | | | | 42.4 | 1.6 | 22.1 | | | | |

Fermentation Products (48 hr) (pHstat)

| Isolate | LB (1% Xylose), pH 5.0 | | | | | | | LB (1% Glucose), pH 5.0 | | | | | | |
|---|---|---|---|---|---|---|---|---|---|---|---|---|---|---|
| | Xylose mM | Lactate mM | Succinate mM | Acetate mM | Ethanol mM | Formate mM | Fumarate μM | Glucose mM | Lactate mM | Succinate mM | Acetate mM | Ethanol mM | Formate mM | Fumarate μM |
| 17C2 | | | | | | | | | | | | | | |
| 17C3 | | | | | | | | | | | | | | |
| 17C4 | | | | | | | | | | | | | | |
| 17C5 | 0.00 | 85.06 | 2.36 | 12.04 | 14.33 | 17.74 | 0.00 | 0.00 | 106.96 | 0.71 | 1.99 | 2.80 | 0.00 | 0.00 |
| 17D1 | | | | | | | | | | | | | | |
| 17D2 | | | | | | | | | | | | | | |
| 17D3 | 0.00 | 83.68 | 1.99 | 16.67 | 7.59 | 0.00 | 0.00 | 0.00 | 67.13 | 0.79 | 6.01 | 0.00 | 0.00 | 0.00 |
| 17E1 | | | | | | | | | | | | | | |
| 17E2 | | | | | | | | | | | | | | |
| 18C1 | | | | | | | | | | | | | | |
| 18C2 | 0.00 | 88.00 | 2.57 | 11.95 | 13.64 | 14.31 | 0.00 | 0.00 | 108.60 | 0.83 | 3.28 | 2.48 | 0.00 | 0.00 |
| 18C4 | | | | | | | | | | | | | | |

TABLE 2-continued

Properties of all the Isolates

| Isolate | | | | | | | | | | | | |
|---|---|---|---|---|---|---|---|---|---|---|---|---|
| 18C5 | | | | | | | | | | | | |
| 18C6 | | | | | | | | | | | | |
| 18D1 | | | | | | | | | | | | |
| 18D4 | | | | | | | | | | | | |
| 18E1 | | | | | | | | | | | | |
| 18E2 | | | | | | | | | | | | |
| 18E3 | | | | | | | | | | | | |
| 19C1 | | | | | | | | | | | | |
| 19D2 | | | | | | | | | | | | |
| 19E2 | | | | | | | | | | | | |
| 21B1 | | | | | | | | | | | | |
| 21B2 | 0.00 | 79.67 | 4.10 | 21.93 | 9.55 | 7.23 | 0.00 | 89.50 | 1.63 | 7.42 | 2.15 | 0.00 |
| 21B3 | | | | | | | | | | | | |
| 21B4 | | | | | | | | | | | | |
| 21C3 | | | | | | | | | | | | |
| 21C4 | | | | | | | | | | | | |
| 21D2 | | | | | | | | | | | | |
| 21D5 | | | | | | | | | | | | |
| 21D6 | | | | | | | | | | | | |
| 22C1 | | | | | | | | | | | | |
| 22C2 | | | | | | | | | | | | |
| 22C3 | | | | | | | | | | | | |
| 22D1 | | | | | | | | | | | | |
| 22D3 | | | | | | | | | | | | |
| 23C1 | | | | | | | | | | | | |
| 23C2 | | | | | | | | | | | | |
| 23C3 | | | | | | | | | | | | |
| 23D1 | | | | | | | | | | | | |
| 23D2 | | | | | | | | | | | | |
| 24B1 | | | | | | | | | | | | |
| 24C1 | | | | | | | | | | | | |
| 24D2 | | | | | | | | | | | | |
| 25C1 | | | | | | | | | | | | |
| 25D2 | | | | | | | | | | | | |
| 25D3 | | | | | | | | | | | | |
| 26C1 | | | | | | | | | | | | |
| 26D1 | 0.00 | 87.47 | 2.27 | 24.42 | 9.28 | 2.68 | 0.00 | 107.47 | 1.06 | 1.71 | 3.01 | 0.00 |
| 26D2 | | | | | | | | | | | | |
| 27C1 | | | | | | | | | | | | |
| 27C2 | | | | | | | | | | | | |
| 27D1 | | | | | | | | | | | | |
| 28C1 | | | | | | | | | | | | |
| 28C2 | | | | | | | | | | | | |
| 28D1 | | | | | | | | | | | | |

TABLE 2-continued

Properties of all the Isolates

Anaerobic Growth

| Isolate | LB Glucose (1%), pH 4.5 | | | LB Xylose (1%), pH 4.5 | | | MS (0.1% YE) (Xylose 1%), pH 5 | | | MS (0.1% YE) (Glucose 1%), pH 5 | | | HCH 10% CSL 1%, pH 5 | | |
|---|---|---|---|---|---|---|---|---|---|---|---|---|---|---|---|
| | O.D. 420 nm | | pH | O.D. 420 nm | | pH | O.D. 420 nm | | pH | O.D. 420 nm | | pH | O.D. 420 nm | | pH |
| | 24 hrs | 48 hrs | 48 hrs | 24 hrs | 48 hrs | 48 hrs | 24 hrs | 48 hrs | 48 hrs | 24 hrs | 48 hrs | 48 hrs | 24 hrs | 48 hrs | 48 hrs |
| 17C2 | | | | | | | | | | | | | | | |
| 17C3 | | | | | | | | | | | | | | | |
| 17C4 | 0.23 | 0.32 | 4.22 | 0.16 | 0.26 | 4.23 | 0.21 | 0.21 | 4.41 | 0.03 | 0.05 | 4.46 | 0.21 | 0.35 | 4.11 |
| 17C5 | 0.27 | 0.42 | 4.15 | 0.21 | 0.27 | 4.21 | 0.36 | 0.31 | 4.50 | 0.12 | 0.13 | 4.48 | 0.12 | 0.26 | 4.14 |
| 17D1 | | | | | | | | | | | | | | | |
| 17D2 | 0.27 | 0.44 | 4.05 | 0.13 | 0.20 | 4.22 | 0.25 | 0.22 | 4.35 | 0.05 | 0.09 | 4.54 | 0.14 | 0.28 | 4.15 |
| 17D3 | 0.10 | 0.32 | 4.22 | 0.10 | 0.16 | 4.24 | 0.19 | 0.19 | 4.45 | 0.08 | 0.07 | 4.59 | 0.04 | 0.21 | 4.15 |
| 17E1 | | | | | | | | | | | | | | | |
| 17E2 | | | | | | | | | | | | | | | |
| 18C1 | 0.21 | 0.32 | 4.23 | 0.21 | 0.23 | 4.28 | 0.19 | 0.21 | 4.33 | 0.07 | 0.08 | 4.54 | 0.25 | 0.37 | 4.10 |
| 18C2 | | | | | | | | | | | | | | | |
| 18C4 | | | | | | | | | | | | | | | |
| 18C5 | 0.07 | 0.12 | 4.39 | 0.07 | 0.18 | 4.41 | 0.40 | 0.50 | 4.61 | 0.05 | 0.07 | 4.60 | 0.10 | 0.24 | 4.14 |
| 18C6 | 0.01 | 0.02 | 4.44 | 0.02 | 0.03 | 4.45 | 0.20 | 0.10 | 4.41 | 0.10 | 0.12 | 4.48 | 0.00 | 0.24 | 4.15 |
| 18D1 | 0.02 | 0.09 | 4.45 | 0.00 | 0.00 | 4.45 | 0.17 | 0.13 | 4.35 | 0.06 | 0.05 | 4.59 | 0.02 | 0.02 | 4.84 |
| 18D4 | | | | | | | | | | | | | | | |
| 18E1 | | | | | | | | | | | | | | | |
| 18E2 | | | | | | | | | | | | | | | |
| 18E3 | | | | | | | | | | | | | | | |
| 19C1 | | | | | | | | | | | | | | | |
| 19D2 | | | | | | | | | | | | | | | |
| 19E2 | | | | | | | | | | | | | | | |
| 21B1 | | | | | | | | | | | | | | | |
| 21B2 | 0.02 | 0.16 | 4.24 | 0.09 | 0.17 | 4.35 | 0.17 | 0.25 | 4.57 | 0.04 | 0.06 | 4.64 | 0.10 | 0.11 | 4.24 |
| 21B3 | | | | | | | | | | | | | | | |
| 21B4 | | | | | | | | | | | | | | | |
| 21C3 | | | | | | | | | | | | | | | |
| 21C4 | | | | | | | | | | | | | | | |
| 21D2 | | | | | | | | | | | | | | | |
| 21D5 | | | | | | | | | | | | | | | |
| 21D6 | | | | | | | | | | | | | | | |
| 22C1 | 0.02 | 0.00 | 4.44 | 0.02 | 0.00 | 4.43 | 0.06 | 0.09 | 4.54 | 0.03 | 0.02 | 4.47 | 0.03 | 0.00 | 4.49 |
| 22C2 | | | | | | | | | | | | | | | |
| 22C3 | | | | | | | | | | | | | | | |
| 22D1 | | | | | | | | | | | | | | | |
| 22D3 | | | | | | | | | | | | | | | |
| 23C1 | | | | | | | | | | | | | | | |
| 23C2 | | | | | | | | | | | | | | | |
| 23C3 | | | | | | | | | | | | | | | |
| 23D1 | | | | | | | | | | | | | | | |
| 23D2 | | | | | | | | | | | | | | | |

TABLE 2-continued

Properties of all the Isolates

| Isolate | LB (Glucose 1%, pH 6.8) | | | | | | | | LB (Glucose 1%, pH 5.0) | | | | | | | | 20% HCH 0.1% YE/Glu pH 5.0[v] plates (48 hrs) | 25% HCH 0.1% YE/Glu pH 5.0 plates (48 hrs) | 50% HCH overlimed 0.1% YE/Glu pH 5.0[v] plates (48 hrs) |
|---|---|---|---|---|---|---|---|---|---|---|---|---|---|---|---|---|---|---|---|
| | 0% Ethanol O.D. 420 nm | | 4% Ethanol(w/w) O.D. 420 nm | | 4.5% Ethanol(w/w) O.D. 420 nm | | 5% Ethanol(w/w) O.D. 420 nm | | 0% Ethanol O.D. 420 nm | | 4% Ethanol(w/w) O.D. 420 nm | | 4.5% Ethanol(w/w) O.D. 420 nm | | 5% Ethanol(w/w) O.D. 420 nm | | | | |
| | 24 hrs | 48 hrs | 24 hrs | 48 hrs | 24 hrs | 48 hrs | 24 hrs | 48 hrs | 24 hrs | 48 hrs | 24 hrs | 48 hrs | 24 hrs | 48 hrs | 24 hrs | 48 hrs | | | |
| 24B1 | | | | | | | | | | | | | | | | | | | |
| 24C1 | | | | | | | | | | | | | | | | | | | |
| 24D2 | | | | | | | | | | | | | | | | | | | |
| 25C1 | | | | | | | | | | | | | | | | | | | |
| 25D2 | | | | | | | | | | | | | | | | | | | |
| 25D3 | | | | | | | | | | | | | | | | | | | |
| 26C1 | | | | | | | | | | | | | | | | | | | |
| 26D1 | | | | | | | | | | | | | | | | | | | |
| 26D2 | 0.23 | 0.26 | 4.24 | 0.17 | 0.25 | 4.35 | 0.13 | 4.50 | 0.10 | 0.11 | 4.51 | 0.25 | 0.31 | 4.19 | | | | | |
| 27C1 | | | | | | | | | | | | | | | | | | | |
| 27C2 | | | | | | | | | | | | | | | | | | | |
| 27D1 | | | | | | | | | | | | | | | | | | | |
| 28C1 | | | | | | | | | | | | | | | | | | | |
| 28C2 | | | | | | | | | | | | | | | | | | | |
| 28D1 | 0.06 | 0.03 | 4.43 | 0.10 | 0.17 | 4.46 | 0.12 | 5.01 | 0.15 | 0.19 | 5.07 | 0.06 | 0.13 | 4.51 | | | | | |
| 17C2 | | | | | | | | | | | | | | | | | | | |
| 17C3 | | | | | | | | | | | | | | | | | | | |
| 17C4 | | | | | | | | | | | | | | | | | | | |
| 17C5 | 1.05 | 1.05 | 0.03 | 0.09 | | | 0.04 | 0.05 | 0.64 | 0.70 | 0.16 | 0.17 | 0.09 | 0.13 | 0.04 | 0.05 | − | − | − |
| 17D1 | | | | | | | | | | | | | | | | | | | |
| 17D2 | | | | | | | | | | | 0.12 | 0.13 | 0.08 | 0.09 | 0.05 | 0.07 | + | + | + |
| 17D3 | 0.75 | 0.85 | 0.14 | 0.37 | 0.04 | 0.03 | 0.03 | 0.04 | 0.60 | 0.70 | | | | | | | − | − | − |
| 17E1 | | | | | | | | | | | | | | | | | | | |
| 17E2 | | | | | | | | | | | | | | | | | | | |
| 18C1 | | | | | | | | | 0.45 | 0.50 | 0.14 | 0.15 | 0.12 | 0.11 | 0.09 | 0.07 | + | + | + |
| 18C2 | | | | | | | | | | | | | | | | | | | |
| 18C4 | | | | | | | | | | | | | | | | | | | |
| 18C5 | | | | | | | | | | | | | | | | | | | |
| 18C6 | | | | | | | | | | | | | | | | | + | + | + |
| 18D1 | | | | | | | | | | | | | | | | | | | |
| 18D4 | | | | | | | | | | | | | | | | | | | |
| 18E1 | | | | | | | | | | | | | | | | | | | |
| 18E2 | | | | | | | | | | | | | | | | | | | |
| 18E3 | | | | | | | | | | | | | | | | | | | |
| 19C1 | | | | | | | | | | | | | | | | | ‡ | − | − |
| 19D2 | | | | | | | | | | | | | | | | | ‡ | − | − |
| 19E2 | | | | | | | | | | | | | | | | | | | |
| 21B1 | 0.65 | 0.80 | 0.04 | 0.58 | 0.05 | 0.03 | 0.03 | 0.03 | 0.50 | 0.50 | 0.13 | 0.15 | 0.05 | 0.05 | 0.04 | 0.03 | + | − | − |
| 21B2 | | | | | | | | | | | | | | | | | | | |
| 21B3 | | | | | | | | | | | | | | | | | | | |
| 21B4 | | | | | | | | | | | | | | | | | − | − | − |

TABLE 2-continued

Properties of all the Isolates

| | Aerobic (pH 5.0) | | | | | | | | | | | | Antibiotic Sensitivity | | | |
|---|---|---|---|---|---|---|---|---|---|---|---|---|---|---|---|---|
| | 25% HCH (0.1% YE) | | | 10% HCH (1% CSL) | | | 25% Overlimed HCH | | | 50% Overlimed HCH (0.1% YE) | | | Tetracycline | Chloramphenicol | Kanamycin | Ampicillin |
| | CFU/ml | | pH | CFU/ml | | pH | CFU/ml | | pH | CFU/ml | | pH | 20 mg/L | 30 mg/L | 50 mg/L | 100 mg/L |
| Isolate | 24 hrs | 48 hrs | 48 hrs | 24 hrs | 48 hrs | 48 hrs | 24 hrs | 48 hrs | 48 hrs | 24 hrs | 48 hrs | 48 hrs | | | | |
| 21C3 | | | | | | | | | | | | | | − | − | − |
| 21C4 | | | | | | | | | | | | | | − | − | − |
| 21D2 | | | | | | | | | | | | | | + | − | − |
| 21D5 | | | | | | | | | | | | | | − | − | − |
| 21D6 | | | | | | | | | | | | | | − | − | − |
| 22C1 | | | | | | | | | | | | | | − | − | − |
| 22C2 | | | | | | | | | | | | | | − | − | − |
| 22C3 | | | | | | | | | | | | | | − | − | − |
| 22D1 | | | | | | | | | | | | | | − | − | − |
| 22D3 | | | | | | | | | | | | | | ++ | − | − |
| 23C1 | | | | | | | | | | | | | | + | − | − |
| 23C2 | | | | | | | | | | | | | | − | − | − |
| 23C3 | | | | | | | | | | | | | | − | − | − |
| 23D1 | | | | | | | | | | | | | | − | − | − |
| 23D2 | | | | | | | | | | | | | | + | − | − |
| 24B1 | | | | | | | | | | | | | | − | − | − |
| 24C1 | | | | | | | | | | | | | | − | − | − |
| 24D2 | | | | | | | | | | | | | | ++ | − | − |
| 25C1 | | | | | | | | | | | | | | + | − | − |
| 25D2 | | | | | | | | | | | | | | − | − | − |
| 25D3 | | | | | | | | | | | | | | ++ | − | − |
| 26C1 | | | | | | | | | | | | | | + | − | − |
| 26D1 | 1.15 | | | | | | | | | | | | | − | − | − |
| 26D2 | | 1.05 | 0.03 | 0.23 | 0.06 | 0.12 | 0.03 | 0.02 | 0.50 | 0.50 | 0.03 | 0.11 | | − | − | − |
| 27C1 | | | | | | | | | | 0.03 | 0.05 | 0.04 | | − | − | − |
| 27D1 | | | | | | | | | | | | | | − | − | − |
| 28C1 | | | | | | | | | | | | | | − | − | − |
| 28C2 | | | | | | | | | | | | | | ++ | − | − |
| 28D1 | | | | | | | | | | | | | | − | − | − |
| 17C2 | | | | | | | | | | | | | | | | |
| 17C3 | | | | | | | | | | | | | | | | |
| 17C4 | | | | | | | | | | | | | | | | |
| 17C5 | | | | | | | | | | | | | | | | |
| 17D1 | | | | | | | | | | | | | | | | |
| 17D2 | | | | | | | | | | | | | | | | |
| 17D3 | | | | | | | | | | | | | | − | − | − |
| 17E1 | | | | | | | | | | | | | | | | |
| 17E2 | | | | | | | | | | | | | | | | |
| 18C1 | | | | | | | | | | | | | − | | − | − |
| 18C2 | | | | | | | | | | | | | − | | − | − |

TABLE 2-continued

Properties of all the Isolates

| | | | | | |
|---|---|---|---|---|---|
| 18C4 | | | | | |
| 18C5 | | | | | |
| 18C6 | | | | | |
| 18D1 | | | | | |
| 18D4 | | | | | |
| 18E1 | | | | | |
| 18E2 | | | | | |
| 18E3 | | | | | |
| 19C1 | | | | | |
| 19D2 | | | | | |
| 19E2 | | | | | |
| 21B1 | | | | | |
| 21B2 | | | — | | — |
| 21B3 | | | | | |
| 21B4 | | | | | |
| 21C3 | | | | | |
| 21C4 | | | | | |
| 21D2 | | | | | |
| 21D5 | | | | | |
| 21D6 | | | | | |
| 22C1 | | | | | |
| 22C2 | | | | | |
| 22C3 | | | | | |
| 22D1 | | | | | |
| 22D3 | | | — | | — |
| 23C1 | | | | | |
| 23C2 | | | | | |
| 23C3 | | | | | |
| 23D1 | | | | | |
| 23D2 | | | | | |
| 24B1 | | | | | |
| 24C1 | | | | | |
| 24D2 | | | | | |
| 25C1 | | | | | |
| 25D2 | | | | | |
| 25D3 | | | | | |
| 26C1 | | | | | |
| 26D1 | | | | | |
| 26D2 | | | | | |
| 27C1 | | | | | |
| 27C2 | | | | | |
| 27D1 | | | — | | — |
| 28C1 | | | | | |
| 28C2 | | | | | |
| 28D1 | | | — | | — |

TABLE 2-continued

Properties of all the Isolates

| Isolate | Identification[a] (16S rRNA) | Xylanase 72 hr | CMCase 72 hr | Cellobiose MS (0.1% YE) pH 5.0 72 hr | Growth at pH 5.0 LB Xylose (1%) Anaerobic O.D. 420 nm 24 hrs | 48 hrs | pH 48 hrs | Aerobic O.D. 420 nm 24 hrs | 48 hrs | pH 48 hrs | LB Glucose (1%) Anaerobic O.D. 420 nm 24 hrs | 48 hrs | pH 48 hrs | Aerobic O.D. 420 nm 24 hrs | 48 hrs | pH 48 hrs |
|---|---|---|---|---|---|---|---|---|---|---|---|---|---|---|---|---|
| 29C1 | | − | − | + | 0.07 | 0.09 | 4.91 | 0.85 | 1.70 | 4.14 | 0.07 | 0.23 | 4.47 | 0.85 | 0.95 | 4.33 |
| 29D1 | | − | − | + | 0.09 | 0.12 | 4.53 | 0.73 | 1.20 | 4.37 | 0.10 | 0.12 | 4.49 | 0.55 | 0.58 | 4.38 |
| 29D2 | | − | − | + | 0.11 | 0.17 | 4.95 | 0.12 | 2.20 | 4.20 | 0.15 | 0.24 | 4.99 | 0.70 | 1.40 | 5.38 |
| 29D3 | | − | − | + | 0.18 | 0.15 | 5.07 | 0.88 | 1.30 | 5.54 | 0.09 | 0.23 | 5.06 | 0.88 | 1.55 | 5.30 |
| 29D5 | | − | − | + | 0.15 | 0.22 | 4.52 | 1.25 | 1.30 | 4.55 | 0.35 | 0.37 | 4.34 | 1.35 | 1.30 | 4.46 |
| 30C1 | | − | − | + | 0.06 | 0.10 | 5.06 | 0.60 | 0.93 | 5.48 | 0.10 | 0.13 | 5.10 | 0.48 | 1.15 | 5.59 |

| Isolate | Stationary Phase Survival LB (Glucose 1%), (microaerobic), pH 5.0 O.D. 420 nm 24 hrs. | 48 hrs | pH 48 hrs | CFU/ml 24 hrs | 48 hrs | Growth at pH 6.8 LB Xylose (1%) Anaerobic O.D. 420 nm 24 hrs | 48 hrs | pH 48 hrs | Aerobic O.D. 420 nm 24 hrs | 48 hrs | pH 48 hrs | LB Glucose (1%) Anaerobic O.D. 420 nm 24 hrs | 48 hrs | pH 48 hrs | Aerobic O.D. 420 nm 24 hrs | 48 hrs | pH 48 hrs |
|---|---|---|---|---|---|---|---|---|---|---|---|---|---|---|---|---|---|
| 29C1 | | | | | | 0.01 | 0.00 | 6.34 | 0.06 | 0.35 | 6.58 | 0.70 | 0.75 | 4.54 | 1.28 | 1.23 | 4.44 |
| 29D1 | | | | | | 0.00 | 0.00 | 6.52 | 1.50 | 2.90 | 4.79 | 0.02 | 0.30 | 4.45 | 1.05 | 1.40 | 4.39 |
| 29D2 | | | | | | 0.08 | 0.10 | 6.48 | 1.00 | 1.25 | 6.00 | 0.07 | 0.08 | 6.45 | 1.07 | 1.35 | 6.21 |
| 29D3 | | | | | | 0.08 | 0.06 | 6.47 | 0.95 | 1.05 | 6.07 | 0.06 | 0.09 | 6.45 | 0.58 | 0.93 | 6.01 |
| 29D5 | | | | | | 0.29 | 0.34 | 4.73 | 1.05 | 1.73 | 4.79 | 0.55 | 0.60 | 4.58 | 1.15 | 1.85 | 4.70 |
| 30C1 | | | | | | 0.05 | 0.10 | 6.46 | 0.60 | 0.70 | 6.15 | 0.03 | 0.06 | 6.51 | 0.65 | 0.63 | 0.06 |

Fermentation Products (48 hr) (pH not Controlled)

| Isolate | LB (1% Xylose), pH 6.8 Xylose mM | Succinate mM | Lactate mM | Formate mM | Acetate mM | Ethanol mM | Fumarate μM | LB (1% Glucose), pH 6.8 Glucose mM | Succinate mM | Lactate mM | Formate mM | Acetate mM | Ethanol mM | Fumarate μM |
|---|---|---|---|---|---|---|---|---|---|---|---|---|---|---|
| 29C1 | | | | | | | | | | | | | | |
| 29D1 | | | | | | | | | | | | | | |
| 29D2 | | | | | | | | | | | | | | |
| 29D3 | | | | | | | | | | | | | | |
| 29D5 | 53.4 | | 12.3 | | 2.0 | | | 43.8 | 1.7 | 14.1 | | | | |
| 30C1 | | | | | | | | | | | | | | |

TABLE 2-continued

Properties of all the Isolates

Fermentation Products (48 hr) (pHstat)

LB (1% Xylose), pH 5.0

| Isolate | Xylose mM | Lactate mM | Succinate mM | Acetate mM | Ethanol mM | Formate mM | Fumarate μM |
|---|---|---|---|---|---|---|---|
| 29C1 | | | | | | | |
| 29D1 | | | | | | | |
| 29D2 | | | | | | | |
| 29D3 | | | | | | | |
| 29D5 | | | | | | | |
| 30C1 | | | | | | | |

LB (1% Glucose), pH 5.0

| | Glucose mM | Lactate mM | Succinate mM | Acetate mM | Ethanol mM | Formate mM | Fumarate μM |
|---|---|---|---|---|---|---|---|
| 29C1 | | | | | | | |
| 29D1 | | | | | | | |
| 29D2 | | | | | | | |
| 29D3 | | | | | | | |
| 29D5 | | | | | | | |
| 30C1 | | | | | | | |

Anaerobic Growth

| Isolate | LB Glucose (1%), pH 4.5 O.D. 420 nm 24 hrs | 48 hrs | pH 48 hrs | LB Xylose (1%), pH 4.5 O.D. 420 nm 24 hrs | 48 hrs | pH 48 hrs | MS (0.1% YE) (Xylose 1%), pH 5 O.D. 420 nm 24 hrs | 48 hrs | pH 48 hrs | MS (0.1% YE) (Glucose 1%), pH 5 O.D. 420 nm 24 hrs | 48 hrs | pH 48 hrs |
|---|---|---|---|---|---|---|---|---|---|---|---|---|
| 29C1 | | | | | | | | | | | | |
| 29D1 | | | | | | | | | | | | |
| 29D2 | | | | | | | | | | | | |
| 29D3 | | | | | | | | | | | | |
| 29D5 | 0.03 | 0.00 | 4.43 | 0.01 | 0.01 | 4.45 | 0.12 | 0.15 | 4.57 | 0.03 | 0.06 | 4.86 |
| 30C1 | | | | | | | | | | 0.05 | 0.08 | 4.67 |

| Isolate | LB (Glucose 1%, pH 6.8) 0% Ethanol O.D. 420 nm 24 hrs 48 hrs | 4.5% Ethanol(w/w) O.D. 420 nm 24 hrs 48 hrs | LB (Glucose 1%, pH 5.0) 0% Ethanol O.D. 420 nm 24 hrs 48 hrs | 4.5% Ethanol(w/w) O.D. 420 nm 24 hrs 48 hrs | 5% Ethanol(w/w) O.D. 420 nm 24 hrs 48 hrs | HCH 10% CSL 1%, pH 5 O.D. 420 nm 24 hrs 48 hrs | pH 48 hrs |
|---|---|---|---|---|---|---|---|

50% HCH

| Isolate | 20% HCH 0.1% YE/Glu pH 5.0[v] plates (48 hrs) | 25% HCH 0.1% YE/Glu pH 5.0[v] plates (48 hrs) | overlimed 0.1% YE/Glu pH 5.0[v] plates (48 hrs) |
|---|---|---|---|
| 29C1 | +++ | − | − |
| 29D1 | − | − | − |
| 29D2 | − | − | − |
| 29D3 | − | − | − |
| 29D5 | − | − | − |
| 30C1 | − | − | − |

TABLE 2-continued

Properties of all the Isolates

| Isolate | 25% HCH, (0.1% YE) CFU/ml 24 hrs | 25% HCH, (0.1% YE) CFU/ml 48 hrs | 25% HCH, (0.1% YE) pH 48 hrs | Aerobic (pH 5.0) 10% HCH, (1% CSL) CFU/ml 24 hrs | 10% HCH, (1% CSL) CFU/ml 48 hrs | 10% HCH, (1% CSL) pH 48 hrs | 25% Overlimed HCH CFU/ml 24 hrs | 25% Overlimed HCH CFU/ml 48 hrs | 25% Overlimed HCH pH 48 hrs | 50% Overlimed HCH (0.1% YE) CFU/ml 24 hrs | 50% Overlimed HCH (0.1% YE) CFU/ml 48 hrs | 50% Overlimed HCH (0.1% YE) pH 48 hrs | Antibiotic Sensitivity Tetracycline 20 mg/L | Chloramphenicol 30 mg/L | Kanamycin 50 mg/L | Ampicillin 100 mg/L |
|---|---|---|---|---|---|---|---|---|---|---|---|---|---|---|---|---|
| 29C1 | | | | | | | | | | | | | | | | |
| 29D1 | | | | | | | | | | | | | | | | |
| 29D2 | | | | | | | | | | | | | | | | |
| 29D3 | | | | | | | | | | | | | | | | |
| 29D5 | | | | | | | | | | | | | | | | |
| 30C1 | | | | | | | | | | | | | | | | |

| Isolate | Identification[a] (16S rRNA) | Xylanase 72 hr | CMCase 72 hr | Cellobiose MS (0.1% YE) pH 5.0 72 hr | Growth at pH 5.0 LB Xylose (1%) Anaerobic O.D. 420 nm 24 hrs | Anaerobic O.D. 420 nm 48 hrs | Anaerobic pH 48 hrs | LB Xylose (1%) Aerobic O.D. 420 nm 24 hrs | Aerobic O.D. 420 nm 48 hrs | Aerobic pH 48 hrs | LB Glucose (1%) Anaerobic O.D. 420 nm 24 hrs | Anaerobic O.D. 420 nm 48 hrs | Anaerobic pH 48 hrs | LB Glucose (1%) Aerobic O.D. 420 nm 24 hrs | Aerobic O.D. 420 nm 48 hrs | Aerobic pH 48 hrs |
|---|---|---|---|---|---|---|---|---|---|---|---|---|---|---|---|---|
| 30D2 | | − | − | + | 0.09 | 0.14 | 5.06 | 0.75 | 1.05 | 5.60 | 0.09 | 0.15 | 5.12 | 0.68 | 1.08 | 5.60 |
| 30D3 | | − | − | + | 0.06 | 0.15 | 4.88 | 0.53 | 0.53 | 6.22 | 0.29 | 0.26 | 4.44 | 0.60 | 0.78 | 4.47 |
| 30D4 | | − | − | + | 0.15 | 0.22 | 5.06 | 0.63 | 0.90 | 5.73 | 0.08 | 0.12 | 5.12 | 0.55 | 0.93 | 5.75 |
| 31C1 | | − | − | + | 0.08 | 0.14 | 5.05 | 0.75 | 1.05 | 5.67 | 0.11 | 0.13 | 5.10 | 0.58 | 0.90 | 5.62 |
| 31C2 | | − | − | + | 0.06 | 0.08 | 4.96 | 0.63 | 0.95 | 5.52 | 0.08 | 0.08 | 5.01 | 0.58 | 1.05 | 4.93 |
| 31C3 | | − | − | + | 0.10 | 0.16 | 5.12 | 0.68 | 0.95 | 5.55 | 0.11 | 0.15 | 5.04 | 0.85 | 1.33 | 5.48 |
| 33D2 | | − | − | + | 0.29 | 0.32 | 4.30 | 1.35 | 1.70 | 4.46 | 0.45 | 0.43 | 4.39 | 1.30 | 2.30 | 4.27 |
| 33D4 | B. coagulans | − | − | − | 0.68 | 0.65 | 4.29 | 1.63 | 1.60 | 4.35 | 0.55 | 0.53 | 4.38 | 1.50 | 1.55 | 4.41 |
| 34D2 | B. coagulans | − | − | − | 0.55 | 0.60 | 4.21 | 1.35 | 1.15 | 4.36 | 0.60 | 0.58 | 4.41 | 1.75 | 1.75 | 4.35 |
| 34D3 | | − | − | + | 0.07 | 0.14 | 4.74 | 0.70 | 0.70 | 4.50 | 0.17 | 0.17 | 4.65 | 1.03 | 1.08 | 4.54 |
| 35C1 | | − | − | − | 0.16 | 0.22 | 4.62 | 1.10 | 1.08 | 4.54 | 0.28 | 0.29 | 4.50 | 1.13 | 2.05 | 4.42 |
| 35C3 | | − | − | + | 0.01 | 0.06 | 4.97 | 0.42 | 0.65 | 4.57 | 0.01 | 0.09 | 4.93 | 2.55 | 2.80 | 4.34 |
| 35D2 | B. coagulans | − | − | + | 0.63 | 0.15 | 4.43 | 1.70 | 1.83 | 4.59 | 0.23 | 0.43 | 4.53 | 1.08 | 2.05 | 4.45 |
| 35D3 | | − | − | + | 0.26 | 0.27 | 4.36 | 1.38 | 1.75 | 4.39 | 0.31 | 0.48 | 4.36 | 1.65 | 1.75 | 4.33 |
| 35D4 | | − | − | + | 0.22 | 0.23 | 4.60 | 0.95 | 0.95 | 4.60 | 0.30 | 0.28 | 4.48 | 1.30 | 1.40 | 4.52 |
| 35D5 | | − | − | − | 0.19 | 0.25 | 4.50 | 1.05 | 1.05 | 4.32 | 0.20 | 0.23 | 4.49 | 0.65 | 0.70 | 4.48 |
| 36D1A | | − | − | | 0.35 | 0.34 | 4.23 | 1.73 | 1.80 | 4.35 | 0.45 | 0.58 | 4.29 | 1.43 | 1.55 | 4.23 |
| 36D1B | | − | − | | 0.25 | 0.28 | 4.35 | 1.30 | 1.38 | 4.44 | 0.38 | 0.40 | 4.29 | 1.08 | 1.00 | 4.26 |
| 36D2 | B. coagulans | − | − | + | 0.48 | 0.43 | 4.33 | 1.63 | 2.53 | 4.29 | 0.48 | 0.45 | 4.41 | 1.23 | 1.50 | 4.42 |
| 37D3 | | − | − | + | 0.13 | 0.18 | 4.48 | 0.98 | 1.00 | 4.33 | 0.19 | 0.33 | 4.38 | 1.15 | 1.30 | 4.35 |
| 38C1 | | − | − | + | 0.10 | 0.13 | 4.49 | 0.75 | 0.80 | 4.57 | 0.22 | 0.26 | 4.45 | 0.70 | 0.75 | 4.42 |
| 38C2 | | − | − | + | 0.06 | 0.07 | 4.92 | 0.75 | 0.85 | 5.63 | 0.02 | 0.07 | 4.94 | 0.60 | 0.70 | 4.99 |
| 38C3 | B. coagulans | − | − | + | 0.24 | 0.25 | 4.40 | 1.70 | 1.80 | 4.44 | 0.45 | 0.43 | 4.34 | 1.35 | 1.75 | 4.42 |
| 38C4 | | − | + | + | 0.04 | 0.11 | 4.72 | 0.43 | 0.83 | 4.95 | 0.06 | 0.08 | 5.07 | 0.60 | 0.75 | 5.48 |
| 38C5 | | − | − | + | 0.04 | 0.07 | 4.69 | 1.00 | 2.05 | 4.41 | 0.11 | 0.18 | 4.53 | 0.80 | 0.83 | 4.53 |

TABLE 2-continued

Properties of all the Isolates

| Isolate | Survival | Anaerobic OD 420 nm 24 hrs | 48 hrs | pH 48 hrs | Aerobic OD 420 nm 24 hrs | 48 hrs | pH 48 hrs | Anaerobic OD 420 nm 24 hrs | 48 hrs | pH 48 hrs | Aerobic OD 420 nm 24 hrs | 48 hrs | pH 48 hrs |
|---|---|---|---|---|---|---|---|---|---|---|---|---|---|
|  |  | LB Xylose (1%) | | | | | | LB Glucose (1%) | | | | | |
| 38C6 | − | 0.13 | 0.21 | 4.52 | 0.98 | 1.05 | 4.50 | 0.15 | 0.26 | 4.49 | 1.00 | 1.10 | 4.41 |
| 38D5 | − | 0.33 | 0.35 | 4.39 | 1.50 | 1.65 | 4.42 | 0.30 | 0.55 | 4.36 | 2.45 | 4.30 | 4.38 |
| 39C2 | − | 0.08 | 0.13 | 4.57 | 1.05 | 1.10 | 4.58 | 0.18 | 0.31 | 4.45 | 1.05 | 1.20 | 4.55 |
| 39C3 | − | 0.00 | 0.00 | 4.94 | 0.80 | 0.00 | 5.02 | 0.15 | 0.35 | 4.43 | 0.90 | 1.10 | 4.50 |
| 39C4 | − | 0.07 | 0.05 | 4.94 | 0.00 | 0.98 | 6.31 | 0.16 | 0.22 | 4.59 | 1.20 | 1.33 | 4.64 |
| 39D1 | + | 0.39 | 0.65 | 4.34 | 2.30 | 2.40 | 4.50 | 0.34 | 0.60 | 4.30 | 1.85 | 1.90 | 4.34 |
| 39D2 | − | 0.00 | 0.00 | 4.95 | 1.15 | 1.75 | 4.44 | 0.02 | 0.02 | 4.99 | 0.00 | 0.00 | 4.99 |
| 39D3 | + | 0.00 | 0.04 | 4.96 | 0.41 | 0.45 | 4.74 | 0.00 | 0.02 | 5.01 | 0.03 | 0.08 | 5.04 |
| 40D2 | − | 0.00 | 0.00 | 4.80 | 1.35 | 2.30 | 4.47 | 0.00 | 0.00 | 4.58 | 1.35 | 2.70 | 4.47 |
| 41C2 | − | 0.07 | 0.12 | 4.57 | 1.10 | 1.15 | 4.52 | 0.11 | 0.30 | 4.43 | 1.05 | 1.20 | 4.51 |
| 41D4 | − | 0.14 | 0.20 | 4.64 | 0.85 | 1.65 | 4.40 | 0.19 | 0.33 | 4.47 | 0.90 | 1.50 | 4.43 |
| 42D1 | − | 0.07 | 0.11 | 4.52 | 1.05 | 1.03 | 4.33 | 0.27 | 0.42 | 4.37 | 1.20 | 1.30 | 4.37 |
| 42D2 | − | 0.20 | 0.18 | 4.56 | 1.05 | 1.55 | 4.41 | 0.17 | 0.32 | 4.46 | 0.45 | 0.90 | 4.41 |
| 42D3 | + | 0.11 | 0.12 | 4.39 | 1.28 | 1.13 | 4.24 | 0.23 | 0.23 | 4.46 | 0.85 | 0.80 | 4.42 |
| 43D1 | − | 0.18 | 0.16 | 4.90 | 1.10 | 0.78 | 5.48 | 0.08 | 0.11 | 4.92 | 0.40 | 0.73 | 4.79 |
| 43D2 | − | 0.09 | 0.09 | 4.51 | 0.50 | 0.80 | 4.54 | 0.25 | 0.30 | 4.45 | 0.68 | 0.70 | 4.58 |
| 43D3 | + | 0.08 | 0.12 | 4.51 | 0.80 | 0.80 | 4.54 | 0.24 | 0.26 | 4.42 | 0.83 | 0.85 | 4.42 |
| 44D2 | + | 0.14 | 0.16 | 4.54 | 1.00 | 1.00 | 4.46 | 0.24 | 0.26 | 4.42 | 0.65 | 0.73 | 4.49 |

Growth at pH 6.8

| Isolate | Stationary Phase Survival — LB (Glucose 1%), (microaerobic), pH 5.0 | | | | | | LB Xylose (1%) | | | | | | LB Glucose (1%) | | | | | |
|---|---|---|---|---|---|---|---|---|---|---|---|---|---|---|---|---|---|---|
|  | O.D. 420 nm 24 hrs | O.D. 420 nm 48 hrs | pH 48 hrs | CFU/ml 24 hrs | CFU/ml 48 hrs | | Anaerobic O.D. 420 nm 24 hrs | 48 hrs | pH 48 hrs | Aerobic O.D. 420 nm 24 hrs | 48 hrs | pH 48 hrs | Anaerobic O.D. 420 nm 24 hrs | 48 hrs | pH 48 hrs | Aerobic O.D. 420 nm 24 hrs | 48 hrs | pH 48 hrs |
| 30D2 |  |  |  |  |  |  | 0.02 | 0.05 | 6.48 | 0.68 | 1.13 | 6.24 | 0.05 | 0.05 | 6.48 | 0.70 | 1.20 | 6.12 |
| 30D3 |  |  |  |  |  |  | 0.00 | 0.00 | 6.53 | 0.00 | 0.00 | 6.54 | 0.00 | 0.00 | 6.71 | 0.00 | 0.00 | 6.71 |
| 30D4 |  |  |  |  |  |  | 0.08 | 0.11 | 6.51 | 0.55 | 1.00 | 6.32 | 0.03 | 0.04 | 6.53 | 0.55 | 0.93 | 6.21 |
| 31C1 |  |  |  |  |  |  | 0.03 | 0.06 | 6.52 | 0.53 | 0.93 | 6.28 | 0.06 | 0.06 | 6.49 | 0.65 | 1.08 | 6.26 |
| 31C2 |  |  |  |  |  |  | 0.06 | 0.11 | 6.37 | 0.48 | 1.05 | 6.23 | 0.06 | 0.07 | 6.37 | 0.53 | 0.85 | 6.02 |
| 31C3 |  |  |  |  |  |  | 0.07 | 0.11 | 6.41 | 0.58 | 0.85 | 6.22 | 0.05 | 0.07 | 6.46 | 0.60 | 1.08 | 6.06 |
| 33D2 |  |  |  |  |  |  | 0.88 | 0.85 | 4.39 | 1.55 | 1.80 | 4.40 | 1.03 | 1.03 | 4.37 | 1.75 | 1.53 | 4.35 |
| 33D4 | 1.70 | 1.70 | 4.41 | 1.4 × 10$^8$ | 1.6 × 10$^6$ |  | 1.05 | 1.13 | 4.52 | 1.95 | 1.90 | 4.57 | 1.15 | 1.15 | 4.41 | 1.93 | 1.95 | 4.45 |
| 34D2 | 1.58 | 1.48 | 4.25 | <10$^4$ | nd |  | 0.95 | 0.98 | 4.51 | 0.95 | 0.73 | 4.38 | 1.15 | 1.15 | 4.40 | 2.30 | 2.40 | 4.24 |
| 34D3 |  |  |  |  |  |  | 0.13 | 0.20 | 4.72 | 0.93 | 1.55 | 4.71 | 0.48 | 0.50 | 4.63 | 0.98 | 0.98 | 4.73 |
| 35C1 |  |  |  |  |  |  | 0.21 | 0.26 | 4.79 | 1.45 | 1.68 | 4.68 | 0.50 | 0.48 | 4.62 | 1.25 | 2.30 | 4.56 |
| 35C3 |  |  |  |  |  |  | 0.00 | 0.00 | 6.38 | 0.25 | 0.55 | 5.65 | 0.11 | 0.12 | 6.39 | 0.00 | 0.04 | 6.75 |
| 35D2 | 1.20 | 1.05 | 4.53 | <10$^4$ | nd |  | 0.78 | 0.93 | 4.63 | 1.60 | 1.70 | 4.45 | 1.03 | 0.98 | 4.52 | 1.95 | 2.08 | 4.48 |
| 35D3 |  |  |  |  |  |  | 0.63 | 1.00 | 4.38 | 1.80 | 1.70 | 4.50 | 1.13 | 1.30 | 4.33 | 2.40 | 3.63 | 4.75 |
| 35D4 |  |  |  |  |  |  | 0.29 | 0.45 | 4.79 | 1.25 | 1.63 | 4.77 | 0.40 | 0.58 | 4.63 | 1.38 | 2.25 | 4.75 |
| 36D5 |  |  |  |  |  |  | 0.26 | 0.27 | 4.60 | 1.03 | 1.18 | 4.32 | 0.55 | 0.50 | 4.57 | 0.93 | 1.08 | 4.33 |
| 36D1A |  |  |  |  |  |  | 0.95 | 0.90 | 4.41 | 1.85 | 2.55 | 4.40 | 1.13 | 1.18 | 4.29 | 1.73 | 1.83 | 4.29 |
| 36D1B | 1.50 | 1.40 | 4.40 | 1 × 10$^4$ | nd |  | 0.63 | 0.68 | 4.37 | 1.85 | 1.88 | 4.42 | 0.80 | 0.85 | 4.27 | 1.53 | 1.33 | 4.33 |
| 36D2 |  |  |  |  |  |  | 1.03 | 1.03 | 4.39 | 2.30 | 2.35 | 4.40 | 1.05 | 1.20 | 4.35 | 2.60 | 2.63 | 4.43 |
| 37D3 |  |  |  |  |  |  | 0.24 | 0.35 | 4.57 | 1.40 | 2.10 | 4.42 | 0.45 | 0.75 | 4.52 | 0.93 | 1.70 | 4.59 |
| 38C1 |  |  |  |  |  |  | 0.21 | 0.28 | 4.65 | 0.70 | 0.80 | 4.77 | 0.25 | 0.35 | 4.51 | 0.90 | 0.80 | 4.69 |

TABLE 2-continued

Properties of all the Isolates

| Isolate | 1 | 2 | 3 | 4 | 5 | 6 | 7 | 8 | 9 | 10 | 11 |
|---|---|---|---|---|---|---|---|---|---|---|---|
| 38C2 | 0.06 | 0.07 | 0.60 | 1.10 | 6.07 | 0.10 | 0.15 | 6.35 | 0.60 | 0.95 | 5.82 |
| 38C3 | 0.73 | 0.75 | 2.05 | 2.70 | 4.17 | 0.80 | 1.05 | 4.39 | 1.55 | 2.50 | 4.13 |
| 38C4 | 0.02 | 0.09 | 0.80 | 1.30 | 5.78 | 0.26 | 0.30 | 5.36 | 0.80 | 0.95 | 5.73 |
| 38C5 |   |   |   |   |   |   |   |   |   |   |   |
| 38C6 | 0.24 | 0.30 | 1.20 | 1.68 | 4.73 | 0.50 | 0.70 | 4.55 | 1.20 | 1.25 | 4.55 |
| 38D5 | 0.65 | 0.80 | 1.63 | 2.45 | 4.45 | 0.75 | 1.15 | 4.27 | 1.60 | 1.58 | 4.36 |
| 39C2 | 0.22 | 0.25 | 1.05 | 1.10 | 4.84 | 0.34 | 0.45 | 4.58 | 1.00 | 1.03 | 4.73 |
| 39C3 | 0.03 | 0.13 | 0.53 | 1.30 | 6.80 | 0.50 | 0.50 | 4.67 | 1.55 | 2.60 | 4.47 |
| 39C4 | 0.02 | 0.00 | 0.20 | 0.17 | 6.40 | 0.50 | 0.65 | 4.62 | 1.18 | 1.35 | 4.49 |
| 39D1 | 1.00 | 1.50 | 1.70 | 1.75 | 6.27 | 0.55 | 1.23 | 4.41 | 2.50 | 2.80 | 4.34 |
| 39D2 | 0.03 | 0.07 | 0.75 | 1.90 | 4.53 | 1.05 | 0.05 | 5.67 | 0.45 | 0.95 | 5.56 |
| 39D3 | 0.06 | 0.06 | 0.68 | 0.65 | 5.67 | 0.09 | 0.14 | 5.72 | 0.70 | 1.05 | 5.91 |
| 40D2 | 0.15 | 0.25 | 1.10 | 1.95 | 5.15 | 0.36 | 0.50 | 4.64 | 1.30 | 1.23 | 4.59 |
| 41C2 | 0.23 | 0.35 | 1.00 | 1.55 | 4.80 | 0.34 | 0.60 | 4.53 | 1.10 | 1.73 | 4.74 |
| 41D4 | 0.11 | 0.19 | 0.17 | 2.40 | 4.91 | 0.35 | 0.60 | 4.61 | 1.50 | 2.60 | 4.44 |
| 42D1 | 0.31 | 0.35 | 1.40 | 1.38 | 4.62 | 0.45 | 0.75 | 4.50 | 1.25 | 1.30 | 4.50 |
| 42D2 | 0.36 | 0.37 | 1.35 | 1.35 | 4.63 | 0.68 | 0.60 | 4.46 | 1.28 | 1.30 | 4.39 |
| 42D3 | 0.40 | 0.43 | 1.20 | 1.15 | 4.38 | 0.58 | 0.21 | 4.44 | 1.18 | 1.05 | 4.31 |
| 43D1 | 0.08 | 0.10 | 0.70 | 1.10 | 4.26 | 0.11 | 0.43 | 6.31 | 0.55 | 0.88 | 5.61 |
| 43D2 | 0.28 | 0.31 | 0.85 | 0.85 | 6.08 | 0.43 | 0.45 | 4.60 | 1.00 | 0.90 | 4.67 |
| 43D3 | 0.26 | 0.32 | 1.23 | 1.80 | 4.79 | 0.45 | 0.30 | 4.56 | 1.25 | 1.80 | 4.49 |
| 44D2 | 0.27 | 0.33 | 0.80 | 1.23 | 4.55 | 0.29 | 0.30 | 4.57 | 1.00 | 1.50 | 4.57 |

Fermentation Products (48 hr) (pH not Controlled)

| | LB (1% Xylose), pH 6.8 | | | | | | | LB (1% Glucose), pH 6.8 | | | | | | |
|---|---|---|---|---|---|---|---|---|---|---|---|---|---|---|
| Isolate | Xylose mM | Succinate mM | Lactate mM | Formate mM | Fumarate μM | Acetate mM | Ethanol mM | Glucose mM | Succinate mM | Lactate mM | Formate mM | Fumarate μM | Acetate mM | Ethanol mM |
| 30D2 | | | | | | | | | | | | | | |
| 30D3 | | | | | | | | | | | | | | |
| 30D4 | | | | | | | | | | | | | | |
| 31C1 | | | | | | | | | | | | | | |
| 31C2 | | | | | | | | | | | | | | |
| 31C3 | | | | | | | | | | | | | | |
| 33D2 | 51.2 | 1.4 | 13.5 | 4.5 | | 3.0 | | 55.1 | 1.3 | 17.9 | | | 2.0 | |
| 33D4 | 46.8 | 2.6 | 12.1 | 26.2** | * | 7.6 | 10.9 | 53.1 | 1.2 | 16.2 | | | | |
| 34D2 | 49.7 | 1.2 | 14.8 | 4.0 | | 3.7 | | 53.9 | 1.2 | 16.9 | | | | |
| 34D3 | | | | | | | | | | | | | | |
| 35C1 | | | | | | | | | | | | | | |
| 35C3 | | | | | | | | | | | | | | |
| 35D2 | 51.3 | 1.5 | 15.3 | * | | 4.0 | | 44.5 | 1.6 | 16.1 | | | | |
| 35D3 | 49.7 | 1.7 | 14.9 | 3.7 | | 4.6 | 5.9 | 40.8 | 1.2 | 19.3 | | | | |
| 35D4 | | | | | | | | | | | | | | |
| 35D5 | | | | | | | | | | | | | | |
| 36D1A | 54.4 | 1.5 | 13.5 | * | | 3.9 | | 41.5 | 1.3 | 20.1 | | | 2.5 | |
| 36D1B | 52.3 | 1.6 | 16.7 | * | | 2.3 | | 43.2 | 1.3 | 22.3 | | | | |
| 36D2 | | | | | | | | | | | | | | |
| 37D3 | | | | | | | | | | | | | | |

TABLE 2-continued

Properties of all the Isolates

| Isolate | | | | | | | | | |
|---|---|---|---|---|---|---|---|---|---|
| 38C1 | | | | | | | | | |
| 38C2 | | | | | | | | | |
| 38C3 | 51.8 | 1.6 | 14.1 | * | 4.6 | 52.7 | 1.4 | 17.0 | 2.6 |
| 38C4 | | | | | | | | | |
| 38C5 | | | | | | | | | |
| 38C6 | 50.3 | 1.6 | 12.2 | 9.4 | 2.2 | 56.2 | 1.7 | 14.5 | |
| 38D5 | 48.0 | 1.6 | 5.9 | | 7.7 | 53.2 | 1.4 | 20.6 | 2.5 |
| 39C2 | | | | | | | | | |
| 39C3 | | | | | | | | | |
| 39C4 | | | | | | | | | |
| 39D1 | 47.8 | 1.6 | 13.9 | 3.9 | 5.2 | 44.9 | 1.6 | 18.2 | * |
| 39D2 | | | | | | | | | |
| 39D3 | | | | | | | | | |
| 40D2 | | | | | | | | | |
| 41C2 | | | | | | | | | |
| 41D4 | | | | | | | | | |
| 42D1 | | | | | | | | | |
| 42D2 | 53.8 | 2.0 | 18.4 | | 2.1 | 47.2 | 1.7 | 17.0 | 2.3 |
| 42D3 | 49.4 | 1.8 | 17.2 | | 2.1 | 45.7 | | 17.1 | 2.5 |
| 43D1 | | | | | | | | | |
| 43D2 | | | | | | | | | |
| 43D3 | | | | | | | | | |
| 44D2 | | | | | | | | | |

Fermentation Products (48 hr) (pHstat)

| | LB (1% Xylose), pH 5.0 | | | | | | | LB (1% Glucose), pH 5.0 | | | | | | |
|---|---|---|---|---|---|---|---|---|---|---|---|---|---|---|
| Isolate | Xylose mM | Lactate mM | Succinate mM | Acetate mM | Ethanol mM | Formate mM | Fumarate μM | Glucose mM | Lactate mM | Succinate mM | Acetate mM | Ethanol mM | Formate mM | Fumarate μM |
| 30D2 | | | | | | | | | | | | | | |
| 30D3 | | | | | | | | | | | | | | |
| 30D4 | | | | | | | | | | | | | | |
| 31C1 | | | | | | | | | | | | | | |
| 31C2 | | | | | | | | | | | | | | |
| 31C3 | | | | | | | | | | | | | | |
| 33D2 | | | | | | | | | | | | | | |
| 33D4 | 0.00 | 71.57 | 3.67 | 27.05 | 17.48 | 22.17 | 0.00 | 0.00 | 104.18 | 1.06 | 9.16 | 3.10 | 0.00 | 0.00 |
| 34D2 | 65.01 | 0.73 | 0.53 | 6.48 | 0.00 | 0.00 | 0.00 | 0.00 | 98.17 | 0.96 | 7.31 | 0.00 | 0.00 | 0.00 |
| 34D3 | | | | | | | | | | | | | | |
| 35C1 | | | | | | | | | | | | | | |
| 35C3 | | | | | | | | | | | | | | |
| 35D2 | 0.51 | 86.33 | 2.67 | 24.42 | 18.33 | 5.71 | 0.00 | 0.00 | 107.00 | 0.76 | 4.00 | 5.48 | 0.00 | 0.00 |
| 35D3 | | | | | | | | | | | | | | |
| 35D4 | | | | | | | | | | | | | | |
| 35D5 | | | | | | | | | | | | | | |
| 36D1A | | | | | | | | | | | | | | |
| 36D1B | | | | | | | | | | | | | | |
| 36D2 | 0.00 | 81.77 | 2.16 | 15.04 | 0.00 | 8.67 | 0.00 | 0.00 | 95.94 | 0.78 | 7.48 | 0.00 | 0.00 | 0.00 |

TABLE 2-continued

Properties of all the Isolates

| Isolate | LB Glucose (1%), pH 4.5 OD 420 nm 24 hrs | 48 hrs | pH 48 hrs | LB Xylose (1%), pH 4.5 OD 420 nm 24 hrs | 48 hrs | pH 48 hrs |
|---|---|---|---|---|---|---|
| 37D3 | | | | | | |
| 38C1 | | | | | | |
| 38C2 | | | | | | |
| 38C3 | 0.00 | 81.56 | 1.17 | 30.00 | 12.29 | 2.13 |
| 38C4 | | | | | | |
| 38C5 | | | | | | |
| 38C6 | | | | | | |
| 38D5 | 31.74 | 35.11 | 1.81 | 11.58 | 2.67 | 2.66 |
| 39C2 | | | | | | |
| 39C3 | | | | | | |
| 39C4 | | | | | | |
| 39D1 | | | | | | |
| 39D2 | | | | | | |
| 39D3 | | | | | | |
| 40D2 | | | | | | |
| 41C2 | | | | | | |
| 41D4 | | | | | | |
| 42D1 | | | | | | |
| 42D2 | | | | | | |
| 42D3 | | | | | | |
| 43D1 | | | | | | |
| 43D2 | 0.00 | 0.00 | 99.08 | 0.60 | 7.53 | 3.74 |
| 43D3 | 0.00 | 0.00 | 99.95 | 0.77 | 7.70 | 3.05 |
| 44D2 | | | | | | |

Anaerobic Growth

| Isolate | LB Glucose (1%), pH 4.5 OD 420 nm 24 hrs | 48 hrs | pH 48 hrs | LB Xylose (1%), pH 4.5 OD 420 nm 24 hrs | 48 hrs | pH 48 hrs | MS (0.1% YE) (Xylose 1%), pH 5 OD 420 nm 24 hrs | 48 hrs | pH 48 hrs | MS (0.1% YE) (Glucose 1%), pH 5 OD 420 nm 24 hrs | 48 hrs | pH 48 hrs | HCH 10% CSL 1%, pH 5 OD 420 nm 24 hrs | 48 hrs | pH 48 hrs |
|---|---|---|---|---|---|---|---|---|---|---|---|---|---|---|---|
| 30D2 | | | | | | | | | | | | | | | |
| 30D3 | | | | | | | | | | | | | | | |
| 30D4 | | | | | | | | | | | | | | | |
| 31C1 | | | | | | | | | | | | | | | |
| 31C2 | | | | | | | | | | | | | | | |
| 31C3 | | | | | | | | | | | | | | | |
| 33D2 | 0.10 | 0.15 | 4.27 | 0.14 | 0.17 | 4.34 | 0.08 | 0.15 | 4.64 | 0.08 | 0.07 | 4.65 | 0.10 | 0.08 | 4.17 |
| 33D3 | 0.10 | 0.25 | 4.15 | 0.15 | 0.22 | 4.35 | 0.15 | 0.17 | 4.62 | 0.08 | 0.08 | 4.63 | 0.15 | 0.12 | 4.15 |
| 33D4 | 0.00 | 0.01 | 4.40 | 0.09 | 0.13 | 4.39 | 0.14 | 0.16 | 4.60 | 0.13 | 0.14 | 4.25 | 0.21 | 0.21 | 3.96 |
| 34C1 | | | | | | | | | | | | | | | |
| 34D2 | 0.00 | 0.00 | 4.43 | 0.00 | 0.00 | 4.41 | 0.10 | 0.17 | 4.61 | 0.03 | 0.04 | 4.82 | 0.19 | 0.15 | 4.18 |
| 34D3 | 0.07 | 0.14 | 4.28 | 0.11 | 0.13 | 4.36 | 0.13 | 0.18 | 4.43 | 0.09 | 0.09 | 4.64 | 0.17 | 0.15 | 4.14 |
| 35C3 | | | | | | | | | | | | | | | |
| 35D2 | | | | | | | | | | | | | | | |
| 35D3 | | | | | | | | | | | | | | | |
| 35D4 | | | | | | | | | | | | | | | |
| 35D5 | | | | | | | | | | | | | | | |

TABLE 2-continued

Properties of all the Isolates

| Isolate | 0% Ethanol O.D. 420 nm 24 hrs | 0% Ethanol O.D. 420 nm 48 hrs | 4% Ethanol(w/w) O.D. 420 nm 24 hrs | 4% Ethanol(w/w) O.D. 420 nm 48 hrs | 4.5% Ethanol(w/w) O.D. 420 nm 24 hrs | 4.5% Ethanol(w/w) O.D. 420 nm 48 hrs | 5% Ethanol(w/w) O.D. 420 nm 24 hrs | 5% Ethanol(w/w) O.D. 420 nm 48 hrs |
|---|---|---|---|---|---|---|---|---|
| 36D1A | | | 0.24 | | 4.32 | 0.17 | 0.21 | |
| 36D1B | | | 0.14 | | 4.28 | 0.10 | 0.12 | |
| 36D2 | | | 0.02 | | 4.43 | 0.07 | 0.04 | |
| 37D3 | | | | | | | | |
| 38C1 | | | | | | | | |
| 38C2 | | | | | | | | |
| 38C3 | | 0.24 | 0.25 | | 4.40 | 1.70 | 1.80 | |
| 38C4 | | | | | | | | |
| 38C5 | | | | | | | | |
| 38C6 | | 0.08 | 0.17 | | 4.32 | 0.12 | 0.10 | |
| 38D5 | | 0.06 | 0.24 | | 4.21 | 0.13 | 0.15 | |
| 39C2 | | | | | | | | |
| 39C3 | | | | | | | | |
| 39C4 | | | | | | | | |
| 39D1 | | 0.07 | 0.30 | | 4.17 | 0.12 | 0.22 | |
| 39D2 | | | | | | | | |
| 39D3 | | | | | | | | |
| 40D2 | | | | | | | | |
| 41C2 | | | | | | | | |
| 41D4 | | | | | | | | |
| 42D1 | | | | | | | | |
| 42D2 | | 0.00 | 0.00 | | 4.45 | 0.01 | 0.00 | |
| 42D3 | | 0.00 | 0.01 | | 4.51 | 0.00 | 0.00 | |
| 43D1 | | | | | | | | |
| 43D2 | | | | | | | | |
| 43D3 | | | | | | | | |
| 44D2 | | | | | | | | |

| Isolate | LB (Glucose 1%, pH 6.8) 0% Ethanol O.D. 420 nm 24 hrs | 48 hrs | 4% Ethanol(w/w) O.D. 420 nm 24 hrs | 48 hrs | LB (Glucose 1%, pH 5.0) 4.5% Ethanol(w/w) O.D. 420 nm 24 hrs | 48 hrs | 5% Ethanol(w/w) O.D. 420 nm 24 hrs | 48 hrs | 20% HCH 0.1% YE/Glu pH 5.0(V) plates (48 hrs) | 25% HCH 0.1% YE/Glu pH 5.0(V) plates (48 hrs) | 50% HCH overlimed 0.1% YE/Glu pH 5.0(V) plates (48 hrs) |
|---|---|---|---|---|---|---|---|---|---|---|---|
| 30D2 | | | | | | | | | − | − | − |
| 30D3 | | | | | | | | | − | + | + |
| 30D4 | | | | | | | | | − | − | − |
| 31C1 | | | | | | | | | − | − | − |
| 31C2 | | | | | | | | | − | − | − |
| 31C3 | | | | | | | | | + | − | − |
| 33D2 | | | | | | | | | ++ | − | − |
| 33D4 | 0.80 | 1.00 | 0.12 | 0.46 | 0.10 | 0.11 | 0.06 | 0.05 | ++ | − | − |
| 34D2 | 0.80 | 1.00 | 0.04 | 0.03 | 0.04 | 0.04 | 0.05 | 0.05 | − | − | − |
| 34D3 | | | | | | | | | + | − | − |
| 35C1 | | | | | | | | | + | + | − |
| 35C3 | 0.85 | 0.95 | 0.15 | 0.49 | 0.05 | 0.14 | 0.00 | 0.13 | | | |
| 35D2 | | | | | | | | | | | |
| 35D3 | | | | | | | | | | | |

TABLE 2-continued

Properties of all the Isolates

| Isolate | Aerobic (pH 5.0) | | | | | | | | Antibiotic Sensitivity | | | |
|---|---|---|---|---|---|---|---|---|---|---|---|---|
| | 25% HCH (0.1% YE) | | 10% HCH (1% CSL) | | 25% Overlimed HCH | | 50% Overlimed HCH (0.1% YE) | | Tetracycline 20 mg/L | Chloramphenicol 30 mg/L | Kanamycin 50 mg/L | Ampicillin 100 mg/L |
| | CFU/ml 24 hrs | 48 hrs pH | CFU/ml 24 hrs | 48 hrs pH | CFU/ml 24 hrs | 48 hrs pH | CFU/ml 24 hrs | 48 hrs pH | | | | |
| 35D4 | | | | | | | | | − | − | − | − |
| 35D5 | | | | | | | | | − | − | − | − |
| 36D1A | | | | | | | | | − | ++ | − | − |
| 36D1B | | | | | | | | | − | + | − | − |
| 36D2 | | | | | | | | | − | + | − | − |
| 37D3 | | | | | | | | | − | − | − | − |
| 38C1 | | | | | | | | | − | − | − | − |
| 38C2 | | | | | | | | | − | − | − | − |
| 38C3 | 0.52 | 0.53 | 0.12 | 0.17 | 0.02 | 0.07 | 0.00 | 0.04 | − | − | − | − |
| 38C4 | | | | | | | | | − | − | − | − |
| 38C5 | | | | | | | | | − | − | − | − |
| 38C6 | | | | | | | | | − | − | − | − |
| 38D5 | | | | | | | | | − | − | − | − |
| 39C2 | | | | | | | | | − | − | − | − |
| 39C3 | | | | | | | | | − | − | − | − |
| 39C4 | | | | | | | | | − | − | − | − |
| 39D1 | | | | | | | | | − | − | − | − |
| 39D2 | | | | | | | | | − | − | − | − |
| 39D3 | | | | | | | | | − | + | + | + |
| 40D2 | | | | | | | | | − | − | − | − |
| 41C2 | | | | | | | | | − | − | − | − |
| 41D4 | | | | | | | | | − | − | − | − |
| 42D1 | | | | | | | | | − | − | − | − |
| 42D2 | | | | | | | | | − | − | − | − |
| 42D3 | | | | | | | | | − | + | − | − |
| 43D1 | | | | | | | | | − | − | − | − |
| 43D2 | | | | | | | | | − | − | − | − |
| 43D3 | | | | | | | | | − | − | − | − |
| 44D2 | | | | | | | | | − | − | − | − |
| 30D2 | | | | | | | | | | | | |
| 30D3 | | | | | | | | | | | | |
| 30D4 | | | | | | | | | | | | |
| 31C1 | | | | | | | | | | | | |
| 31C2 | | | | | | | | | | | | |
| 31C3 | | | | | | | | | | | | |
| 33D2 | | | | | | | | | | | | |
| 33D4 | | | | | | | | | − | − | − | − |
| 34D2 | | | | | | | | | + | − | − | − |
| 34D3 | | | | | | | | | − | − | − | − |
| 35C1 | | | | | | | | | | | | |
| 35C3 | | | | | | | | | | | | |

TABLE 2-continued

Properties of all the Isolates

| Isolate | Identification[a] (16S rRNA) | Xylanase 72 hr | CMCase 72 hr | Cellobiose MS (0.1% YE) pH 5.0 72 hr | | | |
|---|---|---|---|---|---|---|---|
| 35D2 | | | | | | | |
| 35D3 | | | | | | | |
| 35D4 | | | | | | | |
| 35D5 | | | | | | | |
| 36D1A | | | | | | | |
| 36D1B | | | | | | | |
| 36D2 | | | | | | | |
| 37D3 | | | | | | | |
| 38C1 | | | | | | | |
| 38C2 | | | | | | | |
| 38C3 | | | | | | | |
| 38C4 | $10^7$ | — | — | — | $1 \times 10^6$ | $5 \times 10^7$ | $3 \times 10^5$ 4.51 |
| 38C5 | | | | | | | |
| 38C6 | $6 \times 10^6$ 4.80 | | | | | | |
| 38D5 | | | | | | | |
| 39C2 | | | | | | | |
| 39C3 | $3 \times 10^4$ 4.31 | | | | | | |
| 39C4 | $>4 \times 10^7$ | — | — | — | $4 \times 10^7$ | $2 \times 10^6$ | $10^5$ 3.97 $>4 \times 10^7$ $3 \times 10^5$ 4.41 |
| 39D1 | | | | | | | |
| 39D2 | | | | | | | |
| 39D3 | | | | | | | |
| 40D2 | $>4 \times 10^7$ | — | — | — | $5.9 \times 10^6$ 4.44 | | |
| 41C2 | $3 \times 10^7$ | — | — | — | $>4 \times 10^7$ $>4 \times 10^7$ 6.56 | | |
| 41D4 | $>4 \times 10^7$ | — | — | — | $4 \times 10^6$ $4 \times 10^6$ 4.78 | | |
| 42D1 | $1 \times 10^7$ | — | — | — | $>4 \times 10^7$ $>4 \times 10^7$ $>3 \times 10^3$ 4.32 | | |
| 42D2 | | | | | | | |
| 42D3 | | | | | | | |
| 43D1 | | | | | | | |
| 43D2 | | | | | | | |
| 43D3 | | | | | | | |
| 44D2 | | | | | | | |

| | | | | | Growth at pH 5.0 | | | | | | | |
|---|---|---|---|---|---|---|---|---|---|---|---|---|
| | | LB Xylose (1%) | | | | | | LB Glucose (1%) | | | | |
| | | Anaerobic | | | Aerobic | | | Anaerobic | | | Aerobic | |
| | | O.D. 420 nm | | pH | O.D. 420 nm | | pH | O.D. 420 nm | | pH | O.D. 420 nm | pH |
| Isolate | | 24 hrs | 48 hrs | 48 hrs | 24 hrs | 48 hrs | 48 hrs | 24 hrs | 48 hrs | 48 hrs | 24 hrs 48 hrs | 48 hrs |
| 45C1 | | 0.04 | 0.03 | 5.10 | 0.65 | 0.90 | 5.82 | 0.05 | 0.08 | 5.06 | 0.55 1.05 | 5.40 |
| 45C2 | | 0.18 | 0.20 | 4.57 | 0.78 | 0.70 | 4.51 | 0.28 | 0.30 | 4.46 | 0.78 0.85 | 4.42 |
| 45C3 | | 0.10 | 0.13 | 4.97 | 0.35 | 0.37 | 5.80 | 0.11 | 0.22 | 4.84 | 0.53 0.70 | 4.77 |
| 45D2 | | 0.16 | 0.16 | 4.53 | 0.75 | 1.35 | 4.52 | 0.24 | 0.26 | 4.49 | 0.88 1.55 | 4.40 |
| 45D3 | | 0.12 | 0.11 | 4.55 | 0.78 | 0.80 | 4.47 | 0.18 | 0.20 | 4.48 | 0.75 0.80 | 4.44 |
| 46C1 | | 0.25 | 0.25 | 4.22 | 1.53 | 1.60 | 4.25 | 0.32 | 0.32 | 4.34 | 1.35 1.40 | 4.23 |
| 46D1 | | 0.12 | 0.13 | 4.58 | 0.95 | 1.23 | 4.33 | 0.20 | 0.23 | 4.47 | 0.43 0.78 | 4.61 |
| 46D3 | | 0.09 | 0.08 | 4.66 | 1.55 | 2.30 | 4.48 | 0.50 | 0.45 | 4.17 | 1.25 1.20 | 4.31 |

TABLE 2-continued

Properties of all the Isolates

| Isolate | LB (Glucose 1%) O.D. 420 nm 24 hrs | LB (Glucose 1%) O.D. 420 nm 48 hrs | Stationary Phase Survival pH 48 hrs | Stationary Phase Survival (microaerobic), CFU/ml 24 hrs | Stationary Phase Survival (microaerobic), CFU/ml 48 hrs | LB Xylose (1%) Anaerobic O.D. 420 nm 24 hrs | LB Xylose (1%) Anaerobic O.D. 420 nm 48 hrs | LB Xylose (1%) Anaerobic pH 48 hrs | LB Xylose (1%) Aerobic O.D. 420 nm 24 hrs | LB Xylose (1%) Aerobic O.D. 420 nm 48 hrs | LB Xylose (1%) Aerobic pH 48 hrs | Growth at pH 6.8 Anaerobic O.D. 420 nm 24 hrs | Growth at pH 6.8 Anaerobic O.D. 420 nm 48 hrs | Growth at pH 6.8 Anaerobic pH 48 hrs | Growth at pH 6.8 Aerobic O.D. 420 nm 24 hrs | Growth at pH 6.8 Aerobic O.D. 420 nm 48 hrs | Growth at pH 6.8 Aerobic pH 48 hrs |
|---|---|---|---|---|---|---|---|---|---|---|---|---|---|---|---|---|---|
| 46D4 | | | | − | − | 0.22 | 0.24 | 4.42 | 0.90 | 0.85 | 4.43 | 0.34 | 0.34 | 4.45 | 0.93 | 0.90 | 4.33 |
| 47C1 | | | | − | − | 0.26 | 0.27 | 4.15 | 1.60 | 2.10 | 4.27 | 0.40 | 0.40 | 4.26 | 1.00 | 1.40 | 4.29 |
| 47C2 | | | | − | − | 0.16 | 0.17 | 4.41 | 1.60 | 2.30 | 4.40 | 0.30 | 0.30 | 4.23 | 1.18 | 1.10 | 4.25 |
| 48C1 | | | | − | − | 0.26 | 0.32 | 4.13 | 2.15 | 3.40 | 4.26 | 0.35 | 0.42 | 4.21 | 1.50 | 1.40 | 4.23 |
| 48C2 | | | | − | − | 0.12 | 0.17 | 4.53 | 0.90 | 1.50 | 4.65 | 0.40 | 0.41 | 4.30 | 1.60 | 1.55 | 4.34 |
| 48D1 | | | | − | − | 0.12 | 0.15 | 4.50 | 0.65 | 0.73 | 4.52 | 0.26 | 0.31 | 4.42 | 0.90 | 0.80 | 4.41 |
| 49C1 | | | | − | − | 0.22 | 0.25 | 4.15 | 1.50 | 2.25 | 4.36 | 0.40 | 0.40 | 4.15 | 1.45 | 1.40 | 4.19 |
| 49C2 | | | | − | − | 0.15 | 0.28 | 4.31 | 1.45 | 3.10 | 4.50 | 0.12 | 0.45 | 4.16 | 1.03 | 1.05 | 5.55 |
| 49D3 | | | | − | − | 0.42 | 0.47 | 4.24 | 1.70 | 1.60 | 4.23 | 0.40 | 0.43 | 4.30 | 1.70 | 1.40 | 4.36 |
| 49D4sm | | | | − | − | 0.33 | 0.34 | 4.23 | 1.63 | 1.78 | 4.23 | 0.45 | 0.48 | 4.30 | 1.68 | 1.70 | 4.21 |
| 49D4lg | | | | − | − | 0.48 | 0.48 | 4.19 | 1.85 | 1.93 | 4.22 | 0.39 | 0.43 | 4.33 | 1.78 | 2.65 | 4.17 |
| 50C1 | | | | − | − | 0.18 | 0.32 | 4.29 | 1.60 | 2.40 | 4.41 | 0.32 | 0.38 | 4.19 | 1.35 | 1.95 | 4.23 |
| 50C2 | | | | − | − | 0.22 | 0.25 | 4.53 | 1.40 | 3.30 | 4.75 | 0.37 | 0.36 | 4.30 | 1.43 | 1.55 | 4.37 |
| 51C1 | | | | − | − | 0.29 | 0.30 | 4.20 | 1.50 | 1.50 | 4.41 | 0.35 | 0.42 | 4.28 | 1.55 | 1.35 | 4.28 |
| 51D1 | | | | − | − | 0.06 | 0.07 | 5.50 | 0.40 | 0.75 | 5.06 | 0.63 | 0.65 | 4.35 | 1.10 | 1.08 | 4.40 |
| 51D2 | | | | − | − | 0.07 | 0.11 | 4.62 | 1.00 | 1.05 | 4.45 | 0.33 | 0.39 | 4.40 | 1.43 | 1.45 | 4.39 |
| 52D1 | | | | − | − | 0.15 | 0.20 | 4.51 | 0.85 | 0.90 | 4.57 | 0.23 | 0.29 | 4.44 | 0.75 | 0.95 | 4.50 |
| 52D2 | | | | − | − | 0.19 | 0.22 | 4.50 | 0.85 | 0.85 | 4.55 | 0.29 | 0.35 | 4.41 | 0.75 | 0.75 | 4.44 |
| 53C1 | | | | + | + | 0.01 | 0.00 | 5.12 | 0.33 | 0.63 | 5.57 | 0.06 | 0.11 | 5.12 | 0.29 | 0.42 | 5.43 |
| 53C2 | | | | + | + | 0.00 | 0.00 | 5.01 | 0.03 | 0.00 | 4.98 | 0.01 | 0.05 | 5.02 | 0.00 | 0.00 | 5.01 |
| 53C3 | | | | + | + | 0.00 | 0.03 | 5.00 | 0.00 | 0.00 | 4.98 | 0.04 | 0.09 | 5.12 | 0.00 | 0.05 | 5.02 |
| 53C4 | | | | + | + | 0.00 | 0.00 | 5.01 | 0.02 | 0.00 | 4.99 | 0.00 | 0.01 | 5.02 | 0.00 | 0.01 | 5.05 |
| 53C5 | | | | + | + | 0.08 | 0.05 | 5.12 | 0.02 | 0.26 | 5.49 | 0.08 | 0.10 | 5.09 | 0.00 | 0.04 | 5.05 |
| 53D1 | | | | − | − | 0.31 | 0.31 | 4.32 | 1.48 | 2.60 | 4.38 | 0.34 | 0.58 | 4.28 | 1.35 | 1.40 | 4.33 |
| 53D2 | | | | + | + | 0.33 | 0.36 | 4.41 | 1.30 | 1.50 | 4.39 | 0.35 | 0.40 | 4.39 | 1.10 | 1.15 | 4.38 |
| 54C1 | | | | − | − | 0.00 | 0.00 | 5.01 | 0.00 | 1.50 | 4.22 | 0.00 | 0.01 | 5.03 | 0.48 | 1.15 | 4.44 |
| 54D1 | | | | − | − | 0.03 | 0.09 | 4.63 | 0.65 | 1.33 | 4.52 | 0.18 | 0.27 | 4.50 | 0.58 | 1.15 | 4.46 |
| 54D2 | | | | − | − | 0.19 | 0.27 | 4.28 | 1.17 | 1.20 | 4.29 | 0.25 | 0.32 | 4.31 | 1.33 | 1.38 | 4.13 |
| 54D3 | | | | − | − | 0.19 | 0.22 | 4.55 | 1.13 | 2.00 | 4.67 | 0.30 | 0.34 | 4.23 | 1.43 | 1.37 | 4.37 |
| 54D5A | | | | − | − | 0.11 | 0.12 | 4.60 | 0.75 | 0.80 | 4.55 | 0.19 | 0.19 | 4.49 | 0.80 | 0.80 | 4.47 |
| 54D5B | | | | − | − | 0.11 | 0.14 | 4.55 | 0.55 | 0.55 | 4.89 | 0.05 | 0.07 | 5.08 | 0.40 | 1.18 | 5.36 |
| 55C1 | | | | − | − | 0.24 | 0.25 | 4.29 | 1.23 | 1.68 | 4.36 | 0.30 | 0.40 | 4.28 | 1.45 | 1.43 | 4.48 |
| 55C2 | | | | + | + | 0.02 | 0.01 | 5.09 | 0.50 | 0.65 | 5.50 | 0.04 | 0.11 | 5.10 | 0.00 | 0.06 | 5.02 |
| 55D2 | | | | − | − | 0.05 | 0.07 | 4.61 | 0.75 | 1.25 | 4.46 | 0.16 | 0.26 | 4.54 | 0.83 | 1.05 | 4.39 |
| 55D5 | | | | − | − | 0.27 | 0.30 | 4.38 | 1.15 | 1.80 | 4.35 | 0.33 | 0.43 | 4.34 | 1.30 | 1.75 | 4.38 |
| 55D6 | | | | | | | | | | | | | | | | | |
| 56H1 | | | | − | − | 0.13 | 0.15 | 4.63 | 0.03 | 0.00 | 4.97 | 0.02 | 0.01 | 4.99 | 0.01 | 0.06 | 4.96 |
| 45C1 | 0.08 | | | | | 0.43 | 0.13 | 6.16 | 0.90 | 1.18 | 5.66 | 0.22 | 0.23 | 5.37 | 0.93 | 1.25 | 5.50 |
| 45C2 | 0.43 | | | | | | 0.45 | 4.48 | 0.58 | 1.25 | 4.62 | 0.27 | 0.65 | 4.43 | 1.20 | 1.15 | 4.50 |

TABLE 2-continued

Properties of all the Isolates

| Isolate | | | | | | | | | | | | | | | |
|---|---|---|---|---|---|---|---|---|---|---|---|---|---|---|---|
| 45C3 | | | | 0.09 | 0.14 | 6.35 | 0.36 | 0.33 | 6.56 | 0.21 | 0.19 | 5.50 | 0.75 | 0.55 | 5.19 |
| 45D2 | | | | 0.22 | 0.26 | 4.72 | 0.95 | 0.93 | 4.65 | 0.39 | 0.50 | 4.56 | 1.20 | 1.53 | 4.64 |
| 45D3 | | | | 0.28 | 0.33 | 4.72 | 0.80 | 1.25 | 4.57 | 0.32 | 0.33 | 4.58 | 1.20 | 1.75 | 4.45 |
| 46C1 | | | | 0.68 | 0.68 | 4.29 | 1.80 | 1.98 | 4.72 | 0.90 | 0.98 | 4.39 | 1.88 | 1.83 | 4.28 |
| 46D1 | | | | 0.48 | 0.53 | 4.40 | 1.03 | 0.95 | 4.30 | 0.58 | 0.55 | 4.34 | 0.98 | 0.85 | 4.39 |
| 46D3 | | | | 0.55 | 0.60 | 4.64 | 1.50 | 1.80 | 4.58 | 0.70 | 0.75 | 4.31 | 1.55 | 1.35 | 4.29 |
| 46D4 | | | | 0.26 | 0.33 | 4.70 | 0.95 | 1.20 | 4.70 | 0.40 | 0.50 | 4.58 | 1.30 | 2.00 | 4.50 |
| 47C1 | | | | 0.70 | 0.85 | 4.30 | 1.45 | 2.20 | 4.43 | 0.85 | 1.05 | 4.33 | 1.60 | 2.10 | 4.21 |
| 47C2 | | | | 0.60 | 0.70 | 4.50 | 3.80 | 4.60 | 4.39 | 0.70 | 0.85 | 4.26 | 1.85 | 1.75 | 4.36 |
| 48C1 | | | | 0.70 | 0.70 | 4.20 | 1.85 | 2.50 | 4.35 | 0.90 | 1.10 | 4.26 | 1.80 | 1.90 | 4.34 |
| 48C2 | | | | 0.30 | 0.35 | 4.76 | 3.70 | 4.90 | 4.47 | 0.88 | 0.95 | 4.23 | 1.90 | 2.20 | 4.29 |
| 48D1 | | | | 0.28 | 0.35 | 4.67 | 0.80 | 1.20 | 4.71 | 0.35 | 0.37 | 4.59 | 1.05 | 1.20 | 4.80 |
| 49C1 | | | | 0.70 | 0.60 | 4.23 | 1.55 | 2.50 | 4.32 | 0.93 | 1.85 | 4.23 | 1.95 | 1.90 | 4.61 |
| 49C2 | | | | 0.50 | 0.65 | 4.30 | 0.90 | 1.70 | 4.36 | 0.10 | 0.12 | 6.45 | 0.55 | 0.75 | 6.02 |
| 49D3 | 1.30 | 1.95 | 1.55 | 0.73 | 0.80 | 4.35 | 1.75 | 2.60 | 4.54 | 0.90 | 1.00 | 4.23 | 2.00 | 1.85 | 4.39 |
| 49D4sm | 1.35 | 1.90 | 1.55 | 4.28 | 4.28 | 4.32 | <$10^4$ | 4.2 × $10^4$ | <$10^4$ | nd | nd | nd | | | |
| 49D4lg | 1.55 | | | | | | | | | | | | | | |
| 50C1 | | | | 0.70 | 0.73 | 4.22 | 2.05 | 1.75 | 4.22 | 0.95 | 1.05 | 4.30 | 1.95 | 2.20 | 4.30 |
| 50C2 | | | | 0.75 | 0.80 | 4.28 | 2.50 | 3.25 | 4.22 | 1.10 | 1.20 | 4.28 | 2.08 | 2.03 | 4.22 |
| 51C1 | | | | 0.70 | 0.70 | 4.34 | 1.65 | 2.30 | 4.36 | 0.65 | 1.10 | 4.21 | 2.20 | 3.20 | 4.42 |
| 51D1 | | | | 0.38 | 0.50 | 4.48 | 1.85 | 3.00 | 4.54 | 0.75 | 0.90 | 4.35 | 1.60 | 2.15 | 4.45 |
| 51D2 | | | | 0.65 | 0.80 | 4.30 | 1.65 | 2.50 | 4.65 | 0.90 | 0.95 | 4.21 | 1.95 | 1.80 | 4.39 |
| 52D1 | | | | 0.08 | 0.06 | 6.72 | 0.85 | 0.88 | 8.11 | 0.78 | 0.68 | 4.69 | 0.60 | 0.73 | 4.66 |
| 52D2 | | | | 0.14 | 0.35 | 4.39 | 1.05 | 2.10 | 4.63 | 0.35 | 0.43 | 4.62 | 1.00 | 1.95 | 4.48 |
| 53C1 | | | | 0.29 | 0.33 | 4.68 | 0.98 | 1.60 | 4.68 | 0.39 | 0.43 | 4.57 | 0.95 | 1.00 | 4.64 |
| 53C2 | | | | 0.31 | 0.34 | 4.70 | 0.93 | 1.50 | 4.63 | 0.37 | 0.45 | 4.56 | 0.93 | 1.03 | 4.67 |
| 53C3 | | | | 0.09 | 0.12 | 5.91 | 0.95 | 1.00 | 5.29 | 0.23 | 0.28 | 5.25 | 0.83 | 1.03 | 5.57 |
| 53C4 | | | | 0.05 | 0.08 | 6.14 | 0.55 | 0.43 | 5.59 | 0.12 | 0.16 | 5.68 | 0.50 | 0.42 | 5.60 |
| 53C5 | | | | 0.06 | 0.06 | 6.37 | 0.19 | 0.27 | 6.54 | 0.15 | 0.17 | 5.38 | 0.45 | 0.40 | 5.33 |
| 53D1 | | | | 0.07 | 0.05 | 6.17 | 0.80 | 0.75 | 5.13 | 0.12 | 0.12 | 5.63 | 0.70 | 0.58 | 5.32 |
| 53D2 | | | | 0.08 | 0.11 | 6.24 | 0.70 | 0.88 | 6.12 | 0.17 | 0.20 | 5.59 | 0.85 | 1.40 | 5.56 |
| 54C1 | | | | 0.78 | 0.80 | 4.43 | 2.30 | 2.50 | 4.51 | 0.65 | 0.93 | 4.34 | 1.85 | 2.70 | 4.33 |
| 54D1 | | | | 1.03 | 1.03 | 4.33 | 2.25 | 2.95 | 4.52 | 0.68 | 0.98 | 4.40 | 1.60 | 1.85 | 4.47 |
| 54D2 | | | | 0.08 | 0.05 | 6.42 | 0.21 | 0.28 | 6.48 | 0.14 | 0.19 | 5.64 | 0.60 | 0.55 | 5.36 |
| 54D3 | | | | 0.21 | 0.23 | 4.72 | 0.73 | 1.08 | 4.77 | 0.40 | 0.48 | 4.64 | 0.88 | 1.33 | 4.65 |
| 54D5A | | | | 0.53 | 0.63 | 4.25 | 1.65 | 1.65 | 4.40 | 0.83 | 0.88 | 4.36 | 1.55 | 1.65 | 4.28 |
| 54D5B | | | | 0.32 | 0.48 | 4.52 | 1.68 | 2.10 | 4.58 | 0.83 | 0.85 | 4.26 | 1.63 | 1.65 | 4.28 |
| 55C1 | | | | 0.22 | 0.26 | 4.71 | 0.80 | 0.80 | 4.84 | 0.25 | 0.27 | 4.60 | 1.15 | 1.13 | 4.74 |
| 55C2 | | | | 0.31 | 0.33 | 4.57 | 0.50 | 0.85 | 5.01 | 0.00 | 0.01 | 6.43 | 0.17 | 0.60 | 5.29 |
| 55D2 | | | | 0.63 | 0.70 | 4.50 | 1.75 | 2.45 | 4.43 | 0.83 | 0.85 | 4.35 | 1.75 | 1.75 | 4.43 |
| 55D5 | | | | 0.11 | 0.09 | 6.16 | 0.65 | 0.75 | 5.69 | 0.15 | 0.18 | 5.73 | 0.85 | 1.23 | 5.59 |
| 55D6 | | | | 0.14 | 0.29 | 4.37 | 0.80 | 1.08 | 4.81 | 0.26 | 0.38 | 4.70 | 0.85 | 1.40 | 4.70 |
| 56H1 | | | | 0.70 | 0.75 | 4.56 | 1.65 | 2.25 | 4.37 | 0.78 | 0.95 | 4.45 | 1.90 | 2.35 | 4.39 |
| | | | | 0.05 | 0.08 | 6.22 | 0.25 | 0.60 | 4.68 | 0.00 | 0.06 | 5.94 | 0.43 | 0.23 | 5.56 |

TABLE 2-continued

Properties of all the Isolates

Fermentation Products (48 hr) (pH not Controlled)

| Isolate | LB (1% Xylose), pH 6.8 | | | | | | LB (1% Glucose), pH 6.8 | | | | | | |
|---|---|---|---|---|---|---|---|---|---|---|---|---|---|
| | Xylose mM | Succinate mM | Lactate mM | Formate mM | Fumarate µM | Acetate mM | Ethanol mM | Glucose mM | Succinate mM | Lactate mM | Formate mM | Fumarate µM | Acetate mM | Ethanol mM |
| 45C1 | | | | | | | | | | | | | | |
| 45C2 | | | | | | | | | | | | | | |
| 45C3 | | | | | | | | | | | | | | |
| 45D2 | | | | | | | | | | | | | | |
| 45D3 | | | | | | | | | | | | | | |
| 46C1 | 50.2 | 1.6 | 16.1 | 6.1 | | 3.7 | | 56.4 | 1.4 | 18.4 | | | |
| 46D1 | 52.3 | 1.7 | 17.0 | * | | * | 3.3 | 48.4 | 1.7 | 19.8 | | | 2.1 |
| 46D3 | 54.3 | 1.6 | 10.4 | | | 2.3 | | 52.8 | 1.4 | 19.6 | | | |
| 46D4 | | | | | | | | | | | | | | |
| 47C1 | 49.6 | 1.3 | 15.0 | 5.1 | | 4.0 | | 54.2 | 1.3 | 19.1 | | | |
| 47C2 | 50.3 | 2.0 | 4.3 | 11.9 | | 7.1 | | 54.3 | 1.2 | 21.6 | | | 2.9 |
| 48C1 | 47.7 | 1.4 | 16.9 | 6.0 | | 3.5 | | 52.9 | 1.5 | 21.1 | | | |
| 48C2 | 58.0 | 1.1 | 1.4 | 9.2 | | 5.6 | | 53.6 | 1.3 | 22.1 | | | |
| 48D1 | | | | | | | | | | | | | | |
| 49C1 | 48.3 | 1.5 | 17.3 | 5.4 | | 3.4 | | 52.1 | 1.2 | 21.2 | | | |
| 49C2 | | | | | | | | | | | | | | |
| 49D3 | 46.1 | 1.6 | 19.0 | 5.2 | | 4.3 | | 50.9 | 1.2 | 20.6 | | | |
| 49D4sm | 60.3 | * | 18.5 | 5.2 | | 4.1 | | 42.8 | 1.3 | 20.9 | | | |
| 49D4lg | 52.3 | 1.7 | 16.8 | 4.9 | | 4.1 | | 47.7 | 1.5 | 24.4 | | | |
| 50C1 | 46.9 | 1.7 | 15.9 | 6.3 | | 3.9 | | 37.9 | 1.8 | 27.7 | | | |
| 50C2 | 51.1 | | 2.5 | 10.1 | 9.3 | 6.3 | 8.3 | 43.1 | 1.6 | 22.3 | | 9.0 | * |
| 51C1 | 48.4 | 1.3 | 13.3 | 6.0 | | 4.1 | | 48.7 | 1.8 | 21.7 | * | | |
| 51D1 | | | | | | | | | | | | | | |
| 51D2 | | | | | | | | | | | | | | |
| 52D1 | | | | | | | | | | | | | | |
| 52D2 | | | | | | | | | | | | | | |
| 53C1 | | | | | | | | | | | | | | |
| 53C2 | | | | | | | | | | | | | | |
| 53C3 | | | | | | | | | | | | | | |
| 53C4 | | | | | | | | | | | | | | |
| 53C5 | | | | | | | | | | | | | | |
| 53D1 | 42.2 | 1.9 | 13.9 | * | | 5.9 | | 42.1 | 1.7 | 21.7 | | | * |
| 53D2 | 48.8 | 1.7 | 23.4 | 6.3 | | 4.7 | | 41.6 | 1.5 | 19.2 | | | |
| 54C1 | | | | | | | | | | | | | | |
| 54D1 | | | | | | | | | | | | | | |
| 54D2 | 43.0 | 1.6 | 15.8 | 6.0 | | 3.7 | | 41.7 | 1.1 | 22.2 | | | |
| 54D3 | 53.1 | 2.8 | 6.3 | 16.6 | | 7.2 | | 43.7 | 1.7 | 25.1 | 12.6 | | |
| 54D5A | | | | | | | | | | | | | | |
| 54D5B | | | | | | | | | | | | | | |
| 55C1 | 61.6 | 1.1 | 11.0 | 10.6 | | 3.0 | | 62.7 | 3.4 | 22.8 | | | 2.1 |
| 55C2 | | | | | | | | | | | | | | |
| 55D2 | | | | | | | | | | | | | | |
| 55D5 | 55.1 | 1.3 | 11.1 | 4.9 | 10.0 | 4.6 | | 47.5 | 1.5 | 18.2 | | | |

TABLE 2-continued

Properties of all the Isolates

Fermentation Products (48 hr) (pHstat)

| | LB (1% Xylose), pH 5.0 | | | | | | LB (1% Glucose), pH 5.0 | | | | |
|---|---|---|---|---|---|---|---|---|---|---|---|
| Isolate | Xylose mM | Lactate mM | Succinate mM | Acetate mM | Ethanol mM | Formate mM | Fumarate μM | Glucose mM | Succinate mM | Acetate mM | Ethanol mM | Formate mM | Fumarate μM |
| 45C1 | | | | | | | | | | | | | |
| 45C2 | | | | | | | | | | | | | |
| 45C3 | | | | | | | | | | | | | |
| 45D2 | | | | | | | | | | | | | |
| 45D3 | | | | | | | | | | | | | |
| 46C1 | 0.00 | 87.17 | 2.60 | 12.24 | 11.07 | 8.99 | 0.00 | 0.00 | 1.35 | 5.78 | 3.67 | 0.00 | 0.00 |
| 46D1 | | | | | | | | | | | | | |
| 46D3 | | | | | | | | | | | | | |
| 46D4 | | | | | | | | | | | | | |
| 47C1 | 0.00 | 91.72 | 2.61 | 8.37 | 12.44 | 13.14 | 0.00 | 0.00 | 0.93 | 1.04 | 2.45 | 0.00 | 0.00 |
| 47C2 | | | | | | | | | | | | | |
| 48C1 | | | | | | | | | | | | | |
| 48C2 | | | | | | | | | | | | | |
| 48D1 | | | | | | | | | | | | | |
| 49C1 | | | | | | | | | | | | | |
| 49C2 | | | | | | | | | | | | | |
| 49D3 | 0.00 | 83.29 | 2.38 | 17.54 | 18.98 | 10.90 | 0.00 | 0.00 | 0.65 | 2.98 | 4.50 | 0.00 | 0.00 |
| 49D4sm | | | | | | | | | | | | | |
| 49D4lg | 0.00 | 87.35 | 1.84 | 12.00 | 14.90 | 17.83 | 0.00 | 0.00 | 0.83 | 3.25 | 3.69 | 0.00 | 0.00 |
| 50C1 | | | | | | | | | | | | | |
| 50C2 | 22.30 | 5.73 | 3.48 | 37.66 | 32.44 | 62.01 | 0.00 | 0.00 | 1.94 | 1.36 | 5.24 | 0.00 | 0.00 |
| 51C1 | | | | | | | | | | | | | |
| 51D1 | | | | | | | | | | | | | |
| 51D2 | | | | | | | | | | | | | |
| 52D1 | | | | | | | | | | | | | |
| 52D2 | | | | | | | | | | | | | |
| 53C1 | | | | | | | | | | | | | |
| 53C2 | | | | | | | | | | | | | |
| 53C3 | | | | | | | | | | | | | |
| 53C4 | | | | | | | | | | | | | |
| 53C5 | | | | | | | | | | | | | |
| 53D1 | | | | | | | | | | | | | |
| 53D2 | | | | | | | | | | | | | |
| 54C1 | | | | | | | | | | | | | |
| 54D1 | | | | | | | | | | | | | |
| 54D2 | | | | | | | | | | | | | |
| 54D3 | | | | | | | | | | | | | |
| 54D5A | | | | | | | | | | | | | |
| 54D5B | | | | | | | | | | | | | |
| 55C1 | | | | | | | | | | | | | |
| 55D6 | | | | | | | | | | | | | |
| 56H1 | | | | | | | | | | | | | |

TABLE 2-continued

Properties of all the Isolates

| Isolate | LB Glucose (1%), pH 4.5 | | | | LB Xylose (1%), pH 4.5 | | | | Anaerobic Growth | | | | | | | | |
|---|---|---|---|---|---|---|---|---|---|---|---|---|---|---|---|---|---|
| | | | | | | | | | MS (0.1% YE) (Xylose 1%), pH 5 | | | | MS (0.1% YE) (Glucose 1%), pH 5 | | | | HCH 10% CSL 1%, pH 5 | |
| | O.D. 420 nm | | pH | | O.D. 420 nm | | pH | | O.D. 420 nm | | pH | | O.D. 420 nm | | pH | | O.D. 420 nm | | pH |
| | 24 hrs | 48 hrs | 24 hrs | 48 hrs | 24 hrs | 48 hrs | 24 hrs | 48 hrs | 24 hrs | 48 hrs | 48 hrs | 24 hrs | 48 hrs | 48 hrs | 24 hrs | 48 hrs | 48 hrs |
| 55C2 | | | | | | | | | | | | | | | | | |
| 55D2 | | | | | | | | | | | | | | | | | |
| 55D5 | | | | | | | | | | | | | | | | | |
| 55D6 | | | | | | | | | | | | | | | | | |
| 56H1 | 0.00 | 82.82 | 3.12 | | 11.42 | 16.29 | 11.57 | | 0.00 | 0.00 | 96.48 | | 0.56 | 3.82 | | 0.00 | 0.00 | 0.00 |
| 45C1 | | | | | | | | | | | | | | | | | |
| 45C2 | | | | | | | | | | | | | | | | | |
| 45C3 | | | | | | | | | | | | | | | | | |
| 45D2 | | | | | | | | | | | | | | | | | |
| 45D3 | | | | | | | | | | | | | | | | | |
| 46C1 | 0.12 | 0.16 | 4.34 | | 0.11 | 0.12 | 4.38 | | 0.10 | 0.10 | 4.52 | | 0.11 | 0.12 | 4.57 | 0.09 | 0.20 | 4.16 |
| 46D1 | 0.00 | 0.01 | 4.52 | | 0.03 | 0.03 | 4.45 | | 0.00 | 0.01 | 4.39 | | 0.10 | 0.14 | 4.46 | 0.00 | 0.00 | 4.40 |
| 46D3 | 0.17 | 0.21 | 4.29 | | 0.10 | 0.13 | 4.49 | | 0.08 | 0.12 | 4.64 | | 0.14 | 0.20 | 4.65 | 0.13 | 0.11 | 4.16 |
| 46D4 | | | | | | | | | | | | | | | | | |
| 47C1 | 0.15 | 0.17 | 4.28 | | 0.09 | 0.17 | 4.37 | | 0.19 | 0.24 | 4.47 | | 0.14 | 0.18 | 4.49 | 0.16 | 0.26 | 4.16 |
| 47C2 | 0.01 | 0.11 | 4.39 | | 0.01 | 0.09 | 4.47 | | 0.12 | 0.18 | 4.87 | | 0.06 | 0.10 | 4.58 | 0.21 | 0.24 | 4.21 |
| 48C1 | 0.17 | 0.13 | 4.31 | | 0.13 | 0.18 | 4.38 | | 0.16 | 0.19 | 4.47 | | 0.12 | 0.14 | 4.54 | 0.14 | 0.15 | 4.18 |
| 48C2 | 0.06 | 0.12 | 4.41 | | 0.03 | 0.07 | 4.46 | | 0.20 | 0.20 | 4.88 | | 0.10 | 0.11 | 4.60 | 0.15 | 0.18 | 4.19 |
| 48D1 | | | | | | | | | | | | | | | | | |
| 49C1 | 0.19 | 0.17 | 4.32 | | 0.10 | 0.14 | 4.38 | | 0.16 | 0.19 | 4.52 | | 0.12 | 0.15 | 4.53 | 0.12 | 0.15 | 4.18 |
| 49C2 | | | | | | | | | | | | | | | | | |
| 49D3 | 0.08 | 0.24 | 4.27 | | 0.09 | 0.27 | 4.46 | | 0.19 | 0.22 | 4.50 | | 0.13 | 0.19 | 4.51 | 0.27 | 0.28 | 4.17 |
| 49D4sm | 0.16 | 0.26 | 4.33 | | 0.16 | 0.24 | 4.31 | | 0.12 | 0.20 | 4.53 | | 0.11 | 0.15 | 4.57 | 0.04 | 0.11 | 4.14 |
| 49D4lg | 0.17 | 0.21 | 4.30 | | 0.23 | 0.23 | 4.27 | | 0.12 | 0.14 | 4.50 | | 0.09 | 0.16 | 4.50 | 0.11 | 0.19 | 4.20 |
| 50C1 | 0.11 | 0.20 | 4.25 | | 0.09 | 0.13 | 4.39 | | 0.16 | 0.21 | 4.54 | | 0.07 | 0.14 | 4.49 | 0.08 | 0.07 | 4.21 |
| 50C2 | 0.03 | 0.15 | 4.23 | | 0.01 | 0.09 | 4.44 | | 0.12 | 0.14 | 4.77 | | 0.09 | 0.13 | 4.57 | 0.25 | 0.33 | 4.23 |
| 51C1 | 0.16 | 0.19 | 4.27 | | 0.09 | 0.13 | 4.39 | | 0.16 | 0.23 | 4.55 | | 0.14 | 0.18 | 4.53 | 0.21 | 0.21 | 4.21 |
| 51D1 | | | | | | | | | | | | | | | | | |
| 51D2 | | | | | | | | | | | | | | | | | |
| 52D1 | | | | | | | | | | | | | | | | | |
| 52D2 | | | | | | | | | | | | | | | | | |
| 53C1 | | | | | | | | | | | | | | | | | |
| 53C2 | | | | | | | | | | | | | | | | | |
| 53C3 | | | | | | | | | | | | | | | | | |
| 53C4 | | | | | | | | | | | | | | | | | |
| 53C5 | | | | | | | | | | | | | | | | | |
| 53D1 | 0.06 | 0.18 | 4.32 | | 0.10 | 0.13 | 4.45 | | 0.12 | 0.13 | 4.54 | | 0.09 | 0.08 | 4.64 | 0.17 | 0.22 | 4.23 |
| 53D2 | 0.06 | 0.14 | 4.32 | | 0.06 | 0.09 | 4.43 | | 0.11 | 0.15 | 4.53 | | 0.08 | 0.09 | 4.63 | 0.18 | 0.21 | 4.14 |
| 54C1 | | | | | | | | | | | | | | | | | |
| 54D1 | | | | | | | | | | | | | | | | | |

TABLE 2-continued

Properties of all the Isolates

| | LB (Glucose 1%, pH 6.8) | | | | | | | | LB (Glucose 1%, pH 5.0) | | | | | | | | 50% HCH | | |
|---|---|---|---|---|---|---|---|---|---|---|---|---|---|---|---|---|---|---|---|
| | 0% Ethanol O.D. 420 nm | | 4% Ethanol(w/w) O.D. 420 nm | | 4.5% Ethanol(w/w) O.D. 420 nm | | 5% Ethanol(w/w) O.D. 420 nm | | 0% Ethanol O.D. 420 nm | | 4% Ethanol(w/w) O.D. 420 nm | | 4.5% Ethanol(w/w) O.D. 420 nm | | 5% Ethanol(w/w) O.D. 420 nm | | 20% HCH 0.1% YE/Glu pH 5.0(V) plates (48 hrs) | 25% HCH 0.1% YE/Glu pH 5.0(V) plates (48 hrs) | overlimed 0.1% YE/Glu pH 5.0(V) plates (48 hrs) |
| | 24 hrs | 48 hrs | 24 hrs | 48 hrs | 24 hrs | 48 hrs | 24 hrs | 48 hrs | 24 hrs | 48 hrs | 24 hrs | 48 hrs | 24 hrs | 48 hrs | 24 hrs | 48 hrs | | | |
| 54D2 | 0.14 | | 0.17 | 0.02 | | 0.11 | 0.16 | 0.04 | 4.42 | 0.09 | 4.49 | 0.11 | | 0.04 | 4.54 | 0.06 | | | |
| 54D3 | 0.09 | | 0.14 | 0.04 | | 0.07 | 0.11 | 0.03 | 4.45 | 0.04 | 4.69 | 0.04 | | 0.03 | 4.52 | 0.00 | | | 4.12 |
| 54D5A | | | | | | | | | | | | | | | | | | | 4.23 |
| 54D5B | | | | | | | | | | | | | | | | | | | |
| 55C1 | 0.11 | | 0.16 | | | 0.08 | 0.12 | | 4.33 | 0.12 | 4.48 | 0.13 | | | 4.42 | 0.08 | | | 4.13 |
| 55C2 | | | | | | | | | | | | | | | | | | | |
| 55D2 | | | | | | | | | | | | | | | | | | | |
| 55D5 | 0.15 | | 0.20 | 0.04 | | 0.12 | 0.16 | 0.04 | 4.40 | 0.08 | 4.61 | 0.05 | | | 4.50 | 0.16 | | | 4.22 |
| 55D6 | | | | | | | | | | | | | | | | | | | |
| 56H1 | | | | | | | | | | | | | | | | | | | |

| Isolate | 0% Ethanol O.D. 420 nm 24 hrs | 48 hrs | 4% Ethanol(w/w) O.D. 420 nm 24 hrs | 48 hrs | 4.5% Ethanol(w/w) O.D. 420 nm 24 hrs | 48 hrs | 5% Ethanol(w/w) O.D. 420 nm 24 hrs | 48 hrs | 0% Ethanol O.D. 420 nm 24 hrs | 48 hrs | 4% Ethanol(w/w) O.D. 420 nm 24 hrs | 48 hrs | 4.5% Ethanol(w/w) O.D. 420 nm 24 hrs | 48 hrs | 5% Ethanol(w/w) O.D. 420 nm 24 hrs | 48 hrs | 20% HCH | 25% HCH | 50% HCH |
|---|---|---|---|---|---|---|---|---|---|---|---|---|---|---|---|---|---|---|---|
| 45C1 | | | | | | | | | | | | | | | | | | – | – | – |
| 45C2 | | | | | | | | | | | | | | | | | | – | – | – |
| 45C3 | | | | | | | | | | | | | | | | | | – | – | – |
| 45D2 | | | | | | | | | | | | | | | | | | + | – | – |
| 45D3 | | | | | | | | | | | | | | | | | | – | – | – |
| 46C1 | | | | | | | | | | | | | | | | | | + | – | – |
| 46D1 | | | | | | | | | | | | | | | | | | + | – | – |
| 46D3 | | | | | | | | | | | | | | | | | | – | – | – |
| 46D4 | | | | | | | | | | | | | | | | | | – | – | – |
| 47C1 | | | | | | | | | | | | | | | | | | + | – | – |
| 47C2 | | | | | | | | | | | | | | | | | | + | – | – |
| 48C1 | | | | | | | | | | | | | | | | | | + | – | + |
| 48C2 | | | | | | | | | | | | | | | | | | – | – | – |
| 48D1 | | | | | | | | | | | | | | | | | | – | – | – |
| 49C1 | | | | | | | | | | | | | | | | | | + | – | – |
| 49C2 | 0.50 | | 0.02 | 0.02 | 0.04 | 0.04 | 0.04 | 0.04 | 0.15 | 0.40 | 0.10 | 0.04 | 0.03 | 0.04 | 0.05 | 0.04 | + | – | – |
| 49D3 | 0.85 | 0.85 | 0.06 | 0.06 | 0.05 | 0.03 | 0.02 | 0.03 | 0.50 | 0.50 | 0.16 | 0.18 | 0.02 | 0.03 | 0.06 | 0.05 | +++ | + | – |
| 49D4sm | 0.90 | 1.00 | 0.04 | 0.04 | 0.04 | 0.04 | 0.03 | 0.04 | 0.35 | 0.60 | 0.18 | 0.20 | 0.04 | 0.05 | 0.05 | 0.06 | – | + | + |
| 49D4lg | | 1.05 | | | | | | | | | | | | | | | +++ | + | – |
| 50C1 | | | | | | | | | | | | | | | | | | – | – | – |
| 50C2 | | | | | | | | | | | | | | | | | | + | – | – |
| 51C1 | | | | | | | | | | | | | | | | | | – | – | – |
| 51D1 | | | | | | | | | | | | | | | | | | – | – | – |
| 51D2 | | | | | | | | | | | | | | | | | | – | – | – |
| 52D1 | | | | | | | | | | | | | | | | | | – | – | – |
| 52D2 | | | | | | | | | | | | | | | | | | – | – | – |
| 53C1 | | | | | | | | | | | | | | | | | | – | – | – |
| 53C2 | | | | | | | | | | | | | | | | | | – | – | – |
| 53C3 | | | | | | | | | | | | | | | | | | – | – | – |
| 53C4 | | | | | | | | | | | | | | | | | | – | – | – |
| 53C5 | | | | | | | | | | | | | | | | | | – | – | – |

TABLE 2-continued

Properties of all the Isolates

| Isolate | Tetracycline 20 mg/L | Chloramphenicol 30 mg/L | Kanamycin 50 mg/L | Ampicillin 100 mg/L |
|---|---|---|---|---|
| 53D1 | − | − | − | − |
| 53D2 | − | − | − | − |
| 54C1 | − | + | − | − |
| 54D1 | − | − | − | − |
| 54D2 | − | − | − | − |
| 54D3 | − | + | + | − |
| 54D5A | − | − | − | − |
| 54D5B | − | − | − | − |
| 55C1 | − | + | − | − |
| 55C2 | − | − | − | − |
| 55D2 | − | − | − | − |
| 55D5 | − | − | − | − |
| 55D6 | − | − | − | − |
| 56H1 | − | − | − | − |

Aerobic (pH 5.0)

| | 25% HCH, (0.1% YE) | | | 10% HCH, (1% CSL) | | | 25% Overlimed HCH | | | 50% Overlimed HCH | | |
|---|---|---|---|---|---|---|---|---|---|---|---|---|
| | CFU/ml | | pH | CFU/ml | | pH | CFU/ml | | pH | CFU/ml | | pH |
| Isolate | 24 hrs | 48 hrs | 48 hrs | 24 hrs | 48 hrs | 48 hrs | 24 hrs | 48 hrs | 48 hrs | 24 hrs | 48 hrs | 48 hrs |
| 56H1 | | | | | | | 0.56 | 0.60 | 0.17 | 0.21 | 0.06 | 0.06 |
| 45C1 | $1 \times 10^7$ | $6 \times 10^5$ | 4.79 | $>4 \times 10^7$ | $>4 \times 10^7$ | 4.32 | $>4 \times 10^7$ | $10^5$ | 3.98 | | | |
| 45C2 | | | | | | | | | | | | |
| 45C3 | | | | | | | | | | | | |
| 45D2 | | | | | | | | | | | | |
| 45D3 | | | | | | | | | | | | |
| 46C1 | | | | | | | | | | | | |
| 46D1 | | | | | | | | | | | | |
| 46D3 | | | | | | | | | | | | |
| 46D4 | | | | | | | | | | | | |
| 47C1 | | | | | | | | | | | | |
| 47C2 | | | | | | | | | | | | |
| 48C1 | | | | | | | | | | | | |
| 48C2 | | | | | | | | | | | | |
| 48D1 | | | | | | | | | | | | |
| 49C1 | | | | | | | | | | | | |
| 49C2 | | | | | | | | | | | | |
| 49D3 | | | | | | | | | | | | |
| 49D4sm | | | | | | | | | | | | |
| 49D4lg | | | | | | | | | | | | |
| 50C1 | | | | | | | | | | | | |
| 50C2 | | | | | | | | | | | | |
| 51C1 | | | | | | | | | | | | |
| 51D1 | | | | | | | | | | | | |
| 51D2 | | | | | | | | | | | | |
| 52D1 | | | | | | | | | | | | |
| 52D2 | | | | | | | | | | | | |
| 53C1 | | | | | | | | | | | | |

Antibiotic Sensitivity (continued)

| Isolate | Tetracycline 20 mg/L | Chloramphenicol 30 mg/L | Kanamycin 50 mg/L | Ampicillin 100 mg/L |
|---|---|---|---|---|
| 49D3 | + | − | − | − |
| 49D4sm | + | − | − | − |
| 49D4lg | − | − | − | − |

TABLE 2-continued

Properties of all the Isolates

| Isolate | Identification[a] (16S rRNA) | Xylanase 72 hr | CMCase 72 hr | Cellobiose MS (0.1% YE) pH 5.0 72 hr | Growth at pH 5.0 | | | | | | | | | | | |
|---|---|---|---|---|---|---|---|---|---|---|---|---|---|---|---|---|
| | | | | | LB Xylose (1%) | | | | | | LB Glucose (1%) | | | | | |
| | | | | | Anaerobic | | | Aerobic | | | Anaerobic | | | Aerobic | | |
| | | | | | O.D. 420 nm | | pH | O.D. 420 nm | | pH | O.D. 420 nm | | pH | O.D. 420 nm | | pH |
| | | | | | 24 hrs | 48 hrs | 48 hrs | 24 hrs | 48 hrs | 48 hrs | 24 hrs | 48 hrs | 48 hrs | 24 hrs | 48 hrs | 48 hrs |
| 53C2 | | | | | | | | | | | | | | | | |
| 53C3 | | | | | | | | | | | | | | | | |
| 53C4 | | | | | | | | | | | | | | | | |
| 53C5 | | | | | | | | | | | | | | | | |
| 53D1 | | | | | | | | | | | | | | | | |
| 53D2 | | | | | | | | | | | | | | | | |
| 54C1 | | | | | | | | | | | | | | | | |
| 54D1 | | | | | | | | | | | | | | | | |
| 54D2 | | | | | | | | | | | | | | | | |
| 54D3 | | | | | | | | | | | | | | | | |
| 54D5A | | | | | | | | | | | | | | | | |
| 54D5B | | | | | | | | | | | | | | | | |
| 55C1 | | | | | | | | | | | | | | | | |
| 55C2 | | | | | | | | | | | | | | | | |
| 55D2 | | | | | | | | | | | | | | | | |
| 55D5 | | | | | | | | | | | | | | | | |
| 55D6 | | | | | | | | | | | | | | | | |
| 56H1 | | | | | | | | | | | | | | | | |
| 56H3A | B. coagulans | − | − | + | 0.49 | 0.55 | 4.02 | 1.80 | 1.90 | 4.13 | 0.56 | 0.54 | 4.08 | 1.80 | 1.70 | 4.02 |
| 56H3B | B. coagulans | − | − | + | 0.60 | 0.67 | 4.06 | 1.90 | 1.80 | 4.18 | 0.47 | 0.54 | 4.15 | 1.60 | 1.50 | 4.07 |
| 57H1 | B. smithii | + | − | + | 0.13 | 0.17 | 4.62 | 0.50 | 1.70 | 4.1 | 0.34 | 0.33 | 4.24 | 1.30 | 1.30 | 3.98 |
| 57H2 | B. coagulans | + | − | + | 0.52 | 0.54 | 3.93 | 1.80 | 1.60 | 4.09 | 0.62 | 0.62 | 4.03 | 1.80 | 1.90 | 4.25 |
| 57H3 | B. coagulans | − | − | + | 0.38 | 0.35 | 4.21 | 1.90 | 1.45 | 4.25 | 0.31 | 0.28 | 4.37 | 1.50 | 1.50 | 4.34 |
| HCH7 | B. coagulans | − | − | + | 0.31 | 0.33 | 4.27 | 1.45 | 1.50 | 4.30 | 0.32 | 0.28 | 4.21 | 1.15 | 1.20 | 4.31 |
| HCH8 | B. coagulans | − | − | + | 0.34 | 0.34 | 4.18 | 1.10 | 4.00 | 4.50 | 0.33 | 0.31 | 4.18 | 1.55 | 1.60 | 4.37 |
| HCH10 | | − | − | | 0.01 | 0.02 | 4.97 | 0.90 | 0.80 | 7.02 | 0.02 | 0.28 | 4.42 | 1.15 | 1.85 | 4.84 |
| SIC2 | | − | − | | 0.15 | 0.11 | 4.46 | 0.95 | 1.00 | 4.34 | 0.19 | 0.17 | 4.54 | 1.50 | 1.50 | 4.30 |
| SIC3A | | − | − | | 0.09 | 0.07 | 4.63 | 0.30 | 0.40 | 4.80 | 0.08 | 0.08 | 4.66 | 0.25 | 0.55 | 4.57 |
| SIC3B | | − | − | | 0.00 | 0.00 | 4.99 | 0.00 | 0.00 | 5.00 | 0.00 | 0.00 | 5.02 | 0.00 | 0.00 | 5.01 |
| SIC8 | | − | − | | 0.00 | 0.00 | 4.62 | 1.05 | 1.05 | 4.50 | 0.00 | 0.27 | 4.47 | 1.30 | 1.30 | 4.44 |
| SIC9 | | − | − | | 0.17 | 0.16 | 4.70 | 1.35 | 1.95 | 4.47 | 0.27 | 0.36 | 4.46 | 1.25 | 2.40 | 4.40 |
| SID2 | | − | + | | 0.12 | 0.21 | 4.74 | 1.20 | 1.20 | 4.57 | 0.24 | 0.28 | 4.49 | 1.65 | 1.05 | 4.50 |
| SID3 | | − | − | | 0.09 | 0.09 | 5.13 | 0.60 | 1.25 | 5.50 | 0.17 | 0.06 | 5.12 | 1.15 | 1.85 | 5.97 |
| SIIC1 | | − | − | | 0.01 | 0.02 | 4.96 | 0.30 | 0.40 | 5.08 | 0.04 | 0.07 | 4.97 | 1.95 | 0.65 | 4.70 |
| SIID1 | | − | − | | 0.04 | 0.03 | 4.55 | 0.65 | 0.65 | 4.51 | 0.09 | 0.26 | 4.39 | 0.63 | 0.90 | 4.45 |
| Y1 | | − | − | | 0.20 | 0.20 | 4.62 | 0.60 | 0.80 | 4.56 | 0.28 | 0.20 | 4.45 | 0.85 | 0.95 | 4.37 |
| Y2 | | − | − | | 0.17 | 0.18 | 4.51 | 0.95 | 0.95 | 4.49 | 0.21 | 0.24 | 4.40 | 0.95 | 1.05 | 4.40 |
| Y3 | | − | − | | 0.18 | 0.20 | 4.58 | 0.40 | 1.15 | 4.76 | 0.26 | 0.55 | 4.30 | 1.00 | 1.70 | 4.24 |
| Y8 | B. coagulans | − | − | + | | | | | | | | | | | | |

TABLE 2-continued

Properties of all the Isolates

| Isolate | | Stationary Phase Survival | | | | | Anaerobic | | Aerobic | | | |
|---|---|---|---|---|---|---|---|---|---|---|---|---|
| | | LB (Glucose 1%), 48 hrs | | pH, (microaerobic), pH 5.0 | | CFU/ml | | O.D. 420 nm | | O.D. 420 nm | | |
| | | O.D. 420 nm 24 hrs | 48 hrs | 24 hrs | 48 hrs | 24 hrs | 48 hrs | 24 hrs | 48 hrs | pH 48 hrs | 24 hrs | 48 hrs | pH 48 hrs |
| Y11 | | | | | | | | 0.15 | 0.15 | 4.54 | 0.70 | 0.70 | 4.48 | 0.23 | 0.21 | 4.41 | 0.75 | 0.80 | 4.42 |
| Y26 | | | | | | | | 0.13 | 0.16 | 4.50 | 0.70 | 0.70 | 4.51 | 0.26 | 0.25 | 4.40 | 0.95 | 0.97 | 4.42 |
| Y27 | | | | | | | | 0.07 | 0.09 | 4.70 | 0.60 | 0.60 | 4.55 | 0.21 | 0.21 | 4.44 | 0.65 | 0.60 | 4.46 |
| Y33 | | | | | | | | 0.13 | 0.17 | 4.44 | 0.60 | 1.30 | 4.44 | 0.23 | 0.26 | 4.41 | 0.75 | 0.80 | 4.41 |
| Y39 | | | | | | | | 0.34 | 0.33 | 4.22 | 1.25 | 1.85 | 4.27 | 0.55 | 0.50 | 4.24 | 1.50 | 1.55 | 4.18 |
| Y40 | B. coagulans | | | | − | − | | 0.42 | 0.38 | 4.24 | 1.60 | 1.90 | 4.45 | 0.75 | 0.55 | 4.27 | 1.75 | 1.70 | 4.35 |
| Y41 | B. coagulans | | | | − | − | | 0.10 | 0.11 | 4.88 | 0.45 | 0.70 | 6.17 | 0.75 | 0.55 | 4.16 | 2.00 | 1.95 | 4.21 |
| Y42 | | | | | − | − | | 0.09 | 0.17 | 4.59 | 0.90 | 1.00 | 4.45 | 0.09 | 0.10 | 4.63 | 0.60 | 1.05 | 4.42 |
| Y47 | | | | | − | − | | 0.20 | 0.21 | 4.42 | 1.20 | 1.25 | 4.42 | 0.13 | 0.17 | 4.50 | 0.70 | 0.80 | 4.47 |
| Y48 | | | | | − | − | | 0.18 | 0.19 | 4.43 | 1.00 | 1.05 | 4.25 | 0.17 | 0.19 | 4.54 | 0.65 | 0.70 | 4.48 |
| Y49 | | | | | − | − | | 0.21 | 0.19 | 4.45 | 0.95 | 1.05 | 4.26 | 0.20 | 0.18 | 4.49 | 0.60 | 0.70 | 4.52 |
| Y54 | | | | | − | − | | 0.13 | 0.15 | 4.39 | 0.75 | 0.85 | 4.39 | 0.18 | 0.14 | 4.35 | 0.50 | 0.55 | 4.37 |
| Y55 | B. coagulans | | | | − | − | | 0.42 | 0.37 | 4.24 | 1.30 | 1.65 | 4.21 | 0.60 | 0.45 | 4.21 | 1.85 | 1.80 | 4.19 |
| Y56 | B. smithii | | | | + | + | | 0.21 | 0.55 | 4.46 | 0.85 | 2.50 | 4.53 | 0.65 | 0.60 | 4.26 | 1.70 | 1.70 | 4.29 |
| Y61 | | | | | − | − | | 0.16 | 0.19 | 4.47 | 0.75 | 1.45 | 4.38 | 0.25 | 0.29 | 4.40 | 0.75 | 0.75 | 4.40 |
| Y62 | | | | | − | − | | 0.15 | 0.17 | 4.44 | 1.15 | 2.30 | 4.38 | 0.18 | 0.30 | 4.39 | 0.30 | 0.55 | 4.43 |
| Y63 | | | | | − | − | | 0.20 | 0.22 | 4.49 | 1.00 | 1.05 | 4.40 | 0.18 | 0.17 | 4.48 | 0.40 | 0.35 | 4.66 |
| Y64 | | | | | − | − | | 0.14 | 0.13 | 4.61 | 0.06 | 0.19 | 4.54 | 0.13 | 0.17 | 4.59 | 0.10 | 0.29 | 4.46 |
| Y65 | | | | | − | − | | 0.18 | 0.14 | 4.43 | 0.75 | 0.80 | 4.47 | 0.21 | 0.20 | 4.42 | 0.26 | 0.30 | 4.35 |
| Y66 | B. coagulans | | | | + | + | | 0.65 | 0.70 | 4.21 | 1.70 | 1.73 | 4.32 | 0.55 | 0.55 | 4.30 | 2.30 | 2.20 | 4.18 |
| Y67 | | | | | − | − | | 0.13 | 0.14 | 4.61 | 0.03 | 0.28 | 4.54 | 0.12 | 0.16 | 4.55 | 0.03 | 0.22 | 4.57 |
| Y68 | | | | | − | − | | 0.23 | 0.24 | 4.50 | 0.95 | 1.00 | 4.26 | 0.16 | 0.17 | 4.54 | 1.15 | 1.05 | 4.35 |
| Y69 | | | | | − | − | | 0.13 | 0.15 | 4.68 | 1.53 | 2.40 | 4.55 | 0.37 | 0.48 | 4.32 | 1.73 | 1.78 | 4.36 |
| Y70 | | | | | − | − | | 0.18 | 0.18 | 4.49 | 1.00 | 0.95 | 4.31 | 0.19 | 0.19 | 4.47 | 0.90 | 0.88 | 4.34 |
| Y71 | | | | | − | − | | 0.03 | 0.03 | 4.88 | 0.95 | 2.70 | 7.13 | 0.03 | 0.09 | 4.70 | 1.05 | 1.08 | 4.37 |

Growth at pH 6.8

| Isolate | LB Xylose (1%) | | | | | | LB Glucose (1%) | | | | | |
|---|---|---|---|---|---|---|---|---|---|---|---|---|
| | Anaerobic | | | | Aerobic | | | | Anaerobic | | Aerobic | |
| | O.D. 420 nm | | pH | | O.D. 420 nm | | pH | | O.D. 420 nm | | O.D. 420 nm | | pH |
| | 24 hrs | 48 hrs | 48 hrs | | 24 hrs | 48 hrs | 48 hrs | | 24 hrs | 48 hrs | 24 hrs | 48 hrs | 48 hrs |
| 56H3A | 0.72 | 1.00 | 4.08 | | 1.60 | 1.60 | 4.29 | | 0.74 | 1.20 | 2.20 | 2.10 | 4.09 |
| 56H3B | | | | | | | | | | | | | |
| 57H1 | 0.81 | 1.10 | 4.18 | | 2.20 | 1.60 | 4.2 | | 0.76 | 1.00 | 1.80 | 2.10 | 4.1 |
| 57H2 | 0.50 | 0.70 | 4.17 | | 2.00 | 1.90 | 4.19 | | 0.43 | 0.60 | 1.50 | 1.70 | 3.92 |
| 57H3 | 0.73 | 1.00 | 4.12 | | 2.10 | 2.00 | 4.25 | | 0.78 | 1.30 | 2.10 | 1.50 | 4.23 |
| HCH7 | 0.90 | 0.90 | 4.36 | | 1.85 | 2.60 | 4.46 | | 0.90 | 0.90 | 2.00 | 3.10 | 4.31 |
| HCH8 | 0.85 | 1.00 | 4.32 | | 3.70 | 4.00 | 4.31 | | 0.90 | 0.95 | 1.75 | 1.90 | 4.26 |
| HCH10 | 0.80 | 1.10 | 4.26 | | 2.20 | 3.50 | 4.51 | | 0.90 | 0.80 | 1.75 | 2.00 | 4.19 |
| SIC2 | 0.10 | 0.14 | 6.42 | | 0.70 | 0.95 | 6.84 | | 0.04 | 0.08 | 0.85 | 1.35 | 5.25 |
| SIC3A | 0.33 | 0.36 | 4.43 | | 1.80 | 3.40 | 4.34 | | 0.65 | 0.65 | 1.05 | 1.10 | 4.50 |
| SIC3B | 0.55 | 0.60 | 4.43 | | 1.15 | 1.10 | 4.40 | | 0.33 | 0.38 | 1.25 | 1.25 | 4.49 |
| SIC8 | 0.00 | 0.00 | 6.61 | | 0.00 | 0.00 | 6.56 | | 0.00 | 0.00 | 0.00 | 0.00 | 6.76 |
| SIC9 | 0.29 | 0.29 | 4.69 | | 1.65 | 2.50 | 4.35 | | 0.60 | 0.65 | 1.30 | 1.20 | 4.66 |
| SID2 | 0.26 | 0.29 | 4.84 | | 1.80 | 2.70 | 4.70 | | 0.26 | 0.40 | 2.20 | 3.40 | 5.05 |

Additional stationary phase data:
- HCH7: 1.70 / 1.90 O.D.; 4.52 pH; 7.7 × 10⁷ / 7.1 × 10⁵ CFU/ml
- HCH8: 1.90 / 2.05 O.D.; 4.38 pH; 1.2 × 10⁵ / nd CFU/ml
- HCH10: 1.20 / 1.25 O.D.; 4.33 pH; 7.5 × 10⁴ / nd CFU/ml TABLE 2-continued Properties of all the Isolates

| Isolate | Lactate mM | Formate mM | Fumarate μM | Acetate mM | Ethanol mM | Succinate mM | Lactate mM | Glucose mM | Formate mM | Fumarate μM | Acetate mM | Ethanol mM |
|---|---|---|---|---|---|---|---|---|---|---|---|---|
| SID3 | | | | 0.10 | 0.40 | 4.42 | 1.10 | 2.20 | 4.89 | 0.24 | 0.34 | 4.62 | 1.20 | 2.20 | 4.67 |
| SIIC1 | | | | 0.06 | 0.07 | 6.14 | 1.30 | 1.65 | 6.36 | 0.06 | 0.10 | 5.65 | 1.60 | 1.15 | 6.22 |
| SIID1 | | | | 0.08 | 0.08 | 6.22 | 1.25 | 1.50 | 5.43 | 0.10 | 0.13 | 5.71 | 1.70 | 1.50 | 5.75 |
| Y1 | | | | 0.25 | 0.24 | 4.74 | 0.70 | 1.25 | 4.93 | 0.32 | 0.35 | 4.52 | 0.95 | 1.00 | 4.67 |
| Y2 | | | | 0.14 | 0.14 | 4.73 | 0.70 | 1.00 | 4.65 | 0.22 | 0.29 | 4.60 | 0.95 | 1.40 | 4.62 |
| Y3 | | | | 0.25 | 0.27 | 4.64 | 0.75 | 1.10 | 4.83 | 0.28 | 0.28 | 4.47 | 1.10 | 1.20 | 4.65 |
| Y8 | | | | 0.25 | 0.65 | 4.57 | 0.55 | 1.20 | 5.10 | 0.90 | 1.10 | 4.23 | 2.80 | 3.10 | 4.28 |
| Y11 | | | | 0.07 | 0.25 | 4.65 | 0.65 | 1.25 | 4.64 | 0.29 | 0.34 | 4.46 | 1.35 | 1.45 | 4.69 |
| Y26 | | | | 0.25 | 0.20 | 4.61 | 0.65 | 1.20 | 4.64 | 0.31 | 0.34 | 4.53 | 1.25 | 1.45 | 4.67 |
| Y27 | | | | 0.22 | 0.12 | 4.81 | 0.55 | 1.25 | 4.66 | 0.24 | 0.32 | 4.55 | 0.90 | 0.95 | 4.73 |
| Y33 | | | | 0.11 | 0.18 | 4.66 | 0.75 | 1.55 | 4.68 | 0.19 | 0.26 | 4.50 | 0.90 | 1.20 | 4.87 |
| Y39 | | | | 0.16 | 0.80 | 4.26 | 1.10 | 1.10 | 4.52 | 0.80 | 1.05 | 4.43 | 1.60 | 1.80 | 4.38 |
| Y40 | | | | 0.70 | 0.90 | 4.35 | 1.80 | 2.80 | 4.37 | 0.75 | 0.90 | 4.24 | 1.65 | 1.80 | 4.35 |
| Y41 | | | | 0.95 | 0.04 | 5.94 | 0.65 | 0.80 | 6.66 | 0.95 | 1.15 | 4.28 | 3.00 | 3.60 | 4.33 |
| Y47 | 1.60 | nd | | 0.05 | 0.34 | 4.46 | 0.00 | 0.80 | 6.52 | 0.02 | 0.31 | 4.53 | 0.00 | 1.15 | 4.45 |
| Y48 | | | | 0.00 | 0.50 | 4.44 | 1.30 | 1.30 | 4.40 | 0.50 | 0.55 | 4.41 | 0.70 | 0.70 | 4.39 |
| Y49 | | | | 0.00 | 0.37 | 4.43 | 0.60 | 1.40 | 4.35 | 0.50 | 0.55 | 4.47 | 0.00 | 1.15 | 4.50 |
| Y54 | | | | 0.50 | 0.55 | 4.43 | 1.15 | 1.30 | 4.30 | 0.27 | 0.55 | 4.40 | 0.80 | 0.95 | 4.43 |
| Y55 | 1.80 | <10⁴ | | 0.00 | 0.40 | 4.52 | 0.75 | 1.60 | 4.44 | 0.95 | 1.05 | 4.45 | 0.00 | 0.70 | 4.44 |
| Y56 | | | | 0.85 | 0.82 | 4.32 | 1.60 | 1.45 | 4.29 | 0.85 | 0.95 | 4.29 | 2.00 | 2.40 | 4.28 |
| Y61 | | | | 0.22 | 0.40 | 4.62 | 0.95 | 1.35 | 4.72 | 0.26 | 0.32 | 4.29 | 2.40 | 2.60 | 4.20 |
| Y62 | | | | 0.21 | 0.22 | 4.55 | 0.60 | 1.35 | 4.70 | 0.85 | 0.90 | 4.47 | 0.95 | 1.70 | 4.67 |
| Y63 | | | | 0.75 | 0.70 | 4.55 | 1.65 | 1.95 | 4.51 | 0.25 | 0.55 | 4.34 | 1.60 | 1.70 | 4.53 |
| Y64 | | | | 0.38 | 0.55 | 4.40 | 1.00 | 1.20 | 4.41 | 0.00 | 0.10 | 4.51 | 1.10 | 1.25 | 4.57 |
| Y65 | | | | 0.07 | 0.36 | 4.50 | 0.01 | 0.07 | 6.15 | 0.45 | 0.53 | 5.62 | 0.00 | 0.75 | 4.67 |
| Y66 | 1.70 | 2 × 10⁴ | | 0.48 | 0.50 | 4.60 | 1.30 | 1.28 | 4.35 | 0.80 | 0.98 | 4.50 | 1.15 | 1.10 | 4.43 |
| Y67 | | | | 0.83 | 1.03 | 4.24 | 2.00 | 1.95 | 4.75 | 0.95 | 0.00 | 4.33 | 2.00 | 2.30 | 4.23 |
| Y68 | | | | 0.09 | 0.32 | 4.58 | 0.00 | 1.08 | 4.42 | 0.00 | 0.00 | 6.67 | 0.00 | 0.02 | 6.65 |
| Y69 | | | | 0.40 | 0.53 | 4.43 | 1.35 | 1.25 | 4.31 | 0.31 | 0.53 | 4.39 | 1.30 | 1.25 | 4.34 |
| Y70 | | | | 0.39 | 0.45 | 4.79 | 1.50 | 1.88 | 4.81 | 0.70 | 0.95 | 4.32 | 1.85 | 2.65 | 4.46 |
| Y71 | | | | 0.07 | 0.31 | 4.63 | 1.13 | 0.95 | 4.33 | 0.28 | 0.40 | 4.50 | 0.93 | 0.85 | 4.44 |
| | | | | 0.06 | 0.07 | 6.27 | 0.45 | 0.48 | 5.68 | 0.03 | 0.09 | 5.65 | 0.95 | 1.25 | 4.70 |

Fermentation Products (48 hr) (pH not Controlled)

| | LB (1% Xylose), pH 6.8 | | | | | | LB (1% Glucose), pH 6.8 | | | | | |
|---|---|---|---|---|---|---|---|---|---|---|---|---|
| Isolate | Xylose mM | Succinate mM | Lactate mM | Formate mM | Fumarate μM | Acetate mM | Ethanol mM | Glucose mM | Succinate mM | Lactate mM | Formate mM | Fumarate μM | Acetate mM | Ethanol mM |
| 56H3A | | | | | | | | | | | | | | |
| 56H3B | | | | | | | | | | | | | | |
| 57H1 | | | | | | | | | | | | | | |
| 57H2 | | | | | | | | | | | | | | |
| 57H3 | | | | | | | | | | | | | | |
| HCH7 | 46.5 | 1.4 | 12.2 | 4.1 | | 5.3 | | 41.5 | 1.3 | 16.1 | | | * | |
| HCH8 | 48.1 | 1.9 | 14.3 | 3.9 | | 5.3 | | 40.0 | 1.1 | 17.3 | | | 2.8 | |
| HCH10 | 46.6 | 1.6 | 12.9 | 8.7 | 9.0 | 4.5 | | 39.4 | 1.3 | 20.1 | | | 2.0 | |
| SIC2 | | | | | | | | | | | | | | |
| SIC3A | 42.4 | 1.8 | 15.1 | | | * | | 44.9 | 1.6 | 15.5 | | | 2.1 | |

TABLE 2-continued

Properties of all the Isolates

| Isolate | | | | | | | |
|---|---|---|---|---|---|---|---|
| SIC3B | 48.8 | 1.7 | 16.3 | | 3.7 | | |
| SIC8 | | | | | | | |
| SIC9 | 43.2 | 1.4 | 11.5 | | 2.5 | | |
| SID2 | | | | | | | |
| SID3 | | | | | | | |
| SIIC1 | | | | | | | |
| SIID1 | | | | | | | |
| Y1 | | | | | | | |
| Y2 | | | | | | | |
| Y3 | | | | | | | |
| Y8 | 59.6 | 1.7 | 2.4 | | 9.6 | 8.9 | |
| Y11 | | | | | | | |
| Y26 | | | | | | | |
| Y27 | | | | | | | |
| Y33 | | | | | | | |
| Y39 | 53.2 | 1.7 | 14.6 | 6.5 | 4.7 | 50.7 | 1.8 | 20.8 | 2.0 |
| Y40 | 53.2 | 1.6 | 13.9 | 5.6 | 3.7 | 57.6 | 1.5 | 17.6 | * |
| Y41 | 74.0 | 1.5 | 15.6 | * | 3.4 | 56.3 | 1.7 | 22.0 | 2.0 |
| Y42 | | | | | Pyruvate 0.86 | | | | |
| Y47 | 52.0 | 2.0 | 15.8 | * | 7.0 | | 40.7 | 1.6 | 16.0 | * |
| Y48 | 50.5 | 1.6 | 15.8 | * | * | 10.8 | 42.9 | 1.5 | 15.2 | * |
| Y49 | 51.1 | 1.7 | 15.6 | * | 2.3 | | 42.7 | 1.4 | 17.2 | * |
| Y54 | | | | | | 10.4 | | | | |
| Y55 | 57.3 | 1.3 | 14.3 | 4.1 | 2.6 | | 56.1 | 1.5 | 21.1 | |
| Y56 | 51.5 | 1.8 | 5.2 | 9.8 | 10.0 | | 51.2 | 1.6 | 19.6 | 2.2 |
| Y61 | 58.8 | 1.4 | 4.9 | 7.1 | 5.9 | 9.1 | 53.9 | 1.5 | 18.2 | |
| Y62 | | | | | | | | | | |
| Y63 | | | | | | | | | | |
| Y64 | | | | | | | | | | |
| Y65 | 50.0 | 1.7 | 14.5 | * | * | | 55.8 | 2.5 | 15.3 | 2.4 |
| Y66 | 39.5 | 1.5 | 23.4 | 4.4 | 4.1 | | 49.8 | 2.0 | 18.7 | |
| Y67 | | | | | | | | | | |
| Y68 | | | | | | | | | | |
| Y69 | 51.8 | 1.7 | 7.1 | 12.5 | 10.0 | | 49.7 | 2.0 | 20.4 | |
| Y70 | | | | | | | | | | |
| Y71 | | | | | | | | | | |

Fermentation Products (48 hr) (pHstat)

| | LB (1% Xylose), pH 5.0 | | | | | | LB (1% Glucose), pH 5.0 | | | | | |
|---|---|---|---|---|---|---|---|---|---|---|---|---|
| Isolate | Xylose mM | Lactate mM | Succinate mM | Acetate mM | Ethanol mM | Formate mM | Fumarate μM | Glucose mM | Lactate mM | Succinate mM | Acetate mM | Ethanol mM | Formate mM | Fumarate μM |
| 56H3A | 0.00 | 95.54 | 3.25 | 9.19 | 8.04 | 7.57 | 0.00 | 0.00 | 92.38 | 0.83 | 5.18 | 0.00 | 0.00 | 0.00 |
| 56H3B | 0.00 | 84.76 | 3.63 | 16.34 | 10.80 | 11.45 | 0.00 | 0.00 | 95.00 | 0.59 | 4.42 | 0.00 | 0.00 | 0.00 |
| 57H1 | 0.00 | 75.03 | 4.13 | 12.36 | 18.67 | 11.11 | 0.00 | 0.00 | 95.20 | 0.56 | 3.89 | 0.00 | 0.00 | 0.00 |
| 57H2 | 0.00 | 86.62 | 3.90 | 5.63 | 16.90 | 3.25 | 0.00 | 4.42 | 92.09 | 1.35 | 10.48 | 0.00 | 0.00 | 0.00 |

TABLE 2-continued

Properties of all the Isolates

| | | | | | | | | | | |
|---|---|---|---|---|---|---|---|---|---|---|
| 57H3 | 0.00 | 87.91 | 3.08 | 14.96 | 8.71 | 5.42 | 0.00 | 97.17 | 0.55 | 3.66 | 0.00 | 0.00 |
| HCH7 | 0.00 | 63.17 | 2.24 | 27.47 | 15.96 | 14.23 | 0.00 | 94.12 | 0.74 | 1.73 | 2.85 | 0.00 |
| HCH8 | 0.00 | 71.97 | 2.45 | 22.35 | 9.00 | 7.45 | 0.00 | 91.39 | 0.81 | 1.67 | 0.00 | 0.00 |
| HCH10 | 0.00 | 86.23 | 3.92 | 8.23 | 10.19 | 6.74 | 0.00 | 103.11 | 2.77 | 4.63 | 0.00 | 3.56 |
| SIC2 | | | | | | | | | | | | |
| SIC3A | | | | | | | | | | | | |
| SIC3B | | | | | | | | | | | | |
| SIC8 | | | | | | | | | | | | |
| SIC9 | | | | | | | | | | | | |
| SID2 | | | | | | | | | | | | |
| SID3 | | | | | | | | | | | | |
| SIIC1 | | | | | | | | | | | | |
| SIID1 | | | | | | | | | | | | |
| Y1 | | | | | | | | | | | | |
| Y2 | | | | | | | | | | | | |
| Y3 | | | | | | | | | | | | |
| Y8 | 55.11 | 2.22 | 1.32 | 15.61 | 6.12 | 9.80 | 0.00 | 98.49 | 1.19 | 9.49 | 0.00 | 0.00 |
| Y11 | | | | | | | | | | | | |
| Y26 | | | | | | | | | | | | |
| Y27 | | | | | | | | | | | | |
| Y33 | | | | | | | | | | | | |
| Y39 | | | | | | | | | | | | |
| Y40 | 0.42 | 81.51 | 2.24 | 18.59 | 11.31 | 6.02 | 0.00 | 92.60 | 0.70 | 11.42 | 1.89 | 0.00 |
| Y41 | 34.17 | 30.92 | 1.07 | 16.11 | 6.29 | 5.97 | 0.00 | 96.48 | 1.00 | 8.76 | 0.00 | 0.00 |
| Y42 | | | | | | | | | | | | |
| Y47 | | | | | | | | | | | | |
| Y48 | | | | | | | | | | | | |
| Y49 | | | | | | | | | | | | |
| Y54 | | | | | | | | | | | | |
| Y55 | 0.00 | 85.26 | 2.46 | 12.67 | 15.24 | 10.65 | 8.77 | 97.99 | 0.45 | 0.48 | 5.27 | 0.00 |
| Y56 | 27.11 | 25.99 | 1.73 | 28.87 | 7.31 | 11.03 | 0.00 | 91.56 | 0.99 | 10.48 | 0.00 | 0.00 |
| Y61 | | | | | | | | | | | | |
| Y62 | | | | | | | | | | | | |
| Y63 | | | | | | | | | | | | |
| Y64 | | | | | | | | | | | | |
| Y65 | | | | | | | | | | | | |
| Y66 | 0.63 | 89.90 | 2.72 | 10.58 | 11.48 | 12.05 | 0.00 | 107.22 | 1.15 | 2.14 | 3.24 | 0.00 |
| Y67 | | | | | | | | | | | | |
| Y68 | | | | | | | | | | | | |
| Y69 | | | | | | | | | | | | |
| Y70 | | | | | | | | | | | | |
| Y71 | | | | | | | | | | | | |

TABLE 2-continued

Properties of all the Isolates

| | Anaerobic Growth | | | | | | | | | | | | | | |
|---|---|---|---|---|---|---|---|---|---|---|---|---|---|---|---|
| | LB Glucose (1%), pH 4.5 | | | LB Xylose (1%), pH 4.5 | | | MS (0.1% YE) (Xylose 1%), pH 5 | | | MS (0.1% YE) (Glucose 1%), pH 5 | | | HCH 10% CSL 1%, pH 5 | | |
| | O.D. 420 nm | | pH | O.D. 420 nm | | pH | O.D. 420 nm | | pH | O.D. 420 nm | | pH | O.D. 420 nm | | pH |
| Isolate | 24 hrs | 48 hrs | 48 hrs | 24 hrs | 48 hrs | 48 hrs | 24 hrs | 48 hrs | 48 hrs | 24 hrs | 48 hrs | 48 hrs | 24 hrs | 48 hrs | 48 hrs |
| 56H3A | | | | | | | 0.14 | 0.15 | 4.27 | 0.11 | 0.12 | 4.18 | 0.23 | 0.26 | 3.95 |
| 56H3B | | | | | | | | | | | | | 0.31 | 0.31 | 3.96 |
| 57H1 | | | | | | | 0.08 | 0.1 | 4.21 | 0.08 | 0.09 | 4.13 | 0.03 | 0.09 | 3.98 |
| 57H2 | | | | | | | 0.07 | 0.08 | 4.14 | 0.07 | 0.06 | 4.12 | 0.32 | 0.30 | 3.97 |
| 57H3 | | | | | | | 0.18 | 0.2 | 4.21 | 0.15 | 0.16 | 4.17 | 0.28 | 0.28 | 4.05 |
| HCH7 | 0.00 | 0.00 | 4.44 | 0.00 | 0.15 | 4.36 | 0.23 | 0.25 | 4.61 | 0.05 | 0.05 | 4.56 | 0.02 | 0.08 | 4.04 |
| HCH8 | 0.18 | 0.16 | 4.30 | 0.21 | 0.22 | 4.32 | 0.27 | 0.30 | 4.57 | 0.04 | 0.10 | 4.50 | 0.08 | 0.15 | 4.02 |
| HCH10 | 0.02 | 0.08 | 4.39 | 0.01 | 0.06 | 4.42 | 0.15 | 0.17 | 4.52 | 0.02 | 0.09 | 4.50 | | | |
| SIC2 | | | | | | | | | | | | | | | |
| SIC3A | 0.00 | 0.05 | 4.51 | 0.00 | 0.00 | 4.47 | 0.08 | 0.08 | 4.50 | 0.03 | 0.03 | 4.48 | 0.00 | 0.00 | 4.33 |
| SIC3B | 0.02 | 0.05 | 4.51 | 0.00 | 0.00 | 4.46 | 0.05 | 0.01 | 4.84 | 0.04 | 0.03 | 4.48 | 0.00 | 0.00 | 4.34 |
| SIC8 | | | | | | | | | | | | | | | |
| SIC9 | 0.04 | 0.04 | 4.52 | 0.04 | 0.00 | 4.46 | 0.11 | 0.19 | 4.57 | 0.08 | 0.14 | 4.50 | 0.00 | 0.00 | 4.51 |
| SID2 | | | | | | | | | | | | | | | |
| SID3 | | | | | | | | | | | | | | | |
| SIID1 | | | | | | | | | | | | | | | |
| Y1 | | | | | | | | | | | | | | | |
| Y2 | | | | | | | | | | | | | | | |
| Y3 | | | | | | | | | | | | | | | |
| Y8 | 0.16 | 0.17 | 4.28 | 0.08 | 0.12 | 4.49 | 0.09 | 0.06 | 5.29 | 0.10 | 0.12 | 4.59 | 0.05 | 0.13 | 4.09 |
| Y11 | | | | | | | | | | | | | | | |
| Y26 | | | | | | | | | | | | | | | |
| Y27 | | | | | | | | | | | | | | | |
| Y33 | | | | | | | | | | | | | | | |
| Y39 | 0.05 | 0.22 | 4.23 | 0.08 | 0.18 | 4.30 | 0.16 | 0.15 | 4.52 | 0.04 | 0.12 | 4.51 | 0.14 | 0.18 | 4.06 |
| Y40 | 0.08 | 0.24 | 4.27 | 0.12 | 0.20 | 4.39 | 0.12 | 0.10 | 4.53 | 0.03 | 0.13 | 4.55 | 0.15 | 0.14 | 4.08 |
| Y41 | 0.11 | 0.14 | 4.29 | 0.07 | 0.10 | 4.49 | 0.14 | 0.10 | 5.23 | 0.06 | 0.09 | 4.54 | 0.02 | 0.13 | 4.09 |
| Y42 | | | | | | | | | | | | | | | |
| Y47 | 0.03 | 0.00 | 4.45 | 0.03 | 0.02 | 4.49 | 0.10 | 0.09 | 4.58 | 0.05 | 0.07 | 4.54 | 0.00 | 0.00 | 4.50 |
| Y48 | 0.02 | 0.00 | 4.46 | 0.00 | 0.01 | 4.51 | 0.11 | 0.08 | 4.56 | 0.00 | 0.01 | 4.50 | 0.00 | 0.00 | 4.43 |
| Y49 | 0.04 | 0.03 | 4.44 | 0.00 | 0.00 | 4.49 | 0.10 | 0.08 | 4.56 | 0.00 | 0.01 | 4.47 | 0.00 | 0.00 | 4.38 |
| Y54 | | | | | | | | | | | | | | | |
| Y55 | 0.14 | 0.28 | 4.31 | 0.13 | 0.23 | 4.30 | 0.17 | 0.17 | 4.46 | 0.12 | 0.14 | 4.48 | 0.19 | 0.21 | 4.08 |
| Y56 | 0.00 | 0.25 | 4.24 | 0.01 | 0.17 | 4.65 | 0.16 | 0.11 | 4.62 | 0.08 | 0.13 | 4.50 | 0.11 | 0.15 | 4.13 |
| Y61 | 0.00 | 0.01 | 4.46 | 0.00 | 0.00 | 4.49 | 0.14 | 0.18 | 4.65 | 0.07 | 0.16 | 4.45 | 0.02 | 0.03 | 4.14 |
| Y62 | | | | | | | | | | | | | | | |
| Y63 | | | | | | | | | | | | | | | |
| Y64 | | | | | | | | | | | | | | | |
| Y65 | 0.00 | 0.00 | 4.47 | 0.03 | 0.04 | 4.41 | 0.00 | 0.03 | 4.50 | 0.03 | 0.03 | 4.43 | + | + | 4.06 |
| Y66 | 0.20 | 0.28 | 4.25 | 0.16 | 0.18 | 4.33 | 0.17 | 0.18 | 4.51 | 0.10 | 0.08 | 4.42 | 0.16 | 0.20 | 4.08 |

TABLE 2-continued

Properties of all the Isolates

| Isolate | LB (Glucose 1%, pH 6.8) 0% Ethanol O.D. 420 nm 24 hrs | 48 hrs | 4% Ethanol(w/w) O.D. 420 nm 24 hrs | 48 hrs | 4.5% Ethanol(w/w) O.D. 420 nm 24 hrs | 48 hrs | 5% Ethanol(w/w) O.D. 420 nm 24 hrs | 48 hrs | LB (Glucose 1%, pH 5.0) 0% Ethanol O.D. 420 nm 24 hrs | 48 hrs | 4% Ethanol(w/w) O.D. 420 nm 24 hrs | 48 hrs | 4.5% Ethanol(w/w) O.D. 420 nm 24 hrs | 48 hrs | 5% Ethanol(w/w) O.D. 420 nm 24 hrs | 48 hrs | 20% HCH 0.1% YE/Glu pH 5.0[v] plates (48 hrs) | 25% HCH 0.1% YE/Glu pH 5.0[v] plates (48 hrs) | 50% HCH overlimed 0.1% YE/Glu pH 5.0[v] plates (48 hrs) |
|---|---|---|---|---|---|---|---|---|---|---|---|---|---|---|---|---|---|---|---|
| Y67 | | 0.18 | 0.23 | 4.30 | 0.09 | 0.14 | 4.44 | 0.13 | 0.15 | 4.76 | 0.12 | 0.14 | 4.47 | 0.00 | | | | | 4.28 |
| Y68 | | | | | | | | | | | | | | | | | | | |
| Y69 | | | | | | | | | | | | | | | | | | | |
| Y70 | | | | | | | | | | | | | | | | | | | |
| Y71 | | | | | | | | | | | | | | | | | | | |
| 56H3A | | | | | | | | | | 0.62 | 0.63 | 0.14 | 0.15 | 0.09 | 0.11 | 0.03 | 0.03 | +++ | + | − |
| 56H3B | | | | | | | | | | 0.66 | 0.58 | 0.10 | 0.09 | 0.03 | 0.05 | 0.03 | 0.02 | +++ | ++ | − |
| 57H1 | | | | | | | | | | 0.47 | 0.42 | 0.07 | 0.20 | 0.05 | 0.12 | 0.03 | 0.04 | +++ | +++ | − |
| 57H2 | | | | | | | | | | 0.35 | 0.37 | 0.04 | 0.03 | 0.03 | 0.06 | 0.01 | 0.02 | +++ | + | − |
| 57H3 | | | | | | | | | | 0.50 | 0.57 | 0.14 | 0.13 | 0.08 | 0.08 | 0.01 | 0.03 | +++ | ++ | − |
| HCH7 | 0.90 | 0.95 | 0.03 | 0.02 | 0.02 | 0.02 | 0.01 | 0.01 | 0.30 | 0.30 | 0.17 | 0.16 | 0.05 | 0.05 | 0.05 | 0.05 | +++ | ++ | + |
| HCH8 | 1.00 | 1.05 | 0.17 | 0.28 | 0.09 | 0.08 | 0.07 | 0.06 | 0.46 | 0.48 | 0.12 | 0.13 | 0.06 | 0.06 | 0.05 | 0.04 | +++ | ++ | + |
| HCH10 | 0.75 | 0.95 | 0.03 | 0.06 | 0.04 | 0.04 | 0.05 | 0.04 | 0.45 | 0.50 | 0.07 | 0.07 | 0.01 | 0.02 | 0.03 | 0.03 | +++ | ++ | + |
| SIC2 | | | | | | | | | | | | | | | | | | − | − | − |
| SIC3A | | | | | | | | | | | | | | | | | | − | − | − |
| SIC3B | | | | | | | | | | | | | | | | | | − | − | − |
| SIC8 | | | | | | | | | | | | | | | | | | − | − | − |
| SIC9 | | | | | | | | | | | | | | | | | | − | − | − |
| SID2 | | | | | | | | | | | | | | | | | | − | − | − |
| SID3 | | | | | | | | | | | | | | | | | | − | − | − |
| SIIC1 | | | | | | | | | | | | | | | | | | − | − | − |
| SIID1 | | | | | | | | | | | | | | | | | | − | − | − |
| Y1 | | | | | | | | | | | | | | | | | | − | − | − |
| Y2 | | | | | | | | | | | | | | | | | | − | − | − |
| Y3 | | | | | | | | | | | | | | | | | | − | − | − |
| Y8 | 0.80 | 0.90 | 0.03 | 0.08 | 0.04 | 0.04 | 0.02 | 0.02 | 0.77 | 0.85 | 0.22 | 0.21 | 0.10 | 0.11 | 0.09 | 0.11 | + | − | − |
| Y11 | | | | | | | | | | | | | | | | | | − | − | − |
| Y26 | | | | | | | | | | | | | | | | | | − | − | − |
| Y27 | | | | | | | | | | | | | | | | | | − | − | − |
| Y33 | | | | | | | | | | | | | | | | | | − | − | − |
| Y39 | | | | | | | | | | | | | | | | | | − | − | − |
| Y40 | | | | | | | | | | 0.66 | 0.72 | 0.07 | 0.14 | 0.04 | 0.08 | 0.00 | 0.05 | + | − | − |
| Y41 | | | | | | | | | | 0.67 | 0.72 | 0.19 | 0.15 | 0.18 | 0.17 | 0.16 | 0.16 | + | − | + |
| Y42 | | | | | | | | | | | | | | | | | | + | − | − |
| Y47 | | | | | | | | | | | | | | | | | | − | − | − |
| Y48 | | | | | | | | | | | | | | | | | | − | − | − |
| Y49 | | | | | | | | | | | | | | | | | | − | − | − |
| Y54 | | | | | | | | | | | | | | | | | | − | − | − |
| Y55 | 1.10 | 1.20 | 0.30 | 0.34 | 0.09 | 0.28 | 0.03 | 0.04 | 0.65 | 0.70 | 0.14 | 0.13 | 0.06 | 0.06 | 0.07 | 0.07 | + | − | − |
| Y56 | | | | | | | | | | 0.66 | 0.70 | 0.15 | 0.21 | 0.18 | 0.21 | 0.06 | 0.09 | − | − | − |
| Y61 | | | | | | | | | | | | | | | | | | − | − | − |

TABLE 2-continued

Properties of all the Isolates

Aerobic (pH 5.0)

| Isolate | 25% HCH, (0.1% YE) | | 10% HCH, (1% CSL) | | 25% Overlimed HCH | | 50% Overlimed HCH (0.1% YE) | | Antibiotic Sensitivity | | | |
|---|---|---|---|---|---|---|---|---|---|---|---|---|
| | CFU/ml | pH | CFU/ml | pH | CFU/ml | pH | CFU/ml | pH | Tetracycline 20 mg/L | Chloramphenicol 30 mg/L | Kanamycin 50 mg/L | Ampicillin 100 mg/L |
| | 24 hrs | 48 hrs | 48 hrs | 24 hrs | 48 hrs | 48 hrs | 24 hrs | 48 hrs | 48 hrs | 24 hrs | 48 hrs | 48 hrs |
| Y62 | | | | | | | | | | – | – | – |
| Y63 | | | | | | | | | | + | – | – |
| Y64 | | | | | | | | | | ++ | – | – |
| Y65 | | | | | | | | | | + | – | – |
| Y66 | 1.00 | 1.05 | 0.02 | 0.02 | 0.02 | 0.02 | 0.02 | 0.02 | 0.02 | – | – | – |
| Y67 | | | | | | | | | | + | – | – |
| Y68 | | | | | | | | | | + | – | – |
| Y69 | | | | | | | | | | ++ | – | – |
| Y70 | | | | | | | | | 0.02 | – | – | – |
| Y71 | | | | | | | | | | | | |
| 56H3A | | | | | | | | | | | | |
| 56H3B | | | | | | | | | | | | |
| 57H1 | | | | | | | | | | | | |
| 57H2 | | | | | | | | | | | | |
| 57H3 | | | | | | | | | | | | |
| HCH7 | >4 × 10⁷ | 4 × 10⁵ | 3.99 | 3 × 10⁷ | 3 × 10⁶ | 4.51 | >4 × 10⁷ | 6 × 10⁶ | 4.23 | >4 × 10⁷ | 10⁴ | 4.3 |
| HCH8 | 8 × 10⁶ | — | 3.97 | >4 × 10⁷ | 4 × 10⁷ | 4.94 | 10⁷ | 2 × 10⁶ | 4.17 | >4 × 10⁷ | 9 × 10³ | 4.38 |
| HCH10 | >4 × 10⁷ | | 4.18 | 2 × 10⁷ | 3 × 10⁶ | 4.37 | 7 × 10⁶ | 2 × 10⁵ | 4.4 | 10⁵ | 10⁵ | 4.75 |
| SIC2 | | | | | | | | | | – | – | – |
| SIC3A | | | | | | | | | | – | – | – |
| SIC3B | | | | | | | | | | – | – | – |
| SIC8 | | | | | | | | | | | | |
| SIC9 | | | | | | | | | | | | |
| SID2 | | | | | | | | | | | | |
| SID3 | | | | | | | | | | | | |
| SIIC1 | | | | | | | | | | | | |
| SIID1 | | | | | | | | | | | | |
| Y1 | | | | | | | | | | | | |
| Y2 | | | | | | | | | | | | |
| Y3 | | | | | | | | | | | | |
| Y8 | | | | | | | | | | | | |
| Y11 | | | | | | | | | | | | |
| Y26 | | | | | | | | | | | | |
| Y27 | | | | | | | | | | | | |
| Y33 | | | | | | | | | | | | |
| Y39 | | | | | | | | | | | | |
| Y40 | | | | | | | | | | – | | |
| Y41 | | | | | | | | | | | – | – |
| Y42 | | | | | | | | | | | | |
| Y47 | | | | | | | | | | | | |
| Y48 | | | | | | | | | | | | – |

TABLE 2-continued

Properties of all the Isolates

| Isolate | Identification[a] (16S rRNA) | Xylanase 72 hr | CMCase 72 hr | Cellobiose MS (0.1% YE) pH 5.0 72 hr | Growth at pH 5.0 | | | | | | | | | | | |
|---|---|---|---|---|---|---|---|---|---|---|---|---|---|---|---|---|
| | | | | | LB Xylose (1%) | | | | | | LB Glucose (1%) | | | | | |
| | | | | | Anaerobic | | | Aerobic | | | Anaerobic | | | Aerobic | | |
| | | | | | O.D. 420 nm | | pH | O.D. 420 nm | | pH | O.D. 420 nm | | pH | O.D. 420 nm | | pH |
| | | | | | 24 hrs | 48 hrs | 48 hrs | 24 hrs | 48 hrs | 48 hrs | 24 hrs | 48 hrs | 48 hrs | 24 hrs | 48 hrs | 48 hrs |
| Y49 | | | | | | | | | | | | | | | | |
| Y54 | | | | | | | | | | | | | | | | |
| Y55 | | | | | | | | | | | | | | | | |
| Y56 | | | | | | | | | | | | | | | | |
| Y61 | | | | | | | | | | | | | | | | |
| Y62 | | – | | | | | | | | | | | | | | |
| Y63 | | | | | | | | | | | | | | | | |
| Y64 | | | | | | | | | | | | | | | | |
| Y65 | | | | | | | | | | | | | | | | |
| Y66 | | | | | | | | | | | | | | | | |
| Y67 | | – | | | | | | | | | | | | | | |
| Y68 | | | | | | | | | | | | | | | | |
| Y69 | | – | | | | | | | | | | | | | | |
| Y70 | | | | | | | | | | | | | | | | |
| Y71 | | | | | | | | | | | | | | | | |
| Y72 | | – | – | | 0.31 | 0.31 | 4.38 | 1.68 | 2.70 | 4.42 | 0.39 | 0.39 | 4.36 | 1.80 | 1.68 | 4.30 |
| Y73 | | – | – | | 0.12 | 0.12 | 4.91 | 0.60 | 1.70 | 6.63 | 0.55 | 0.65 | 4.29 | 0.60 | 0.58 | 4.20 |
| Y75 | | – | – | | 0.14 | 0.14 | 4.56 | 1.10 | 1.20 | 4.47 | 0.25 | 0.25 | 4.46 | 1.03 | 0.98 | 4.54 |
| Y77 | | – | – | | 0.18 | 0.15 | 4.45 | 0.98 | 1.03 | 4.31 | 0.14 | 0.17 | 4.54 | 0.63 | 0.65 | 4.50 |
| Y78 | | – | – | | 0.18 | 0.20 | 4.58 | 1.33 | 1.40 | 4.45 | 0.36 | 0.38 | 4.32 | 1.50 | 1.43 | 4.28 |
| Y79 | | – | – | | 0.15 | 0.21 | 4.59 | 0.95 | 1.55 | 4.58 | 0.26 | 0.34 | 4.36 | 1.30 | 1.80 | 4.27 |
| Y81 | | – | – | | 0.17 | 0.17 | 4.53 | 0.83 | 0.95 | 4.27 | 0.22 | 0.26 | 4.39 | 0.53 | 0.58 | 4.38 |
| Y82 | | – | – | | 0.33 | 0.35 | 4.33 | 1.48 | 2.60 | 4.49 | 0.34 | 0.39 | 4.28 | 1.15 | 1.60 | 4.32 |
| Y83 | | – | – | | 0.12 | 0.11 | 4.87 | 0.28 | 0.58 | 4.93 | 0.58 | 0.65 | 4.34 | 1.80 | 1.88 | 4.16 |
| Y84 | | – | – | | 0.16 | 0.14 | 4.45 | 0.60 | 0.75 | 4.40 | 0.11 | 0.12 | 4.46 | 0.78 | 0.80 | 4.53 |
| Y85 | | – | – | | 0.35 | 0.39 | 4.28 | 1.60 | 1.65 | 4.36 | 0.55 | 0.63 | 4.28 | 1.60 | 1.63 | 4.27 |
| Y87 | | – | – | | 0.12 | 0.10 | 4.87 | 0.38 | 0.40 | 5.36 | 0.53 | 0.58 | 4.35 | 1.83 | 1.90 | 4.21 |
| pH 4 isolates | | | | | | | | | | | | | | | | |
| p4-54 | | | | | | | | | | | | | | | | |
| p4-56 | | | | | | | | | | | | | | | | |
| p4-61 | | | | | | | | | | | | | | | | |
| p4-62 | | | | | 0.65 | 0.70 | 4.20 | 1.60 | 1.60 | 4.10 | 0.60 | 0.55 | 4.18 | 1.60 | 1.65 | 4.13 |
| p4-63 | | | | | | | | | | | | | | | | |
| p4-70B | | | | | | | | | | | | | | | | |
| p4-72A | | | | | | | | | | | | | | | | |
| p4-72B | | | | | | | | | | | | | | | | |
| p4-73A | | | | | | | | | | | | | | | | |
| p4-73B | | | | | | | | | | | | | | | | |

TABLE 2-continued

Properties of all the Isolates

| | Stationary Phase Survival | | | | | LB Xylose (1%) | | | | | | LB Glucose (1%) | | | | | |
|---|---|---|---|---|---|---|---|---|---|---|---|---|---|---|---|---|---|
| | LB (Glucose 1%), (microaerobic), pH 5.0 | | | | | Anaerobic | | | Aerobic | | | Anaerobic | | | Aerobic | | |
| | O.D. 420 nm | | pH | CFU/ml | | O.D. 420 nm | | pH | O.D. 420 nm | | pH | O.D. 420 nm | | pH | O.D. 420 nm | | pH |
| Isolate | 24 hrs. | 48 hrs | 48 hrs | 24 hrs | 48 hrs | 24 hrs | 48 hrs | 48 hrs | 24 hrs | 48 hrs | 48 hrs | 24 hrs | 48 hrs | 48 hrs | 24 hrs | 48 hrs | 48 hrs |
| p4-73C | | | | | | 0.50 | 0.50 | 4.11 | 2.03 | 1.47 | 4.11 | 0.60 | 0.65 | 4.01 | 1.75 | 1.55 | 4.11 |
| p4-74A | | | | | | 0.37 | 0.45 | 4.15 | 2.25 | 1.55 | 4.10 | 0.60 | 0.63 | 4.05 | 1.70 | 1.75 | 4.04 |
| p4-74B | | | | | | 0.65 | 0.70 | 4.17 | 1.87 | 1.45 | 4.01 | 0.53 | 0.60 | 4.21 | 1.70 | 1.27 | 3.98 |
| p4-85 | | | | | | 0.32 | 0.29 | 4.08 | 1.35 | 1.25 | 3.93 | 0.36 | 0.45 | 3.99 | 1.20 | 1.17 | 3.90 |
| p4-102A | | | | | | − | | | | | | | | | | | |
| p4-102B | | | | | | + | | | | | | | | | | | |
| B. coagulans (W) | | | | | | − | − | | | | | | | | | | |
| B. coagulans (T) | | | | | | − | − | | | | | | | | | | |

Growth at pH 6.8

| | Stationary Phase Survival | | | | | LB Xylose (1%) | | | | | | LB Glucose (1%) | | | | | |
|---|---|---|---|---|---|---|---|---|---|---|---|---|---|---|---|---|---|
| | LB (Glucose 1%), (microaerobic), pH 5.0 | | | | | Anaerobic | | | Aerobic | | | Anaerobic | | | Aerobic | | |
| | O.D. 420 nm | | pH | CFU/ml | | O.D. 420 nm | | pH | O.D. 420 nm | | pH | O.D. 420 nm | | pH | O.D. 420 nm | | pH |
| Isolate | 24 hrs. | 48 hrs | 48 hrs | 24 hrs | 48 hrs | 24 hrs | 48 hrs | 48 hrs | 24 hrs | 48 hrs | 48 hrs | 24 hrs | 48 hrs | 48 hrs | 24 hrs | 48 hrs | 48 hrs |
| Y72 | | | | | | 0.65 | 0.80 | 4.39 | 2.50 | 2.95 | 4.43 | 0.88 | 0.93 | 4.33 | 1.95 | 1.85 | 4.30 |
| Y73 | | | | | | 0.07 | 0.08 | 6.01 | 1.75 | 0.40 | 6.14 | 0.80 | 1.03 | 4.26 | 3.60 | 4.80 | 4.94 |
| Y75 | | | | | | 0.22 | 0.27 | 4.56 | 1.10 | 1.05 | 4.68 | 0.28 | 0.32 | 4.60 | 1.13 | 1.10 | 4.68 |
| Y77 | | | | | | 0.39 | 0.45 | 4.45 | 1.15 | 1.18 | 4.33 | 0.33 | 0.38 | 4.58 | 0.78 | 1.10 | 4.43 |
| Y78 | | | | | | 0.55 | 0.68 | 4.70 | 0.75 | 0.78 | 4.95 | 0.80 | 0.95 | 4.33 | 1.60 | 1.60 | 4.45 |
| Y79 | | | | | | 0.09 | 0.37 | 4.68 | 0.75 | 1.00 | 4.85 | 0.55 | 0.68 | 4.40 | 1.35 | 2.55 | 4.35 |
| Y81 | | | | | | 0.30 | 0.35 | 4.35 | 1.63 | 1.43 | 4.32 | 0.29 | 0.60 | 4.38 | 1.25 | 1.20 | 4.23 |
| Y82 | | | | | | 0.14 | 0.48 | 4.42 | 0.50 | 1.23 | 4.67 | 0.53 | 0.75 | 4.31 | 1.95 | 1.90 | 4.24 |
| Y83 | | | | | | 0.09 | 0.12 | 5.88 | 0.85 | 0.88 | 6.82 | 0.85 | 1.08 | 4.20 | 2.45 | 3.25 | 4.19 |
| Y84 | | | | | | 0.33 | 0.53 | 4.44 | 0.60 | 1.10 | 4.33 | 0.00 | 0.19 | 4.58 | 1.05 | 1.05 | 4.49 |
| Y85 | | | | | | 0.60 | 0.80 | 4.28 | 1.15 | 1.35 | 4.49 | 0.75 | 1.05 | 4.29 | 1.80 | 1.75 | 4.37 |
| Y87 | | | | | | 0.06 | 0.05 | 5.98 | 0.45 | 0.45 | 6.74 | 1.03 | 1.18 | 4.21 | 2.55 | 3.45 | 4.25 |
| pH 4 isolates | | | | | | | | | | | | | | | | | |
| p4-54 | 0.48 | 0.73 | 4.81 | 6.4 × 10⁵ | 10⁵ | 0.90 | 0.90 | 4.17 | 2.07 | 1.85 | 4.07 | 1.03 | 1.15 | 4.24 | 2.03 | 1.55 | 4.03 |
| p4-56 | 1.60 | 1.85 | 4.27 | 5.7 × 10⁵ | 9 × 10⁵ | | | | | | | | | | | | |
| p4-61 | 1.40 | 1.40 | 4.19 | 3.2 × 10⁶ | <10⁵ | | | | | | | | | | | | |
| p4-62 | 1.80 | 2.75 | 4.32 | 1.3 × 10⁶ | 1.9 × 10⁷ | | | | | | | | | | | | |
| p4-63 | 1.43 | 1.40 | 4.36 | 2.8 × 10⁵ | nd | | | | | | | | | | | | |
| p4-70B | 1.33 | 1.53 | 4.34 | 2.2 × 10⁷ | 2.9 × 10⁶ | | | | | | | | | | | | |
| p4-72A | 1.40 | 1.35 | 4.36 | 7.6 × 10⁶ | 10⁵ | | | | | | | | | | | | |
| p4-72B | 1.70 | 1.50 | 4.18 | 2.2 × 10⁶ | <10⁵ | | | | | | | | | | | | |
| p4-73A | 1.55 | 1.48 | 4.21 | <10⁴ | nd | | | | | | | | | | | | |
| p4-73B | 1.38 | 1.30 | 4.26 | 1.1 × 10⁵ | nd | | | | | | | | | | | | |
| p4-73C | 1.80 | 2.35 | 4.43 | 2.5 × 10⁷ | 5 × 10⁶ | | | | | | | | | | | | |
| p4-74A | | | | | | | | | | | | | | | | | |
| p4-74B | 1.45 | 1.88 | 4.29 | 5.1 × 10⁶ | 2.1 × 10⁸ | 1.07 | 0.95 | 4.13 | 2.20 | 1.95 | 4.19 | 1.10 | 1.13 | 4.13 | 2.20 | 1.85 | 4.00 |

TABLE 2-continued

Properties of all the Isolates

| Isolate | | | | | | | | | | | | | | | |
|---|---|---|---|---|---|---|---|---|---|---|---|---|---|---|---|
| p4-85 | 1.68 | 1.50 | 4.18 | 1.05 | 0.95 | 4.16 | 3.10 | 3.70 | 4.03 | 1.10 | 1.10 | 4.18 | 2.30 | 1.90 | 3.95 |
| p4-102A | 1.23 | 1.33 | 4.24 | 0.80 | 0.90 | 4.28 | 2.03 | 2.00 | 4.15 | 1.00 | 1.10 | 4.25 | 1.77 | 1.70 | 4.09 |
| p4-102B | | | | 0.77 | 0.77 | 4.18 | 1.97 | 1.35 | 4.05 | 0.95 | 0.95 | 4.21 | 1.50 | 1.20 | 3.89 |
| B. coagulans (W) | | | | | | | | | $1.8 \times 10^6$ | | | | | | |
| B. coagulans (T) | | | | | | | | | $1.3 \times 10^4$ | | | | | | |
|  | | | | | | | | | $<10^5$ | | | | | | |
|  | | | | | | | | | nd | | | | | | |

Fermentation Products (48 hr) (pH not Controlled)

| | LB (1% Xylose), pH 6.8 | | | | | | | LB (1% Glucose), pH 6.8 | | | | | | |
|---|---|---|---|---|---|---|---|---|---|---|---|---|---|---|
| Isolate | Xylose mM | Succinate mM | Lactate mM | Formate mM | Fumarate μM | Acetate mM | Ethanol mM | Glucose mM | Succinate mM | Lactate mM | Formate mM | Fumarate μM | Acetate mM | Ethanol mM |
| Y72 | 26.0 | * | 2.9 | 7.9 | | 4.7 | | 50.9 | 1.2 | 18.5 | | | | |
| Y73 | | | | | | | | | | | | | | |
| Y75 | | | | | | | | | | | | | | |
| Y77 | | | | | | | | | | | | | | |
| Y78 | 49.9 | 1.4 | 1.9 | 12.0 | | 7.3 | | 54.8 | | 18.5 | | | * | |
| Y79 | | | | | | | | | | | | | | |
| Y81 | | | | | | | | | | | | | | |
| Y82 | | | | | | | | | | | | | | |
| Y83 | | | | | | | | | | | | | | |
| Y84 | | | | | | | | | | | | | | |
| Y85 | 51.7 | 2.0 | 17.9 | 3.6 | | 2.3 | | 37.5 | 1.7 | 20.3 | | | * | |
| Y87 | | | | | 9.80 | | | | | | | | | |
| pH 4 isolates | | | | | | | | | | | | | | |
| p4-54 | | | | | | | | | | | | | | |
| p4-56 | | | | | | | | | | | | | | |
| p4-61 | 59.90 | 2.40 | 12.50 | 4.30 | | 4.30 | | 46.80 | 1.20 | 18.70 | | | | |
| p4-62 | 52.10 | 1.60 | 23.20 | | | 4.90 | | 45.90 | 1.30 | 18.00 | | | | |
| p4-63 | 58.20 | 1.50 | 14.70 | | | 5.40 | | 48.90 | 1.20 | 16.70 | | | | |
| p4-70B | 59.30 | | 14.00 | | | 5.20 | | 45.90 | | 22.00 | | | | |
| p4-72A | | | | | | | | | | | | | | |
| p4-72B | | | | | | | | | | | | | | |
| p4-73A | | | | | | | | | | | | | | |
| p4-73B | | | | | | | | | | | | | | |
| p4-73C | | | | | | | | | | | | | | |
| p4-74A | 59.60 | 1.40 | 14.90 | 4.20 | | 4.20 | 2.50 | 36.30 | 1.20 | 18.80 | | | * | |
| p4-74B | 48.60 | 1.30 | 13.00 | 6.00 | | 4.80 | * | 41.80 | 1.30 | 18.70 | | | | |
| p4-85 | 49.50 | 1.10 | 5.10 | 6.80 | | 6.50 | * | 51.90 | 1.10 | 21.40 | | | | |
| p4-102A | | | | | | | | | | | | | | |

TABLE 2-continued

Properties of all the Isolates

| Isolate | LB (1% Xylose), pH 5.0 | | | | | | LB (1% Glucose), pH 5.0 | | | | | |
|---|---|---|---|---|---|---|---|---|---|---|---|---|
| | Xylose mM | Lactate mM | Succinate mM | Acetate mM | Ethanol mM | Formate mM | Fumarate µM | Glucose mM | Lactate mM | Succinate mM | Acetate mM | Ethanol mM | Formate mM | Fumarate µM |
| Y72 | | | | | | | | | | | | | | |
| Y73 | | | | | | | | | | | | | | |
| Y75 | | | | | | | | | | | | | | |
| Y77 | | | | | | | | | | | | | | |
| Y78 | | | | | | | | | | | | | | |
| Y79 | | | | | | | | | | | | | | |
| Y81 | | | | | | | | | | | | | | |
| Y82 | | | | | | | | | | | | | | |
| Y83 | | | | | | | | | | | | | | |
| Y84 | | | | | | | | | | | | | | |
| Y85 | | | | | | | | | | | | | | |
| Y87 | | | | | | | | | | | | | | |
| pH 4 isolates | | | | | | | | | | | | | | |
| p4-54 | | | | | | | | | | | | | | |
| p4-56 | | | | | | | | | | | | | | |
| p4-61 | | | | | | | | | | | | | | |
| p4-62 | | | | | | | | | | | | | | |
| p4-63 | | | | | | | | | | | | | | |
| p4-70B | | | | | | | | | | | | | | |
| p4-72A | | | | | | | | | | | | | | |
| p4-72B | | | | | | | | | | | | | | |
| p4-73A | | | | | | | | | | | | | | |
| p4-73B | | | | | | | | | | | | | | |
| p4-73C | | | | | | | | | | | | | | |
| p4-74A | | | | | | | | | | | | | | |
| p4-74B | | | | | | | | | | | | | | |
| p4-85 | | | | | | | | | | | | | | |
| p4-102A | | | | | | | | | | | | | | |
| p4-102B B. coagulans (W) | | | | | | | | | | | | | | |
| B. coagulans (T) | | | | | | | | | | | | | | |

TABLE 2-continued

Properties of all the Isolates

|  | LB Glucose (1%), pH 4.5 | | LB Xylose (1%), pH 4.5 | | Anaerobic Growth MS (0.1% YE) (Xylose 1%), pH 5 | | MS (0.1% YE) (Glucose 1%), pH 5 | | HCH 10% CSL 1%, pH 5 | |
|---|---|---|---|---|---|---|---|---|---|---|
|  | O.D. 420 nm | pH | O.D. 420 nm | pH | O.D. 420 nm | pH | O.D. 420 nm | pH | O.D. 420 nm | pH |
| Isolate | 24 hrs | 48 hrs | 48 hrs | 24 hrs | 48 hrs | 48 hrs | 24 hrs | 48 hrs | 48 hrs | 24 hrs | 48 hrs | 48 hrs | 24 hrs | 48 hrs | 48 hrs |
| p4-102B B. coagulans (W) | 66.17 | 0.00 | 0.00 | 3.50 | 0.00 | 0.00 | 0.00 | 0.00 | 97.99 | 2.82 | 4.21 | 0.00 | 0.00 | 0.00 | 0.00 |
| B. coagulans (T) | 50.42 | 0.00 | 1.49 | 6.30 | 0.00 | 0.00 | 0.00 | 0.00 | 98.62 | 2.94 | 5.89 | 3.82 | 0.00 | 0.00 | 0.00 |
| Y72 | 0.08 | 0.10 | 4.31 | 0.00 | 0.00 | 4.43 | 0.15 | 0.18 | 4.61 | 0.08 | 0.08 | 4.42 | 0.16 | 0.12 | 4.06 |
| Y73 | | | | | | | | | | | | | | | |
| Y75 | | | | | | | | | | | | | | | |
| Y77 | | | | | | | | | | | | | | | |
| Y78 | 0.13 | 0.19 | 4.32 | 0.15 | 0.21 | 4.44 | 0.16 | 0.20 | 4.67 | 0.07 | 0.07 | 4.44 | + | + | 4.05 |
| Y79 | | | | | | | | | | | | | | | |
| Y81 | | | | | | | | | | | | | | | |
| Y82 | | | | | | | | | | | | | | | |
| Y83 | | | | | | | | | | | | | | | |
| Y84 | | | | | | | | | | | | | | | |
| Y85 | 0.19 | 0.28 | 4.19 | 0.08 | 0.16 | 4.32 | 0.19 | 0.23 | 4.44 | 0.08 | 0.08 | 4.37 | 0.13 | 0.16 | 4.10 |
| Y87 | | | | | | | | | | | | | | | |
| pH 4 isolates | | | | | | | | | | | | | | | |
| p4-54 | | | | | | | | | | | | | | | |
| p4-56 | | | | | | | | | | | | | | | |
| p4-61 | | | | | | | | | | | | | | | |
| p4-62 | | | | | | | | | | | | | | | |
| p4-63 | | | | | | | | | | | | | | | |
| p4-70B | | | | | | | | | | | | | | | |
| p4-72A | | | | | | | | | | | | | | | |
| p4-72B | | | | | | | | | | | | | | | |
| p4-73A | | | | | | | | | | | | | | | |
| p4-73B | | | | | | | | | | | | | | | |
| p4-73C | | | | | | | | | | | | | | | |
| p4-74A | | | | | | | | | | | | | | | |
| p4-74B | | | | | | | | | | | | | | | |
| p4-85 | | | | | | | | | | | | | | | |
| p4- | | | | | | | | | | | | | | | |

TABLE 2-continued

Properties of all the Isolates

| Isolate | LB (Glucose 1%, pH 6.8) | | | | | | | 0% Ethanol | | LB (Glucose 1%, pH 5.0) | | | | | | | 20% HCH 0.1% YE/Glu pH 5.0^(V) plates (48 hrs) | 25% HCH 0.1% YE/Glu pH 5.0^(V) plates (48 hrs) | 50% HCH overlimed 0.1% YE/Glu pH 5.0^(V) plates (48 hrs) |
|---|---|---|---|---|---|---|---|---|---|---|---|---|---|---|---|---|---|---|---|
| | 0% Ethanol | | 4% Ethanol(w/w) | | 4.5% Ethanol(w/w) | | 5% Ethanol(w/w) | | | 4% Ethanol(w/w) | | 4.5% Ethanol(w/w) | | 5% Ethanol(w/w) | | | | | |
| | O.D. 420 nm | | O.D. 420 nm | | O.D. 420 nm | | O.D. 420 nm | | O.D. 420 nm | O.D. 420 nm | | O.D. 420 nm | | O.D. 420 nm | | | | | |
| | 24 hrs | 48 hrs | 24 hrs | 48 hrs | 24 hrs | 48 hrs | 24 hrs | 48 hrs | 24 hrs | 48 hrs | 24 hrs | 48 hrs | 24 hrs | 48 hrs | 24 hrs | 48 hrs | | | |
| Y72 | | | | | | | | | | | | | | | | | ++ | − | − |
| Y73 | | | | | | | | | | | | | | | | | + | − | − |
| Y75 | | | | | | | | | | | | | | | | | − | − | − |
| Y77 | | | | | | | | | | | | | | | | | + | − | − |
| Y78 | | | | | | | | | | | | | | | | | ++ | + | − |
| Y79 | | | | | | | | | | | | | | | | | ++ | − | − |
| Y81 | | | | | | | | | | | | | | | | | + | + | − |
| Y82 | | | | | | | | | | | | | | | | | ++ | − | − |
| Y84 | | | | | | | | | | | | | | | | | − | − | − |
| Y85 | | | | | | | | | | | | | | | | | +++ | − | − |
| Y87 | | | | | | | | | | | | | | | | | | | |
| pH 4 isolates | | | | | | | | | | | | | | | | | | | |
| p4-54 | | | | | | | 0.03 | 0.03 | 0.02 | 0.01 | 0.01 | 0.01 | 0.02 | 0.02 | | | | | |
| p4-56 | | | | | | | 0.18 | 0.18 | 0.07 | 0.08 | 0.05 | 0.05 | 0.04 | 0.05 | | | | | |
| p4-61 | | | | | | | 0.70 | 0.70 | 0.10 | 0.12 | 0.05 | 0.07 | 0.05 | 0.05 | | | | | |
| p4-62 | | | | | | | 0.28 | 0.50 | 0.24 | 0.25 | 0.08 | 0.07 | 0.05 | 0.06 | | | | | |
| p4-63 | | | | | | | 0.60 | 0.35 | 0.14 | 0.14 | 0.07 | 0.07 | 0.03 | 0.03 | | | | | |
| p4-70B | | | | | | | 0.65 | 0.55 | 0.01 | 0.00 | 0.03 | 0.04 | 0.03 | 0.03 | | | | | |
| p4-72A | | | | | | | 0.03 | 0.65 | 0.08 | 0.07 | 0.08 | 0.09 | 0.04 | 0.04 | | | | | |
| p4-72B | | | | | | | 0.31 | 0.03 | 0.04 | 0.05 | 0.05 | 0.04 | 0.03 | 0.03 | | | | | |
| p4-73A | | | | | | | 0.26 | 0.35 | 0.02 | 0.03 | 0.04 | 0.02 | 0.03 | 0.02 | | | | | |
| p4-73B | | | | | | | | 0.31 | 0.07 | 0.08 | 0.05 | 0.05 | 0.02 | 0.03 | | | | | |

102A
p4-102B
B. coagulans (W)
B. coagulans (T)

TABLE 2-continued

Properties of all the Isolates

| Isolate | 25% HCH, (0.1% YE) | | 10% HCH, (1% CSL) | | 25% Overlimed HCH | | 50% Overlimed HCH (0.1% YE) | | Antibiotic Sensitivity | | | |
|---|---|---|---|---|---|---|---|---|---|---|---|---|
| | | | | | | | | | Tetracycline 20 mg/L | Chloramphenicol 30 mg/L | Kanamycin 50 mg/L | Ampicillin 100 mg/L |
| | CFU/ml | pH | CFU/ml | pH | CFU/ml | pH | CFU/ml | pH | | | | |
| | 24 hrs | 48 hrs | 48 hrs | 24 hrs | 48 hrs | 48 hrs | 24 hrs | 48 hrs | 48 hrs | 24 hrs | 48 hrs | 48 hrs |

| Isolate | | | | | | | | | | | | | |
|---|---|---|---|---|---|---|---|---|---|---|---|---|---|
| p4-73C | | | | | | | | | 0.13 | 0.30 | 0.09 | 0.04 | 0.03 | 0.03 | 0.08* | 0.10* |
| p4-74A | | | | | | | | | 0.45 | 0.50 | 0.04 | 0.04 | 0.03 | 0.04 | 0.02 | 0.02 |
| p4-74B | | | | | | | | | 0.45 | 0.45 | 0.04 | 0.04 | 0.03 | 0.03 | 0.02 | 0.03 |
| p4-85 | | | | | | | | | 0.55 | 0.55 | 0.23 | 0.20 | 0.14 | 0.12 | 0.12 | 0.13 |
| p4-102A | | | | | | | | | 0.70 | 0.75 | 0.04 | 0.03 | 0.03 | 0.03 | 0.03 | 0.02 |
| p4-102B | | | | | | | | | | | | | | | | |
| B. coagulans (W) | | | | | | | | | 0.45 | 0.50 | 0.06 | 0.03 | 0.02 | 0.03 | 0.04 | 0.03 |
| B. coagulans (T) | | | | | | | | | | | | | | | | |

Aerobic (pH 5.0)

| pH 4 isolates | 24 hrs | 48 hrs | 48 hrs | 24 hrs | 48 hrs | 48 hrs | 24 hrs | 48 hrs | 48 hrs | 24 hrs | 48 hrs | 48 hrs | | | | |
|---|---|---|---|---|---|---|---|---|---|---|---|---|---|---|---|---|
| p4-54 | 10⁶ | 2 × 10⁵ | 4.73 | 10⁶ | 3 × 10⁵ | 4.07 | 8 × 10⁵ | 2 × 10⁵ | 4.72 | 5 × 10⁵ | 5 × 10⁵ | 4.65 | — | — | — | — |
| p4-56 | 5 × 10⁵ | 3 × 10⁶ | 4.74 | >4 × 10⁷ | >4 × 10⁷ | 4.93 | 4 × 10⁷ | 5 × 10⁵ | 4.42 | 6 × 10⁵ | 5 × 10⁵ | 4.64 | — | — | — | — |
| p4-61 | 10⁷ | 6 × 10⁴ | 4.34 | 7 × 10⁵ | 4 × 10³ | 4.06 | 1 × 10⁵ | 2 × 10⁵ | 4.72 | 1 × 10⁶ | 7 × 10⁵ | 4.66 | — | — | — | — |
| p4-62 | 4 × 10⁷ | — | 4.42 | 3 × 10⁶ | 4 × 10³ | 4.06 | >4 × 10⁷ | 103.00 | 4.20 | 4 × 10⁵ | 3 × 10⁵ | 4.62 | — | — | — | — |
| p4-63 | | | | | | | | | | | | | | | | |

TABLE 2-continued

Properties of all the Isolates

| | | | | | | | | | | | | | | | | | | | |
|---|---|---|---|---|---|---|---|---|---|---|---|---|---|---|---|---|---|---|---|
| p4-70B | | | | | | | | | | | | | – | – | – | – | – | – | – |
| p4-72A | $10^6$ | $4 \times 10^4$ | 4.63 | $>4 \times 10^7$ | $1 \times 10^7$ | 5.08 | $3 \times 10^5$ | $5 \times 10^6$ | 4.48 | $3 \times 10^4$ | $3 \times 10^5$ | 4.65 | – | – | – | – | – | – | – |
| p4-72B | | $10^3$ | 4.52 | $1 \times 10^6$ | – | 4.05 | $>4 \times 10^7$ | – | 4.17 | $10^5$ | $3 \times 10^5$ | 4.66 | | | | | | | |
| p4-73A | $1 \times 10^7$ | – | 4.41 | $>4 \times 10^7$ | $4 \times 10^6$ | 4.64 | $>4 \times 10^7$ | – | 4.19 | $10^3$ | $10^5$ | 4.65 | | | | | | | |
| p4-73B | $3 \times 10^7$ | – | 4.31 | $2 \times 10^5$ | $10^5$ | 4.07 | $3 \times 10^5$ | – | 4.35 | – | – | 4.49 | | | | | | | |
| p4-73C | $>4 \times 10^7$ | $2 \times 10^7$ | 4.19 | $2 \times 10^6$ | $3 \times 10^3$ | 4.26 | $3 \times 10^7$ | $10^7$ | 4.13 | $10^3$ | $10^5$ | 4.65 | | | | | | | |
| p4-74A | $>3 \times 10^7$ | – | 4.76 | $7 \times 10^5$ | $6 \times 10^3$ | 4.40 | $3 \times 10^6$ | – | 4.37 | $10^3$ | $2 \times 10^3$ | 4.64 | | | | | | | |
| p4-74B | – | – | 4.38 | $>4 \times 10^7$ | $7 \times 10^4$ | 4.74 | $>4 \times 10^7$ | $2 \times 10^5$ | 4.29 | $2 \times 10^5$ | $5 \times 10^5$ | 4.68 | | | | | | | |
| p4-85 | $>3 \times 10^7$ | $10^5$ | 4.66 | $6 \times 10^5$ | $4 \times 10^5$ | 4.13 | $3 \times 10^7$ | $5 \times 10^3$ | 4.55 | $2 \times 10^5$ | $10^5$ | 4.66 | | | | | | | |
| p4-102A | $2 \times 10^7$ | – | 4.79 | $5 \times 10^7$ | $10^5$ | 4.33 | $4 \times 10^5$ | $1 \times 10^7$ | 4.62 | $10^5$ | – | 4.66 | | | | | | | |
| p4-102B | $5 \times 10^3$ | | | | | | | | | | | | | | | | | | |
| *B. coagulans* (W) | | | | | | | | | | | | | | | | | | | |
| *B. coagulans* (T) | | | | | | | | | | | | | | | | | | | |

TABLE 3

Selected Properties of Isolates Close to *Bacillus coagulans* Grouped on Their 16S rRNA Sequence Similarity

| | | | Growth on Cellobiose MS (0.1% YE) pH 5.0 | Growth at pH 5.0 | | | | | | | | | | |
|---|---|---|---|---|---|---|---|---|---|---|---|---|---|---|
| | | | | LB Xylose (1%) | | | | | | LB Glucose (1%) | | | | |
| | | | | Anaerobic | | | Aerobic | | | Anaerobic | | | Aerobic | | |
| | | | | O.D. 420 nm | | pH | O.D. 420 nm | | pH | O.D. 420 nm | | pH | O.D. 420 nm | | pH |
| Isolate | Xylanase 72 hr | CMCase 72 hr | 72 hr | 24 hrs | 48 hrs | 48 hrs | 24 hrs | 48 hrs | 48 hrs | 24 hrs | 48 hrs | 48 hrs | 24 hrs | 48 hrs | 48 hrs |
| Group 1 | | | | | | | | | | | | | | | |
| 1D2 | − | − | ++ | 0.30 | 0.32 | 4.22 | 1.90 | 2.15 | 4.28 | 0.38 | 0.36 | 4.37 | 1.48 | 3.00 | 4.26 |
| 1D6B | − | − | − | 0.15 | 0.31 | 4.18 | 1.75 | 3.90 | 4.39 | 0.19 | 0.43 | 4.30 | 0.59 | 0.80 | 4.16 |
| 2D1 | − | − | ++ | 0.33 | 0.26 | 4.38 | 2.10 | 3.20 | 4.32 | 0.44 | 0.42 | 4.26 | 1.80 | 1.80 | 4.23 |
| 3F2 | − | − | − | 0.38 | 0.41 | 4.15 | 1.90 | 1.95 | 4.17 | 0.52 | 0.51 | 4.23 | 1.85 | 3.50 | 4.20 |
| 13E1Lg | − | − | + | 0.34 | 0.36 | 4.24 | 1.98 | 1.90 | 4.15 | 0.53 | 0.58 | 4.17 | 0.95 | 1.00 | 4.30 |
| 17C5 | − | − | + | 0.34 | 0.33 | 4.29 | 2.15 | 2.30 | 4.33 | 0.62 | 0.65 | 4.35 | 2.52 | 3.23 | 4.23 |
| 17D3 | − | − | + | 0.65 | 0.61 | 4.30 | 1.90 | 1.80 | 4.39 | 0.50 | 0.50 | 4.24 | 1.38 | 1.55 | 4.35 |
| 26D2 | − | − | − | 0.42 | 0.28 | 4.20 | 2.00 | 2.20 | 4.34 | 0.75 | 0.72 | 4.14 | 1.85 | 1.70 | 4.34 |
| 38C3 | − | − | + | 0.24 | 0.25 | 4.40 | 1.70 | 1.80 | 4.44 | 0.45 | 0.43 | 4.34 | 1.35 | 1.75 | 4.42 |
| 56H3A | − | − | +++ | 0.49 | 0.55 | 4.02 | 1.80 | 1.90 | 4.13 | 0.56 | 0.54 | 4.08 | 1.80 | 1.70 | 4.02 |
| 57H3 | + | − | ++ | 0.52 | 0.54 | 3.93 | 1.80 | 1.60 | 4.09 | 0.62 | 0.62 | 4.03 | 1.80 | 1.90 | 4.25 |
| 57H1 | − | − | ++ | 0.60 | 0.67 | 4.06 | 1.90 | 1.80 | 4.18 | 0.47 | 0.54 | 4.15 | 1.60 | 1.50 | 4.07 |
| Group 2 | | | | | | | | | | | | | | | |
| Y 66 | − | − | +++ | 0.65 | 0.70 | 4.21 | 1.70 | 1.73 | 4.32 | 0.55 | 0.55 | 4.30 | 2.30 | 2.20 | 4.18 |
| Group 3 | | | | | | | | | | | | | | | |
| Y 55 | − | − | +++ | 0.42 | 0.37 | 4.24 | 1.30 | 1.65 | 4.21 | 0.60 | 0.45 | 4.21 | 1.85 | 1.80 | 4.19 |
| Group 4 | | | | | | | | | | | | | | | |
| 7D4 | − | − | + | 0.48 | 0.45 | 4.34 | 1.90 | 1.75 | 4.38 | 0.52 | 0.70 | 4.43 | 1.85 | 1.73 | 4.31 |
| 18C2 | − | − | + | 0.63 | 0.52 | 4.25 | 1.55 | 1.55 | 4.39 | 0.40 | 0.40 | 4.36 | 1.58 | 1.65 | 4.34 |
| Group 5 | | | | | | | | | | | | | | | |
| 1F2 | − | − | + | 0.40 | 0.45 | 4.12 | 2.10 | 2.30 | 4.13 | 0.43 | 0.66 | 4.26 | 1.93 | 1.93 | 4.19 |
| 6C1 | − | − | ++ | 0.52 | 0.50 | 4.36 | 2.57 | 2.03 | 4.25 | 1.25 | 0.61 | 4.42 | 1.80 | 2.78 | 4.46 |
| 6F2 | − | − | + | 0.45 | 0.60 | 4.53 | 1.71 | 2.35 | 4.62 | 0.40 | 0.63 | 4.19 | 2.15 | 3.08 | 4.22 |
| 33D4 | − | − | + | 0.68 | 0.65 | 4.29 | 1.63 | 1.60 | 4.35 | 0.55 | 0.53 | 4.38 | 1.50 | 1.55 | 4.41 |
| 34D2 | − | − | − | 0.00 | 0.00 | 4.95 | 1.15 | 1.75 | 4.44 | 0.02 | 0.02 | 4.99 | 0.00 | 0.00 | 4.99 |
| HCH7 | − | − | +++ | 0.38 | 0.35 | 4.21 | 1.90 | 1.45 | 4.25 | 0.31 | 0.28 | 4.37 | 1.50 | 1.50 | 4.34 |
| HCH8 | − | − | +++ | 0.31 | 0.33 | 4.27 | 1.45 | 1.50 | 4.30 | 0.32 | 0.28 | 4.21 | 1.15 | 1.20 | 4.31 |
| Group 6 | | | | | | | | | | | | | | | |
| 1C4 | − | − | ++ | 0.45 | 0.58 | 4.30 | 1.95 | 1.80 | 4.30 | 0.31 | 0.40 | 4.31 | 1.60 | 1.85 | 4.33 |
| Group 7 | | | | | | | | | | | | | | | |
| 1D7 | − | − | ++ | 0.40 | 0.40 | 4.26 | 1.85 | 2.00 | 4.23 | 0.55 | 0.66 | 4.32 | 1.90 | 3.40 | 4.25 |
| Group 8 | | | | | | | | | | | | | | | |
| 6H2 | − | − | + | 0.31 | 0.37 | 4.20 | 1.50 | 1.45 | 4.35 | 0.38 | 0.40 | 4.35 | 1.78 | 1.73 | 4.37 |
| 21B2 | − | − | + | 0.73 | 0.75 | 4.26 | 1.78 | 2.60 | 4.29 | 0.80 | 0.78 | 4.15 | 1.60 | 1.63 | 4.32 |
| HCH10 | − | − | +++ | 0.34 | 0.34 | 4.18 | 1.10 | 4.00 | 4.50 | 0.33 | 0.31 | 4.18 | 1.55 | 1.60 | 4.37 |
| Group 9 | | | | | | | | | | | | | | | |
| 35D2 | − | − | ++ | 0.63 | 0.15 | 4.43 | 1.70 | 1.83 | 4.59 | 0.23 | 0.43 | 4.53 | 1.08 | 2.05 | 4.45 |
| Group 10 | | | | | | | | | | | | | | | |
| 57H2 | + | − | ++ | 0.13 | 0.17 | 4.62 | 0.50 | 1.70 | 4.10 | 0.34 | 0.33 | 4.24 | 1.30 | 1.30 | 3.98 |
| Group 11 | | | | | | | | | | | | | | | |
| 7C8 | − | − | ++ | 0.49 | 0.50 | 4.28 | 2.30 | 2.18 | 4.52 | 0.04 | 0.65 | 4.40 | 2.15 | 1.87 | 4.40 |
| 7G1 | − | − | + | 0.42 | 0.50 | 4.29 | 2.55 | 2.15 | 4.39 | 0.40 | 0.56 | 4.39 | 2.10 | 2.93 | 4.34 |
| Group 12 | | | | | | | | | | | | | | | |
| 7F1 | − | − | + | 0.27 | 0.26 | 4.34 | 1.63 | 1.80 | 4.32 | 0.35 | 0.40 | 4.36 | 1.50 | 1.43 | 4.36 |
| 36D2 | − | − | ++ | 0.48 | 0.43 | 4.33 | 1.63 | 2.53 | 4.29 | 0.48 | 0.45 | 4.41 | 1.23 | 1.50 | 4.42 |
| Y 40 | − | − | +++ | 0.42 | 0.38 | 4.24 | 1.60 | 1.90 | 4.45 | 0.75 | 0.55 | 4.27 | 1.75 | 1.70 | 4.35 |
| *B. coagulans* (W) | − | − | +++ | No Growth | | | | | | | | | | | |

TABLE 3-continued

Selected Properties of Isolates Close to *Bacillus coagulans* Grouped on Their 16S rRNA Sequence Similarity

| | Fermentation Products (48 hrs) (pHstat) pH 5.0 | | | | | | | | | | | |
|---|---|---|---|---|---|---|---|---|---|---|---|---|
| | LB + 1% Xylose | | | | | | LB + 1% Glucose | | | | | |
| Isolate | Xylose mM | Lactate mM | Succinate mM | Acetate mM | Ethanol mM | Formate mM | Glucose mM | Lactate mM | Succinate mM | Acetate mM | Ethanol mM | Formate mM |
| Group 1 | | | | | | | | | | | | |
| 1D2 | 0.00 | 74.97 | 0.00 | 10.00 | 17.18 | 9.14 | 0.00 | 88.02 | 0.00 | 3.91 | 0.00 | 0.00 |
| 1D6B | 0.00 | 94.01 | 3.78 | 3.35 | 20.58 | 0.00 | 0.00 | 99.78 | 0.97 | 4.90 | 9.07 | 0.00 |
| 2D1 | 0.00 | 87.16 | 3.37 | 13.05 | 7.62 | 8.79 | 0.00 | 94.28 | 0.97 | 7.76 | 3.41 | 0.00 |
| 3F2 | 0.00 | 85.14 | 3.41 | 9.88 | 10.03 | 6.15 | 0.00 | 99.37 | 1.03 | 8.39 | 0.00 | 0.00 |
| 13E1Lg | 0.00 | 90.82 | 2.53 | 12.33 | 11.08 | 11.42 | 0.00 | 106.15 | 0.67 | 3.87 | 3.91 | 0.00 |
| 17C5 | 0.00 | 85.06 | 2.36 | 12.04 | 14.33 | 17.74 | 0.00 | 106.96 | 0.71 | 1.99 | 2.80 | 0.00 |
| 17D3 | 0.00 | 83.68 | 1.99 | 16.67 | 7.59 | 0.00 | 0.00 | 67.13 | 0.79 | 6.01 | 0.00 | 0.00 |
| 26D2 | 0.00 | 87.47 | 2.27 | 24.42 | 9.28 | 2.68 | 0.00 | 107.47 | 1.06 | 1.71 | 3.01 | 0.00 |
| 38C3 | 0.00 | 81.56 | 1.17 | 30.00 | 12.29 | 2.13 | 0.00 | 99.08 | 0.60 | 7.53 | 3.74 | 0.00 |
| 56H3A | 0.00 | 95.54 | 3.25 | 9.19 | 8.04 | 7.57 | 0.00 | 92.38 | 0.83 | 5.18 | 0.00 | 0.00 |
| 57H3 | 0.00 | 87.91 | 3.08 | 14.96 | 8.71 | 5.42 | 0.00 | 97.17 | 0.55 | 3.66 | 0.00 | 0.00 |
| 57H1 | 0.00 | 75.03 | 4.13 | 12.36 | 18.67 | 11.11 | 0.00 | 95.20 | 0.56 | 3.89 | 0.00 | 0.00 |
| Group 2 | | | | | | | | | | | | |
| Y 66 | 0.63 | 89.90 | 2.72 | 10.58 | 11.48 | 12.05 | 0.00 | 107.22 | 1.15 | 2.14 | 3.24 | 0.00 |
| Group 3 | | | | | | | | | | | | |
| Y 55 | 0.00 | 85.26 | 2.46 | 12.67 | 15.24 | 10.65 | 8.77 | 97.99 | 0.45 | 0.48 | 5.27 | 0.00 |
| Group 4 | | | | | | | | | | | | |
| 7D4 | 10.68 | 78.89 | 1.64 | 7.21 | 6.42 | 0.00 | 9.49 | 86.46 | 0.60 | 0.72 | 4.56 | 0.00 |
| 18C2 | 0.00 | 88.00 | 2.57 | 11.95 | 13.64 | 14.31 | 0.00 | 108.60 | 0.83 | 3.28 | 2.48 | 0.00 |
| Group 5 | | | | | | | | | | | | |
| 1F2 | 0.00 | 93.27 | 2.26 | 9.81 | 13.28 | 3.46 | 0.00 | 97.35 | 0.86 | 7.88 | 0.00 | 0.00 |
| 6C1 | 0.00 | 85.58 | 2.12 | 12.06 | 17.51 | 3.53 | 0.00 | 100.01 | 0.47 | 7.12 | 2.95 | 0.00 |
| 6F2 | 15.19 | 13.16 | 2.95 | 24.70 | 18.58 | 34.83 | 0.00 | 98.41 | 0.71 | 5.11 | 0.00 | 0.00 |
| 33D4 | 0.00 | 71.57 | 3.67 | 27.05 | 17.48 | 22.17 | 0.00 | 104.18 | 1.06 | 9.16 | 3.10 | 0.00 |
| 34D2 | 65.01 | 0.73 | 0.53 | 6.48 | 0.00 | 0.00 | 0.00 | 98.17 | 0.96 | 7.31 | 0.00 | 0.00 |
| HCH7 | 0.00 | 63.17 | 2.24 | 27.47 | 15.96 | 14.23 | 0.00 | 94.12 | 0.74 | 1.73 | 2.85 | 0.00 |
| HCH8 | 0.00 | 71.97 | 2.45 | 22.35 | 9.00 | 7.45 | 0.00 | 91.39 | 0.81 | 1.67 | 0.00 | 0.00 |
| Group 6 | | | | | | | | | | | | |
| 1C4 | 0.00 | 77.47 | 1.79 | 10.55 | 10.41 | 11.91 | 0.00 | 89.16 | 0.72 | 8.52 | 0.00 | 0.00 |
| Group 7 | | | | | | | | | | | | |
| 1D7 | 0.32 | 71.01 | 1.72 | 9.50 | 10.11 | 8.15 | 0.00 | 91.17 | 0.79 | 0.00 | 0.00 | 0.00 |
| Group 8 | | | | | | | | | | | | |
| 6H2 | 0.00 | 71.74 | 2.55 | 25.47 | 7.56 | 0.00 | 0.00 | 89.76 | 2.78 | 13.22 | 0.00 | 0.00 |
| 21B2 | 0.00 | 79.67 | 4.10 | 21.93 | 9.55 | 7.23 | 0.00 | 89.50 | 1.63 | 7.42 | 2.15 | 0.00 |
| HCH10 | 0.00 | 86.23 | 3.92 | 8.23 | 10.19 | 6.74 | 0.00 | 103.11 | 2.77 | 4.63 | 0.00 | 0.00 |
| Group 9 | | | | | | | | | | | | |
| 35D2 | 0.51 | 86.33 | 2.67 | 24.42 | 18.33 | 5.71 | 0.00 | 107.00 | 0.78 | 4.00 | 5.48 | 0.00 |
| Group 10 | | | | | | | | | | | | |
| 57H2 | 0.00 | 86.62 | 3.90 | 5.63 | 16.90 | 3.25 | 4.42 | 92.09 | 1.35 | 10.48 | 0.00 | 0.00 |
| Group 11 | | | | | | | | | | | | |
| 7C8 | 0.00 | 73.62 | 2.48 | 28.41 | 7.64 | 0.00 | 0.00 | 88.04 | 0.65 | 12.26 | 0.00 | 0.00 |
| 7G1 | 0.00 | 79.88 | 1.98 | 18.91 | 9.26 | 1.93 | 0.00 | 92.23 | 0.77 | 6.73 | 4.76 | 0.00 |
| Group 12 | | | | | | | | | | | | |
| 7F1 | 0.00 | 78.30 | 2.33 | 20.71 | 5.92 | 0.00 | 0.00 | 94.94 | 0.78 | 7.80 | 0.00 | 0.00 |
| 36D2 | 0.00 | 81.77 | 2.16 | 15.04 | 0.00 | 8.67 | 0.00 | 95.94 | 0.78 | 7.48 | 0.00 | 0.00 |
| Y 40 | 0.42 | 81.51 | 2.24 | 18.59 | 11.31 | 6.02 | 0.00 | 92.60 | 0.70 | 11.42 | 1.89 | 0.00 |
| *B. coagulans* (W) | 66.17 | 0.00 | 0.00 | 3.50 | 0.00 | 0.00 | 0.00 | 97.99 | 2.82 | 4.21 | 3.82 | 0.00 |

TABLE 3-continued

Selected Properties of Isolates Close to *Bacillus coagulans* Grouped on Their 16S rRNA Sequence Similarity

| | Growth at pH 6.8 | | | | | |
|---|---|---|---|---|---|---|
| | LB Xylose (1%) Anaerobic | | | LB Glucose (1%) Anaerobic | | |
| | O.D. 420 nm | | pH | O.D. 420 nm | | pH |
| | 24 hrs | 48 hrs | 48 hrs | 24 hrs | 48 hrs | 48 hrs |
| Group 1 | | | | | | |
| 1D2 | 1.15 | 1.05 | 4.28 | 1.35 | 1.20 | 4.25 |
| 1D6B | 0.40 | 0.75 | 4.27 | 0.85 | 1.03 | 4.23 |
| 2D1 | 0.95 | 0.95 | 4.44 | 1.20 | 1.15 | 4.27 |
| 3F2 | 1.10 | 1.20 | 4.19 | 1.15 | 1.10 | 4.07 |
| 13E1Lg | 0.85 | 1.00 | 4.38 | 1.03 | 1.00 | 4.26 |
| 17C5 | 1.00 | 0.77 | 4.27 | 1.20 | 1.13 | 4.30 |
| 17D3 | 0.88 | 0.55 | 4.35 | 1.50 | 1.28 | 4.31 |
| 26D2 | 1.30 | 1.15 | 4.38 | 1.35 | 1.40 | 4.36 |
| 38C3 | 0.73 | 0.75 | 4.47 | 0.80 | 1.05 | 4.39 |
| 56H3A | 0.72 | 1.00 | 4.08 | 0.74 | 1.2 | 4.06 |
| 57H3 | 0.73 | 1.00 | 4.12 | 0.78 | 1.30 | 4.14 |
| 57H1 | 0.81 | 1.10 | 4.18 | 0.76 | 1.00 | 4.03 |
| Group 2 | | | | | | |
| Y 66 | 0.83 | 1.03 | 4.24 | 0.80 | 0.98 | 4.33 |
| Group 3 | | | | | | |
| Y 55 | 0.85 | 0.82 | 4.32 | 0.95 | 1.05 | 4.29 |
| Group 4 | | | | | | |
| 7D4 | 0.83 | 0.95 | 4.41 | 0.74 | 1.37 | 4.32 |
| 18C2 | 1.13 | 0.83 | 4.36 | 1.17 | 1.44 | 4.32 |
| Group 5 | | | | | | |
| 1F2 | 1.10 | 1.05 | 4.27 | 1.30 | 1.30 | 4.33 |
| 6C1 | 1.03 | 1.40 | 4.36 | 0.73 | 0.92 | 4.16 |
| 6F2 | 0.53 | 0.58 | 4.43 | 0.93 | 1.03 | 4.28 |
| 33D4 | 1.05 | 1.13 | 4.52 | 1.15 | 1.15 | 4.41 |
| 34D2 | 0.03 | 0.07 | 5.67 | 0.09 | 0.05 | 5.67 |
| HCH7 | 0.90 | 0.90 | 4.36 | 0.90 | 0.90 | 4.43 |
| HCH8 | 0.85 | 1.00 | 4.32 | 0.90 | 0.95 | 4.35 |
| Group 6 | | | | | | |
| 1C4 | 1.30 | 1.50 | 4.38 | 1.15 | 1.23 | 4.36 |
| Group 7 | | | | | | |
| 1D7 | 1.00 | 1.10 | 4.29 | 1.20 | 1.40 | 4.18 |
| Group 8 | | | | | | |
| 6H2 | 0.65 | 0.83 | 4.32 | 0.90 | 1.03 | 4.32 |
| 21B2 | 1.25 | 1.28 | 4.39 | 1.00 | 1.15 | 4.34 |
| HCH10 | 0.80 | 1.10 | 4.26 | 0.90 | 0.80 | 4.23 |
| Group 9 | | | | | | |
| 35D2 | 0.78 | 0.93 | 4.63 | 1.03 | 0.98 | 4.52 |
| Group 10 | | | | | | |
| 57H2 | 0.50 | 0.70 | 4.17 | 0.43 | 0.60 | 3.97 |
| Group 11 | | | | | | |
| 7C8 | 0.29 | 2.10 | 4.31 | 0.00 | 1.23 | 4.45 |
| 7G1 | 0.73 | 0.90 | 4.38 | 0.73 | 0.95 | 4.42 |
| Group 12 | | | | | | |
| 7F1 | 0.83 | 0.85 | 4.47 | 0.80 | 1.05 | 4.36 |
| 36D2 | 1.03 | 1.03 | 4.39 | 1.05 | 1.20 | 4.35 |
| Y 40 | 0.95 | 0.90 | 4.35 | 0.75 | 0.90 | 4.43 |
| *B. coagulans* (W) | | | | | | |

TABLE 3-continued

Selected Properties of Isolates Close to *Bacillus coagulans* Grouped on Their 16S rRNA Sequence Similarity

| | Anaerobic Growth | | | | | | | | | Aerobic Growth in HCH | | |
|---|---|---|---|---|---|---|---|---|---|---|---|---|
| | MS (0.1% YE) (Xylose 1%), pH 5.0 | | | MS (0.1% YE) (Glucose 1%), pH 5.0 | | | HCH 10%, CSL 1%, pH 5.0 | | | 20% HCH 0.1% YE/Glu | 25% HCH 0.1% YE/Glu | 50% HCH overlimed 0.1% YE/Glu |
| | O.D. 420 cm | | pH | O.D. 420 nm | | pH | O.D. 420 nm | | pH | pH 5.0 | pH 5.0 | pH 5.0 |
| Isolate | 24 hrs | 48 hrs | 48 hrs | 24 hrs | 48 hrs | 48 hrs | 24 hrs | 48 hrs | 48 hrs | plates (48 hrs) | plates (48 hrs) | plates (48 hrs) |
| Group 1 | | | | | | | | | | | | |
| 1D2 | 0.09 | 0.19 | 4.61 | 0.09 | 0.08 | 4.42 | 0.27 | 0.32 | 4.19 | +++ | − | − |
| 1D6B | 0.11 | 0.12 | 4.56 | 0.08 | 0.05 | 4.60 | 0.29 | 0.45 | 4.17 | +++ | + | − |
| 2D1 | 0.16 | 0.20 | 4.69 | 0.10 | 0.06 | 4.48 | 0.32 | 0.33 | 4.29 | +++ | + | − |
| 3F2 | 0.10 | 0.11 | 4.51 | 0.06 | 0.06 | 4.45 | 0.12 | 0.14 | 4.21 | + | − | − |
| 13E1Lg | 0.10 | 0.14 | 4.50 | 0.10 | 0.14 | 4.43 | 0.21 | 0.26 | 4.09 | ++ | + | + |
| 17C5 | 0.36 | 0.31 | 4.50 | 0.12 | 0.13 | 4.48 | 0.12 | 0.26 | 4.14 | − | − | − |
| 17D3 | 0.19 | 0.19 | 4.45 | 0.08 | 0.07 | 4.59 | 0.04 | 0.21 | 4.15 | − | − | − |
| 26D2 | 0.13 | 0.14 | 4.50 | 0.10 | 0.11 | 4.51 | 0.25 | 0.31 | 4.19 | − | − | − |
| 38C3 | 0.45 | 0.43 | 4.34 | 0.07 | 0.12 | 4.62 | 0.11 | 0.15 | 4.16 | − | − | − |
| 56H3A | 0.14 | 0.15 | 4.27 | 0.11 | 0.12 | 4.18 | 0.23 | 0.26 | 3.95 | +++ | + | − |
| 57H3 | 0.18 | 0.20 | 4.21 | 0.15 | 0.16 | 4.17 | 0.32 | 0.30 | 3.97 | +++ | + | − |
| 57H1 | 0.08 | 0.10 | 4.21 | 0.08 | 0.09 | 4.13 | 0.31 | 0.31 | 3.96 | +++ | ++ | − |
| Group 2 | | | | | | | | | | | | |
| Y 66 | 0.17 | 0.18 | 4.51 | 0.10 | 0.08 | 4.42 | 0.16 | 0.20 | 4.08 | + | − | − |
| Group 3 | | | | | | | | | | | | |
| Y 55 | 0.17 | 0.17 | 4.46 | 0.12 | 0.14 | 4.48 | 0.19 | 0.21 | 4.08 | + | − | − |
| Group 4 | | | | | | | | | | | | |
| 7D4 | 0.22 | 0.24 | 4.53 | 0.10 | 0.09 | 4.47 | 0.17 | 0.15 | 4.10 | ++ | + | − |
| 18C2 | 0.19 | 0.21 | 4.33 | 0.07 | 0.08 | 4.54 | 0.25 | 0.37 | 4.10 | + | + | + |
| Group 5 | | | | | | | | | | | | |
| 1F2 | 0.17 | 0.24 | 4.53 | 0.17 | 0.13 | 4.50 | 0.30 | 0.26 | 4.17 | +++ | ++ | + |
| 6C1 | 0.20 | 0.20 | 4.48 | 0.11 | 0.12 | 4.43 | 0.05 | 0.10 | 4.10 | + | + | − |
| 6F2 | 0.15 | 0.20 | 4.57 | 0.09 | 0.09 | 4.47 | 0.04 | 0.07 | 4.12 | + | − | − |
| 33D4 | 0.15 | 0.17 | 4.62 | 0.08 | 0.08 | 4.63 | 0.15 | 0.12 | 4.15 | − | − | − |
| 34D2 | 0.14 | 0.16 | 4.60 | 0.13 | 0.14 | 4.25 | 0.21 | 0.21 | 3.96 | +++ | + | − |
| HCH7 | 0.23 | 0.25 | 4.61 | 0.05 | 0.05 | 4.56 | 0.28 | 0.28 | 4.05 | ++ | − | − |
| HCH8 | 0.27 | 0.30 | 4.57 | 0.04 | 0.10 | 4.50 | 0.02 | 0.08 | 4.04 | +++ | ++ | + |
| Group 6 | | | | | | | | | | | | |
| 1C4 | 0.13 | 0.22 | 4.66 | 0.15 | 0.16 | 4.50 | 0.34 | 0.39 | 4.14 | +++ | + | + |
| Group 7 | | | | | | | | | | | | |
| 1D7 | 0.22 | 0.29 | 4.62 | 0.12 | 0.13 | 4.47 | 0.17 | 0.24 | 4.19 | − | − | − |
| Group 8 | | | | | | | | | | | | |
| 6H2 | 0.19 | 0.17 | 4.45 | 0.08 | 0.07 | 4.49 | 0.08 | 0.00 | 4.10 | + | − | − |
| 21B2 | 0.17 | 0.25 | 4.57 | 0.04 | 0.06 | 4.64 | 0.10 | 0.11 | 4.24 | +++ | ++ | + |
| HCH10 | 0.15 | 0.17 | 4.52 | 0.02 | 0.09 | 4.50 | 0.08 | 0.15 | 4.02 | − | − | − |
| Group 9 | | | | | | | | | | | | |
| 35D2 | 0.10 | 0.17 | 4.61 | 0.03 | 0.04 | 4.82 | 0.19 | 0.15 | 4.18 | + | − | − |
| Group 10 | | | | | | | | | | | | |
| 57H2 | 0.07 | 0.08 | 4.14 | 0.07 | 0.06 | 4.12 | 0.03 | 0.09 | 3.98 | +++ | ++ | − |
| Group 11 | | | | | | | | | | | | |
| 7C8 | 0.09 | 0.12 | 4.30 | 0.10 | 0.14 | 4.29 | 0.20 | 0.22 | 3.98 | − | − | − |
| 7G1 | 0.18 | 0.18 | 4.45 | 0.12 | 0.13 | 4.45 | 0.17 | 0.22 | 3.97 | + | + | − |
| Group 12 | | | | | | | | | | | | |
| 7F1 | 0.10 | 0.12 | 4.52 | 0.07 | 0.09 | 4.50 | 0.11 | 0.10 | 4.12 | + | − | − |
| 36D2 | 0.11 | 0.18 | 4.55 | 0.04 | 0.04 | 4.50 | 0.17 | 0.17 | 4.13 | + | − | − |
| Y 40 | 0.12 | 0.10 | 4.53 | 0.03 | 0.13 | 4.55 | 0.15 | 0.14 | 4.08 | + | − | − |
| *B. coagulans* (W) | | | | | | | | | | + | − | − |

TABLE 3-continued

Selected Properties of Isolates Close to *Bacillus coagulans* Grouped on Their 16S rRNA Sequence Similarity

| | Anaerobic Growth at pH 4.5 | | | | | | Ethanol tolerance LB (Glucose 1%, pH 5.0) | | | | | | | |
|---|---|---|---|---|---|---|---|---|---|---|---|---|---|---|
| | | | | | | | 0% Ethanol | | 4% Ethanol(w/w) | | | | | |
| | LB Glucose (1%) | | | LB Xylose (1%) | | | O.D. | O.D. | O.D. | O.D. | 4.5% Ethanol(w/ w) O.D. 420 nm | | 5% Ethanol(w/w) O.D. 420 nm | |
| | O.D. 420 nm | | pH | O.D. 420 nm | | pH | 420 nm | 420 nm | 420 nm | 420 nm | | | | |
| Isolate | 24 hrs | 48 hrs | 48 hrs | 24 hrs | 48 hrs | 48 hrs | 24 hrs | 48 hrs | 24 hrs | 48 hrs | 24 hrs | 48 hrs | 24 hrs | 48 hrs |
| Group 1 | | | | | | | | | | | | | | |
| 1D2 | 0.04 | 0.17 | 4.46 | 0.04 | 0.11 | 4.42 | 0.68 | 0.70 | 0.26 | 0.27 | 0.17 | 0.16 | 0.09 | 0.15 |
| 1D6B | 0.05 | 0.10 | 4.41 | 0.08 | 0.02 | 4.42 | 0.54 | 0.50 | 0.11 | 0.15 | 0.08 | 0.08 | 0.07 | 0.12 |
| 2D1 | 0.04 | 0.06 | 4.49 | 0.08 | 0.15 | 4.47 | 0.54 | 0.58 | 0.25 | 0.24 | 0.07 | 0.07 | 0.07 | 0.07 |
| 3F2 | 0.14 | 0.15 | 4.32 | 0.12 | 0.19 | 4.27 | 0.58 | 0.66 | 0.30 | 0.34 | 0.02 | 0.11 | 0.01 | 0.01 |
| 13E1Lg | 0.19 | 0.22 | 4.23 | 0.16 | 0.15 | 4.23 | 0.65 | 0.65 | 0.26 | 0.26 | 0.16 | 0.15 | 0.09 | 0.10 |
| 17C5 | 0.27 | 0.42 | 4.15 | 0.21 | 0.27 | 4.21 | 0.64 | 0.70 | 0.16 | 0.17 | 0.09 | 0.13 | 0.04 | 0.05 |
| 17D3 | 0.10 | 0.32 | 4.22 | 0.10 | 0.16 | 4.24 | 0.60 | 0.70 | 0.12 | 0.13 | 0.08 | 0.09 | 0.05 | 0.07 |
| 26D2 | 0.23 | 0.26 | 4.24 | 0.17 | 0.25 | 4.35 | 0.50 | 0.50 | 0.03 | 0.11 | 0.03 | 0.03 | 0.05 | 0.04 |
| 38C3 | 0.24 | 0.25 | 4.40 | 1.70 | 1.80 | 4.44 | 0.52 | 0.53 | 0.12 | 0.17 | 0.02 | 0.07 | 0.00 | 0.04 |
| 56H3A | | | | | | | 0.62 | 0.63 | 0.14 | 0.15 | 0.09 | 0.11 | 0.03 | 0.03 |
| 57H3 | | | | | | | 0.38 | 0.40 | 0.28 | 0.23 | 0.17 | 0.17 | 0.11 | 0.11 |
| 57H1 | | | | | | | 0.26 | 0.51 | 0.23 | 0.24 | 0.13 | 0.13 | 0.09 | 0.10 |
| Group 2 | | | | | | | | | | | | | | |
| Y 66 | 0.20 | 0.28 | 4.25 | 0.16 | 0.18 | 4.33 | 0.50 | 0.55 | 0.18 | 0.20 | 0.04 | 0.05 | 0.02 | 0.02 |
| Group 3 | | | | | | | | | | | | | | |
| Y 55 | 0.14 | 0.28 | 4.31 | 0.13 | 0.23 | 4.30 | 0.65 | 0.70 | 0.14 | 0.13 | 0.06 | 0.06 | 0.07 | 0.07 |
| Group 4 | | | | | | | | | | | | | | |
| 7D4 | 0.26 | 0.26 | 4.25 | 0.18 | 0.23 | 4.40 | 0.40 | 0.50 | 0.17 | 0.17 | 0.10 | 0.10 | 0.05 | 0.04 |
| 18C2 | 0.21 | 0.32 | 4.23 | 0.21 | 0.23 | 4.28 | 0.45 | 0.50 | 0.14 | 0.15 | 0.12 | 0.11 | 0.09 | 0.07 |
| Group 5 | | | | | | | | | | | | | | |
| 1F2 | 0.14 | 0.26 | 4.32 | 0.12 | 0.18 | 4.36 | 0.46 | 0.48 | 0.12 | 0.13 | 0.06 | 0.06 | 0.05 | 0.04 |
| 6C1 | 0.02 | 0.03 | 4.47 | 0.01 | 0.04 | 4.50 | 0.47 | 0.49 | 0.14 | 0.14 | 0.07 | 0.07 | 0.09 | 0.08 |
| 6F2 | 0.11 | 0.15 | 4.44 | 0.15 | 0.22 | 4.37 | 0.50 | 0.55 | 0.04 | 0.06 | 0.02 | 0.02 | 0.01 | 0.00 |
| 33D4 | 0.10 | 0.25 | 4.15 | 0.15 | 0.22 | 4.35 | 0.58 | 0.64 | 0.18 | 0.16 | 0.10 | 0.11 | 0.06 | 0.05 |
| 34D2 | | | | | | | 0.55 | 0.60 | 0.13 | 0.13 | 0.05 | 0.06 | 0.03 | 0.03 |
| HCH7 | 0.00 | 0.00 | 4.44 | 0.00 | 0.15 | 4.36 | 0.40 | 0.40 | 0.06 | 0.09 | 0.02 | 0.07 | 0.03 | 0.03 |
| HCH8 | 0.18 | 0.16 | 4.30 | 0.21 | 0.22 | 4.32 | 0.30 | 0.30 | 0.17 | 0.16 | 0.05 | 0.05 | 0.05 | 0.05 |
| Group 6 | | | | | | | | | | | | | | |
| 1C4 | 0.03 | 0.24 | 4.35 | 0.06 | 0.19 | 4.37 | 0.60 | 0.60 | 0.02 | 0.01 | 0.05 | 0.07 | 0.04 | 0.03 |
| Group 7 | | | | | | | | | | | | | | |
| 1D7 | 0.10 | 0.12 | 4.44 | 0.11 | 0.18 | 4.43 | 0.35 | 0.45 | 0.18 | 0.18 | 0.11 | 0.13 | 0.04 | 0.02 |
| Group 8 | | | | | | | | | | | | | | |
| 6H2 | 0.03 | 0.08 | 4.48 | 0.04 | 0.14 | 4.42 | 0.50 | 0.50 | 0.13 | 0.15 | 0.05 | 0.05 | 0.04 | 0.03 |
| 21B2 | 0.02 | 0.16 | 4.24 | 0.09 | 0.17 | 4.35 | 0.45 | 0.50 | 0.07 | 0.07 | 0.01 | 0.02 | 0.03 | 0.03 |
| HCH10 | 0.02 | 0.08 | 4.39 | 0.01 | 0.06 | 4.42 | 0.40 | 0.40 | 0.12 | 0.12 | 0.04 | 0.04 | 0.05 | 0.05 |
| Group 9 | | | | | | | | | | | | | | |
| 35D2 | 0.00 | 0.00 | 4.43 | 0.00 | 0.00 | 4.41 | 0.60 | 0.64 | 0.07 | 0.17 | 0.05 | 0.14 | 0.00 | 0.13 |
| Group 10 | | | | | | | | | | | | | | |
| 57H2 | | | | | | | 0.35 | 0.40 | 0.19 | 0.19 | 0.14 | 0.16 | 0.05 | 0.03 |
| Group 11 | | | | | | | | | | | | | | |
| 7C8 | | | | | | | 0.35 | 0.50 | 0.19 | 0.23 | 0.16 | 0.17 | 0.08 | 0.06 |
| 7G1 | 0.03 | 0.14 | 4.38 | 0.02 | 0.15 | 4.40 | 0.45 | 0.45 | 0.11 | 0.13 | 0.11 | 0.11 | 0.08 | 0.06 |
| Group 12 | | | | | | | | | | | | | | |
| 7F1 | 0.06 | 0.15 | 4.42 | 0.14 | 0.15 | 4.37 | 0.50 | 0.52 | 0.21 | 0.22 | 0.12 | 0.14 | 0.06 | 0.07 |
| 36D2 | 0.01 | 0.02 | 4.43 | 0.07 | 0.04 | 4.42 | 0.00 | 0.00 | 0.01 | 0.00 | 0.00 | 0.00 | 0.00 | 0.00 |
| Y 40 | 0.08 | 0.24 | 4.27 | 0.12 | 0.20 | 4.39 | 0.66 | 0.72 | 0.07 | 0.14 | 0.04 | 0.08 | 0.00 | 0.05 |
| *B. coagulans* (W) | | | | | | | | | | | | | | |

Blank Column indicates that the experiment was not performed

TABLE 4

Growth and Fermentation Profile of Selected isolates in 3% Glucose

3% Glucose In LB medium in pH stat at pH 5.0, 50° C.

| Isolate | Identification (16S rRNA) | O.D. 420 nm | | | | Glucose (mM) | | | | Lactate (mM) | | |
|---|---|---|---|---|---|---|---|---|---|---|---|---|
| | | 0 hr | 24 hr | 48 hr | 72 hr | 0 hr | 24 hr | 48 hr | 72 hr | 24 hr | 48 hr | 72 hr |
| 1C4 | B. coagulans | 0.02 | 2.89 | 2.89 | 2.89 | 176.24 | 58.09 | 51.11 | 46.78 | 192.77 | 199.26 | 205.95 |
| 1D1 | B. coagulans | 0.02 | 2.72 | 2.71 | 2.58 | 174.11 | 37.47 | 33.90 | 29.51 | 228.22 | 224.03 | 222.87 |
| 1D2 | B. coagulans | 0.02 | 3.03 | 2.76 | 2.64 | 176.07 | 47.03 | 19.58 | 14.61 | 215.56 | 252.98 | 256.44 |
| 1D5 | | 0.01 | 1.70 | 1.37 | 1.38 | 174.82 | 43.09 | 22.90 | 15.18 | 223.19 | 248.77 | 264.18 |
| 1D6B | B. coagulans | 0.02 | 3.71 | 3.36 | 3.15 | 169.29 | 76.83 | 39.14 | 25.90 | 151.07 | 204.32 | 221.92 |
| 1D7 | B. coagulans | 0.02 | 2.63 | 2.31 | 2.42 | 172.94 | 76.67 | 64.12 | 62.39 | 170.70 | 182.30 | 179.42 |
| 1F2 | B. coagulans | 0.02 | 2.38 | 2.28 | 2.27 | 177.71 | 36.89 | 22.61 | 17.06 | 233.09 | 247.17 | 249.65 |
| 2D1 | B. coagulans | 0.03 | 4.03 | 3.39 | 3.02 | 180.44 | 22.15 | 0.00 | 0.00 | 247.78 | 282.56 | 278.80 |
| 2D2 | B. coagulans | 0.01 | 3.63 | 2.60 | 2.60 | 169.40 | 67.93 | 33.70 | 25.01 | 169.40 | 219.58 | 231.80 |
| 2D3 | B. coagulans | 0.02 | 2.28 | 2.14 | 1.93 | 174.73 | 84.42 | 39.71 | 26.38 | 147.28 | 224.31 | 247.03 |
| 2D10 | | 0.01 | 2.50 | 2.20 | 2.08 | 169.96 | 81.62 | 69.34 | 67.02 | 148.36 | 174.33 | 173.49 |
| 2F2 | | 0.01 | 1.66 | 1.92 | 1.71 | 169.83 | 126.53 | 92.86 | 85.17 | 64.00 | 120.19 | 129.44 |
| 3F2 | B. coagulans | 0.03 | 3.16 | 2.73 | 2.83 | 175.08 | 28.66 | 13.71 | 8.84 | 247.76 | 266.07 | 278.20 |
| 4D3 | | 0.02 | 2.73 | 3.09 | 3.13 | 173.85 | 64.71 | 43.39 | 27.47 | 160.66 | 195.50 | 218.17 |
| 5D2 | | 0.02 | 3.26 | 3.19 | 2.75 | 165.32 | 72.55 | 11.20 | 0.00 | 156.55 | 255.23 | 273.09 |
| 5D10 | | 0.02 | 1.61 | 1.20 | 1.21 | 165.16 | 89.81 | 64.69 | 51.66 | 128.33 | 166.94 | 186.24 |
| 5D13 | | 0.02 | 2.21 | 2.42 | 2.47 | 165.66 | 109.42 | 57.76 | 27.91 | 94.25 | 183.84 | 231.50 |
| 6C1 | B. coagulans | 0.03 | 2.48 | 2.39 | 2.71 | 164.66 | 82.61 | 67.81 | 61.54 | 134.80 | 154.69 | 155.56 |
| 6F1L | | 0.01 | 2.08 | 2.19 | 2.42 | 166.88 | 68.03 | 59.79 | 48.90 | 163.55 | 170.57 | 188.41 |
| 6H1B | | 0.01 | 2.82 | 2.96 | 3.31 | 165.64 | 75.09 | 58.85 | 42.51 | 145.83 | 169.10 | 189.17 |
| 6H2 | B. coagulans | 0.01 | 3.08 | 3.31 | 3.30 | 166.37 | 60.73 | 54.93 | 48.49 | 171.88 | 180.57 | 186.49 |
| 7C4 | | 0.01 | 3.02 | 3.05 | 3.05 | 165.15 | 44.51 | 28.64 | 21.68 | 197.29 | 222.76 | 227.40 |
| 7C8 | B. coagulans | 0.01 | 3.33 | 3.40 | 3.30 | 168.10 | 51.44 | 21.03 | 10.78 | 185.94 | 233.23 | 243.16 |
| 7D3 | | 0.01 | 2.83 | 3.20 | 2.97 | 167.63 | 71.50 | 11.45 | 0.00 | 157.98 | 253.37 | 260.33 |
| 7D4 | B. coagulans | 0.02 | 1.70 | 1.70 | 1.90 | 166.66 | 101.06 | 87.75 | 86.35 | 107.47 | 117.93 | 119.98 |
| 7F1 | B. coagulans | 0.01 | 2.31 | 2.36 | 2.15 | 164.70 | 115.85 | 75.15 | 72.58 | 83.67 | 135.33 | 144.80 |
| 7G1 | B. coagulans | 0.01 | 2.73 | 2.52 | 2.31 | 165.13 | 69.49 | 13.21 | 0.00 | 152.17 | 258.80 | 277.91 |
| 8F1 | | 0.02 | 1.97 | 1.81 | 1.85 | 166.69 | 58.65 | 25.07 | 2.01 | 167.26 | 238.30 | 277.45 |
| 13E1L | B. coagulans | 0.01 | 3.67 | 2.30 | 2.29 | 176.30 | 12.01 | 0.00 | 0.00 | 270.53 | 290.53 | 291.24 |
| 14E2 | | 0.01 | 2.36 | 2.39 | 2.27 | 165.96 | 77.99 | 63.28 | 62.14 | 127.45 | 150.01 | 146.44 |
| 16C2 | | 0.01 | 2.41 | 2.32 | 2.42 | 165.04 | 71.21 | 53.58 | 49.94 | 155.22 | 185.51 | 180.26 |
| 17C4 | | 0.02 | 1.75 | 1.76 | 2.10 | 167.41 | 71.74 | 66.05 | 51.22 | 162.44 | 168.64 | 190.14 |
| 17C5 | B. coagulans | 0.02 | 2.44 | 2.69 | 2.68 | 166.23 | 12.05 | 0.00 | 0.00 | 258.17 | 276.29 | 272.99 |
| 17D2 | | 0.02 | 2.07 | 1.84 | 2.06 | 173.53 | 20.29 | 12.82 | 14.20 | 242.82 | 254.26 | 253.88 |
| 17D3 | B. coagulans | 0.01 | 2.47 | 2.36 | 1.79 | 172.34 | 35.54 | 28.89 | 28.04 | 219.63 | 234.43 | 231.68 |
| 18C2 | B. coagulans | 0.02 | 2.10 | 1.98 | 1.98 | 174.74 | 68.78 | 65.69 | 62.02 | 175.31 | 181.57 | 185.98 |
| 18C5 | | 0.02 | 2.70 | 2.18 | 2.06 | 181.53 | 47.29 | 17.12 | 9.22 | 212.38 | 256.54 | 257.31 |
| 18D1 | | 0.02 | 3.15 | 3.20 | 3.08 | 171.34 | 44.46 | 21.28 | 15.78 | 211.01 | 242.28 | 241.68 |
| 21B2 | B. coagulans | 0.01 | 0.96 | 1.07 | 2.25 | 179.10 | 111.59 | 104.59 | 38.28 | 110.39 | 114.58 | 222.23 |
| 26D2 | B. coagulans | 0.02 | 1.09 | 1.30 | 1.51 | 173.68 | 87.15 | 86.11 | 84.82 | 146.33 | 144.26 | 143.65 |
| 33D4 | B. coagulans | 0.02 | 2.37 | 1.93 | 1.93 | 174.28 | 42.77 | 28.99 | 23.55 | 217.46 | 231.18 | 231.36 |
| 34D2 | B. coagulans | 0.01 | 3.27 | 2.94 | 2.49 | 165.75 | 78.27 | 33.35 | 24.31 | 154.80 | 231.32 | 244.63 |

| Isolate | Acetate (mM) | | | | Succinate (mM) | | | | Formate (mM) | | | Ethanol (mM) | | | 2,3-Butanediol (mM) | | |
|---|---|---|---|---|---|---|---|---|---|---|---|---|---|---|---|---|---|
| | 0 hr | 24 hr | 48 hr | 72 hr | 0 hr | 24 hr | 48 hr | 72 hr | 24 hr | 48 hr | 72 hr | 24 hr | 48 hr | 72 hr | 24 hr | 48 hr | 72 hr |
| 1C4 | 1.37 | 0.48 | 1.02 | 1.37 | 0.00 | 0.32 | 0.22 | 0.30 | 0.00 | 0.00 | 0.00 | 3.86 | 4.06 | 3.70 | 0.00 | 0.00 | 0.00 |
| 1D1 | 1.19 | 0.00 | 1.13 | 2.25 | 0.00 | 0.24 | 0.25 | 0.26 | 0.00 | 0.00 | 0.00 | 4.74 | 5.08 | 3.49 | 0.00 | 0.00 | 0.00 |
| 1D2 | 1.32 | 0.00 | 0.00 | 0.00 | 0.00 | 0.22 | 0.22 | 0.24 | 0.00 | 0.00 | 0.00 | 4.71 | 5.44 | 5.58 | 0.00 | 0.00 | 0.00 |
| 1D5 | 1.26 | 0.00 | 0.00 | 0.00 | 0.00 | 0.47 | 0.41 | 0.43 | 0.00 | 0.00 | 0.00 | 2.37 | 4.53 | 3.74 | 0.00 | 0.00 | 0.00 |
| 1D6B | 0.83 | 0.00 | 3.96 | 7.08 | 1.23 | 2.66 | 3.01 | 2.94 | 0.00 | 0.00 | 0.00 | 6.46 | 10.95 | 11.77 | 0.00 | 0.00 | 0.00 |
| 1D7 | 1.48 | 0.00 | 0.00 | 0.00 | 0.00 | 0.39 | 0.40 | 0.36 | 0.00 | 0.00 | 0.00 | 2.75 | 3.65 | 3.91 | 0.00 | 0.00 | 0.00 |
| 1F2 | 1.30 | 0.00 | 2.12 | 3.63 | 0.00 | 0.37 | 0.37 | 0.30 | 0.00 | 0.00 | 0.00 | 4.00 | 4.48 | 4.73 | 0.00 | 0.00 | 0.00 |
| 2D1 | 1.03 | 0.00 | 7.05 | 6.22 | 1.22 | 0.56 | 1.05 | 1.12 | 0.00 | 0.00 | 0.00 | 1.90 | 6.95 | 6.58 | 1.27 | 2.00 | 2.99 |
| 2D2 | 0.86 | 0.00 | 0.00 | 0.00 | 1.12 | 0.70 | 0.89 | 0.93 | 0.00 | 0.00 | 0.00 | 1.14 | 1.96 | 2.52 | 1.14 | 1.34 | 2.09 |
| 2D3 | 0.85 | 0.00 | 0.00 | 0.00 | 1.14 | 0.40 | 0.39 | 0.40 | 0.00 | 0.00 | 0.00 | 0.86 | 2.27 | 1.81 | 0.76 | 0.83 | 1.19 |
| 2D10 | 0.86 | 0.00 | 0.00 | 0.00 | 1.28 | 0.32 | 0.31 | 0.31 | 0.00 | 0.00 | 0.00 | 0.96 | 1.58 | 1.69 | 1.09 | 0.92 | 1.16 |
| 2F2 | 0.90 | 0.00 | 0.00 | 3.66 | 1.12 | 0.48 | 0.63 | 0.61 | 0.00 | 0.00 | 0.00 | 0.73 | 1.86 | 1.46 | 0.73 | 2.24 | 1.98 |
| 3F2 | 1.57 | 0.00 | 1.10 | 2.07 | 0.00 | 0.41 | 0.35 | 0.31 | 0.00 | 0.00 | 0.00 | 6.06 | 5.08 | 3.08 | 0.00 | 0.00 | 0.00 |
| 4D3 | 0.84 | 0.00 | 0.00 | 0.00 | 1.43 | 0.00 | 1.20 | 1.44 | 0.00 | 0.00 | 0.00 | 1.81 | 0.00 | 4.37 | 1.14 | 1.89 | 0.99 |
| 5D2 | 0.91 | 0.00 | 0.00 | 0.00 | 1.19 | 0.48 | 0.31 | 0.00 | 0.00 | 0.00 | 0.00 | 1.59 | 2.75 | 4.82 | 0.48 | 0.91 | 2.92 |
| 5D10 | 0.94 | 0.00 | 0.00 | 0.00 | 1.42 | 0.56 | 0.00 | 0.00 | 0.00 | 0.00 | 0.00 | 0.85 | 0.93 | 1.42 | 0.78 | 0.79 | 1.06 |
| 5D13 | 0.84 | 7.02 | 8.01 | 10.27 | 1.22 | 2.09 | 2.83 | 3.30 | 0.00 | 0.00 | 0.00 | 0.00 | 0.00 | 0.00 | 0.38 | 0.79 | 0.69 |
| 6C1 | 0.86 | 0.00 | 0.00 | 0.00 | 1.20 | 0.47 | 0.47 | 0.47 | 0.00 | 0.00 | 0.00 | 0.00 | 1.27 | 0.00 | 2.45 | 1.42 | 2.78 |
| 6F1L | 0.92 | 3.73 | 0.00 | 0.00 | 1.30 | 0.00 | 0.91 | 0.96 | 0.00 | 0.00 | 0.00 | 2.01 | 1.86 | 2.90 | 1.07 | 0.93 | 1.08 |
| 6H1B | 0.94 | 0.00 | 0.00 | 0.00 | 1.19 | 0.62 | 0.88 | 0.68 | 0.00 | 0.00 | 0.00 | 0.83 | 1.31 | 2.57 | 1.40 | 1.71 | 2.57 |
| 6H2 | 0.79 | 0.00 | 0.00 | 0.00 | 1.34 | 0.66 | 0.00 | 0.70 | 0.00 | 0.00 | 0.00 | 1.42 | 1.62 | 2.02 | 1.40 | 1.31 | 1.33 |
| 7C4 | 0.97 | 0.00 | 3.87 | 4.69 | 1.29 | 2.02 | 1.69 | 1.15 | 0.00 | 0.00 | 0.00 | 2.29 | 2.67 | 3.45 | 1.04 | 3.50 | 1.79 |
| 7C8 | 0.76 | 0.00 | 0.00 | 4.44 | 1.34 | 1.21 | 2.09 | 2.55 | 0.00 | 0.00 | 0.00 | 2.41 | 2.93 | 3.54 | 1.03 | 1.65 | 2.85 |

TABLE 4-continued

Growth and Fermentation Profile of Selected isolates in 3% Glucose

| 7D3 | 0.93 | 3.13 | 0.00 | 6.45 | 2.23 | 0.52 | 0.72 | 0.73 | 0.00 | 0.00 | 0.00 | 2.04 | 3.79 | 5.77 | 0.60 | 3.28 | 3.65 |
|---|---|---|---|---|---|---|---|---|---|---|---|---|---|---|---|---|---|
| 7D4 | 0.00 | 0.00 | 0.00 | 0.00 | 1.53 | 0.44 | 0.41 | 0.44 | 0.00 | 0.00 | 0.00 | 1.55 | 0.00 | 0.53 | 1.66 | 1.44 | 2.02 |
| 7F1 | 0.83 | 0.00 | 0.00 | 0.00 | 1.01 | 0.00 | 0.60 | 0.60 | 0.00 | 0.00 | 0.00 | 10.83 | 1.96 | 2.94 | 1.88 | 1.40 | 1.50 |
| 7G1 | 0.00 | 0.00 | 0.00 | 4.39 | 2.54 | 0.22 | 0.29 | 0.35 | 0.00 | 0.00 | 0.00 | 1.44 | 3.38 | 3.93 | 0.68 | 0.97 | 1.74 |
| 8F1 | 1.35 | 0.00 | 0.00 | 0.00 | 3.60 | 0.34 | 0.37 | 0.35 | 0.00 | 0.00 | 0.00 | 0.00 | 1.03 | 1.31 | 0.77 | 0.89 | 1.13 |
| 13E1L | 1.24 | 0.50 | 1.07 | 1.02 | 0.00 | 0.28 | 0.26 | 0.21 | 4.76 | 4.11 | 0.00 | 8.60 | 5.03 | 7.96 | 0.00 | 0.00 | 0.00 |
| 14E2 | 0.00 | 0.00 | 5.09 | 4.02 | 1.46 | 0.93 | 1.73 | 1.09 | 0.00 | 0.00 | 0.00 | 2.52 | 1.97 | 3.22 | 1.28 | 1.91 | 2.02 |
| 16C2 | 11.12 | 0.98 | 0.00 | 2.77 | 0.61 | 1.10 | 1.64 | 1.58 | 0.00 | 0.00 | 0.00 | 0.00 | 1.34 | 2.09 | 0.00 | 0.00 | 1.82 |
| 17C4 | 3.33 | 1.84 | 0.57 | 0.00 | 1.05 | 1.02 | 0.00 | 0.72 | 0.00 | 0.00 | 0.00 | 10.31 | 4.06 | 2.43 | 0.00 | 0.00 | 0.84 |
| 17C5 | 0.50 | 0.00 | 0.00 | 5.13 | 0.00 | 0.00 | 0.70 | 0.00 | 3.47 | 3.12 | 0.00 | 0.00 | 7.07 | 11.05 | 0.00 | 0.00 | 1.20 |
| 17D2 | 0.00 | 0.95 | 0.89 | 0.00 | 1.14 | 0.40 | 0.62 | 1.63 | 4.73 | 2.55 | 0.00 | 4.38 | 8.32 | 2.34 | 0.00 | 0.00 | 1.08 |
| 17D3 | 1.16 | 2.13 | 2.25 | 2.40 | 0.00 | 0.78 | 0.91 | 1.14 | 3.46 | 3.93 | 0.00 | 8.96 | 10.28 | 9.78 | 0.00 | 0.00 | 0.00 |
| 18C2 | 2.39 | 0.00 | 0.00 | 0.73 | 0.00 | 0.42 | 0.45 | 0.52 | 0.00 | 0.00 | 0.00 | 1.69 | 1.98 | 2.02 | 0.00 | 0.00 | 0.00 |
| 18C5 | 1.57 | 0.00 | 2.00 | 2.97 | 0.00 | 0.57 | 0.69 | 0.83 | 0.00 | 0.00 | 0.00 | 0.99 | 1.73 | 1.58 | 0.00 | 0.00 | 0.00 |
| 18D1 | 1.23 | 0.00 | 2.64 | 3.66 | 0.00 | 0.71 | 0.94 | 0.95 | 0.00 | 0.00 | 0.00 | 4.22 | 4.19 | 4.33 | 0.00 | 0.00 | 0.00 |
| 21B2 | 1.79 | 0.00 | 0.48 | 0.00 | 0.00 | 0.41 | 0.51 | 0.60 | 0.00 | 0.00 | 0.00 | 0.67 | 0.81 | 2.99 | 0.00 | 0.00 | 0.00 |
| 26D2 | 1.24 | 2.00 | 1.97 | 1.62 | 0.00 | 1.25 | 1.36 | 0.00 | 0.00 | 0.00 | 0.00 | 4.02 | 3.98 | 3.99 | 0.00 | 0.00 | 0.00 |
| 33D4 | 1.37 | 2.31 | 2.99 | 4.60 | 0.00 | 0.59 | 0.61 | 0.69 | 0.00 | 0.00 | 0.00 | 6.46 | 8.60 | 8.05 | 0.00 | 0.00 | 0.00 |
| 34D2 | 0.00 | 0.00 | 0.00 | 0.00 | 0.00 | 0.37 | 0.34 | 0.33 | 0.00 | 0.00 | 0.00 | 1.14 | 2.50 | 2.58 | 0.00 | 0.00 | 0.00 |

3% Glucose In LB medium In pH stat at pH 5.0, 50° C.

| Isolate | Identification (16S rRNA) | O.D. 420 nm | | | | Glucose (mM) | | | | Lactate (mM) | | |
|---|---|---|---|---|---|---|---|---|---|---|---|---|
| | | 0 hr | 24 hr | 48 hr | 72 hr | 0 hr | 24 hr | 48 hr | 72 hr | 24 hr | 48 hr | 72 hr |
| 35D2 | B. coagulans | 0.02 | 1.84 | 2.18 | 2.18 | 168.44 | 87.26 | 71.33 | 59.21 | 135.46 | 155.82 | 165.85 |
| 36D1 | B. coagulans | 0.02 | 3.35 | 2.34 | 1.86 | 167.70 | 54.67 | 0.00 | 0.00 | 196.11 | 290.74 | 289.20 |
| 36D2 | B. coagulans | 0.02 | 2.76 | 2.22 | 2.32 | 161.94 | 62.81 | 54.01 | 53.39 | 165.25 | 174.82 | 177.79 |
| 38D5 | | 0.01 | 2.09 | 1.67 | 1.89 | 165.95 | 119.72 | 53.38 | 52.58 | 75.90 | 188.58 | 187.39 |
| 39D1 | | 0.02 | 2.85 | 2.23 | 2.28 | 167.84 | 74.41 | 51.54 | 51.02 | 163.67 | 198.37 | 195.62 |
| 39D1A | | 0.01 | 2.87 | 2.30 | 2.17 | 167.75 | 65.97 | 17.75 | 17.87 | 177.09 | 254.00 | 246.61 |
| 46C1 | | 0.02 | 2.63 | 2.04 | 2.05 | 164.24 | 70.38 | 28.56 | 23.24 | 149.85 | 214.75 | 224.92 |
| 47C1 | | 0.02 | 2.35 | 1.98 | 1.88 | 171.63 | 92.01 | 59.90 | 52.67 | 112.03 | 167.42 | 176.28 |
| 49D3 | | 0.03 | 1.64 | 0.55 | 2.01 | 158.86 | 71.47 | 57.61 | 38.42 | 138.48 | 166.72 | 191.80 |
| 49D4L | | 0.02 | 2.80 | 3.17 | 3.69 | 162.56 | 49.03 | 30.03 | 7.01 | 182.38 | 209.69 | 248.58 |
| 53D1 | | 0.02 | 2.78 | 2.36 | 2.46 | 160.61 | 47.87 | 31.34 | 28.11 | 172.43 | 197.96 | 195.68 |
| 53D2 | | 0.01 | 1.67 | 1.59 | 1.48 | 156.66 | 113.21 | 101.81 | 100.16 | 75.64 | 98.74 | 93.41 |
| 56H3A | B. coagulans | 0.01 | 2.92 | 2.95 | 2.83 | 156.67 | 47.42 | 28.93 | 26.54 | 185.78 | 211.29 | 216.12 |
| 57H1 | B. coagulans | 0.01 | 2.75 | 2.82 | 2.86 | 155.47 | 68.22 | 39.02 | 22.49 | 153.33 | 200.79 | 223.46 |
| 57H2 | B. smithii | 0.02 | 1.04 | 1.16 | 1.17 | 161.39 | 125.15 | 111.12 | 102.07 | 59.20 | 82.11 | 96.38 |
| 57H3 | B. coagulans | 0.01 | 2.70 | 3.22 | 3.01 | 156.04 | 48.01 | 22.05 | 9.14 | 188.81 | 225.99 | 243.11 |
| HCH7 | B. coagulans | 0.02 | 3.29 | 2.89 | 2.65 | 155.54 | 38.14 | 11.22 | 9.55 | 200.07 | 233.69 | 233.07 |
| HCH8 | B. coagulans | 0.02 | 3.86 | 3.10 | 2.86 | 159.81 | 15.32 | 0.00 | 0.00 | 236.98 | 258.46 | 253.82 |
| HCH10 | B. coagulans | 0.01 | 3.89 | 3.75 | 3.31 | 157.54 | 71.16 | 7.74 | 0.00 | 142.82 | 254.02 | 258.27 |
| Y-8 | B. coagulans | 0.01 | 3.06 | 3.10 | 2.63 | 156.81 | 18.80 | 0.00 | 0.00 | 226.21 | 256.64 | 256.62 |
| Y-39 | | 0.02 | 1.74 | 2.39 | 3.10 | 156.91 | 71.30 | 65.81 | 34.04 | 143.42 | 150.40 | 195.98 |
| Y-40 | B. coagulans | 0.01 | 3.47 | 3.11 | 3.10 | 158.61 | 0.00 | 0.23 | 0.00 | 259.37 | 262.26 | 258.36 |
| Y-41 | B. coagulans | 0.01 | 2.84 | 3.46 | 3.44 | 169.63 | 17.80 | 0.00 | 0.00 | 267.03 | 290.90 | 303.79 |
| Y-55 | B. coagulans | 0.01 | 2.99 | 3.73 | 3.75 | 172.89 | 94.86 | 13.03 | 0.00 | 126.73 | 257.09 | 275.77 |
| Y-56 | B. smithii | 0.01 | 3.45 | 3.05 | 3.15 | 175.77 | 44.29 | 20.47 | 10.09 | 211.91 | 245.32 | 253.01 |
| Y-66 | B. coagulans | 0.01 | 3.62 | 2.75 | 2.73 | 174.41 | 60.72 | 0.00 | 0.00 | 182.19 | 279.13 | 275.82 |
| Y-72 | | 0.02 | 0.30 | 2.71 | 3.81 | 176.76 | 166.90 | 72.38 | 19.53 | 17.84 | 160.16 | 241.83 |
| Y-82 | | 0.01 | 0.40 | 2.00 | 2.34 | 174.86 | 161.87 | 44.13 | 24.46 | 17.80 | 208.92 | 233.92 |
| Y-85 | | 0.01 | 1.25 | 2.32 | 3.41 | 175.00 | 122.56 | 101.74 | 71.95 | 82.56 | 103.32 | 139.97 |
| P4-62 | | 0.02 | 2.62 | 2.63 | 2.86 | 176.00 | 69.14 | 58.58 | 48.77 | 174.10 | 187.38 | 201.49 |
| P4-74B | B. coagulans | 0.03 | 4.27 | 3.90 | 3.66 | 171.79 | 0.07 | 0.00 | 0.00 | 281.21 | 275.66 | 271.64 |
| P4-85 | | 0.02 | 4.38 | 2.88 | 2.53 | 176.49 | 3.32 | 0.00 | 0.00 | 277.17 | 286.37 | 289.00 |
| P4-102A | | 0.02 | 6.23 | 5.92 | 5.10 | 176.27 | 30.15 | 0.00 | 0.00 | 201.03 | 226.19 | 225.62 |
| P4-102B | B. coagulans | 0.03 | 4.10 | 3.00 | 2.53 | 174.00 | 17.27 | 0.00 | 0.00 | 258.57 | 291.08 | 291.12 |
| B. coagulans 7050 | ATCC 7050 | 0.02 | 3.41 | 1.96 | 1.72 | 172.24 | 23.45 | 0.00 | 0.00 | 252.91 | 283.57 | 279.32 |

| Isolate | Acetate (mM) | | | | Succinate (mM) | | | | Formate (mM) | | | Ethanol (mM) | | | 2,3-Butanediol (mM) | | |
|---|---|---|---|---|---|---|---|---|---|---|---|---|---|---|---|---|---|
| | 0 hr | 24 hr | 48 hr | 72 hr | 0 hr | 24 hr | 48 hr | 72 hr | 24 hr | 48 hr | 72 hr | 24 hr | 48 hr | 72 hr | 24 hr | 48 hr | 72 hr |
| 35D2 | 1.76 | 1.91 | 3.49 | 5.98 | 0.00 | 0.56 | 0.77 | 0.86 | 0.00 | 0.00 | 0.00 | 1.77 | 2.19 | 2.44 | 0.00 | 0.00 | 0.00 |
| 36D1 | 1.52 | 0.00 | 0.00 | 0.00 | 0.00 | 0.29 | 0.39 | 0.35 | 0.00 | 0.00 | 0.00 | 1.41 | 2.59 | 2.44 | 0.00 | 0.00 | 0.00 |
| 36D2 | 2.53 | 0.00 | 0.00 | 0.00 | 0.00 | 0.51 | 0.00 | 0.00 | 0.00 | 0.00 | 0.00 | 1.77 | 1.04 | 1.81 | 0.00 | 0.00 | 0.00 |
| 38D5 | 1.29 | 0.00 | 4.52 | 4.72 | 0.00 | 0.37 | 0.41 | 0.44 | 0.00 | 0.00 | 0.00 | 0.00 | 2.05 | 2.03 | 0.00 | 0.00 | 0.00 |
| 39D1 | 1.57 | 0.00 | 0.00 | 0.00 | 0.00 | 0.00 | 0.22 | 0.23 | 0.19 | 0.00 | 0.00 | 0.00 | 0.00 | 0.00 | 0.00 | 0.00 | 0.00 |
| 39D1A | 1.48 | 0.00 | 0.00 | 1.09 | 0.00 | 0.21 | 0.24 | 0.29 | 0.00 | 0.00 | 0.00 | 1.43 | 2.01 | 1.91 | 0.00 | 0.00 | 0.00 |
| 46C1 | 1.18 | 0.00 | 13.36 | 16.56 | 0.00 | 0.00 | 2.57 | 2.26 | 0.00 | 0.00 | 0.00 | 0.00 | 3.67 | 0.00 | 0.00 | 0.00 | 0.00 |
| 47C1 | 1.18 | 8.67 | 0.00 | 0.00 | 0.00 | 0.75 | 0.00 | 0.00 | 0.00 | 0.00 | 0.00 | 0.00 | 5.73 | 5.03 | 0.00 | 0.00 | 0.00 |
| 49D3 | 0.97 | 5.32 | 0.00 | 0.00 | 0.00 | 0.34 | 0.75 | 0.74 | 0.00 | 0.00 | 0.00 | 0.00 | 21.99 | 2.58 | 0.00 | 0.00 | 0.00 |
| 49D4L | 1.80 | 8.13 | 6.56 | 0.00 | 0.00 | 2.79 | 0.34 | 2.40 | 0.00 | 0.00 | 0.00 | 24.18 | 0.00 | 8.68 | 0.00 | 0.00 | 0.00 |

TABLE 4-continued

Growth and Fermentation Profile of Selected isolates in 3% Glucose

| 53D1 | 2.72 | 4.97 | 0.00 | 5.94 | 0.00 | 2.42 | 1.79 | 1.79 | 0.00 | 0.00 | 0.00 | 6.90 | 29.17 | 13.53 | 0.00 | 0.00 | 0.00 |
|---|---|---|---|---|---|---|---|---|---|---|---|---|---|---|---|---|---|
| 53D2 | 1.41 | 0.00 | 0.00 | 0.00 | 0.00 | 0.65 | 0.50 | 0.76 | 0.00 | 0.00 | 0.00 | 0.00 | 0.00 | 0.00 | 0.00 | 0.00 | 0.00 |
| 56H3A | 1.53 | 0.00 | 4.90 | 5.90 | 0.00 | 0.25 | 0.33 | 0.60 | 0.00 | 0.00 | 0.00 | 7.63 | 3.47 | 5.92 | 0.00 | 0.00 | 0.00 |
| 57H1 | 1.80 | 5.51 | 0.00 | 0.00 | 0.00 | 0.14 | 0.00 | 0.00 | 0.00 | 0.00 | 0.00 | 3.04 | 4.01 | 4.93 | 0.00 | 0.00 | 0.00 |
| 57H2 | 0.00 | 13.52 | 9.49 | 9.21 | 0.00 | 1.15 | 1.15 | 1.05 | 0.00 | 0.00 | 0.00 | 0.00 | 0.00 | 0.00 | 0.00 | 0.00 | 0.00 |
| 57H3 | 1.87 | 0.00 | 0.00 | 0.00 | 0.00 | 0.33 | 0.38 | 33.54 | 0.00 | 0.00 | 0.00 | 0.00 | 5.65 | 7.02 | 0.00 | 0.00 | 0.00 |
| HCH7 | 7.01 | 5.87 | 8.10 | 10.43 | 0.00 | 1.04 | 1.04 | 0.88 | 0.00 | 0.00 | 0.00 | 11.97 | 13.44 | 17.81 | 0.00 | 0.00 | 0.00 |
| HCH8 | 7.85 | 12.22 | 10.29 | 4.60 | 0.00 | 0.36 | 0.51 | 0.41 | 0.00 | 0.00 | 0.00 | 7.76 | 7.88 | 9.04 | 0.00 | 0.00 | 0.00 |
| HCH10 | 0.00 | 7.47 | 5.23 | 10.15 | 0.00 | 0.70 | 0.64 | 0.80 | 0.00 | 0.00 | 0.00 | 2.58 | 4.77 | 6.57 | 0.00 | 0.00 | 0.00 |
| Y-8 | 1.13 | 0.00 | 4.49 | 6.20 | 0.00 | 1.20 | 1.46 | 1.20 | 0.00 | 0.00 | 0.00 | 8.49 | 7.66 | 5.26 | 0.00 | 0.00 | 0.00 |
| Y-39 | 1.10 | 4.35 | 0.00 | 0.00 | 0.00 | 0.50 | 0.41 | 0.77 | 0.00 | 0.00 | 0.00 | 0.00 | 1.92 | 4.78 | 0.00 | 0.00 | 0.00 |
| Y-40 | 1.15 | 7.24 | 4.46 | 0.00 | 0.00 | 0.23 | 0.24 | 0.23 | 0.00 | 0.00 | 0.00 | 6.40 | 3.98 | 7.22 | 0.00 | 0.00 | 0.00 |
| Y-41 | 0.88 | 0.49 | 2.11 | 2.74 | 0.00 | 0.99 | 1.96 | 0.58 | 0.00 | 0.00 | 0.00 | 5.50 | 7.84 | 7.50 | 0.00 | 0.00 | 0.00 |
| Y-55 | 0.99 | 0.00 | 1.69 | 2.21 | 0.00 | 0.62 | 0.84 | 0.86 | 5.23 | 4.05 | 4.60 | 8.76 | 17.76 | 21.64 | 0.00 | 0.00 | 0.00 |
| Y-56 | 1.12 | 2.44 | 4.50 | 7.23 | 0.00 | 0.78 | 1.12 | 1.18 | 0.00 | 0.00 | 0.00 | 5.08 | 6.07 | 7.34 | 0.00 | 0.00 | 0.00 |
| Y-66 | 1.18 | 0.00 | 1.75 | 3.79 | 0.00 | 0.47 | 0.58 | 0.77 | 0.00 | 0.00 | 0.00 | 3.36 | 6.64 | 6.00 | 0.00 | 0.00 | 0.00 |
| Y-72 | 0.86 | 0.00 | 0.00 | 2.04 | 0.00 | 0.53 | 0.81 | 1.13 | 0.00 | 0.00 | 0.00 | 0.00 | 6.21 | 7.04 | 0.00 | 0.00 | 0.00 |
| Y-82 | 0.80 | 0.00 | 1.16 | 1.10 | 0.00 | 0.51 | 0.35 | 0.33 | 0.00 | 4.64 | 5.05 | 0.00 | 5.08 | 7.31 | 0.00 | 0.00 | 0.00 |
| Y-85 | 1.19 | 0.00 | 0.00 | 1.83 | 0.00 | 0.52 | 0.55 | 1.12 | 0.00 | 0.00 | 0.00 | 0.00 | 0.00 | 3.99 | 0.00 | 0.00 | 0.00 |
| P4-62 | 1.64 | 0.00 | 0.00 | 0.00 | 0.00 | 0.21 | 0.21 | 0.23 | 0.00 | 0.00 | 0.00 | 4.40 | 5.38 | 5.86 | 0.00 | 0.00 | 0.00 |
| P4-74B | 1.38 | 1.31 | 4.90 | 9.03 | 0.00 | 0.29 | 0.26 | 0.33 | 0.00 | 0.00 | 0.00 | 6.92 | 6.97 | 6.69 | 0.00 | 0.00 | 0.00 |
| P4-85 | 1.06 | 0.00 | 1.11 | 1.10 | 0.00 | 0.23 | 0.33 | 0.30 | 5.09 | 0.00 | 0.00 | 7.16 | 10.45 | 4.83 | 0.00 | 0.00 | 0.00 |
| P4-102A | 0.87 | 1.99 | 11.95 | 13.36 | 0.00 | 1.64 | 1.86 | 2.04 | 7.73 | 23.68 | 20.84 | 43.58 | 61.70 | 64.19 | 0.00 | 0.00 | 0.00 |
| P4-102B | 1.26 | 0.00 | 1.67 | 2.91 | 0.00 | 0.41 | 0.40 | 0.46 | 0.00 | 0.00 | 0.00 | 4.73 | 7.16 | 7.75 | 0.00 | 0.00 | 0.00 |
| *B. coagulans* 7050 | 1.00 | 3.23 | 5.50 | 7.79 | 0.00 | 1.18 | 1.59 | 1.27 | 0.00 | 0.00 | 0.00 | 6.35 | 6.35 | 2.80 | 0.00 | 0.00 | 0.00 |

TABLE 5

Growth and Fermentation Profile of Selected Isolates in 3% Xylose

3% Xylose in LB medium in pH stat at pH 5.0, 50° C.

| | O.D. 420 nm | | | | Xylose (mM) | | | | Lactate (mM) | | |
|---|---|---|---|---|---|---|---|---|---|---|---|
| Isolate | 0 hr | 24 hr | 48 hr | 72 hr | 0 hr | 24 hr | 48 hr | 72 hr | 24 hr | 48 hr | 72 hr |
| 1C4 | 0.02 | 3.30 | 3.05 | 3.30 | 198.04 | 70.80 | 31.67 | 8.92 | 159.01 | 213.36 | 240.63 |
| 1D1 | 0.02 | 4.06 | 3.30 | 3.57 | 191.04 | 82.28 | 23.97 | 1.60 | 146.90 | 221.63 | 247.95 |
| 1D2 | 0.02 | 3.59 | 3.36 | 2.89 | 199.09 | 46.56 | 0.00 | 0.00 | 182.46 | 247.44 | 244.15 |
| 1D5 | 0.01 | 2.88 | 2.93 | 2.51 | 0.00 | 112.98 | 36.61 | 19.40 | 100.23 | 205.51 | 229.89 |
| 1D7 | 0.02 | 1.13 | 2.32 | 2.58 | 200.80 | 158.28 | 104.53 | 77.16 | 39.00 | 95.66 | 134.90 |
| 1F2 | 0.02 | 3.24 | 3.13 | 3.01 | 204.03 | 51.68 | 0.21 | 0.00 | 184.85 | 260.54 | 260.30 |
| 1D6B | 0.01 | 3.75 | 4.05 | 3.89 | 194.86 | 107.31 | 32.58 | 2.21 | 111.28 | 206.19 | 244.51 |
| 2D1 | 0.02 | 2.72 | 2.81 | 2.85 | 196.39 | 93.89 | 39.11 | 15.77 | 131.14 | 202.93 | 238.33 |
| 2D2 | 0.01 | 1.44 | 1.34 | 2.09 | 198.71 | 173.03 | 130.64 | 109.37 | 20.29 | 25.86 | 35.80 |
| 2D3 | 0.01 | 1.48 | 2.08 | 2.35 | 195.14 | 126.70 | 69.09 | 35.67 | 94.06 | 157.19 | 208.66 |
| 2D10 | 0.01 | 1.76 | 3.49 | 3.61 | 197.69 | 160.92 | 67.99 | 25.10 | 44.39 | 147.83 | 209.94 |
| 2F2 | 0.01 | 0.78 | 1.45 | 1.91 | 194.70 | 163.22 | 116.30 | 91.81 | 49.86 | 63.00 | 105.08 |
| 3F2 | 0.03 | 4.09 | 3.43 | 3.52 | 195.70 | 17.36 | 2.10 | 0.45 | 235.61 | 260.38 | 259.21 |
| 4D3 | 0.01 | 2.09 | 2.25 | 2.60 | 195.34 | 128.47 | 94.63 | 77.60 | 63.63 | 103.16 | 127.50 |
| 5D2 | 0.01 | 1.37 | 2.29 | 2.58 | 196.06 | 116.13 | 75.01 | 36.63 | 81.81 | 134.07 | 189.63 |
| 5D10 | 0.02 | 2.70 | 2.54 | 2.12 | 195.86 | 131.26 | 52.64 | 34.40 | 61.76 | 166.05 | 190.66 |
| 5D13 | 0.01 | 1.02 | 1.57 | 1.69 | 198.11 | 180.55 | 135.85 | 115.31 | 27.68 | 79.68 | 107.85 |
| 6C1 | 0.02 | 4.19 | 4.16 | 4.31 | 196.72 | 96.08 | 16.95 | 0.00 | 119.29 | 213.74 | 231.73 |
| 6F1L | 0.02 | 2.30 | 2.75 | 2.55 | 196.47 | 117.77 | 56.36 | 39.06 | 74.42 | 163.91 | 185.04 |
| 6H1B | 0.01 | 1.87 | 2.55 | 2.35 | 196.47 | 133.05 | 100.35 | 86.82 | 54.09 | 92.46 | 106.59 |
| 6H2 | 0.01 | 2.27 | 2.97 | 3.14 | 192.05 | 111.90 | 56.77 | 33.03 | 72.77 | 137.68 | 171.47 |
| 7C4 | 0.01 | 2.19 | 3.51 | 4.03 | 199.13 | 134.61 | 65.14 | 30.99 | 62.15 | 152.14 | 193.44 |
| 7C8 | 0.01 | 1.98 | 2.45 | 2.59 | 199.44 | 119.90 | 83.12 | 62.27 | 60.39 | 105.45 | 135.23 |
| 7D3 | 0.01 | 1.26 | 2.38 | 2.90 | 194.82 | 119.52 | 74.07 | 32.44 | 67.14 | 130.86 | 191.69 |
| 7D4 | 0.02 | 1.23 | 2.65 | 2.50 | 194.70 | 148.94 | 116.42 | 80.87 | 36.19 | 87.43 | 129.07 |
| 7F1 | 0.02 | 2.42 | 3.40 | 3.12 | 197.01 | 121.73 | 61.88 | 41.48 | 61.87 | 137.34 | 158.32 |
| 7G1 | 0.02 | 1.14 | 1.79 | 1.70 | 197.33 | 133.21 | 105.95 | 91.26 | 46.15 | 73.85 | 91.00 |
| 8F1 | 0.02 | 1.02 | 2.43 | 2.43 | 198.66 | 151.90 | 101.94 | 52.54 | 22.49 | 87.44 | 152.41 |
| 13E1L | 0.01 | 5.06 | 3.33 | 2.97 | 196.25 | 0.00 | 0.00 | 0.00 | 241.35 | 242.87 | 246.23 |
| 14E2 | 0.01 | 0.92 | 1.85 | 1.98 | 195.53 | 155.75 | 135.40 | 117.03 | 24.32 | 44.45 | 62.41 |
| 16C2 | 0.01 | 2.90 | 2.99 | 2.93 | 206.54 | 105.83 | 49.55 | 22.32 | 112.09 | 182.43 | 217.00 |
| 17C4 | 0.01 | 2.46 | 1.59 | 1.48 | 197.34 | 59.12 | 30.42 | 23.73 | 169.79 | 206.72 | 212.93 |
| 17C5 | 0.02 | 3.82 | 3.54 | 3.34 | 197.76 | 78.79 | 10.17 | 0.00 | 138.60 | 233.43 | 248.24 |
| 17D2 | 0.02 | 3.64 | 3.53 | 3.32 | 195.12 | 64.10 | 14.22 | 0.00 | 159.96 | 224.02 | 239.41 |
| 17D3 | 0.02 | 3.08 | 3.42 | 3.25 | 196.40 | 75.93 | 25.71 | 0.00 | 135.80 | 192.63 | 223.73 |
| 18C2 | 0.02 | 2.76 | 2.25 | 2.39 | 198.88 | 75.48 | 41.49 | 20.34 | 164.10 | 210.87 | 239.06 |
| 18C5 | 0.02 | 2.44 | 2.93 | 2.29 | 209.13 | 114.37 | 38.66 | 13.50 | 92.05 | 203.67 | 238.84 |

TABLE 5-continued

Growth and Fermentation Profile of Selected Isolates in 3% Xylose

| | | | | | | | | | | | | |
|---|---|---|---|---|---|---|---|---|---|---|---|---|
| 18D1 | 0.02 | 2.91 | 3.61 | 3.69 | 200.24 | 91.67 | 33.22 | 0.87 | 102.95 | 180.17 | 222.37 | |
| 21B2 | 0.01 | 0.92 | 3.12 | 3.39 | 199.36 | 149.90 | 87.25 | 27.91 | 26.97 | 111.92 | 189.89 | |

| | Acetate (mM) | | | | Succinate (mM) | | | | Formate (mM) | | | Ethanol (mM) | | |
|---|---|---|---|---|---|---|---|---|---|---|---|---|---|---|
| Isolate | 0 hr | 24 hr | 48 hr | 72 hr | 0 hr | 24 hr | 48 hr | 72 hr | 24 hr | 48 hr | 72 hr | 24 hr | 48 hr | 72 hr |
| 1C4 | 1.47 | 5.42 | 5.84 | 7.92 | 0.00 | 1.16 | 1.53 | 1.64 | 10.59 | 5.66 | 0.00 | 17.05 | 27.40 | 27.41 |
| 1D1 | 1.23 | 10.13 | 15.04 | 22.62 | 0.00 | 1.90 | 2.88 | 2.44 | 9.33 | 7.71 | 6.79 | 16.20 | 23.54 | 23.36 |
| 1D2 | 1.16 | 10.67 | 16.81 | 22.58 | 0.00 | 1.94 | 1.91 | 2.06 | 13.72 | 11.40 | 9.29 | 28.57 | 36.87 | 40.28 |
| 1D5 | 0.00 | 9.58 | 19.88 | 20.53 | 0.00 | 2.63 | 3.95 | 3.65 | 7.41 | 0.00 | 0.00 | 12.34 | 16.25 | 14.64 |
| 1D7 | 1.20 | 6.08 | 10.46 | 16.73 | 0.00 | 1.33 | 0.97 | 0.57 | 0.00 | 0.00 | 0.00 | 1.80 | 6.89 | 7.74 |
| 1F2 | 1.43 | 6.09 | 4.75 | 5.17 | 0.00 | 1.51 | 1.75 | 1.83 | 11.20 | 9.71 | 7.29 | 14.85 | 25.87 | 23.31 |
| 1D6B | 0.83 | 3.16 | 0.00 | 0.00 | 0.95 | 3.10 | 5.02 | 5.03 | 3.58 | 0.00 | 2.24 | 11.64 | 20.10 | 20.24 |
| 2D1 | 0.93 | 6.11 | 7.53 | 8.19 | 0.96 | 1.61 | 2.94 | 3.45 | 6.24 | 2.14 | 4.24 | 11.59 | 16.61 | 18.05 |
| 2D2 | 0.71 | 8.73 | 9.23 | 14.20 | 1.01 | 1.14 | 1.77 | 2.66 | 15.42 | 19.02 | 29.22 | 9.44 | 9.84 | 17.65 |
| 2D3 | 1.02 | 3.07 | 0.00 | 0.00 | 0.96 | 1.28 | 2.63 | 3.39 | 2.34 | 2.28 | 2.56 | 5.89 | 9.81 | 12.68 |
| 2D10 | 0.79 | 3.83 | 8.79 | 10.79 | 1.01 | 0.85 | 2.59 | 3.06 | 3.46 | 3.86 | 0.00 | 5.06 | 12.88 | 14.51 |
| 2F2 | 0.99 | 2.97 | 3.47 | 3.84 | 0.99 | 0.62 | 0.85 | 1.25 | 3.57 | 5.39 | 2.47 | 2.79 | 2.20 | 4.46 |
| 3F2 | 0.00 | 3.69 | 3.56 | 3.66 | 0.00 | 2.41 | 2.65 | 2.73 | 11.21 | 9.75 | 7.80 | 23.69 | 14.97 | 24.07 |
| 4D3 | 0.83 | 13.61 | 21.23 | 26.18 | 1.13 | 1.79 | 3.43 | 4.12 | 0.00 | 0.00 | 0.00 | 6.22 | 9.51 | 10.53 |
| 5D2 | 0.77 | 11.17 | 16.88 | 25.75 | 1.22 | 1.37 | 2.10 | 2.51 | 0.00 | 2.26 | 0.00 | 4.49 | 4.68 | 6.67 |
| 5D10 | 0.75 | 4.76 | 11.41 | 15.00 | 1.19 | 2.14 | 4.46 | 5.08 | 2.24 | 2.60 | 0.00 | 4.73 | 13.82 | 14.74 |
| 5D13 | 0.82 | 5.99 | 5.42 | 7.41 | 1.22 | 2.02 | 4.20 | 3.84 | 0.00 | 0.00 | 0.00 | 0.00 | 0.00 | 0.00 |
| 6C1 | 0.90 | 5.09 | 8.93 | 13.72 | 1.18 | 2.68 | 4.07 | 3.85 | 3.03 | 5.03 | 5.97 | 17.48 | 29.69 | 30.87 |
| 6F1L | 0.98 | 5.01 | 11.63 | 13.62 | 1.23 | 2.08 | 3.79 | 4.28 | 3.18 | 2.52 | 0.00 | 4.69 | 11.16 | 12.41 |
| 6H1B | 0.00 | 12.92 | 21.02 | 24.90 | 1.18 | 1.57 | 3.19 | 3.84 | 0.00 | 0.00 | 0.00 | 4.41 | 6.45 | 6.55 |
| 6H2 | 0.94 | 16.28 | 30.42 | 38.90 | 1.09 | 2.18 | 4.54 | 5.77 | 2.72 | 2.09 | 0.00 | 8.53 | 13.58 | 16.13 |
| 7C4 | 0.92 | 8.18 | 16.01 | 20.31 | 1.24 | 1.62 | 3.19 | 3.72 | 2.04 | 2.56 | 2.25 | 5.80 | 16.05 | 19.63 |
| 7C8 | 0.00 | 16.28 | 27.69 | 37.59 | 0.00 | 1.02 | 2.55 | 2.57 | 3.52 | 3.92 | 0.00 | 6.83 | 8.73 | 13.62 |
| 7D3 | 0.94 | 10.21 | 17.67 | 23.44 | 1.23 | 1.17 | 2.14 | 2.60 | 0.00 | 0.00 | 0.00 | 3.63 | 5.69 | 7.86 |
| 7D4 | 0.87 | 4.13 | 5.18 | 9.99 | 0.96 | 0.98 | 1.76 | 2.62 | 0.00 | 0.00 | 0.00 | 0.00 | 1.33 | 1.42 |
| 7F1 | 0.87 | 8.79 | 14.86 | 17.47 | 0.95 | 1.92 | 2.90 | 3.62 | 0.00 | 1.20 | 0.69 | 2.86 | 9.67 | 11.59 |
| 7G1 | 0.86 | 11.60 | 15.24 | 17.02 | 0.96 | 0.00 | 1.19 | 1.24 | 1.83 | 1.30 | 0.61 | 5.09 | 2.81 | 3.49 |
| 8F1 | 1.09 | 4.94 | 7.94 | 11.60 | 1.01 | 1.25 | 3.89 | 5.54 | 3.21 | 2.17 | 2.79 | 1.97 | 5.12 | 8.43 |
| 13E1L | 0.00 | 26.00 | 30.28 | 29.43 | 0.00 | 1.90 | 2.09 | 2.02 | 9.19 | 9.61 | 6.72 | 26.60 | 23.59 | 25.08 |
| 14E2 | 0.82 | 8.96 | 11.88 | 16.19 | 0.94 | 0.91 | 1.55 | 2.20 | 0.00 | 0.00 | 0.00 | 0.00 | 0.00 | 2.06 |
| 16C2 | 1.20 | 0.00 | 3.15 | 6.06 | 1.29 | 5.99 | 5.35 | 5.52 | 0.00 | 0.00 | 0.00 | 10.75 | 15.68 | 15.01 |
| 17C4 | 2.24 | 4.47 | 4.70 | 5.93 | 1.07 | 2.88 | 3.48 | 3.60 | 8.93 | 10.49 | 10.07 | 13.50 | 14.02 | 10.82 |
| 17C5 | 0.88 | 3.47 | 3.22 | 3.71 | 1.07 | 2.38 | 2.43 | 2.77 | 4.99 | 3.68 | 0.00 | 11.40 | 19.89 | 19.10 |
| 17D2 | 0.97 | 3.16 | 3.45 | 5.23 | 1.09 | 1.96 | 2.82 | 2.45 | 6.62 | 5.48 | 3.33 | 15.35 | 26.82 | 19.32 |
| 17D3 | 0.00 | 29.18 | 50.37 | 59.77 | 0.77 | 2.24 | 3.30 | 3.77 | 0.00 | 0.00 | 0.00 | 7.58 | 8.42 | 7.53 |
| 18C2 | 1.34 | 4.36 | 4.95 | 6.28 | 0.00 | 2.37 | 2.58 | 2.92 | 9.43 | 14.15 | 10.34 | 15.94 | 20.12 | 17.78 |
| 18C5 | 1.23 | 9.09 | 17.58 | 20.23 | 0.00 | 2.82 | 4.62 | 5.45 | 8.00 | 8.66 | 7.66 | 9.22 | 17.18 | 20.65 |
| 18D1 | 1.13 | 33.54 | 60.88 | 70.36 | 0.00 | 1.70 | 2.53 | 3.28 | 7.26 | 8.14 | 5.17 | 15.14 | 23.94 | 24.36 |
| 21B2 | 1.42 | 11.11 | 34.62 | 64.76 | 0.00 | 1.60 | 4.00 | 5.63 | 4.43 | 2.76 | 0.00 | 2.11 | 6.73 | 9.89 |

3% Xylose in LB medium in pH stat at pH 5.0, 50° C.

| | O.D. 420 nm | | | | Xylose (mM) | | | | Lactate (mM) | | |
|---|---|---|---|---|---|---|---|---|---|---|---|
| Isolate | 0 hr | 24 hr | 48 hr | 72 hr | 0 hr | 24 hr | 48 hr | 72 hr | 24 hr | 48 hr | 72 hr |
| 26D2 | 0.02 | 2.82 | 3.02 | 2.85 | 203.44 | 95.23 | 52.16 | 24.93 | 125.00 | 175.43 | 205.06 |
| 33D4 | 0.02 | 2.62 | 3.19 | 2.88 | 200.16 | 137.62 | 24.87 | 0.00 | 69.95 | 219.38 | 248.77 |
| 34D2 | 0.01 | 0.20 | 0.30 | 0.40 | 197.60 | 198.18 | 199.87 | 194.03 | 0.59 | 0.54 | 0.47 |
| 35D2 | 0.01 | 2.21 | 2.38 | 2.19 | 198.02 | 128.54 | 84.63 | 65.13 | 77.65 | 130.47 | 155.68 |
| 36D1 | 0.02 | 3.36 | 4.03 | 4.01 | 200.76 | 81.73 | 0.00 | 0.38 | 129.07 | 241.25 | 242.89 |
| 36D2 | 0.02 | 3.48 | 3.06 | 3.11 | 162.91 | 90.26 | 26.60 | 0.00 | 140.29 | 227.94 | 258.52 |
| 38D5 | 0.01 | 1.44 | 3.49 | 3.15 | 203.00 | 161.87 | 86.71 | 43.90 | 37.83 | 142.04 | 193.31 |
| 39D1 | 0.02 | 2.74 | 2.96 | 2.78 | 198.38 | 121.74 | 64.90 | 40.22 | 79.04 | 159.28 | 192.71 |
| 39D1A | 0.01 | 1.55 | 3.06 | 3.34 | 198.64 | 134.11 | 64.56 | 15.53 | 48.13 | 143.63 | 209.56 |
| 46C1 | 0.02 | 2.54 | 2.57 | 2.39 | 168.08 | 124.32 | 48.56 | 17.79 | 95.00 | 202.94 | 246.05 |
| 47C1 | 0.01 | 2.88 | 2.93 | 2.76 | 165.40 | 107.63 | 35.06 | 3.32 | 110.29 | 216.32 | 259.27 |
| 49D3 | 0.02 | 2.74 | 2.71 | 2.74 | 164.70 | 136.00 | 89.68 | 71.61 | 92.23 | 141.13 | 166.79 |
| 49D4L | 0.02 | 3.29 | 3.21 | 3.55 | 217.14 | 78.74 | 56.38 | 44.90 | 157.29 | 184.40 | 200.48 |
| 53D1 | 0.02 | 3.20 | 3.51 | 3.58 | 207.55 | 111.13 | 39.36 | 7.13 | 91.56 | 189.61 | 229.02 |
| 53D2 | 0.01 | 1.35 | 2.81 | 2.45 | 175.60 | 137.36 | 72.16 | 38.97 | 39.53 | 129.06 | 178.83 |
| 56H3A | 0.01 | 3.57 | 4.23 | 3.56 | 177.38 | 88.32 | 15.76 | 0.10 | 113.00 | 206.99 | 230.99 |
| 57H1 | 0.01 | 2.75 | 4.32 | 4.04 | 205.55 | 105.93 | 22.27 | 0.65 | 97.34 | 196.67 | 227.65 |
| 57H2 | 0.01 | 0.20 | 0.30 | 0.30 | 201.23 | 199.97 | 198.29 | 196.08 | 1.33 | 1.38 | 1.59 |
| 57H3 | 0.01 | 2.72 | 3.47 | 3.84 | 179.77 | 105.18 | 50.95 | 14.53 | 85.38 | 158.64 | 208.60 |
| HCH7 | 0.01 | 3.97 | 3.33 | 2.95 | 179.30 | 48.00 | 0.15 | 0.00 | 142.82 | 207.50 | 207.24 |
| HCH8 | 0.01 | 4.73 | 3.98 | 3.51 | 182.16 | 23.94 | 0.20 | 0.00 | 185.64 | 216.75 | 219.76 |
| HCH10 | 0.01 | 3.98 | 4.94 | 4.41 | 181.33 | 94.19 | 13.87 | 0.41 | 100.73 | 215.99 | 234.37 |
| Y-8 | 0.01 | 0.20 | 2.88 | 6.16 | 189.03 | 179.73 | 155.63 | 49.66 | 0.00 | 9.57 | 33.73 |
| Y-39 | 0.02 | 2.68 | 3.01 | 1.87 | 180.89 | 109.71 | 14.37 | 0.00 | 94.31 | 214.38 | 229.71 |

TABLE 5-continued

Growth and Fermentation Profile of Selected Isolates in 3% Xylose

| Y-40 | 0.01 | 4.14 | 4.31 | 4.07 | 180.42 | 49.60 | 0.00 | 0.27 | 150.86 | 218.17 | 220.43 |
|---|---|---|---|---|---|---|---|---|---|---|---|
| Y-41 | 0.01 | 0.35 | 2.44 | 3.32 | 205.00 | 211.83 | 192.47 | 128.98 | 0.00 | 10.96 | 34.23 |
| Y-55 | 0.02 | 3.54 | 3.93 | 3.66 | 199.65 | 111.01 | 0.00 | 0.00 | 101.19 | 240.64 | 239.00 |
| Y-56 | 0.01 | 0.60 | 1.32 | 1.95 | 190.83 | 182.65 | 148.17 | 124.73 | 4.15 | 10.30 | 23.13 |
| Y-66 | 0.02 | 1.82 | 1.51 | 2.44 | 195.94 | 98.04 | 75.57 | 40.17 | 93.61 | 116.93 | 170.22 |
| Y-72 | 0.01 | 0.61 | 2.51 | 2.56 | 197.15 | 188.37 | 133.56 | 88.55 | 7.88 | 41.78 | 58.69 |
| Y-82 | 0.01 | 0.51 | 2.06 | 2.57 | 195.95 | 179.19 | 132.05 | 104.29 | 3.87 | 11.66 | 19.71 |
| Y-85 | 0.01 | 1.55 | 1.68 | 1.88 | 195.69 | 141.76 | 106.31 | 95.88 | 51.69 | 82.33 | 90.96 |
| P4-62 | 0.02 | 1.33 | 3.87 | 4.18 | 198.61 | 133.57 | 62.38 | 23.40 | 41.73 | 140.33 | 192.57 |
| P4-74B | 0.03 | 6.40 | 6.60 | 6.12 | 199.04 | 48.40 | 0.00 | 0.00 | 173.33 | 234.25 | 236.20 |
| P4-85 | 0.02 | 4.28 | 4.59 | 4.01 | 198.14 | 57.61 | 0.00 | 0.00 | 152.57 | 243.37 | 243.72 |
| P4-102A | 0.03 | 2.42 | 2.79 | 2.61 | 193.86 | 94.62 | 45.90 | 22.18 | 80.86 | 118.30 | 146.40 |
| P4-102B | 0.03 | 5.52 | 4.41 | 4.06 | 197.66 | 45.00 | 0.00 | 0.00 | 186.09 | 247.25 | 247.55 |
| *B. coagulans* 7050 | 0.01 | 0.40 | 0.40 | 0.40 | 197.58 | 198.65 | 197.19 | 196.17 | 0.38 | 0.00 | 0.00 |

| | Acetate (mM) | | | | Succinate (mM) | | | | Formate (mM) | | | Ethanol (mM) | | |
|---|---|---|---|---|---|---|---|---|---|---|---|---|---|---|
| Isolate | 0 hr | 24 hr | 48 hr | 72 hr | 0 hr | 24 hr | 48 hr | 72 hr | 24 hr | 48 hr | 72 hr | 24 hr | 48 hr | 72 hr |
| 26D2 | 1.52 | 32.07 | 52.20 | 65.12 | 0.00 | 1.57 | 2.24 | 2.28 | 0.00 | 0.00 | 0.00 | 6.03 | 6.91 | 7.50 |
| 33D4 | 1.63 | 11.21 | 29.89 | 36.76 | 0.00 | 1.90 | 3.04 | 3.26 | 9.92 | 8.69 | 6.71 | 6.73 | 20.21 | 20.28 |
| 34D2 | 0.80 | 3.51 | 4.39 | 4.46 | 0.00 | 0.72 | 0.54 | 0.41 | 2.88 | 0.00 | 0.00 | 0.00 | 0.00 | 0.00 |
| 35D2 | 1.32 | 10.88 | 14.61 | 14.84 | 0.00 | 1.16 | 1.84 | 2.12 | 6.91 | 4.01 | 3.71 | 9.68 | 14.70 | 16.14 |
| 36D1 | 1.11 | 3.62 | 2.81 | 3.86 | 0.00 | 1.30 | 1.87 | 1.82 | 9.60 | 11.16 | 8.73 | 18.41 | 29.75 | 29.50 |
| 36D2 | 1.76 | 20.33 | 26.33 | 37.81 | 0.00 | 2.05 | 2.89 | 3.30 | 5.26 | 4.36 | 8.75 | 15.97 | 15.38 | 15.89 |
| 38D5 | 1.56 | 5.29 | 14.48 | 23.32 | 0.00 | 0.86 | 1.94 | 2.55 | 6.27 | 7.87 | 12.77 | 2.27 | 6.77 | 8.59 |
| 39D1 | 1.20 | 2.32 | 0.00 | 1.07 | 0.00 | 1.73 | 2.98 | 3.27 | 5.61 | 12.07 | 11.24 | 12.36 | 23.65 | 25.84 |
| 39D1A | 1.21 | 5.74 | 10.37 | 18.44 | 0.00 | 1.17 | 3.00 | 4.15 | 6.64 | 12.97 | 14.97 | 6.11 | 16.27 | 23.85 |
| 46C1 | 11.30 | 4.92 | 5.90 | 5.39 | 0.00 | 2.49 | 4.09 | 4.18 | 3.28 | 5.83 | 2.28 | 18.43 | 24.26 | 30.99 |
| 47C1 | 0.00 | 6.58 | 4.20 | 9.42 | 0.00 | 2.71 | 4.57 | 4.92 | 8.42 | 5.97 | 7.16 | 7.72 | 37.87 | 27.75 |
| 49D3 | 0.89 | 19.52 | 27.46 | 27.38 | 0.00 | 2.22 | 2.73 | 3.17 | 5.32 | 5.14 | 0.00 | 10.10 | 13.73 | 9.62 |
| 49D4L | 0.00 | 5.12 | 9.88 | 7.47 | 0.00 | 1.16 | 2.58 | 2.22 | 10.35 | 7.59 | 7.75 | 18.62 | 20.98 | 29.73 |
| 53D1 | 0.00 | 33.40 | 68.38 | 79.67 | 0.00 | 3.19 | 4.81 | 4.76 | 6.66 | 0.00 | 0.00 | 5.71 | 9.40 | 21.76 |
| 53D2 | 0.00 | 7.88 | 11.88 | 13.57 | 0.00 | 0.00 | 2.63 | 3.45 | 4.71 | 8.46 | 6.98 | 2.98 | 11.04 | 13.13 |
| 56H3A | 0.00 | 19.55 | 34.82 | 42.22 | 0.00 | 0.00 | 2.37 | 2.29 | 6.95 | 6.82 | 4.35 | 13.24 | 18.44 | 19.11 |
| 57H1 | 0.82 | 10.02 | 19.33 | 23.62 | 0.66 | 1.27 | 1.94 | 2.18 | 9.85 | 12.20 | 9.99 | 26.30 | 51.53 | 57.16 |
| 57H2 | 1.26 | 2.08 | 1.60 | 1.86 | 0.00 | 0.00 | 0.00 | 0.79 | 0.00 | 6.04 | 0.00 | 0.00 | 0.00 | 0.00 |
| 57H3 | 0.87 | 13.64 | 27.02 | 34.37 | 0.00 | 0.00 | 2.40 | 2.30 | 6.29 | 2.62 | 11.38 | 7.76 | 15.60 | 17.06 |
| HCH7 | 1.43 | 41.29 | 59.37 | 62.52 | 0.00 | 2.45 | 3.44 | 3.44 | 9.32 | 8.31 | 5.77 | 23.38 | 29.18 | 28.14 |
| HCH8 | 1.53 | 52.18 | 56.99 | 64.03 | 0.00 | 2.40 | 2.16 | 2.98 | 0.00 | 0.00 | 0.00 | 24.96 | 16.11 | 16.44 |
| HCH10 | 0.00 | 4.55 | 0.00 | 0.00 | 0.00 | 3.60 | 4.83 | 4.59 | 12.20 | 9.23 | 8.89 | 12.96 | 24.54 | 25.84 |
| Y-8 | 1.72 | 8.86 | 28.90 | 116.80 | 0.00 | 0.00 | 0.00 | 5.73 | 0.00 | 26.45 | 93.70 | 0.00 | 13.26 | 57.24 |
| Y-39 | 5.16 | 14.07 | 24.97 | 28.33 | 0.00 | 0.00 | 4.49 | 4.91 | 4.49 | 0.00 | 0.00 | 6.98 | 14.34 | 14.05 |
| Y-40 | 1.75 | 26.68 | 35.98 | 34.23 | 0.00 | 2.20 | 3.76 | 4.11 | 5.49 | 9.59 | 8.02 | 16.23 | 24.98 | 24.95 |
| Y-41 | 1.00 | 3.85 | 17.82 | 45.48 | 0.00 | 0.50 | 1.13 | 1.97 | 0.00 | 14.02 | 21.27 | 0.00 | 7.27 | 23.45 |
| Y-55 | 1.01 | 23.69 | 38.07 | 38.92 | 0.76 | 1.64 | 2.36 | 1.99 | 10.67 | 13.09 | 10.27 | 12.04 | 20.80 | 16.92 |
| Y-56 | 0.92 | 9.69 | 20.18 | 29.39 | 1.46 | 1.11 | 1.30 | 1.65 | 8.76 | 15.15 | 25.47 | 3.22 | 7.67 | 13.00 |
| Y-66 | 1.03 | 26.56 | 30.55 | 34.09 | 0.00 | 1.33 | 1.27 | 1.64 | 8.15 | 7.87 | 7.70 | 8.06 | 9.68 | 11.32 |
| Y-72 | 1.20 | 5.58 | 17.06 | 35.04 | 0.68 | 0.93 | 3.39 | 3.85 | 5.77 | 28.87 | 47.12 | 0.00 | 32.04 | 56.85 |
| Y-82 | 0.00 | 8.72 | 24.28 | 39.50 | 0.00 | 0.58 | 1.93 | 2.68 | 9.42 | 26.01 | 26.81 | 2.58 | 18.55 | 25.58 |
| Y-85 | 1.00 | 3.17 | 2.86 | 4.49 | 0.84 | 1.58 | 2.56 | 2.84 | 6.88 | 0.00 | 0.00 | 5.04 | 8.71 | 7.09 |
| P4-62 | 1.62 | 6.32 | 12.17 | 17.50 | 0.00 | 0.69 | 0.99 | 1.50 | 3.69 | 1.85 | 0.00 | 6.65 | 23.35 | 36.38 |
| P4-74B | 1.73 | 14.64 | 21.00 | 21.43 | 0.00 | 0.94 | 1.12 | 1.19 | 10.95 | 10.25 | 11.14 | 27.32 | 33.23 | 32.27 |
| P4-85 | 1.67 | 15.79 | 25.85 | 25.93 | 0.00 | 1.38 | 2.08 | 2.04 | 10.46 | 11.68 | 11.16 | 20.49 | 23.29 | 24.24 |
| P4-102A | 1.79 | 11.49 | 23.69 | 30.31 | 0.00 | 1.25 | 1.35 | 1.29 | 9.70 | 10.47 | 7.80 | 24.69 | 25.12 | 30.93 |
| P4-102B | 1.66 | 1.08 | 1.15 | 1.67 | 0.00 | 1.85 | 2.03 | 2.05 | 6.07 | 6.70 | 6.42 | 38.04 | 42.19 | 42.41 |
| *B. coagulans* 7050 | 1.49 | 4.59 | 4.70 | 4.39 | 0.00 | 1.10 | 0.81 | 0.56 | 3.68 | 4.80 | 0.00 | 0.00 | 0.00 | 0.00 |

TABLE 6

Fermentation Profile of Selected Isolates in 5% Sugars

5% Glucose in LB medium in pH stat at pH 5.0, 50° C.

| | O.D. at 420 nm | | | | | Glucose Remaining (mM) | | | | | Lactate (mM) | | | |
|---|---|---|---|---|---|---|---|---|---|---|---|---|---|---|
| Isolate | 0 h | 24 h | 48 h | 72 h | 96 h | 0 h | 24 h | 48 h | 72 h | 96 h | 24 h | 48 h | 72 h | 96 h |
| 2D1 | 0.04 | 3.33 | 2.99 | 2.55 | 2.54 | 269.30 | 175.27 | 127.15 | 98.45 | 91.57 | 203.84 | 293.69 | 295.88 | 316.67 |
| 3F2 | 0.03 | 3.48 | 2.95 | 2.95 | 2.95 | 272.27 | 122.46 | 98.78 | 93.36 | 92.52 | 254.50 | 298.31 | 309.04 | 315.19 |
| 13E1L | 0.02 | 2.92 | 3.38 | 3.67 | 3.83 | 271.09 | 117.16 | 69.97 | 47.36 | 32.44 | 258.76 | 326.71 | 362.52 | 385.17 |
| 17C5 | 0.03 | 2.64 | 2.92 | 2.94 | 3.06 | 271.16 | 121.89 | 105.45 | 92.18 | 87.73 | 235.90 | 281.39 | 304.76 | 307.77 |

TABLE 6-continued

Fermentation Profile of Selected Isolates in 5% Sugars

| 18C2 | 0.03 | 2.03 | 2.14 | 2.15 | 2.27 | 271.72 | 140.72 | 133.35 | 144.43 | 132.90 | 200.94 | 212.12 | 223.88 | 236.72 |
|---|---|---|---|---|---|---|---|---|---|---|---|---|---|---|
| 33D4 | 0.02 | 2.71 | 2.60 | 2.62 | 2.63 | 271.35 | 189.24 | 141.29 | 126.94 | 119.64 | 218.42 | 239.43 | 245.66 |
| 36D1 | 0.02 | 3.33 | 2.92 | 2.83 | 2.85 | 273.23 | 151.22 | 88.83 | 66.12 | 49.55 | 208.06 | 315.86 | 347.65 | 371.63 |
| HCH7 | 0.03 | 2.71 | 2.75 | 2.74 | 2.85 | 282.52 | 150.87 | 138.40 | 139.58 | 138.10 | 206.71 | 238.26 | 239.04 | 236.24 |
| HCH8 | 0.02 | 4.03 | 2.68 | 2.55 | 2.89 | 289.89 | 121.49 | 96.97 | 95.02 | 94.36 | 275.57 | 311.64 | 315.39 | 316.40 |
| HCH10 | 0.01 | 3.32 | 3.33 | 2.93 | 2.60 | 272.50 | 213.97 | 147.00 | 123.55 | 112.27 | 132.73 | 211.50 | 253.85 | 262.81 |
| Y-40 | 0.01 | 3.87 | 3.11 | 3.11 | 3.09 | 272.64 | 154.45 | 103.20 | 100.64 | 100.08 | 199.59 | 288.27 | 284.26 | 281.25 |
| p4-74B | 0.01 | 4.04 | 3.77 | 3.93 | 4.06 | 272.31 | 108.11 | 78.94 | 62.15 | 47.43 | 283.24 | 331.10 | 361.09 | 379.76 |
| p4-85 | 0.01 | 2.89 | 2.52 | 2.29 | 1.95 | 275.06 | 156.03 | 119.02 | 112.90 | 112.47 | 208.56 | 271.78 | 279.40 | 283.35 |
| p4-102B | 0.03 | 4.24 | 4.15 | 3.59 | 3.49 | 277.61 | 120.03 | 36.27 | 14.06 | 0.00 | 269.55 | 406.68 | 440.01 | 458.41 |

5% Glucose in LB medium in pH stat at pH 5.0, 50° C.

| | Acetate (mM) | | | | Succinate (mM) | | | | Formate (mM) | | | | Ethanol (mM) | | | |
|---|---|---|---|---|---|---|---|---|---|---|---|---|---|---|---|---|
| Isolate | 24 h | 48 h | 72 h | 96 h | 24 h | 48 h | 72 h | 96 h | 24 h | 48 h | 72 h | 96 h | 24 h | 48 h | 72 h | 96 h |
| 2D1 | 0.00 | 0.00 | 0.00 | 0.00 | 0.00 | 0.00 | 0.00 | 0.97 | 0.00 | 0.00 | 0.00 | 0.00 | 0.00 | 6.43 | 0.00 | 5.39 |
| 3F2 | 0.00 | 0.00 | 0.00 | 0.00 | 0.00 | 0.00 | 0.00 | 0.00 | 4.79 | 0.00 | 0.00 | 0.00 | 2.10 | 1.91 | 2.42 | 2.80 |
| 13E1L | 0.99 | 0.00 | 0.00 | 0.00 | 0.00 | 0.00 | 0.00 | 0.00 | 2.73 | 4.04 | 3.07 | 0.64 | 4.99 | 22.50 | 15.27 | 15.99 |
| 17C5 | 0.00 | 0.90 | 1.14 | 1.66 | 0.00 | 0.00 | 0.00 | 0.00 | 0.94 | 0.45 | 0.00 | 0.00 | 1.87 | 6.65 | 7.50 | 8.19 |
| 18C2 | 0.00 | 0.00 | 0.00 | 0.00 | 0.00 | 0.00 | 0.00 | 0.00 | 0.00 | 0.00 | 0.00 | 0.00 | 4.57 | 2.54 | 2.32 | 2.72 |
| 33D4 | 0.00 | 0.02 | 0.00 | 1.57 | 0.00 | 0.00 | 0.00 | 0.00 | 0.00 | 0.00 | 0.00 | 0.00 | 1.24 | 5.96 | 6.57 | 6.85 |
| 36D1 | 0.00 | 0.00 | 0.00 | 6.38 | 0.00 | 0.00 | 0.00 | 0.00 | 0.00 | 0.00 | 0.00 | 0.00 | 1.42 | 2.91 | 1.92 | 8.69 |
| HCH7 | 2.13 | 0.13 | 0.74 | 0.23 | 0.00 | 0.00 | 0.00 | 0.00 | 0.00 | 0.00 | 0.00 | 0.00 | 3.85 | 6.05 | 5.96 | 5.81 |
| HCH8 | 0.00 | 0.00 | 0.00 | 0.00 | 0.31 | 0.30 | 0.57 | 0.35 | 0.00 | 0.00 | 0.00 | 0.00 | 8.25 | 10.25 | 8.20 | 11.61 |
| HCH10 | 0.00 | 1.15 | 3.95 | 8.32 | 0.00 | 0.00 | 0.00 | 0.00 | 0.00 | 0.00 | 0.00 | 0.00 | 1.11 | 3.13 | 7.11 | 7.33 |
| Y-40 | 0.00 | 0.01 | 2.24 | 1.87 | 0.00 | 0.00 | 0.00 | 0.00 | 0.00 | 0.00 | 0.00 | 0.00 | 1.35 | 3.18 | 7.90 | 3.44 |
| p4-74B | 0.00 | 0.64 | 1.20 | 3.10 | 0.00 | 0.00 | 0.00 | 0.00 | 0.00 | 0.00 | 0.00 | 0.00 | 4.72 | 6.27 | 9.20 | 8.56 |
| p4-85 | 0.00 | 0.00 | 0.00 | 0.00 | 0.00 | 0.00 | 0.00 | 0.00 | 0.00 | 0.00 | 0.00 | 0.00 | 1.45 | 2.36 | 7.26 | 3.38 |
| p4-102B | 0.00 | 0.00 | 1.29 | 1.99 | 0.00 | 0.00 | 0.00 | 0.00 | 2.10 | 8.47 | 9.84 | 2.92 | 8.62 | 21.12 | 19.53 |

5% Xylose LB medium in pH stat at pH 5.0, 50° C.

| | O.D at 420 nm | | | | | Xylose Remaining (mM) | | | | | Lactate (mM) | | | |
|---|---|---|---|---|---|---|---|---|---|---|---|---|---|---|
| Isolate | 0 h | 24 h | 48 h | 72 h | 96 h | 0 h | 24 h | 48 h | 72 h | 96 h | 24 h | 48 h | 72 h | 96 h |
| 2D1 | 0.02 | 2.93 | 3.28 | 2.99 | 2.90 | 317.66 | 215.81 | 156.18 | 128.64 | 109.75 | 140.44 | 214.80 | 245.42 | 273.82 |
| 3F2 | 0.03 | 3.17 | 2.95 | 3.09 | 3.36 | 327.03 | 158.84 | 105.73 | 87.07 | 65.35 | 205.75 | 284.90 | 306.82 | 339.37 |
| 13E1L | 0.04 | 3.66 | 4.64 | 4.10 | 4.71 | 332.60 | 171.20 | 83.70 | 57.60 | 44.31 | 162.76 | 300.36 | 342.21 | 357.54 |
| 17C5 | 0.03 | 4.62 | 5.60 | 5.32 | 5.59 | 331.71 | 193.84 | 118.61 | 86.27 | 69.26 | 156.73 | 288.71 | 332.43 | 354.65 |
| 18C2 | 0.03 | 2.46 | 2.52 | 2.55 | 2.56 | 319.62 | 190.32 | 148.52 | 126.44 | 122.19 | 177.25 | 239.21 | 264.70 | 332.83 |
| 33D4 | 0.02 | 2.99 | 4.63 | 3.79 | 3.69 | 330.34 | 248.38 | 129.61 | 87.97 | 71.25 | 136.00 | 273.55 | 333.85 | 356.49 |
| 36D1 | 0.02 | 4.02 | 4.24 | 4.33 | 3.87 | 320.19 | 203.09 | 110.61 | 64.58 | 51.95 | 146.45 | 266.12 | 293.88 | 306.06 |
| HCH7 | 0.03 | 5.25 | 4.22 | 3.96 | 4.17 | 335.83 | 177.73 | 104.81 | 95.17 | 90.63 | 176.08 | 281.96 | 278.97 | 288.19 |
| HCH8 | 0.03 | 4.88 | 4.27 | 4.13 | 4.10 | 330.93 | 134.93 | 88.75 | 82.87 | 79.75 | 249.64 | 308.13 | 300.33 | 300.93 |
| HCH10 | 0.01 | 4.85 | 5.59 | 5.50 | 4.94 | 321.57 | 217.93 | 110.01 | 65.79 | 52.86 | 126.12 | 233.14 | 293.80 | 302.34 |
| Y-40 | 0.01 | 4.17 | 4.94 | 5.03 | 4.93 | 323.05 | 196.40 | 70.58 | 38.04 | 23.82 | 152.99 | 294.47 | 314.51 | 330.72 |
| p4-74B | 0.02 | 6.55 | 6.08 | 5.87 | 5.72 | 321.82 | 148.02 | 72.03 | 60.59 | 56.78 | 214.07 | 265.01 | 275.75 | 277.14 |
| p4-85 | 0.01 | 3.64 | 4.77 | 4.86 | 4.65 | 323.71 | 230.65 | 118.44 | 89.54 | 75.00 | 115.46 | 219.46 | 259.09 | 274.48 |
| p4-102B | 0.02 | 5.22 | 4.88 | 4.96 | 4.38 | 321.80 | 166.53 | 76.53 | 49.14 | 36.32 | 194.55 | 280.62 | 322.79 | 338.50 |

5% Xylose LB medium in pH stat at pH 5.0, 50° C.

| | Acetate (mM) | | | | Succinate (mM) | | | | Formate (mM) | | | | Ethanol (mM) | | | |
|---|---|---|---|---|---|---|---|---|---|---|---|---|---|---|---|---|
| Isolate | 24 h | 48 h | 72 h | 96 h | 24 h | 48 h | 72 h | 96 h | 24 h | 48 h | 72 h | 96 h | 24 h | 48 h | 72 h | 96 h |
| 2D1 | 5.10 | 5.81 | 5.28 | 6.44 | 0.88 | 1.74 | 2.19 | 2.37 | 3.72 | 3.25 | 3.81 | 3.17 | 11.27 | 15.45 | 19.53 | 19.55 |
| 3F2 | 2.70 | 2.65 | 1.44 | 2.79 | 1.14 | 1.51 | 1.57 | 1.74 | 8.49 | 9.30 | 6.87 | 7.59 | 14.21 | 17.92 | 18.08 | 19.21 |
| 13E1L | 7.48 | 22.35 | 24.63 | 24.74 | 3.27 | 3.41 | 4.76 | 4.41 | 8.76 | 10.22 | 9.89 | 9.62 | 20.97 | 21.16 | 26.14 | 22.19 |
| 17C5 | 0.00 | 0.05 | 2.58 | 3.01 | 3.09 | 4.67 | 4.90 | 4.46 | 10.29 | 11.65 | 12.70 | 9.92 | 13.10 | 16.31 | 17.00 | 16.47 |
| 18C2 | 2.40 | 2.60 | 1.69 | 2.56 | 1.33 | 1.56 | 1.74 | 2.10 | 8.06 | 8.18 | 5.41 | 5.55 | 11.36 | 14.16 | 14.98 | 14.81 |
| 33D4 | 0.64 | 8.39 | 10.29 | 8.80 | 0.00 | 0.00 | 0.00 | 0.00 | 4.55 | 3.55 | 4.47 | 0.00 | 0.00 | 19.80 | 18.17 | 18.96 |
| 36D1 | 0.72 | 0.57 | 1.33 | 2.40 | 0.21 | 0.31 | 0.23 | 0.97 | 4.42 | 3.00 | 0.00 | 0.00 | 20.91 | 30.98 | 27.48 | 30.86 |
| HCH7 | 30.60 | 40.65 | 46.15 | 41.07 | 3.50 | 3.50 | 4.85 | 5.10 | 2.92 | 6.43 | 0.00 | 0.00 | 14.76 | 20.90 | 19.75 | 18.92 |
| HCH8 | 34.92 | 42.26 | 41.77 | 43.16 | 0.00 | 0.00 | 0.00 | 0.00 | 4.13 | 0.00 | 0.00 | 0.00 | 18.38 | 17.54 | 17.76 | 15.02 |
| HCH10 | 2.72 | 1.53 | 1.71 | 2.68 | 1.07 | 2.75 | 3.62 | 1.74 | 8.37 | 9.00 | 9.08 | 5.04 | 18.12 | 24.50 | 28.69 | 25.93 |
| Y-40 | 17.96 | 31.08 | 32.41 | 38.18 | 0.75 | 1.36 | 1.52 | 2.09 | 5.14 | 4.70 | 6.03 | 4.54 | 16.43 | 28.27 | 20.25 | 29.30 |
| p4-74B | 13.74 | 17.63 | 19.69 | 19.29 | 0.27 | 0.37 | 0.35 | 0.60 | 12.05 | 12.66 | 13.43 | 10.02 | 27.20 | 29.59 | 23.65 | 28.33 |
| p4-85 | 7.93 | 13.02 | 15.40 | 15.78 | 0.43 | 1.21 | 1.39 | 1.25 | 4.29 | 2.16 | 0.00 | 0.00 | 8.73 | 11.95 | 11.97 | 14.99 |
| p4-102B | 0.00 | 0.00 | 0.00 | 6.28 | 0.99 | 0.70 | 1.39 | 2.57 | 4.70 | 3.02 | 5.39 | 10.45 | 32.81 | 41.37 | 41.57 | 39.35 |

TABLE 7

Growth and Fermentation of Selected Isolates in Minimal Salts medium

3% Glucose in minimal medium + 1% corn steep liquor in pH stat at pH 5.0, 50° C.

| | O.D. at 420 nm | | | | | Glucose (mM) | | | | | Lactate (mM) | | | | | Acetate (mM) | |
|---|---|---|---|---|---|---|---|---|---|---|---|---|---|---|---|---|---|
| Isolates | 0 h | 24 h | 48 h | 72 h | 96 h | 0 h | 24 h | 48 h | 72 h | 96 h | 0 h | 24 h | 48 h | 72 h | 96 h | 0 h | 24 h |
| 3F2 | 0.03 | 2.16 | 1.76 | 1.67 | 1.78 | 167.51 | 77.33 | 49.49 | 36.62 | 26.30 | 11.99 | 157.35 | 198.19 | 225.63 | 236.27 | 0.00 | 0.00 |
| 13E1L | 0.03 | 1.15 | 1.46 | 1.90 | 2.23 | 166.19 | 121.75 | 117.60 | 93.68 | 77.28 | 11.14 | 84.53 | 88.44 | 112.56 | 131.71 | 0.00 | 0.00 |
| 17C5 | 0.03 | 2.43 | 2.83 | 3.00 | 3.03 | 165.81 | 99.55 | 59.50 | 30.06 | 9.22 | 12.06 | 118.90 | 176.61 | 228.01 | 254.37 | 0.00 | 0.30 |
| 36D1 | 0.02 | 3.26 | 3.44 | 3.09 | 2.96 | 164.81 | 70.26 | 0.00 | 0.00 | 0.00 | 11.39 | 173.42 | 285.20 | 278.40 | 272.69 | 0.78 | 0.00 |
| HCH7 | 0.02 | 1.37 | 1.17 | 1.17 | 1.38 | 164.92 | 103.42 | 90.67 | 89.24 | 84.64 | 12.03 | 109.02 | 127.98 | 126.18 | 133.14 | 0.00 | 0.00 |
| HCH8 | 0.02 | 2.45 | 2.17 | 1.96 | 1.63 | 164.94 | 93.76 | 68.81 | 60.92 | 55.63 | 11.77 | 128.83 | 168.31 | 181.86 | 186.80 | 0.00 | 0.00 |
| HCH10 | 0.02 | 2.07 | 1.73 | 1.85 | 1.87 | 164.08 | 123.57 | 77.76 | 56.41 | 40.24 | 11.61 | 78.11 | 154.37 | 191.19 | 215.94 | 0.00 | 0.48 |
| P4-74B | 0.01 | 2.53 | 1.94 | 1.83 | 1.59 | 164.68 | 54.33 | 11.85 | 0.00 | 0.00 | 11.36 | 192.94 | 267.00 | 285.59 | 278.79 | 0.00 | 0.00 |
| P4-85 | 0.02 | 3.40 | 3.59 | 3.63 | 3.40 | 164.97 | 91.31 | 56.27 | 38.93 | 31.87 | 12.18 | 128.68 | 178.66 | 204.70 | 205.90 | 0.00 | 0.00 |
| P4-102B | 0.02 | 2.99 | 2.81 | 2.74 | 2.28 | 165.02 | 93.30 | 26.76 | 0.00 | 0.00 | 11.41 | 129.08 | 243.15 | 279.61 | 276.23 | 0.00 | 0.00 |
| Y-40 | 0.01 | 1.49 | 1.18 | 1.72 | 2.53 | 163.69 | 96.26 | 85.61 | 74.29 | 32.92 | 11.26 | 127.00 | 139.33 | 151.38 | 209.76 | 0.00 | 0.00 |
| Y-55 | 0.01 | 1.48 | 1.58 | 2.45 | 3.04 | 166.04 | 104.27 | 98.75 | 77.72 | 45.41 | 11.86 | 103.86 | 105.63 | 129.40 | 175.42 | 0.00 | 0.44 |

3% Glucose in minimal medium + 1% corn steep liquor in pH stat at pH 5.0, 50° C.

| | Acetate (mM) | | | Succinate (mM) | | | | | Formate (mM) | | | | | Ethanol (mM) | | | |
|---|---|---|---|---|---|---|---|---|---|---|---|---|---|---|---|---|---|
| Isolates | 48 h | 72 h | 96 h | 0 h | 24 h | 48 h | 72 h | 96 h | 0 h | 24 h | 48 h | 72 h | 96 h | 0 h | 24 h | 48 h | 72 h | 96 h |
| 3F2 | 0.00 | 0.00 | 0.56 | 0.00 | 0.28 | 0.29 | 0.34 | 0.47 | 0.00 | 0.00 | 0.00 | 0.00 | 0.00 | 0.00 | 3.77 | 3.71 | 0.00 | 5.18 |
| 13E1L | 0.00 | 1.27 | 2.14 | 0.00 | 0.54 | 0.74 | 1.11 | 1.54 | 0.00 | 0.00 | 0.00 | 0.00 | 0.00 | 0.00 | 0.00 | 0.00 | 6.01 | 7.35 |
| 17C5 | 0.88 | 1.94 | 2.19 | 0.00 | 0.36 | 0.34 | 0.59 | 0.54 | 0.00 | 0.00 | 0.00 | 0.00 | 0.00 | 0.00 | 2.61 | 4.05 | 5.38 | 4.25 |
| 36D1 | 0.39 | 2.72 | 6.03 | 0.00 | 0.58 | 0.66 | 0.80 | 0.87 | 0.00 | 0.00 | 0.00 | 0.00 | 0.00 | 0.00 | 2.22 | 3.05 | 2.53 | 5.43 |
| HCH7 | 0.00 | 0.00 | 1.02 | 0.00 | 0.38 | 0.55 | 0.65 | 0.49 | 0.00 | 0.00 | 0.00 | 0.00 | 0.00 | 0.00 | 2.15 | 3.55 | 1.70 | 5.62 |
| HCH8 | 0.00 | 0.00 | 0.00 | 0.00 | 0.26 | 0.30 | 0.32 | 0.25 | 0.00 | 0.00 | 0.00 | 0.00 | 0.00 | 0.00 | 2.56 | 3.83 | 0.00 | 4.96 |
| HCH10 | 0.00 | 0.00 | 0.00 | 0.00 | 0.69 | 0.55 | 0.48 | 0.53 | 0.00 | 0.00 | 0.00 | 0.00 | 0.00 | 0.00 | 1.43 | 4.90 | 0.00 | 6.31 |
| P4-74B | 0.00 | 0.66 | 1.08 | 0.00 | 0.33 | 0.00 | 0.43 | 0.41 | 0.00 | 0.00 | 0.00 | 0.00 | 0.00 | 0.00 | 1.24 | 0.00 | 1.34 | 1.05 |
| P4-85 | 0.50 | 2.52 | 3.15 | 0.00 | 0.36 | 0.48 | 0.62 | 0.82 | 0.00 | 0.00 | 0.00 | 0.00 | 0.00 | 0.00 | 0.00 | 6.12 | 10.00 | 5.81 |
| P4-102B | 0.64 | 1.73 | 6.91 | 0.00 | 1.02 | 1.18 | 1.20 | 1.58 | 0.00 | 0.00 | 0.00 | 0.00 | 0.00 | 0.00 | 1.81 | 2.16 | 11.94 | 2.63 |
| Y-40 | 0.45 | 0.67 | 0.75 | 0.00 | 0.98 | 0.36 | 0.46 | 0.73 | 0.00 | 0.00 | 0.00 | 0.00 | 0.00 | 0.00 | 1.28 | 1.06 | 15.26 | 2.67 |
| Y-55 | 0.00 | 1.41 | 1.06 | 0.00 | 0.32 | 0.42 | 0.48 | 0.85 | 0.00 | 0.00 | 0.00 | 0.00 | 0.00 | 0.00 | 5.67 | 3.31 | 3.03 | 6.47 |

3% Xylose in minimal medium + 1% corn steep liquor in pH stat at pH 5.0, 50° C.

| | O.D. at 420 nm | | | | | Xylose (mM) | | | | | Lactate (mM) | | | | | Acetate (mM) |
|---|---|---|---|---|---|---|---|---|---|---|---|---|---|---|---|---|
| Isolates | 0 h | 24 h | 48 h | 72 h | 96 h | 0 h | 24 h | 48 h | 72 h | 96 h | 0 h | 24 h | 48 h | 72 h | 96 h | 0 h |
| 3F2 | 0.04 | 4.58 | 4.57 | 4.21 | 3.85 | 193.47 | 69.51 | 0.00 | 0.00 | 0.00 | 10.73 | 167.83 | 260.48 | 254.23 | 257.56 | 0.00 |
| 13E1L | 0.02 | 0.71 | 1.34 | 1.65 | 2.40 | 197.80 | 175.09 | 153.74 | 142.33 | 120.10 | 11.02 | 34.30 | 60.72 | 60.26 | 82.50 | 0.00 |
| 17C5 | 0.03 | 4.06 | 4.21 | 3.86 | 3.62 | 191.95 | 52.87 | 0.00 | 0.00 | 0.00 | 9.94 | 177.08 | 257.90 | 261.66 | 256.24 | 0.00 |
| 36D1 | 0.02 | 3.73 | 3.95 | 3.50 | 2.93 | 196.40 | 85.93 | 4.57 | 0.45 | 0.00 | 9.24 | 117.72 | 239.09 | 257.96 | 249.65 | 0.00 |
| HCH7 | 0.02 | 3.90 | 3.97 | 3.28 | 2.70 | 194.18 | 63.06 | 0.35 | 0.00 | 0.00 | 10.04 | 135.68 | 223.07 | 221.72 | 218.98 | 0.00 |
| HCH8 | 0.01 | 4.47 | 4.88 | 4.42 | 3.95 | 194.29 | 55.15 | 0.31 | 0.00 | 0.00 | 10.25 | 153.25 | 229.78 | 229.66 | 224.58 | 0.00 |
| HCH10 | 0.01 | 2.81 | 2.63 | 2.44 | 2.45 | 190.98 | 124.30 | 47.13 | 22.85 | 10.99 | 10.12 | 76.25 | 183.05 | 216.15 | 231.05 | 0.00 |
| P4-74B | 0.04 | 3.14 | 4.34 | 4.19 | 4.19 | 197.87 | 138.18 | 39.43 | 0.00 | 0.00 | 11.05 | 79.60 | 212.61 | 256.33 | 252.24 | 0.00 |
| P4-85 | 0.02 | 3.83 | 4.89 | 3.52 | 3.28 | 193.62 | 94.25 | 0.24 | 0.00 | 0.00 | 9.91 | 113.89 | 249.07 | 250.53 | 245.21 | 0.00 |
| P4-102B | 0.03 | 1.24 | 2.24 | 2.30 | 2.12 | 195.16 | 159.75 | 78.97 | 56.09 | 20.27 | 10.86 | 69.15 | 135.95 | 193.42 | 231.93 | 0.00 |
| Y-40 | 0.02 | 2.74 | 3.88 | 3.94 | 3.37 | 197.14 | 88.37 | 22.57 | 0.00 | 0.00 | 10.04 | 99.10 | 193.36 | 231.18 | 233.96 | 0.00 |
| Y-55 | 0.01 | 2.82 | 4.22 | 3.94 | 3.60 | 198.42 | 115.24 | 22.73 | 0.00 | 0.00 | 9.56 | 78.74 | 205.27 | 238.17 | 236.64 | 0.00 |

3% Xylose in minimal medium + 1% corn steep liquor in pH stat at pH 5.0, 50° C.

| | Acetate (mM) | | | | Succinate (mM) | | | | | Formate (mM) | | | | | Ethanol (mM) | | | |
|---|---|---|---|---|---|---|---|---|---|---|---|---|---|---|---|---|---|---|
| Isolates | 24 h | 48 h | 72 h | 96 h | 0 h | 24 h | 48 h | 72 h | 96 h | 0 h | 24 h | 48 h | 72 h | 96 h | 0 h | 24 h | 48 h | 72 h | 96 h |
| 3F2 | 0.00 | 1.24 | 3.98 | 7.59 | 0.00 | 3.04 | 2.28 | 3.25 | 4.67 | 0.00 | 3.39 | 0.00 | 0.00 | 0.00 | 0.00 | 19.78 | 22.98 | 21.34 | 21.66 |
| 13E1L | 4.06 | 7.45 | 7.60 | 12.15 | 0.00 | 0.84 | 1.57 | 1.64 | 2.35 | 0.00 | 0.00 | 0.00 | 0.00 | 0.00 | 0.00 | 4.24 | 4.60 | 4.70 | 5.23 |
| 17C5 | 1.77 | 3.35 | 6.15 | 8.88 | 0.00 | 0.00 | 2.27 | 3.10 | 5.06 | 0.00 | 3.26 | 0.00 | 0.00 | 0.00 | 0.00 | 19.30 | 22.78 | 21.57 | 19.70 |
| 36D1 | 0.00 | 0.00 | 0.00 | 0.00 | 0.00 | 2.89 | 3.88 | 5.05 | 0.00 | 0.00 | 0.00 | 0.00 | 0.00 | 0.00 | 16.42 | 28.59 | 27.92 | 22.26 |
| HCH7 | 16.98 | 27.01 | 28.70 | 30.09 | 0.00 | 4.59 | 7.76 | 6.76 | 9.92 | 0.00 | 4.83 | 5.80 | 4.15 | 3.08 | 0.00 | 26.51 | 37.23 | 36.31 | 35.51 |
| HCH8 | 17.58 | 26.58 | 26.18 | 26.00 | 0.00 | 3.54 | 6.40 | 5.68 | 7.33 | 0.00 | 2.99 | 3.59 | 2.92 | 0.00 | 0.00 | 21.56 | 30.00 | 29.84 | 29.01 |
| HCH10 | 3.20 | 3.51 | 4.37 | 7.52 | 0.00 | 0.00 | 2.56 | 3.25 | 4.06 | 0.00 | 3.53 | 2.39 | 0.00 | 0.00 | 0.00 | 7.74 | 14.54 | 14.76 | 15.43 |
| P4-74B | 6.15 | 9.04 | 13.21 | 17.84 | 0.00 | 0.57 | 0.78 | 0.78 | 0.74 | 0.00 | 1.53 | 0.00 | 0.00 | 0.00 | 0.00 | 12.41 | 18.60 | 22.63 | 20.21 |

TABLE 7-continued

Growth and Fermentation of Selected Isolates in Minimal Salts medium

| | | | | | | | | | | | | | | | | | | | |
|---|---|---|---|---|---|---|---|---|---|---|---|---|---|---|---|---|---|---|---|
| P4-85 | 5.00 | 5.19 | 5.72 | 5.86 | 0.00 | 2.79 | 5.71 | 7.47 | 10.03 | 0.00 | 4.01 | 5.32 | 4.64 | 4.06 | 0.00 | 12.95 | 28.64 | 28.13 | 27.81 |
| P4-102B | 0.00 | 5.36 | 8.15 | 6.91 | 0.00 | 2.24 | 2.51 | 4.26 | 4.05 | 0.00 | 0.00 | 0.00 | 0.00 | 0.00 | 0.00 | 4.08 | 7.80 | 8.46 | 8.92 |
| Y-40 | 7.50 | 8.16 | 9.94 | 12.19 | 0.00 | 3.01 | 3.47 | 3.83 | 4.46 | 0.00 | 5.24 | 5.12 | 4.83 | 5.71 | 0.00 | 14.19 | 26.61 | 30.43 | 31.74 |
| Y-55 | 4.52 | 4.98 | 9.31 | 12.80 | 0.00 | 0.00 | 7.04 | 5.69 | 7.19 | 0.00 | 1.27 | 0.00 | 0.00 | 0.00 | 0.00 | 6.75 | 19.93 | 20.96 | 12.80 |

TABLE 8

Growth and Fermentation of Selected isolates in Hemicellulose Hydrolysate

25% HCH in minimal medium + 1% corn steep liquor in pH stat at pH 5.0, 50° C.

| | Glucose (mM) | | | | | Xylose (mM) | | | | |
|---|---|---|---|---|---|---|---|---|---|---|
| Isolates | 0 h | 24 h | 48 h | 72 h | 96 h | 0 h | 24 h | 48 h | 72 h | 96 h |
| 13E1L | 15.09 | 0.00 | 0.00 | 0.00 | 0.00 | 122.18 | 91.48 | 12.16 | 0.62 | 0.41 |
| 17C5 | 17.29 | 0.00 | 0.00 | 0.00 | 0.00 | 128.62 | 105.68 | 63.79 | 18.49 | 0.00 |
| 36D1 | 14.88 | 0.00 | 0.00 | 0.00 | 0.00 | 119.98 | 105.23 | 57.68 | 14.26 | 0.62 |
| Y-40 | 14.61 | 0.00 | 0.00 | 0.00 | 0.00 | 118.09 | 97.24 | 15.23 | 0.93 | 0.54 |
| P4-74B | 15.24 | 0.00 | 0.00 | 0.00 | 0.00 | 121.29 | 111.72 | 111.56 | 104.40 | 78.09 |
| P4-102B | 14.98 | 0.00 | 0.00 | 0.00 | 0.00 | 120.34 | 109.42 | 97.64 | 87.44 | 68.68 |

| | Lactate (mM) | | | | | Acetate (mM) | | | | |
|---|---|---|---|---|---|---|---|---|---|---|
| Isolates | 0 h | 24 h | 48 h | 72 h | 96 h | 0 h | 24 h | 48 h | 72 h | 96 h |
| 13E1L | 15.20 | 102.73 | 201.42 | 220.94 | 216.00 | 42.74 | 42.07 | 48.24 | 51.05 | 50.57 |
| 17C5 | 13.64 | 90.50 | 168.29 | 207.08 | 215.48 | 47.98 | 51.21 | 54.58 | 54.78 | 58.01 |
| 36D1 | 15.09 | 76.89 | 146.22 | 203.26 | 211.88 | 42.35 | 44.11 | 46.74 | 49.53 | 53.34 |
| Y-40 | 15.32 | 85.28 | 198.51 | 218.60 | 216.38 | 43.00 | 44.99 | 48.15 | 49.71 | 50.93 |
| P4-74B | 15.44 | 75.14 | 74.01 | 78.57 | 112.01 | 44.70 | 50.89 | 45.89 | 50.16 | 51.38 |
| P4-102B | 14.53 | 78.53 | 91.86 | 113.59 | 130.58 | 42.75 | 43.53 | 47.50 | 51.39 | 49.85 |

50% Over-limed HCH in minimal medium + 1% corn steep liquor in pH stat at pH 5.0, 50° C.

| | Glucose (mM) | | | | | Xylose (mM) | | | | |
|---|---|---|---|---|---|---|---|---|---|---|
| Isolates | 0 h | 24 h | 48 h | 72 h | 96 h | 0 h | 24 h | 48 h | 72 h | 96 h |
| 13E1L | 23.75 | 0.00 | 0.00 | 0.00 | 0.00 | 157.16 | 92.59 | 1.17 | 1.12 | 1.02 |
| 17C5 | 21.52 | 0.00 | 0.00 | 0.00 | 0.00 | 149.40 | 83.98 | 0.00 | 0.00 | 0.00 |
| 36D1 | 22.49 | 0.00 | 0.00 | 0.00 | 0.00 | 149.01 | 73.50 | 1.01 | 0.71 | 0.00 |
| Y-40 | 22.21 | 0.00 | 0.00 | 0.00 | 0.00 | 147.30 | 38.87 | 0.78 | 0.80 | 0.00 |
| P4-74B | 27.00 | 0.00 | 0.00 | 0.00 | 0.00 | 179.39 | 169.87 | 167.86 | 128.98 | 93.65 |
| P4-102B | 24.79 | 0.00 | 0.00 | 0.00 | 0.00 | 164.96 | 147.79 | 124.81 | 86.65 | 65.70 |

| | Lactate (mM) | | | | | Acetate (mM) | | | | |
|---|---|---|---|---|---|---|---|---|---|---|
| Isolates | 0 h | 24 h | 48 h | 72 h | 96 h | 0 h | 24 h | 48 h | 72 h | 96 h |
| 13E1L | 8.53 | 150.87 | 260.05 | 264.00 | 263.53 | 24.22 | 23.19 | 29.57 | 36.11 | 29.69 |
| 17C5 | 11.51 | 137.99 | 250.31 | 251.42 | 251.76 | 23.96 | 23.76 | 19.78 | 32.13 | 35.80 |
| 36D1 | 9.35 | 164.61 | 258.86 | 254.54 | 252.80 | 25.81 | 25.08 | 26.88 | 28.32 | 29.80 |
| Y-40 | 10.28 | 191.72 | 237.46 | 239.63 | 231.16 | 25.89 | 27.50 | 35.09 | 36.24 | 37.49 |
| P4-74B | 7.46 | 78.70 | 85.71 | 94.45 | 133.26 | 25.69 | 30.98 | 36.53 | 35.50 | 39.67 |
| P4-102B | 9.99 | 92.79 | 131.21 | 161.61 | 167.00 | 28.73 | 25.83 | 36.63 | 40.55 | 40.00 |

25% HCH in minimal medium + 1% corn steep liquor in pH stat at pH 5.0, 50° C.

| | Arabinose (mM) | | | | | Succinate (mM) | | | | |
|---|---|---|---|---|---|---|---|---|---|---|
| Isolates | 0 h | 24 h | 48 h | 72 h | 96 h | 0 h | 24 h | 48 h | 72 h | 96 h |
| 13E1L | 15.67 | 0.00 | 0.00 | 0.00 | 0.00 | 0.00 | 0.00 | 3.77 | 3.00 | 3.29 |
| 17C5 | 17.04 | 0.00 | 0.00 | 0.00 | 0.00 | 0.00 | 0.67 | 0.94 | 1.01 | 0.93 |
| 36D1 | 14.88 | 0.88 | 0.00 | 0.00 | 0.00 | 0.00 | 0.00 | 2.92 | 0.00 | 2.47 |
| Y-40 | 14.05 | 12.70 | 4.75 | 1.28 | 1.45 | 0.00 | 2.39 | 2.38 | 3.44 | 2.88 |
| P4-74B | 15.37 | 0.00 | 0.00 | 0.00 | 0.00 | 0.00 | 2.49 | 0.00 | 2.21 | 0.00 |
| P4-102B | 14.44 | 0.00 | 0.00 | 0.00 | 0.00 | 0.00 | 2.30 | 2.50 | 2.49 | 2.89 |

TABLE 8-continued

Growth and Fermentation of Selected isolates in Hemicellulose Hydrolysate

| | Ethanol (mM) | | | | | Formate (mM) | | | | |
|---|---|---|---|---|---|---|---|---|---|---|
| Isolates | 0 h | 24 h | 48 h | 72 h | 96 h | 0 h | 24 h | 48 h | 72 h | 96 h |
| 13E1L | 0.00 | 1.72 | 10.96 | 4.76 | 3.78 | 3.02 | 0.00 | 4.51 | 4.87 | 4.18 |
| 17C5 | 0.00 | 0.00 | 0.00 | 0.00 | 0.00 | 4.56 | 4.39 | 0.00 | 0.00 | 0.00 |
| 36D1 | 0.00 | 4.36 | 0.63 | 3.33 | 1.97 | 3.24 | 0.00 | 0.00 | 0.00 | 0.00 |
| Y-40 | 0.00 | 0.84 | 6.21 | 4.13 | 7.38 | 3.08 | 4.31 | 3.13 | 4.97 | 4.27 |
| P4-74B | 0.00 | 0.00 | 2.94 | 3.97 | 1.49 | 3.55 | 6.50 | 6.30 | 5.28 | 6.21 |
| P4-102B | 0.00 | 0.00 | 0.53 | 1.64 | 3.44 | 2.97 | 5.20 | 6.47 | 4.68 | 5.36 |

50% Over-limed HCH in minimal medium + 1% corn steep liquor in pH stat at pH 5.0, 50° C.

| | Arabinose (mM) | | | | | Succinate (mM) | | | | |
|---|---|---|---|---|---|---|---|---|---|---|
| Isolates | 0 h | 24 h | 48 h | 72 h | 96 h | 0 h | 24 h | 48 h | 72 h | 96 h |
| 13E1L | 7.94 | 0.00 | 0.00 | 0.00 | 0.00 | 0.00 | 0.00 | 0.00 | 0.00 | 0.00 |
| 17C5 | 10.69 | 0.00 | 0.00 | 0.00 | 0.00 | 0.00 | 1.08 | 2.23 | 2.30 | 3.00 |
| 36D1 | 7.31 | 0.00 | 0.00 | 0.00 | 0.00 | 0.00 | 0.00 | 0.00 | 0.00 | 0.00 |
| Y-40 | 7.09 | 3.02 | 1.26 | 1.07 | 1.01 | 0.00 | 0.00 | 0.00 | 0.00 | 0.00 |
| P4-74B | 9.27 | 0.00 | 0.00 | 0.00 | 0.00 | 0.00 | 0.00 | 0.00 | 0.00 | 0.00 |
| P4-102B | 10.37 | 0.00 | 0.00 | 0.00 | 0.00 | 0.00 | 0.00 | 0.00 | 0.00 | 0.00 |

| | Ethanol (mM) | | | | | Formate (mM) | | | | |
|---|---|---|---|---|---|---|---|---|---|---|
| Isolates | 0 h | 24 h | 48 h | 72 h | 96 h | 0 h | 24 h | 48 h | 72 h | 96 h |
| 13E1L | 0.00 | 0.00 | 0.00 | 0.00 | 0.00 | 0.00 | 0.00 | 0.00 | 0.00 | 0.00 |
| 17C5 | 0.00 | 0.00 | 0.00 | 8.64 | 0.00 | 4.67 | 4.50 | 0.00 | 0.00 | 0.67 |
| 36D1 | 0.00 | 0.00 | 0.00 | 0.00 | 0.00 | 0.00 | 0.00 | 0.00 | 0.00 | 0.00 |
| Y-40 | 0.00 | 0.00 | 0.00 | 0.00 | 0.00 | 0.00 | 0.00 | 0.00 | 0.00 | 0.00 |
| P4-74B | 0.00 | 0.00 | 0.00 | 0.00 | 0.00 | 0.00 | 0.00 | 0.00 | 0.00 | 0.00 |
| P4-102B | 0.00 | 0.00 | 0.00 | 0.00 | 0.00 | 0.00 | 0.00 | 0.00 | 0.00 | 0.00 |

The 25% hemicellulose hydrolysate was derived from batch T6-#5
The 50% overlimed hemicellulose hydrolysate was derived from batch BCI-Nov. 99

TABLE 9

Fermentation profile of 3% glucose in LB medium and in minimal medium with 1% corn steep liquor at pH 5.0 and 50° C.

| Isolates | Medium | Cell mass g/L | Glucose utilized mM | Lactate mM | Acetate mM | Ethanol mM | Glucose consumption mmol L$^{-1}$ h$^{-1}$ | Volumetric productivity mmol L$^{-1}$ h$^{-1}$ (Lactate) | Specific productivity mmol g$^{-1}$ h$^{-1}$ (Lactate) | Specific glucose consumption rate mmol g$^{-1}$ h$^{-1}$ | Yield (%) Lactate | Total |
|---|---|---|---|---|---|---|---|---|---|---|---|---|
| 17C5 | LB | 2.14 | 173.23 | 278.25 | 9.36 | 6.92 | 17.46 | 28.29 | 30.54 | 18.85 | 80.31 | 85.10 |
| | MM | 1.18 | 144.19 | 209.80 | 1.85 | 8.14 | 2.96 | 4.87 | 22.88 | 13.90 | 72.75 | 76.47 |
| 36D1 | LB | 1.42 | 169.30 | 278.58 | 4.86 | 5.13 | 5.86 | 9.63 | 44.50 | 27.08 | 82.27 | 85.37 |
| | MM | 1.34 | 162.50 | 271.05 | 5.88 | 6.35 | 3.76 | 6.23 | 29.79 | 17.99 | 83.40 | 87.27 |
| P4-74B | LB | 2.17 | 166.49 | 274.42 | 12.35 | 6.04 | 11.72 | 19.16 | 41.48 | 25.37 | 82.41 | 87.99 |
| | MM | 1.28 | 161.13 | 261.94 | 5.05 | 4.68 | 5.15 | 8.91 | 31.81 | 18.39 | 81.28 | 84.35 |
| P4-102B | LB | 1.18 | 171.15 | 280.43 | 5.05 | 5.58 | 3.72 | 7.87 | 33.22 | 15.69 | 81.93 | 85.61 |
| | MM | 1.17 | 166.61 | 268.70 | 3.35 | 4.87 | 2.80 | 4.60 | 28.00 | 17.03 | 80.64 | 83.57 |

LB - Rich medium
MM—Minimal medium

TABLE 10

Fermentation profile of 3% xylose in LB medium and in minimal medium with 1% corn steep liquor at pH 5.0 and 50° C.

| Isolates | Medium | Dry Cell mass g/L | Xylose utilized mM | Lactate mM | Acetate mM | Ethanol mM | Xylose consumption mmol L$^{-1}$ h$^{-1}$ | Volumetric productivity mmol L$^{-1}$ h$^{-1}$ (Lactate) | Specific productivity mmol g$^{-1}$ h$^{-1}$ (Lactate) | Specific Xylose consumption rate mmol g$^{-1}$ h$^{-1}$ | Yield (%) Lactate | Total |
|---|---|---|---|---|---|---|---|---|---|---|---|---|
| 17C5 | LB | 2.25 | 199.78 | 253.84 | 9.20 | 20.61 | 7.54 | 9.16 | 11.48 | 9.45 | 76.24 | 85.65 |
| | MM | 1.65 | 200.82 | 256.07 | 11.60 | 14.60 | 4.79 | 5.10 | 11.67 | 10.96 | 76.51 | 84.83 |

TABLE 10-continued

Fermentation profile of 3% xylose in LB medium and in minimal medium with 1% corn steep liquor at pH 5.0 and 50° C.

| Isolates | Medium | Dry Cell mass g/L | Xylose utilized mM | Lactate mM | Acetate mM | Ethanol mM | Xylose consumption mmol L$^{-1}$ h$^{-1}$ | Volumetric productivity mmol L$^{-1}$ h$^{-1}$ (Lactate) | Specific productivity mmol g$^{-1}$ h$^{-1}$ (Lactate) | Specific Xylose consumption rate mmol g$^{-1}$ h$^{-1}$ | Yield (%) Lactate | Yield (%) Total |
|---|---|---|---|---|---|---|---|---|---|---|---|---|
| 36D1 | LB | 1.48 | 203.10 | 240.82 | 11.21 | 24.23 | 4.90 | 5.63 | 16.61 | 14.47 | 71.14 | 81.84 |
|  | MM | 1.81 | 201.81 | 228.67 | 16.60 | 34.91 | 6.21 | 6.79 | 13.02 | 11.91 | 67.98 | 84.57 |
| P4-74B | LB | 2.49 | 190.89 | 229.97 | 28.41 | 22.96 | 7.51 | 9.03 | 7.06 | 5.87 | 72.28 | 88.92 |
|  | MM | 1.83 | 201.79 | 245.87 | 22.38 | 16.88 | 4.97 | 5.91 | 7.45 | 6.26 | 73.11 | 84.97 |
| P4-102B | LB | 2.11 | 190.36 | 241.15 | 8.20 | 40.49 | 7.75 | 9.58 | 15.04 | 12.17 | 76.01 | 92.20 |
|  | MM | 0.99 | 181.27 | 225.15 | 8.26 | 6.15 | 2.19 | 2.62 | 9.57 | 7.99 | 74.53 | 80.21 |

LB - Rich medium
MM—Minimal medium

TABLE 11

Isomeric form of lactic acid produced by second generation biocatalysts

| Strain | concentration (mM) L (+) | concentration (mM) D (−) | Ratio L/D | Ratio D/L |
|---|---|---|---|---|
| Glucose – minimal medium | | | | |
| 17C5 | 13.40 | 0.00 | 1.00 | 0.00 |
| 36D1 | 7.80 | 0.35 | 0.96 | 0.04 |
| P4-74B | 11.60 | 0.40 | 0.97 | 0.03 |
| P4-102B | 13.90 | 0.00 | 1.00 | 0.00 |
| LB + glucose medium | | | | |
| 17C5 | 13.00 | 0.35 | 0.97 | 0.03 |
| 36D1 | 10.60 | 0.00 | 1.00 | 0.00 |
| P4-74B | 13.30 | 0.35 | 0.97 | 0.03 |
| P4-102B | 14.30 | 0.40 | 0.97 | 0.03 |

Glucose concentration was 3% in both media. Lactic acid isomer was determined by HPLC using a chiral column.

TABLE 12

$^{13}$C-enrichment ratios for fermentation products produced from $^{13}C_1$-xylose

| | | Isotope Enrichment Ratio | | | | |
|---|---|---|---|---|---|---|
| | | Strain 36D1 | | Strain P4-102B | | |
| Product | Carbon Position | Non-growing | Growing | Non-growing | Growing | E. coli W3110 |
| Lactate | C-1 | 4.5 | 4.9 | 5.6 | 5.1 | 10.8 |
|  | C-2 | 1.0 | 1.0 | 1.0 | 1.0 | 1.0 |
|  | C-3 | 15.9 | 17.3 | 12.6 | 13.2 | 11.3 |
| Acetate | C-1 | 1.0 | 1.0 | 1.0 | 1.0 | 1.0 |
|  | C-2 | 10.2* | 14.7* | 4.8* | 9.1 | 4.6 |
| Ethanol | C-1 | 1.0 | 1.0 | 1.0 | 1.0 | 1.0 |
|  | C-2 | 39.0* | 10.0 | 15.2 | 11.1 | 5.8 |

Second generation biocatalyst, strain 36D1 or P4-102B, was grown in LB+Xylose to mid-exponential phase in a pH-stat at pH 5.0 at 50° C. For the experiment with non-growing cells, 40 ml of culture was centrifuged and the cells were washed with 5.0 ml of LB. The cells were resuspended in 4.75 ml of LB-xylose (1%). Enough $^{13}C_1$-xylose was added to the culture to bring the xylose concentration to 1.2% and the $^{13}$C-enrichment to 20.8%. For the experiment with growing cells, cells from 0.5 ml of the mid-exponential phase culture were removed from the pH-stat, washed with equal volume of LB, and resuspended in 4.75 ml of LB-Xylose medium. Both fermentations were carried out at 50° C. with manual addition of 1.0 N KOH to maintain the pH between 6.0 and 7.0. When acid production stopped, cells were removed by centrifugation and the supernatant was subjected to HPLC for product analysis and also to $^{13}$C-NMR for identification of the $^{13}$C-enrichment. $^{13}C_1$ propionate (50 mM) served as a reference.

For E. coli W3110, 20 ml of cells were grown under anaerobic conditions in LB+Xylose until late-exponential phase at 37° C. Cells were collected by centrifugation, washed once with LB and resuspended in 5.0 ml of LB-Xylose with $^{13}$C-enrichment. Fermentation was carried out at 37° C. with manual pH control between 6.0 and 7.0.

All enrichment ratios were based on the natural abundance of $^{13}$C at the indicated positions with C-2 of lactate and C-1 of acetate and ethanol as reference. *represents that the $C_1$-carbon of acetic acid and ethanol was not labeled or the amount of label at the C1-position was below the detection limit. The presented value was computed based on the sensitivity of the instrument for $^{13}$C.

TABLE 13

SSF profile of strain 36D1 in mineral salts medium at different pH and temperature

| | | Fermentation products (mM) | | | | | Volumetric productivity | % Yield | |
|---|---|---|---|---|---|---|---|---|---|
| | | Lactate | Acetate | Succinate | Formate | Ethanol | of Lactate (mmol $L^{-1}h^{-1}$) | Lactate | Total |
| pH | Temp. (° C.) | | | | | | | | |
| 4.5 | 50 | 182.76 | 7.55 | 1.45 | 0.00 | 8.95 | 5.54 ± 0.16 | 82.24 | 90.32 |
| 5.0 | 50 | 141.25 | 14.59 | 1.80 | 15.32 | 22.04 | 6.17 ± 0.09 | 63.56 | 80.86 |
| 5.5 | 50 | 113.92 | 27.61 | 4.22 | 58.15 | 29.53 | 5.96 ± 0.45 | 51.26 | 78.88 |
| 6.0 | 50 | 66.66 | 36.55 | 3.54 | 90.66 | 34.83 | 4.05 ± 0.24 | 30.00 | 63.71 |
| 7.0 | 50 | 4.89 | 19.57 | 0.37 | 17.42 | 7.11 | 0.87 ± 0.14 | 2.20 | 14.37 |
| Temp. (° C.) | pH | | | | | | | | |
| 30 | 5.0 | 122.24 | 12.20 | 1.62 | 0.00 | 7.70 | 1.50 ± 0.04 | 55.00 | 64.70 |
| 37 | 5.0 | 137.98 | 9.05 | 1.73 | 0.00 | 19.68 | 2.50 ± 0.14 | 62.09 | 75.80 |
| 43 | 5.0 | 146.03 | 11.53 | 1.53 | 11.96 | 24.78 | 4.32 ± 0.08 | 65.71 | 82.74 |
| 50 | 5.0 | 141.25 | 14.59 | 1.80 | 15.32 | 22.04 | 6.17 ± 0.09 | 63.56 | 80.86 |
| 55 | 5.0 | 152.94 | 11.97 | 1.31 | 0.00 | 12.23 | 8.66 ± 0.08 | 69.82 | 80.30 |
| 60 | 5.0 | 105.95 | 12.39 | 0.60 | 0.00 | 2.35 | 7.22 ± 0.16 | 47.68 | 54.58 |

Batch fermentation was carried out for 96 hrs.

TABLE 14

Sugar cane bagasse hemicellulose hydrolysate fermentation by *Bacillus* sp. strain 17C5[a]
(Sheet 1 of 1)

| Sugar[b] | Sugar consumed (mM) | | | Net Production (mM)[c] | | | | | Lactate |
|---|---|---|---|---|---|---|---|---|---|
| (mM) | Glucose | Xylose | Arabinose | Lactate | Acetate | Ethanol | Formate | Succinate | Yield (%)[d] |
| 256 | 32.5 ± 1.6 | 224.5 ± 9.8 | 4.5 ± 0.4 | 403.7 ± 5.6 | 7.0 ± 1.2 | 2.5 ± 0.5 | 7.8 ± 2.6 | 4.8 ± 0.8 | 90 |
| 412 | 50.8 ± 1.2 | 349.1 ± 9.9 | 5.5 ± 0.3 | 617.4 ± 18.4 | 0.6 ± 0.6 | 5.2 ± 1.0 | 9.5 ± 4.5 | 7.7 ± 0.4 | 89 |
| 483 | 60.3 | 340.4 | 4.7 | 600.2 | 1.0 | 3.9 | 11.1 | 9.1 | 86 |

[a]Fermentations at three concentrations of total sugar (50° C. and pH 5.0). Averages with standard deviations are based on three independent fermentations. A single fermentation was conducted with the highest sugar concentration, 483 mM.
[b]Sugar concentration at the beginning of fermentation.
[c]Lime-treated sugar cane bagasse hemicellulose hydrolysate contained 66 mM acetate. Corn steep liquor at 0.5% final concentration in the fermentations contained 5.5 mM lactate, 0.2 mM acetate and 0.025 mM succinate. Appropriate amounts of these compounds were subtracted to obtain the net production by the biocatalyst. Carbon recovery as products (excluding cells) averaged 90%.
[d]Product yield was calculated as a percentage of the maximum theoretical yield assuming 2 lactates per glucose and 1.67 lactates per pentose.

We claim:

1. An isolated microorganism selected from *Bacillus* isolates 17C5 (ATCC PTA-5826), 36D1 (ATCC PTA-5827) or P4-102B (ATCC PTA-5828).

2. The isolated microorganism according to claim 1, wherein said microorganism is *Bacillus* isolate 36D1 (ATCC PTA-5827).

3. The isolated microorganism according to claim 1, wherein said microorganism is *Bacillus* isolate P4-102B (ATCC PTA-5828).

4. The isolated microorganism according to claim 1, wherein said microorganism is *Bacillus* isolate 17C5 (ATCC PTA-5826).

5. A composition comprising a microorganism selected from *Bacillus* isolates 17C5 (ATCC PTA-5826), 36D1 (ATCC PTA-5827) or P4-102B (ATCC PTA-5828) and culture medium.

6. The composition according to claim 5, wherein said microorganism is Bacillus isolate 36D1 (ATCC PTA-5827).

7. The composition according to claim 5, wherein said microorganism is *Bacillus* isolate P4-102B (ATCC PTA-5828).

8. The composition according to claim 5, wherein said microorganism is *Bacillus* isolate 17C5 (ATCC PTA-5826).

9. A method of producing L(+)-lactic acid comprising the steps of:
1) providing a microorganism selected from *Bacillus* isolates 17C5 (ATCC PTA-5826), 36D1 (ATCC PTA-5827) or P4-102B (ATCC PTA-5828); and
2) culturing said microorganism in the presence of at least one carbon source capable of being converted to said L(+)-lactic acid under conditions suitable for the production of said L(+)-lactic acid.

10. The method according to claim 9, further comprising the step of recovering the L(+)-lactic acid.

11. The method according to claim 9, wherein said microorganism is *Bacillus* isolate 36D1 (ATCC PTA-5827).

12. The method according to claim 9, wherein said microorganism is *Bacillus* isolate P4-102B (ATCC PTA-5828).

13. The method according to claim 9, wherein said microorganism is *Bacillus* isolate 17C5 (ATCC PTA-5826).

* * * * *

UNITED STATES PATENT AND TRADEMARK OFFICE
CERTIFICATE OF CORRECTION

| | | |
|---|---|---|
| PATENT NO. | : 7,098,009 B2 | Page 1 of 1 |
| APPLICATION NO. | : 10/793568 | |
| DATED | : August 29, 2006 | |
| INVENTOR(S) | : Keelnatham T. Shanmugam et al. | |

It is certified that error appears in the above-identified patent and that said Letters Patent is hereby corrected as shown below:

<u>Title page,</u>
Item (57), Line 2, "acid high yield" should read --acid at high yield--.

<u>Column 8,</u>
Line 60, "G3Phosphatase" should read --G3P phosphatase--.

<u>Column 14,</u>
Line 49, "Bemoist and Chambon" should read --Bernoist and Chambon--.

<u>Column 18,</u>
Line 48, "(B. coagulans IDSP)" should read --(B. coagulans IDSp)--.

Signed and Sealed this

Twenty-seventh Day of March, 2007

JON W. DUDAS
*Director of the United States Patent and Trademark Office*

SEQUENCE LISTING

<160> NUMBER OF SEQ ID NOS: 44

<210> SEQ ID NO 1
<211> LENGTH: 990
<212> TYPE: DNA
<213> ORGANISM: Bacillus
<220> FEATURE:
<221> NAME/KEY: exon
<222> LOCATION: (1)..(990)
<223> OTHER INFORMATION: DNA sequence of d-ldh from strain Bacillus sp.
      P4-102B (990 bp)

<400> SEQUENCE: 1

```
atg aga aaa gtt gtt gcc tat gag acg agg gcg gat gaa ttc ccc tta      48
Met Arg Lys Val Val Ala Tyr Glu Thr Arg Ala Asp Glu Phe Pro Leu
1               5                   10                  15 ttt caa aag ttt gcg aga aaa ttt gat ttg gat atc aag tat gtg gat      96
Phe Gln Lys Phe Ala Arg Lys Phe Asp Leu Asp Ile Lys Tyr Val Asp
            20                  25                  30
```

```
gat gtg tta acc cct caa acg gca gtg gaa gca aaa ggg gct gaa gcg       144
Asp Val Leu Thr Pro Gln Thr Ala Val Glu Ala Lys Gly Ala Glu Ala
         35                  40                  45 gtg acg atc ctt ggg aat tat ccg gtg ggc gcc gaa act ttt atg gct       192
Val Thr Ile Leu Gly Asn Tyr Pro Val Gly Ala Glu Thr Phe Met Ala
 50                  55                  60 tta aga gat gcc agt gta aaa tat att ggc ttg agg act gca ggg tat       240
Leu Arg Asp Ala Ser Val Lys Tyr Ile Gly Leu Arg Thr Ala Gly Tyr
 65                  70                  75                  80 aat cat atc gat cag gaa gcc gcc aaa gca tat ggc att cgt ttt tcg       288
Asn His Ile Asp Gln Glu Ala Ala Lys Ala Tyr Gly Ile Arg Phe Ser
                 85                  90                  95 aat gtg gcg tat tcg ccc tat tgt gtt gcc gat ttt gca acg atg ctg       336
Asn Val Ala Tyr Ser Pro Tyr Cys Val Ala Asp Phe Ala Thr Met Leu
            100                 105                 110 att ttg atg tgt gta agg aaa gca aaa cag atc tta agc cgt gtg gag       384
Ile Leu Met Cys Val Arg Lys Ala Lys Gln Ile Leu Ser Arg Val Glu
        115                 120                 125 gca caa gat ttt tct gtg gaa ggg att cag ggc agg gaa atg cat aac       432
Ala Gln Asp Phe Ser Val Glu Gly Ile Gln Gly Arg Glu Met His Asn
130                 135                 140 tta acg atc ggg att att ggc gcc ggc aga atc ggc agt att gtt gcg       480
Leu Thr Ile Gly Ile Ile Gly Ala Gly Arg Ile Gly Ser Ile Val Ala
145                 150                 155                 160 aaa aat ttg tcc ggt ttt ggc tgc aac atc att gca cac gat acc gtt       528
Lys Asn Leu Ser Gly Phe Gly Cys Asn Ile Ile Ala His Asp Thr Val
                165                 170                 175 gaa aga gat gaa ttg cgc ggc att ttg aaa tat gta tct ttg gat gaa       576
Glu Arg Asp Glu Leu Arg Gly Ile Leu Lys Tyr Val Ser Leu Asp Glu
            180                 185                 190 ctg ctg aag gaa agc gat gtg ata acc atc cac aca ccc tta ttt gat       624
Leu Leu Lys Glu Ser Asp Val Ile Thr Ile His Thr Pro Leu Phe Asp
        195                 200                 205 cgt aca tac cat atg att aac cag gat cgg att gca aaa atg aag gac       672
Arg Thr Tyr His Met Ile Asn Gln Asp Arg Ile Ala Lys Met Lys Asp
210                 215                 220 ggc gtt tgc atc atc aat tgt tcc cgt ggt gcc gta gtg gat acg gat       720
Gly Val Cys Ile Ile Asn Cys Ser Arg Gly Ala Val Val Asp Thr Asp
225                 230                 235                 240 gcg ctt atc gca ggg att gag gcg ggg aaa gtc ggc gct gcc ggg att       768
Ala Leu Ile Ala Gly Ile Glu Ala Gly Lys Val Gly Ala Ala Gly Ile
                245                 250                 255 gat gta ctg gaa gat gag gaa ggg att ttt cat tat gac cgc cgc acg       816
Asp Val Leu Glu Asp Glu Glu Gly Ile Phe His Tyr Asp Arg Arg Thr
            260                 265                 270 gat att ttg gcc cac cac cag ctg gct att ctg aga tct ttt ccc aat       864
Asp Ile Leu Ala His His Gln Leu Ala Ile Leu Arg Ser Phe Pro Asn
        275                 280                 285 gtg atc gtc acg ccg cac act gcg ttt tac acc gat cag gcg gtt agc       912
Val Ile Val Thr Pro His Thr Ala Phe Tyr Thr Asp Gln Ala Val Ser
290                 295                 300 gat atg gtg gaa atg gcg cta aca tcg ctt gta tcc ttt atg gag acg       960
Asp Met Val Glu Met Ala Leu Thr Ser Leu Val Ser Phe Met Glu Thr
305                 310                 315                 320 ggg aag agc agg tgg gag ata aaa tca tga                                990
Gly Lys Ser Arg Trp Glu Ile Lys Ser
                325

<210> SEQ ID NO 2
<211> LENGTH: 329
```

```
<212> TYPE: PRT
<213> ORGANISM: Bacillus
<220> FEATURE:
<221> NAME/KEY: MISC_FEATURE
<222> LOCATION: (1)..(329)
<223> OTHER INFORMATION: Sequence of D-LDH from Bacillus sp. P4-102B
      (329 amino acids)

<400> SEQUENCE: 2
```

Met Arg Lys Val Val Ala Tyr Glu Thr Arg Ala Asp Glu Phe Pro Leu
1               5                   10                  15

Phe Gln Lys Phe Ala Arg Lys Phe Asp Leu Asp Ile Lys Tyr Val Asp
            20                  25                  30

Asp Val Leu Thr Pro Gln Thr Ala Val Glu Ala Lys Gly Ala Glu Ala
        35                  40                  45

Val Thr Ile Leu Gly Asn Tyr Pro Val Gly Ala Glu Thr Phe Met Ala
    50                  55                  60

Leu Arg Asp Ala Ser Val Lys Tyr Ile Gly Leu Arg Thr Ala Gly Tyr
65                  70                  75                  80

Asn His Ile Asp Gln Glu Ala Ala Lys Ala Tyr Gly Ile Arg Phe Ser
                85                  90                  95

Asn Val Ala Tyr Ser Pro Tyr Cys Val Ala Asp Phe Ala Thr Met Leu
            100                 105                 110

Ile Leu Met Cys Val Arg Lys Ala Lys Gln Ile Leu Ser Arg Val Glu
        115                 120                 125

Ala Gln Asp Phe Ser Val Glu Gly Ile Gln Gly Arg Glu Met His Asn
    130                 135                 140

Leu Thr Ile Gly Ile Ile Gly Ala Gly Arg Ile Gly Ser Ile Val Ala
145                 150                 155                 160

Lys Asn Leu Ser Gly Phe Gly Cys Asn Ile Ile Ala His Asp Thr Val
                165                 170                 175

Glu Arg Asp Glu Leu Arg Gly Ile Leu Lys Tyr Val Ser Leu Asp Glu
            180                 185                 190

Leu Leu Lys Glu Ser Asp Val Ile Thr Ile His Thr Pro Leu Phe Asp
        195                 200                 205

Arg Thr Tyr His Met Ile Asn Gln Asp Arg Ile Ala Lys Met Lys Asp
    210                 215                 220

Gly Val Cys Ile Ile Asn Cys Ser Arg Gly Ala Val Val Asp Thr Asp
225                 230                 235                 240

Ala Leu Ile Ala Gly Ile Glu Ala Gly Lys Val Gly Ala Ala Gly Ile
                245                 250                 255

Asp Val Leu Glu Asp Glu Glu Gly Ile Phe His Tyr Asp Arg Arg Thr
            260                 265                 270

Asp Ile Leu Ala His His Gln Leu Ala Ile Leu Arg Ser Phe Pro Asn
        275                 280                 285

Val Ile Val Thr Pro His Thr Ala Phe Tyr Thr Asp Gln Ala Val Ser
    290                 295                 300

Asp Met Val Glu Met Ala Leu Thr Ser Leu Val Ser Phe Met Glu Thr
305                 310                 315                 320

Gly Lys Ser Arg Trp Glu Ile Lys Ser
                325

```
<210> SEQ ID NO 3
<211> LENGTH: 525
<212> TYPE: DNA
<213> ORGANISM: Bacillus
<220> FEATURE:
```

<210> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 17D3
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..()
<223> OTHER INFORMATION: y = t or c
<220> FEATURE:
<221> NAME/KEY: misc_feature
<222> LOCATION: (468)..()
<223> OTHER INFORMATION: y = t or c

<400> SEQUENCE: 3
tcctggctca ggacgaacgc tggcggcgtg cctaatacat gcaagtcgtg cggaccttt       60 aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttykgctgt cacttacaga tgggcccgcg gcgcattagc    240
twgttggtgg ggtaayggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggygc cttgacggta    480
cccggccaga agccacggc taactacgtg ccagcagccg cggta                     525

<210> SEQ ID NO 4
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 18C2
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (468)..(468)
<223> OTHER INFORMATION: y = t or c

<400> SEQUENCE: 4
tcctggctca ggacgaacgc tggcggcgtg cctaatacat gcaagtcgtg cggaccttt       60 aaaagcttgc ttttaaaagg ttagcggcgg acgggtgagt aacacgtggg caacctgcct    120

```
gtaagatcgg gataacgccg ggaaaccggg gctaataccg gatagttttt tcctccgcat    180
ggaggaaaaa ggaaagacgg cttykgctgt cacttacaga tgggcccgcg gcgcattagc    240
tagttggtgg ggtaacggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggygc cttgacggta    480
cccggccaga aagccacggc taactacgtg ccagcagccg cggta                    525

<210> SEQ ID NO 5
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 21B2
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c

<400> SEQUENCE: 5
tcctggctca ggacgaacgc tggcggcgtg cctaatacat gcaagtcgtg cggaccttt     60 aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttcggctgt cacttacaga tgggcccgcg gcgcattagc    240
twgttggtgg ggtaayggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggcgc cttgacggta    480
cccggccaga aagccacggc taactacgtg ccagcagccg cggta                    525

<210> SEQ ID NO 6
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 26D2
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
```

<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 6

| | | | | | |
|---|---|---|---|---|---|
| tcctggctca | ggacgaacgc | tggcggcgtg | cctaatacat | gcaagtcgtg | cggaccttttt 60 |
| aaaagcttgc | ttttaaaagg | ttagcggcgg | acgggtgagt | aacacgtggg | caacctgcct 120 |
| gtaagatcgg | gataacgccg | ggaaaccggg | gctaataccg | gatagttttt | tcctccgcat 180 |
| ggaggaaaaa | ggaaagacgg | cttykgctgt | cacttacaga | tgggcccgcg | gcgcattagc 240 |
| twgttggtgg | ggtaayggct | caccaaggca | acgatgcgta | gccgacctga | gagggtgatc 300 |
| ggccacattg | ggactgagac | acggcccaaa | ctcctacggg | aggcagcagt | agggaatctt 360 |
| ccgcaatgga | cgaaagtctg | acggagcaac | gccgcgtgag | tgaagaaggc | cttcgggtcg 420 |
| taaaactctg | ttgccgggga | agaacaagtg | ccgttcgaac | agggcggygc | cttgacggta 480 |
| cccggccaga | aagccacggc | taactacgtg | ccagcagccg | cggta | 525 |

<210> SEQ ID NO 7
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 33D4
<220> FEATURE:
<221> NAME/KEY: misc_feature
<222> LOCATION: (204)..(204)
<223> OTHER INFORMATION: y = to or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t

<400> SEQUENCE: 7

| | | | | | |
|---|---|---|---|---|---|
| tcctggctca | ggacgaacgc | tggcggcgtg | cctaatacat | gcaagtcgtg | cggaccttttt 60 |
| aaaagcttgc | ttttaaaagg | ttagcggcgg | acgggtgagt | aacacgtggg | caacctgcct 120 |
| gtaagatcgg | gataacgccg | ggaaaccggg | gctaataccg | gatagttttt | tcctccgcat 180 |
| ggaggaaaaa | ggaaagacgg | cttykgctgt | cacttacaga | tgggcccgcg | gcgcattagc 240 |
| twgttggtgg | ggtaacggct | caccaaggca | acgatgcgta | gccgacctga | gagggtgatc 300 |
| ggccacattg | ggactgagac | acggcccaaa | ctcctacggg | aggcagcagt | agggaatctt 360 |
| ccgcaatgga | cgaaagtctg | acggagcaac | gccgcgtgag | tgaagaaggc | cttcgggtcg 420 |
| taaaactctg | ttgccgggga | agaacaagtg | ccgttcgaac | agggcggcgc | cttgacggta 480 |
| cccggccaga | aagccacggc | taactacgtg | ccagcagccg | cggta | 525 |

<210> SEQ ID NO 8
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 34D2
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t

<400> SEQUENCE: 8

| tcctggctca | ggacgaacgc | tggcggcgtg | cctaatacat | gcaagtcgtg | cggaccttt  | 60  |
| aaaagcttgc | ttttaaaagg | ttagcggcgg | acgggtgagt | aacacgtggg | caacctgcct | 120 |
| gtaagatcgg | gataacgccg | ggaaaccggg | gctaataccg | gatagttttt | tcctccgcat | 180 |
| ggaggaaaaa | ggaaagacgg | cttykgctgt | cacttacaga | tgggcccgcg | gcgcattagc | 240 |
| twgttggtgg | ggtaacggct | caccaaggca | acgatgcgta | gccgacctga | gagggtgatc | 300 |
| ggccacattg | ggactgagac | acggcccaaa | ctcctacggg | aggcagcagt | agggaatctt | 360 |
| ccgcaatgga | cgaaagtctg | acggagcaac | gccgcgtgag | tgaagaaggc | cttcgggtcg | 420 |
| taaaactctg | ttgccgggga | agaacaagtg | ccgttcgaac | agggcggcgc | cttgacggta | 480 |
| cccggccaga | aagccacggc | taactacgtg | ccagcagccg | cggta      |            | 525 |

<210> SEQ ID NO 9
<211> LENGTH: 523
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 35D2
<220> FEATURE:
<221> NAME/KEY: misc_feature
<222> LOCATION: (59)..(59)
<223> OTHER INFORMATION: k = g or t
<220> FEATURE:
<221> NAME/KEY: misc_feature
<222> LOCATION: (254)..(254)
<223> OTHER INFORMATION: y = t or c

<400> SEQUENCE: 9

| tcctggctca | ggacgaacgc | tggcggcgtg | cctaatacat | gcaagtcgtg | cggrccttkt | 60  |
| aaaggctgct | tttaaaagtt | agcggcggac | gggtgagtaa | cacgtgggca | acctgcctgt | 120 |
| aagactggga | taacgccggg | aaaccggggc | taataccrga | tagttttttc | ctccgcatgg | 180 |
| aggaaaaagg | aaaggcggct | tcggctgcca | cttacagatg | ggcccgcggc | gcattagcta | 240 |
| gttggcgggg | taayggccca | ccaaggcaac | gatgcgtagc | cgacctgaga | gggtgatcgg | 300 |

```
ccacattggg actgagacac ggcccaaact cctacgggag gcagcagtag ggaatcttcc    360
gcaatggacg aaagtctgac ggagcaacgc cgcgtgagtg aagaaggcct tcgggtcgta    420
aaactctgtt gccggggaag aacaagtgcc gttcgaacag gcggcgcct tgacggtacc    480 cggccagaaa gccacggcta actacgtgcc agcagccgcg gta                     523
```

```
<210> SEQ ID NO 10
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 36D2
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c

<400> SEQUENCE: 10
```

```
tcctggctca ggacgaacgc tggcggcgtg cctaatacat gcaagtcgtg cggacctttt    60
aaaagcttgc ttttaaaagg ttagcggcgg acgggtgagt aacacgtggg caacctgcct   120
gtaagatcgg gataacgccg ggaaaccggg gctaataccg gatagttttt tcctccgcat   180
ggaggaaaaa ggaaagacgg cttykgctgt cacttacaga tgggcccgcg gcgcattagc   240
twgttggtgg ggtaayggct caccaaggca acgatgcgta gccgacctga gagggtgatc   300
ggccacattg ggactgagac acggcccaaa ctcctacggg aggcagcagt agggaatctt   360
ccgcaatgga cgaaagtctg acggagcaac gccgcgtgag tgaagaaggc cttcgggtcg   420
taaaactctg ttgccgggga agaacaagtg ccgttcgaac agggcggcgc cttgacggta   480
cccggccaga aagccacggc taactacgtg ccagcagccg cggta                   525
```

```
<210> SEQ ID NO 11
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate Y40
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
```

```
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = to or c

<400> SEQUENCE: 11
tcctggctca ggacgaacgc tggcggcgtg cctaatacat gcaagtcgtg cggacctttt      60
aaaagcttgc ttttaaaagg ttagcggcgg acgggtgagt aacacgtggg caacctgcct     120
gtaagatcgg gataacgccg ggaaaccggg gctaataccg gatagttttt tcctccgcat     180
ggaggaaaaa ggaaagacgg cttykgctgt cacttacaga tgggcccgcg gcgcattagc     240
twgttggtgg ggtaayggct caccaaggca acgatgcgta gccgacctga gagggtgatc     300
ggccacattg ggactgagac acggcccaaa ctcctacggg aggcagcagt agggaatctt     360
ccgcaatgga cgaaagtctg acggagcaac gccgcgtgag tgaagaaggc cttcgggtcg     420
taaaactctg ttgccgggga agaacaagtg ccgttcgaac agggcggcgc cttgacggta     480
cccggccaga aagccacggc taactacgtg ccagcagccg cggta                    525

<210> SEQ ID NO 12
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate Y55
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t

<400> SEQUENCE: 12
tcctggctca ggacgaacgc tggcggcgtg cctaatacat gcaagtcgtg cggacctttt      60
aaaagcttgc ttttaaaagg ttagcggcgg acgggtgagt aacacgtggg caacctgcct     120
gtaagatcgg gataacgccg ggaaaccggg gctaataccg gatagttttt tcctccgcat     180
ggaggaaaaa ggaaagacgg cttykgctgt cacttacaga tgggcccgcg gcgcattagc     240
tagttggtgg ggtaacggct caccaaggca acgatgcgta gccgacctga gagggtgatc     300
ggccacattg ggactgagac acggcccaaa ctcctacggg aggcagcagt agggaatctt     360
ccgcaatgga cgaaagtctg acggagcaac gccgcgtgag tgaagaaggc cttcgggtcg     420
taaaactctg ttgccgggga agaacaagtg ccgttcgaac agggcggcgc cttgacggta     480
cccggccaga aagccacggc taactacgtg ccagcagccg cggta                    525

<210> SEQ ID NO 13
<211> LENGTH: 525
<212> TYPE: DNA
<213> ORGANISM: Bacillus
<220> FEATURE:
<221> NAME/KEY: misc_feature
<222> LOCATION: (1)..(525)
```

```
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate Y66
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (468)..(468)
<223> OTHER INFORMATION: y = t or c

<400> SEQUENCE: 13
tcctggctca ggacgaacgc tggcggcgtg cctaatacat gcaagtcgtg cggacctttt      60
aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttykgctgt cacttacaga tgggcccgcg gcgcattagc    240
twgttggtgg ggtaacggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggygc cttgacggta    480
cccggccaga aagccacggc taactacgtg ccagcagccg cggta                    525

<210> SEQ ID NO 14
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate HCH10
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c

<400> SEQUENCE: 14
tcctggctca ggacgaacgc tggcggcgtg cctaatacat gcaagtcgtg cggacctttt      60
aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttcggctgt cacttacaga tgggcccgcg gcgcattagc    240
twgttggtgg ggtaayggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
```

```
taaaactctg ttgccgggga agaacaagtg ccgttcgaac agggcggcgc cttgacggta    480
cccggccaga aagccacggc taactacgtg ccagcagccg cggta                    525
```

```
<210> SEQ ID NO 15
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate HCH7
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t

<400> SEQUENCE: 15
```

```
tcctggctca ggacgaacgc tggcggcgtg cctaatacat gcaagtcgtg cggacctttt    60
aaaagcttgc ttttaaaagg ttagcggcgg acgggtgagt aacacgtggg caacctgcct   120
gtaagatcgg gataacgccg ggaaaccggg gctaataccg gatagttttt cctccgcat    180 ggaggaaaaa ggaaagacgg cttykgctgt cacttacaga tgggcccgcg gcgcattagc   240
twgttggtgg ggtaacggct caccaaggca acgatgcgta gccgacctga gagggtgatc   300
ggccacattg ggactgagac acggcccaaa ctcctacggg aggcagcagt agggaatctt   360
ccgcaatgga cgaaagtctg acggagcaac gccgcgtgag tgaagaaggc cttcgggtcg   420
taaaactctg ttgccgggga agaacaagtg ccgttcgaac agggcggcgc cttgacggta   480
cccggccaga aagccacggc taactacgtg ccagcagccg cggta                    525
```

```
<210> SEQ ID NO 16
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate HCH8
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t

<400> SEQUENCE: 16
```

```
tcctggctca ggacgaacgc tggcggcgtg cctaatacat gcaagtcgtg cggaccttttt      60 aaaagcttgc ttttaaaagg ttagcggcgg acgggtgagt aacacgtggg caacctgcct     120
gtaagatcgg gataacgccg ggaaaccggg gctaataccg gatagttttt tcctccgcat     180
ggaggaaaaa ggaaagacgg cttykgctgt cacttacaga tgggcccgcg gcgcattagc     240
twgttggtgg ggtaacggct caccaaggca acgatgcgta gccgacctga gagggtgatc     300
ggccacattg ggactgagac acggcccaaa ctcctacggg aggcagcagt agggaatctt     360
ccgcaatgga cgaaagtctg acggagcaac gccgcgtgag tgaagaaggc cttcgggtcg     420
taaaactctg ttgccgggga agaacaagtg ccgttcgaac agggcggcgc cttgacggta     480
cccggccaga aagccacggc taactacgtg ccagcagccg cggta                      525
```

<210> SEQ ID NO 17
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 1C4
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t

<400> SEQUENCE: 17

```
tcctggctca ggacgaacgc tggcggcgtg cctaatacat gcaagtcgtg cggaccttttt      60 aaaagcttgc ttttaaaagg ttagcggcgg acgggtgagt aacacgtggg caacctgcct     120
gtaagatcgg gataacgccg ggaaaccggg gctaataccg gatagttttt tcctccgcat     180
ggaggaaaaa ggaaagacgg cttckgctgt cacttacaga tgggcccgcg gcgcattagc     240
twgttggtgg ggtaacggct caccaaggca acgatgcgta gccgacctga gagggtgatc     300
ggccacattg ggactgagac acggcccaaa ctcctacggg aggcagcagt agggaatctt     360
ccgcaatgga cgaaagtctg acggagcaac gccgcgtgag tgaagaaggc cttcgggtcg     420
taaaactctg ttgccgggga agaacaagtg ccgttcgaac agggcggcgc cttgacggta     480
cccggccaga aagccacggc taactacgtg ccagcagccg cggta                      525
```

<210> SEQ ID NO 18
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 1D7
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (256)..(256)
<223> OTHER INFORMATION: y = t or c

<400> SEQUENCE: 18

```
tcctggctca ggacgaacgc tggcggcgtg cctaatacat gcaagtcgtg cggaccttttt      60 aaaagcttgc ttttaaaagg ttagcggcgg acgggtgagt aacacgtggg caacctgcct     120
gtaagatcgg gataacgccg ggaaaccggg gctaataccg gatagttttt tcctccgcat     180
ggaggaaaaa ggaaagacgg cttckgctgt cacttacaga tgggcccgcg gcgcattagc     240
tagttggtgg ggtaayggct caccaaggca acgatgcgta gccgacctga gagggtgatc     300
ggccacattg ggactgagac acggcccaaa ctcctacggg aggcagcagt agggaatctt     360
ccgcaatgga cgaaagtctg acggagcaac gccgcgtgag tgaagaaggc cttcgggtcg     420
taaaactctg ttgccgggga agaacaagtg ccgttcgaac agggcggtgc cttgacggta     480
cccggccaga aagccacggc taactacgtg ccagcagccg cggta                     525
```

<210> SEQ ID NO 19
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 1F2
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t

<400> SEQUENCE: 19

```
tcctggctca ggacgaacgc tggcggcgtg cctaatacat gcaagtcgtg cggaccttttt      60 aaaagcttgc ttttaaaagg ttagcggcgg acgggtgagt aacacgtggg caacctgcct     120
gtaagatcgg gataacgccg ggaaaccggg gctaataccg gatagttttt tcctccgcat     180
ggaggaaaaa ggaaagacgg cttykgctgt cacttacaga tgggcccgcg gcgcattagc     240
twgttggtgg ggtaacggct caccaaggca acgatgcgta gccgacctga gagggtgatc     300
ggccacattg ggactgagac acggcccaaa ctcctacggg aggcagcagt agggaatctt     360
ccgcaatgga cgaaagtctg acggagcaac gccgcgtgag tgaagaaggc cttcgggtcg     420
taaaactctg ttgccgggga agaacaagtg ccgttcgaac agggcggcgc cttgacggta     480
cccggccaga aagccacggc taactacgtg ccagcagccg cggta                     525
```

<210> SEQ ID NO 20
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:

```
<221> NAME/KEY: misc_feature
<222> LOCATION: (1)..(525)
<223> OTHER INFORMATION: Bacillus isolate 6C1
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t

<400> SEQUENCE: 20
tcctggctca ggacgaacgc tggcggcgtg cctaatacat gcaagtcgtg cggacctttt      60
aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttykgctgt cacttacaga tgggcccgcg gcgcattagc    240
twgttggtgg ggtaacggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggcgc cttgacggta    480
cccggccaga aagccacggc taactacgtg ccagcagccg cggta                   525

<210> SEQ ID NO 21
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 6F2
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t

<400> SEQUENCE: 21
tcctggctca ggacgaacgc tggcggcgtg cctaatacat gcaagtcgtg cggacctttt      60
aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttykgctgt cacttacaga tgggcccgcg gcgcattagc    240
twgttggtgg ggtaacggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggcgc cttgacggta    480
```
cccggccaga aagccacggc taactacgtg ccagcagccg cggta        525

<210> SEQ ID NO 22
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 6H2
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c

<400> SEQUENCE: 22
tcctggctca ggacgaacgc tggcggcgtg cctaatacat gcaagtcgtg cggaccttt     60 aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttcggctgt cacttacaga tgggcccgcg gcgcattagc    240
twgttggtgg ggtaayggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggcgc cttgacggta    480
cccggccaga aagccacggc taactacgtg ccagcagccg cggta                    525

<210> SEQ ID NO 23
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 7C8

<400> SEQUENCE: 23
tcctggctca ggacgaacgc tggcggcgtg cctaatacat gcaagtcgtg cggaccttt     60 aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttcggctgt cacttacaga tgggcccgcg gcgcattagc    240
tagttggtgg ggtaacggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggcgc cttgacggta    480
cccggccaga aagccacggc taactacgtg ccagcagccg cggta                    525

<210> SEQ ID NO 24
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 7D4
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (468)..(468)
<223> OTHER INFORMATION: y = t or c

<400> SEQUENCE: 24
tcctggctca ggacgaacgc tggcggcgtg cctaatacat gcaagtcgtg cggaccttt      60 aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttykgctgt cacttacaga tgggcccgcg gcgcattagc    240
tagttggtgg ggtaacggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggygc cttgacggta    480
cccggccaga aagccacggc taactacgtg ccagcagccg cggta                    525

<210> SEQ ID NO 25
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 7F1
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c

<400> SEQUENCE: 25
tcctggctca ggacgaacgc tggcggcgtg cctaatacat gcaagtcgtg cggaccttt      60

```
aaaagcttgc ttttaaaagg ttagcggcgg acgggtgagt aacacgtggg caacctgcct      120
gtaagatcgg gataacgccg ggaaaccggg gctaataccg gatagttttt tcctccgcat      180
ggaggaaaaa ggaaagacgg cttykgctgt cacttacaga tgggcccgcg gcgcattagc      240
twgttggtgg ggtaayggct caccaaggca acgatgcgta gccgacctga gagggtgatc      300
ggccacattg ggactgagac acggcccaaa ctcctacggg aggcagcagt agggaatctt      360
ccgcaatgga cgaaagtctg acggagcaac gccgcgtgag tgaagaaggc cttcgggtcg      420
taaaactctg ttgccgggga agaacaagtg ccgttcgaac agggcggcgc cttgacggta      480
cccggccaga aagccacggc taactacgtg ccagcagccg cggta                    525
```

```
<210> SEQ ID NO 26
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 7G1
<220> FEATURE:
<221> NAME/KEY: misc_feature
<222> LOCATION: (256)..(256)
<223> OTHER INFORMATION: y = t or c

<400> SEQUENCE: 26
tcctggctca ggacgaacgc tggcggcgtg cctaatacat gcaagtcgtg cggaccttt       60 aaaagcttgc ttttaaaagg ttagcggcgg acgggtgagt aacacgtggg caacctgcct     120
gtaagatcgg gataacgccg ggaaaccggg gctaataccg gatagttttt tcctccgcat     180
ggaggaaaaa ggaaagacgg cttcggctgt cacttacaga tgggcccgcg gcgcattagc     240
tagttggtgg ggtaayggct caccaaggca acgatgcgta gccgacctga gagggtgatc     300
ggccacattg ggactgagac acggcccaaa ctcctacggg aggcagcagt agggaatctt     360
ccgcaatgga cgaaagtctg acggagcaac gccgcgtgag tgaagaaggc cttcgggtcg     420
taaaactctg ttgccgggga agaacaagtg ccgttcgaac agggcggcgc cttgacggta     480
cccggccaga aagccacggc taactacgtg ccagcagccg cggta                    525
```

```
<210> SEQ ID NO 27
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 10H1
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
```

<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 27

| | | | | | |
|---|---|---|---|---|---|
| tcctggctca | ggacgaacgc | tgcggcgtg | cctaatacat | gcaagtcgtg | cggaccttt      60 |
| aaaagcttgc | ttttaaaagg | ttagcggcgg | acgggtgagt | aacacgtggg | caacctgcct   120 |
| gtaagatcgg | gataacgccg | ggaaaccggg | gctaataccg | gatagttttt | tcctccgcat   180 |
| ggaggaaaaa | ggaaagacgg | cttykgctgt | cacttacaga | tgggcccgcg | gcgcattagc   240 |
| twgttggtgg | ggtaayggct | caccaaggca | acgatgcgta | gccgacctga | gagggtgatc   300 |
| ggccacattg | ggactgagac | acggcccaaa | ctcctacggg | aggcagcagt | agggaatctt   360 |
| ccgcaatgga | cgaaagtctg | acggagcaac | gccgcgtgag | tgaagaaggc | cttcgggtcg   420 |
| taaaactctg | ttgccgggga | agaacaagtg | ccgttcgaac | agggcggygc | cttgacggta   480 |
| cccggccaga | aagccacggc | taactacgtg | ccagcagccg | cggta | 525 |

<210> SEQ ID NO 28
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 10H3
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 28

| | | | | | |
|---|---|---|---|---|---|
| tcctggctca | ggacgaacgc | tgcggcgtg | cctaatacat | gcaagtcgtg | cggaccttt      60 |
| aaaagcttgc | ttttaaaagg | ttagcggcgg | acgggtgagt | aacacgtggg | caacctgcct   120 |
| gtaagatcgg | gataacgccg | ggaaaccggg | gctaataccg | gatagttttt | tcctccgcat   180 |
| ggaggaaaaa | ggaaagacgg | cttykgctgt | cacttacaga | tgggcccgcg | gcgcattagc   240 |
| twgttggtgg | ggtaayggct | caccaaggca | acgatgcgta | gccgacctga | gagggtgatc   300 |
| ggccacattg | ggactgagac | acggcccaaa | ctcctacggg | aggcagcagt | agggaatctt   360 |
| ccgcaatgga | cgaaagtctg | acggagcaac | gccgcgtgag | tgaagaaggc | cttcgggtcg   420 |

```
taaaactctg ttgccgggga agaacaagtg ccgttcgaac agggcggygc cttgacggta    480
cccggccaga aagccacggc taactacgtg ccagcagccg cggta                    525
```

<210> SEQ ID NO 29
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 9H3A
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 29

```
tcctggctca ggacgaacgc tggcggcgtg cctaatacat gcaagtcgtg cggacctttt    60
aaaagcttgc ttttaaaagg ttagcggcgg acgggtgagt aacacgtggg caacctgcct   120
gtaagatcgg gataacgccg ggaaaccggg gctaataccg gatagttttt tcctccgcat   180
ggaggaaaaa ggaaagacgg cttykgctgt cacttacaga tgggcccgcg gcgcattagc   240
twgttggtgg ggtaayggct caccaaggca acgatgcgta gccgacctga gagggtgatc   300
ggccacattg ggactgagac acggcccaaa ctcctacggg aggcagcagt agggaatctt   360
ccgcaatgga cgaaagtctg acggagcaac gccgcgtgag tgaagaaggc cttcgggtcg   420
taaaactctg ttgccgggga agaacaagtg ccgttcgaac agggcggygc cttgacggta   480
cccggccaga aagccacggc taactacgtg ccagcagccg cggta                    525
```

<210> SEQ ID NO 30
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 1D2
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)

```
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 30
tcctggctca ggacgaacgc tggcggcgtg cctaatacat gcaagtcgtg cggaccttt      60 aaaagcttgc ttttaaaagg ttagcggcgg acgggtgagt aacacgtggg caacctgcct   120
gtaagatcgg gataacgccg ggaaaccggg gctaataccg gatagttttt tcctccgcat   180
ggaggaaaaa ggaaagacgg cttykgctgt cacttacaga tgggcccgcg gcgcattagc   240
twgttggtgg ggtaayggct caccaaggca acgatgcgta gccgacctga gagggtgatc   300
ggccacattg ggactgagac acggcccaaa ctcctacggg aggcagcagt agggaatctt   360
ccgcaatgga cgaaagtctg acggagcaac gccgcgtgag tgaagaaggc cttcgggtcg   420
taaaactctg ttgccgggga agaacaagtg ccgttcgaac agggcggygc cttgacggta   480
cccggccaga aagccacggc taactacgtg ccagcagccg cggta              525

<210> SEQ ID NO 31
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 13E1Lg
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 31
tcctggctca ggacgaacgc tggcggcgtg cctaatacat gcaagtcgtg cggaccttt      60 aaaagcttgc ttttaaaagg ttagcggcgg acgggtgagt aacacgtggg caacctgcct   120
gtaagatcgg gataacgccg ggaaaccggg gctaataccg gatagttttt tcctccgcat   180
ggaggaaaaa ggaaagacgg cttykgctgt cacttacaga tgggcccgcg gcgcattagc   240
twgttggtgg ggtaayggct caccaaggca acgatgcgta gccgacctga gagggtgatc   300
```

```
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggygc cttgacggta    480
cccggccaga aagccacggc taactacgtg ccagcagccg cggta                    525
```

<210> SEQ ID NO 32
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 38C3
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 32

```
tcctggctca ggacgaacgc tggcggcgtg cctaatacat gcaagtcgtg cggacctttt    60
aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttykgctgt cacttacaga tgggcccgcg gcgcattagc    240
twgttggtgg ggtaayggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggygc cttgacggta    480
cccggccaga aagccacggc taactacgtg ccagcagccg cggta                    525
```

<210> SEQ ID NO 33
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 1D6B
<220> FEATURE:
<221> NAME/KEY: misc_feature
<222> LOCATION: (204)..(204)

```
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 33
tcctggctca ggacgaacgc tggcggcgtg cctaatacat gcaagtcgtg cggacctttt      60
aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttykgctgt cacttacaga tgggcccgcg gcgcattagc    240
twgttggtgg ggtaayggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggygc cttgacggta    480
cccggccaga aagccacggc taactacgtg ccagcagccg cggta                    525

<210> SEQ ID NO 34
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 2D1
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 34
tcctggctca ggacgaacgc tggcggcgtg cctaatacat gcaagtcgtg cggacctttt      60
aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
```

```
ggaggaaaaa ggaaagacgg cttykgctgt cacttacaga tgggcccgcg gcgcattagc      240
twgttggtgg ggtaayggct caccaaggca acgatgcgta gccgacctga gagggtgatc      300
ggccacattg ggactgagac acggcccaaa ctcctacggg aggcagcagt agggaatctt      360
ccgcaatgga cgaaagtctg acggagcaac gccgcgtgag tgaagaaggc cttcgggtcg      420
taaaactctg ttgccgggga agaacaagtg ccgttcgaac agggcggygc cttgacggta      480
cccggccaga aagccacggc taactacgtg ccagcagccg cggta                     525
```

```
<210> SEQ ID NO 35
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 3F2
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 35
tcctggctca ggacgaacgc tggcggcgtg cctaatacat gcaagtcgtg cggacctttt      60
aaaagcttgc ttttaaaagg ttagcggcgg acgggtgagt aacacgtggg caacctgcct     120
gtaagatcgg gataacgccg ggaaaccggg gctaataccg gatagttttt tcctccgcat     180
ggaggaaaaa ggaaagacgg cttykgctgt cacttacaga tgggcccgcg gcgcattagc     240
twgttggtgg ggtaayggct caccaaggca acgatgcgta gccgacctga gagggtgatc     300
ggccacattg ggactgagac acggcccaaa ctcctacggg aggcagcagt agggaatctt     360
ccgcaatgga cgaaagtctg acggagcaac gccgcgtgag tgaagaaggc cttcgggtcg     420
taaaactctg ttgccgggga agaacaagtg ccgttcgaac agggcggygc cttgacggta     480
cccggccaga aagccacggc taactacgtg ccagcagccg cggta                    525

<210> SEQ ID NO 36
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
```

```
<223> OTHER INFORMATION: Bacillus isolate 17C5
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 36
tcctggctca ggacgaacgc tggcggcgtg cctaatacat gcaagtcgtg cggacctttt      60
aaaagcttgc ttttaaaagg ttagcggcgg acgggtgagt aacacgtggg caacctgcct    120
gtaagatcgg gataacgccg ggaaaccggg gctaataccg gatagttttt tcctccgcat    180
ggaggaaaaa ggaaagacgg cttykgctgt cacttacaga tgggcccgcg gcgcattagc    240
twgttggtgg ggtaayggct caccaaggca acgatgcgta gccgacctga gagggtgatc    300
ggccacattg ggactgagac acggcccaaa ctcctacggg aggcagcagt agggaatctt    360
ccgcaatgga cgaaagtctg acggagcaac gccgcgtgag tgaagaaggc cttcgggtcg    420
taaaactctg ttgccgggga agaacaagtg ccgttcgaac agggcggygc cttgacggta    480
cccggccaga aagccacggc taactacgtg ccagcagccg cggta                    525

<210> SEQ ID NO 37
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate 36D1
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 37
tcctggctca ggacgaacgc tggcggcgtg cctaatacat gcaagtcgtg cggacctttt      60
```

```
aaaagcttgc ttttaaaagg ttagcggcgg acgggtgagt aacacgtggg caacctgcct      120
gtaagatcgg gataacgccg ggaaaccggg gctaataccg gatagttttt tcctccgcat      180
ggaggaaaaa ggaaagacgg cttykgctgt cacttacaga tgggcccgcg gcgcattagc      240
twgttggtgg ggtaayggct caccaaggca acgatgcgta gccgacctga gaggtgatc       300 ggccacattg ggactgagac acggcccaaa ctcctacggg aggcagcagt agggaatctt      360
ccgcaatgga cgaaagtctg acggagcaac gccgcgtgag tgaagaaggc cttcgggtcg      420
taaaactctg ttgccgggga agaacaagtg ccgttcgaac agggcggygc cttgacggta      480
cccggccaga aagccacggc taactacgtg ccagcagccg cggta                      525
```

```
<210> SEQ ID NO 38
<211> LENGTH: 525
<212> TYPE: DNA
<213> ORGANISM: Bacillus
<220> FEATURE:
<221> NAME/KEY: misc_feature
<222> LOCATION: (1)..(525)
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate P4-74B
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 38
tcctggctca ggacgaacgc tggcggcgtg cctaatacat gcaagtcgtg cggacctttt       60
aaaagcttgc ttttaaaagg ttagcggcgg acgggtgagt aacacgtggg caacctgcct      120
gtaagatcgg gataacgccg ggaaaccggg gctaataccg gatagttttt tcctccgcat      180
ggaggaaaaa ggaaagacgg cttykgctgt cacttacaga tgggcccgcg gcgcattagc      240
twgttggtgg ggtaayggct caccaaggca acgatgcgta gccgacctga gaggtgatc       300 ggccacattg ggactgagac acggcccaaa ctcctacggg aggcagcagt agggaatctt      360
ccgcaatgga cgaaagtctg acggagcaac gccgcgtgag tgaagaaggc cttcgggtcg      420
taaaactctg ttgccgggga agaacaagtg ccgttcgaac agggcggygc cttgacggta      480
cccggccaga aagccacggc taactacgtg ccagcagccg cggta                      525
```

```
<210> SEQ ID NO 39
<211> LENGTH: 525
<212> TYPE: DNA
<213> ORGANISM: Bacillus
<220> FEATURE:
<221> NAME/KEY: misc_feature
<222> LOCATION: (1)..(525)
```

```
<223> OTHER INFORMATION: 525 bp DNA fragment encoding 16S rRNA molecule
<220> FEATURE:
<221> NAME/KEY: misc_feature
<222> LOCATION: (1)..(525)
<223> OTHER INFORMATION: Bacillus isolate P4-102B
<220> FEATURE:
<221> NAME/KEY: misc_feature
<222> LOCATION: (204)..(204)
<223> OTHER INFORMATION: y = t or c
<220> FEATURE:
<221> NAME/KEY: misc_feature
<222> LOCATION: (205)..(205)
<223> OTHER INFORMATION: k = g or t
<220> FEATURE:
<221> NAME/KEY: misc_feature
<222> LOCATION: (242)..(242)
<223> OTHER INFORMATION: w = a or t
<220> FEATURE:
<221> NAME/KEY: misc_feature
<222> LOCATION: (256)..(256)
<223> OTHER INFORMATION: y = t or c
<220> FEATURE:
<221> NAME/KEY: misc_feature
<222> LOCATION: (468)..(468)
<223> OTHER INFORMATION: y = t or c

<400> SEQUENCE: 39
tcctggctca ggacgaacgc tggcggcgtg cctaatacat gcaagtcgtg cggaccttt     60 aaaagcttgc ttttaaaagg ttagcggcgg acgggtgagt aacacgtggg caacctgcct   120
gtaagatcgg gataacgccg ggaaaccggg gctaataccg gatagttttt tcctccgcat   180
ggaggaaaaa ggaaagacgg cttykgctgt cacttacaga tgggcccgcg gcgcattagc   240
twgttggtgg ggtaayggct caccaaggca acgatgcgta gccgacctga gagggtgatc   300
ggccacattg ggactgagac acggcccaaa ctcctacggg aggcagcagt agggaatctt   360
ccgcaatgga cgaaagtctg acggagcaac gccgcgtgag tgaagaaggc cttcgggtcg   420
taaaactctg ttgccgggga agaacaagtg ccgttcgaac agggcggygc cttgacggta   480
cccggccaga aagccacggc taactacgtg ccagcagccg cggta                   525

<210> SEQ ID NO 40
<211> LENGTH: 1549
<212> TYPE: DNA
<213> ORGANISM: Bacillus
<220> FEATURE:
<221> NAME/KEY: misc_feature
<222> LOCATION: (1)..(1549)
<223> OTHER INFORMATION: 1549 bp DNA fragment encoding 16S rRNA molecule
<220> FEATURE:
<221> NAME/KEY: misc_feature
<222> LOCATION: (1)..(1549)
<223> OTHER INFORMATION: Bacillus isolate 17C5
<220> FEATURE:
<221> NAME/KEY: misc_feature
<222> LOCATION: (216)..(216)
<223> OTHER INFORMATION: y = t or c
<220> FEATURE:
<221> NAME/KEY: misc_feature
<222> LOCATION: (217)..(217)
<223> OTHER INFORMATION: k = g or t
<220> FEATURE:
<221> NAME/KEY: misc_feature
<222> LOCATION: (254)..(254)
<223> OTHER INFORMATION: w = a or t
<220> FEATURE:
<221> NAME/KEY: misc_feature
<222> LOCATION: (268)..(268)
<223> OTHER INFORMATION: y = t or c
<220> FEATURE:
<221> NAME/KEY: misc_feature
<222> LOCATION: (1461)..(1461)
<223> OTHER INFORMATION: y = to or c
```

<220> FEATURE:
<221> NAME/KEY: misc_feature
<222> LOCATION: (1535)..(1535)
<223> OTHER INFORMATION: y = t or c

<400> SEQUENCE: 40

```
tggagagttt gatcctggct caggacgaac gctggcggcg tgcctaatac atgcaagtcg      60
tgcggacctt ttaaaagctt gcttttaaaa ggttagcggc ggacgggtga gtaacacgtg     120
ggcaacctgc ctgtaagatc gggataacgc cgggaaaccg gggctaatac cggatagttt    180
tttcctccgc atggaggaaa aggaaagac ggcttykgct gtcacttaca gatgggcccg     240
cggcgcatta gctwgttggt ggggtaaygg ctcaccaagg caacgatgcg tagccgacct    300
gagagggtga tcggccacat tgggactgag acacggccca aactcctacg ggaggcagca    360
gtagggaatc ttccgcaatg gacgaaagtc tgacggagca acgccgcgtg agtgaagaag    420
gccttcgggt cgtaaaactc tgttgccggg aagaacaag tgccgttcga acagggcggc     480
gccttgacgg tacccggcca gaaagccacg gctaactacg tgccagcagc cgcggtaata    540
cgtaggtggc aagcgttgtc cggaattatt gggcgtaaag cgcgcgcagg cggcttctta    600
agtctgatgt gaaatcttgc ggctcaaccg caagcggtca ttggaaactg ggaggcttga    660
gtgcagaaga ggagagtgga attccacgtg tagcggtgaa atgcgtagag atgtggagga    720
acaccagtgg cgaaggcggc tctctggtct gtaactgacg ctgaggcgcg aaagcgtggg    780
gagcaaacag gattagatac cctggtagtc cacgccgtaa acgatgagtg ctaagtgtta    840
gagggtttcc gccctttagt gctgcagcta acgcattaag cactccgcct ggggagtacg    900
gccgcaaggc tgaaactcaa aggaattgac ggggcccgc acaagcggtg gagcatgtgg     960
tttaattcga agcaacgcga agaaccttac caggtcttga catcctctga cctccctgga   1020
gacagggcct tccccttcgg gggacagagt gacaggtggt gcatggttgt cgtcagctcg   1080
tgtcgtgaga tgttgggtta agtcccgcaa cgagcgcaac ccttgacctt agttgccagc   1140
attsagttgg gcactctaag gtgactgccg gtgacaaacc ggaggaaggt ggggatgacg   1200
tcaaatcatc atgccccta tgacctgggc tacacacgtg ctacaatgga tggtacaaag   1260
ggctgcgaga ccgcgaggtt aagccaatcc cagaaaacca ttcccagttc ggattgcagg   1320
ctgcaacccg cctgcatgaa gccggaatcg ctagtaatcg cggatcagca tgccgcggtg   1380
aatacgttcc cgggccttgt acacaccgcc cgtcacacca cgagagtttg taacacccga   1440
agtcggtgag gtaacctta yggagccagc cgccgaaggt gggacagatg attgggggtga   1500
agtcgtaaca aggtagccgt atcggaaggt gcggytggat cacctcctt               1549
```

<210> SEQ ID NO 41
<211> LENGTH: 1548
<212> TYPE: DNA
<213> ORGANISM: Bacillus
<220> FEATURE:
<221> NAME/KEY: misc_feature
<222> LOCATION: (1)..(1548)
<223> OTHER INFORMATION: 1548 bp DNA fragment encoding 16S rRNA molecule
<220> FEATURE:
<221> NAME/KEY: misc_feature
<222> LOCATION: (1)..(1548)
<223> OTHER INFORMATION: Bacillus isolate 36D1

<400> SEQUENCE: 41

```
gagtttgatc ctggctcagg acgaacgctg gcggcgtgcc taatacatgc aagtcgtgcg     60
gaccttttaa aagcttgctt ttaaaaggtt agcggcggac gggtgagtaa cacgtgggta   120
```

-continued

| | |
|---|---|
| acctgcctgt aagatcggga taacgccggg aaaccggggc taatatcgga tagttttttc | 180 |
| ctccgcatgg aggaaaaagg aaagacggct tttgctgtca cttacagatg ggcccgcggc | 240 |
| gcattagcta gttggtgggg taacggctca ccaaggcaac gatgcgtagc cgacctgaga | 300 |
| gggtgatcgg ccacattggg actgagacac ggcccaaact cctacgggag gcagcagtag | 360 |
| ggaatcttcc gcaatggacg aaagtctgac ggagcaacgc cgcgtgagtg aagaaggcct | 420 |
| tcgggtcgta aaactctgtt gccggggaag aacaagtgcc gttcgaacag gcggcgcct | 480 |
| tgacggtacc cggccagaaa gccacggcta actacgtgcc agcagccgcg gtaatacgta | 540 |
| ggtggcaagc gttgtccgga attattgggc gtaaagcgcg cgcaggcggt ttcttaagtc | 600 |
| tgatgtgaaa tcttgcggct caaccgcaag cggtcattgg aaactggggg cttgagtgc | 660 |
| agaagaggag agtggaattc cacgtgtagc ggtgaaatgc gtagagatgt ggaggaacac | 720 |
| cagtggcgaa ggcggctctc tggtctgtaa ctgacgctga gcgcgaaag cgtggggagc | 780 |
| aaacaggatt agataccctg gtagtccacg ccgtaaacga tgagtgctaa gtgttagagg | 840 |
| gtttccgccc tttagtgctg cagctaacgc attaagcact ccgcctgggg agtacggccg | 900 |
| caaggctgaa actcaaagga attgacgggg cccgcacaa gcggtggagc atgtggttta | 960 |
| attcgaagca acgcgaagaa ccttaccagg tcttgacatc ctctgacctc cctggagaca | 1020 |
| gggccttccc cttcggggga cagagtgaca ggtggtgcat ggttgtcgtc agctcgtgtc | 1080 |
| gtgagatgtt gggttaagtc ccgcaacgag cgcaacccctt gaccttagtt gccagcattc | 1140 |
| agttgggcac tctaaggtga ctgccggtga caaaccggag gaaggtgggg atgacgtcaa | 1200 |
| atcatcatgc cccttatgac ctgggctaca cacgtgctac aatggatggt acaaagggct | 1260 |
| gcgagaccgc gaggttaagc caatcccaga aaaccattcc cagttcggat tgcaggctgc | 1320 |
| aacccgcctg catgaagccg gaatcgctag taatcgcgga tcagcatgcc gcggtgaata | 1380 |
| cgttcccggg ccttgtacac accgcccgtc acaccacgag agtttgtaac acccgaagtc | 1440 |
| ggtgaggtaa cctttacgga gccagccgcc gaaggtggga cagatgattg gggtgaagtc | 1500 |
| gtaacaaggt agccgtatcg gaaggtgcgg ctggatcacc tcctttct | 1548 |

<210> SEQ ID NO 42
<211> LENGTH: 1548
<212> TYPE: DNA
<213> ORGANISM: Bacillus
<220> FEATURE:
<221> NAME/KEY: misc_feature
<222> LOCATION: (1)..(1548)
<223> OTHER INFORMATION: Bacillus isolate P4-102B
<220> FEATURE:
<221> NAME/KEY: misc_feature
<222> LOCATION: (1)..(1548)
<220> FEATURE:
<221> NAME/KEY: misc_feature
<222> LOCATION: (1)..(1548)
<223> OTHER INFORMATION: 1548 bp DNA fragment encoding 16S rRNA molecule

<400> SEQUENCE: 42

| | |
|---|---|
| gagtttgatc ctggctcagg acgaacgctg gcggcgtgcc taatacatgc aagtcgtgcg | 60 |
| gaccttttaa aagcttgctt ttaaaaggtt agcggcggac gggtgagtaa cacgtgggta | 120 |
| acctgcctgt aagatcggga taacgccggg aaaccggggc taataccgga tagttttttc | 180 |
| ttccgcatgg aggaaaaagg aaagacggct tcggctgtca cttacagatg ggcccgcggc | 240 |
| gcattagcta gttggtgggg taatggctca ccaaggcaac gatgcgtagc cgacctgaga | 300 |
| gggtgatcgg ccacattggg actgagacac ggcccaaact cctacgggag gcagcagtag | 360 |

```
ggaatcttcc gcaatggacg aaagtctgac ggagcaacgc cgcgtgagtg aagaaggcct      420
tcgggtcgta aaactctgtt gccggggaag aacaagtgcc gttcgaatag ggcggcgcct      480
tgacggtacc cggccagaaa gccacggcta actacgtgcc agcagccgcg gtaatacgta      540
ggtggcaagc gttgtccgga attattgggc gtaaagcgcg cgcaggcggc ttcttaagtc      600
tgatgtgaaa tcttgcggct caaccgcaag tggtcattgg aaactgggag gcttgagtgc      660
agaagaggag agtggaattc cacgtgtagc ggtgaaatgc gtagagatgt ggaggaacac      720
cagtggcgaa ggcggctctc tggtctgtaa ctgacgctga ggcgcgaaag cgtggggagc      780
aaacaggatt agataccctg gtagtccacg ccgtaaacga tgagtgctaa gtgttagagg      840
gtttccgccc tttagtgctg cagctaacgc attaagcact ccgcctgggg agtacggccg      900
caaggctgaa actcaaagga attgacgggg cccgcacaa gcggtggagc atgtggttta      960
attcgaagca acgcgaagaa ccttaccagg tcttgacatc ctctgacctc cctggagaca     1020
gggccttccc cttcggggga cagagtgaca ggtggtgcat ggttgtcgtc agctcgtgtc     1080
gtgagatgtt gggttaagtc cgcaacgag cgcaacccett gaccttagtt gccagcattc     1140
agttgggcac tctaaggtga ctgccggtga caaaccggag gaaggtgggg atgacgtcaa     1200
atcatcatgc cccttatgac ctgggctaca cacgtgctac aatggatggt acaaagggct     1260
gcgagaccgc gaggttaagc caatcccaga aaaccattcc cagttcggat tgcaggctgc     1320
aacccgcctg catgaagccg gaatcgctag taatcgcgga tcagcatgcc gcggtgaata     1380
cgttcccggg ccttgtacac accgcccgtc acaccacgag agtttgtaac acccgaagtc     1440
ggtgaggtaa cctttacgga gccagccgcc gaaggtggga cagatgattg gggtgaagtc     1500
gtaacaaggt agccgtatcg gaaggtgcgg ctggatcacc tcctttct                  1548
```

<210> SEQ ID NO 43
<211> LENGTH: 19
<212> TYPE: DNA
<213> ORGANISM: E. coli
<220> FEATURE:
<221> NAME/KEY: misc_feature
<222> LOCATION: (1)..(19)
<223> OTHER INFORMATION: Primer based on E. coli 16S rRNA
<220> FEATURE:
<221> NAME/KEY: misc_feature
<222> LOCATION: (1)..(19)
<223> OTHER INFORMATION: Artificial sequence

<400> SEQUENCE: 43
gagtttgatc ctggctcag                                                    19

<210> SEQ ID NO 44
<211> LENGTH: 20
<212> TYPE: DNA
<213> ORGANISM: E. coli
<220> FEATURE:
<221> NAME/KEY: misc_feature
<222> LOCATION: (1)..(20)
<223> OTHER INFORMATION: Primer based on E. coli 16S rRNA
<220> FEATURE:
<221> NAME/KEY: misc_feature
<222> LOCATION: (1)..(20)
<223> OTHER INFORMATION: Artificial sequence

<400> SEQUENCE: 44
agaaaggagg tgatccagcc                                                   20